(12) United States Patent
Betageri et al.

(10) Patent No.: US 6,284,768 B1
(45) Date of Patent: Sep. 4, 2001

(54) SRC FAMILY SH2 DOMAIN INHIBITORS

(75) Inventors: Rajashekhar Betageri, Bethel, CT (US); Pierre L. Beaulieu, Rosemere (CA); Jean-Marie Ferland, Saint Laurent (CA); Montse Llinas-Brunet, Pierrefonds (CA); Neil Moss, Ridgefield, CT (US); Usha Patel, Brookfield, CT (US); John R. Proudfoot, Newtown, CT (US); Mario Cardozo, Brookfield, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/438,647

(22) Filed: Nov. 12, 1999

Related U.S. Application Data

(62) Division of application No. 09/208,113, filed on Dec. 9, 1998, now Pat. No. 6,054,470.
(60) Provisional application No. 60/069,971, filed on Dec. 18, 1997.

(51) Int. Cl.[7] ............... A61K 31/435; A61K 31/44; C07D 401/12

(52) U.S. Cl. .......... 514/277; 514/332; 514/336; 514/337; 514/339; 546/256; 546/268.1; 546/276.4; 546/276.7; 546/277.4

(58) Field of Search ............... 546/256, 264, 546/268.1, 276.4, 276.7, 277.4; 514/277, 332, 336, 337, 339

Primary Examiner—Alan L. Rotman
Assistant Examiner—Rita Desai
(74) Attorney, Agent, or Firm—Robert P. Raymond; Anthony P. Bottino; Alan R. Stempel

(57) ABSTRACT

This invention relates to compounds of formula (I):

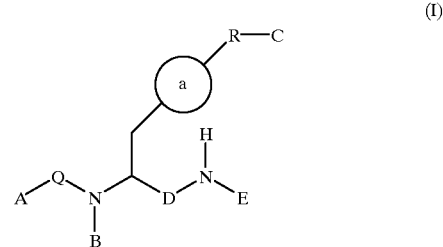

wherein Ring a, A, B, C, D, E, R and Q are defined herein. These compounds possess the ability to disrupt the interaction between regulatory proteins possessing one or more SH2 domains and their native ligands.

10 Claims, No Drawings

SRC FAMILY SH2 DOMAIN INHIBITORS

RELATED APPLICATION DATA

This application is a divisional application of U.S. application Ser. No. 09/208,113 now U.S. Pat. No. 6,054,470 filed Dec. 9, 1998 which in turn claims benefit to U.S. Provisional Application No. 60/069,971 filed Dec. 18, 1997.

TECHNICAL FIELD OF THE INVENTION

This invention relates to compounds that bind to the Src family SH2 domains of particular regulatory proteins. Specifically, the compounds of this invention possess the ability to disrupt the interaction between regulatory proteins possessing one or more SH2 domains and their native ligands. Accordingly, the compounds of this invention are useful for the treatment and prevention of neoplastic and chronic inflammatory diseases. In one embodiment, this invention relates to a novel class of Src family SH2 inhibitors and pharmaceutical compositions comprising these compounds. This invention also relates to methods for producing these Src family SH2 inhibitors. Because of their ability to target Src family SH2 domains, the compounds and pharmaceutical compositions of this invention are particularly well suited as agonists and antagonists of tyrosine-kinase dependent regulatory proteins containing Src family SH2 binding domains.

BACKGROUND OF THE INVENTION

The activation of cells by growth factors, mitogens and antigens resulting in proliferation and differentiation is often dependent on inducible tyrosine kinase activity. This tyrosine kinase activity increases the phosphotyrosine content of many receptor-like and cytoplasmic regulatory proteins. Often, the physical association of such regulatory proteins is mediated through those phosphotyrosine residues. The interaction between a regulatory protein and a tyrosine kinase is often a critical step in initiating and modulating cellular signal transduction pathways.

The receptor-mediated activation of cells is often dependent on inducible tyrosine kinase activity. Activation of tyrosine kinase signal transduction pathways result in a transient increase in intracellular tyrosine phosphorylation on selective subsets of regulatory proteins. This tyrosine phosphorylation of proteins provides multiple means of regulation. For example, tyrosine phosphorylation may modulate the enzymatic activity of proteins, as in the case of p56lck (sometimes referred to herein as "Lck"), PLCγ, and P1-3-kinase. In addition to enzyme regulation through covalent modification, one of the major roles for tyrosine phosphorylation is to create a binding site for Src homology 2 domains ("SH2 domains"). SH2 domains are homologous motifs of approximately 100 amino acids, which recognize and bind to the phosphorylated sequences present on regulatory proteins and growth factor receptors (D. Anderson et al., *Science*, 250, pp. 979–82 (1990)). A particularly important subset of proteins containing SH2 domains is the Src family of proteins ("Src family").

One of the primary purposes of the Src family phosphoprotein/SH2 domain interaction is to initiate the association of proteins into an activation complex, often around the intracellular domain of the receptor itself. This role of the Src family SH2 domain mediates and organizes the ordered, physical assembly of the various proteins in the activation complex. The activity of a number of immunologically important Src family SH2 domain-containing proteins, including Src, Fyn, Fgr, Yes, Lyn, Hck and Lck, is mediated in this way. P56lck is of particular interest because it has been associated with the signal transduction cascade needed for T-cell activation mediated by the T-cell receptor (TCR) (D. B. Straus et al., *Cell* 70, pp. 585–93 (1992)).

Disrupting the interaction between Src family SH2 domains and their phosphotyrosine-bearing native ligands (referred to herein as "Src family SH2 domain inhibition") represents a unique therapeutic approach to immunomodulation and the treatment or prevention of disorders associated with aberrant cellular transduction modulated by Src family SH2 domain binding interactions, such as certain autoimmune and inflammatory disorders, cancer and diabetes. However, despite considerable effort being devoted to this field of endeavor, no suitable drug candidates have yet emerged.

One major hurdle in this drug discovery effort has been the necessary inclusion of a phosphorylated tyrosine residue (sometimes abbreviated herein as "pTyr"), or a phosphorylated analog thereof, to perform the crucial role of the native phosphotyrosine in the phosphotyrosine-containing ligands of Src family SH2 domain-containing regulatory proteins. However, agents containing phosphotyrosine, other phosphorylated α-amino acid residues, or phosphorylated analogs thereof, are not optimal therapeutic agents because the presence of the phosphorylated moiety substantially impedes their cell penetrability. In addition, the phosphate moiety tends to be metabolically unstable and therefore, results in premature degradation of the therapeutic agent. In contrast, the absence of a phosphate moiety is often associated with agents having poor binding affinity and lack of potency. Prior attempts at producing therapeutic agents containing phosphotyrosyl mimetics have met with only marginal success, including the attempted use of the conformationally constrained pTyr analogue, $N^\alpha$-acetyl pTyr amide (T. R. Burke, Jr. et al., *J. Med. Chem.*, 38, pp. 1386–96 (1995)). Another attempt to produce an active compound containing a phosphotyrosyl mimetic replaced pTyr with (2-malonyl)Tyr (B. Ye et al., *J. Med. Chem.*, 38, pp. 4270–75 (1995)). The production of compounds containing other types of phosphate mimics include the use of $NO_2$, $CH_2CONHOH$, $NH_2$, $CH_2COOH$, $CH_2SO_3H$, $CH_2PO_3H_2$, $CHOHPO_3H_2$, $CF_2PO_3H_2$ and $OPSO_2H_2$ (T. Gilmer et al., *J. Biol. Chem.*, 269(50), pp. 31711–19 (1994)), and $CH_2CH(COOH)_2$ (Charifson et al., *Biochemistry*, 36, pp. 6283–93 (1997)). However, until now, no effective replacement or mimic for the critical phosphotyrosine residue has been reported in connection with a Src family SH2 inhibitor so that cellular or in-vivo activity was clearly demonstrated. Recently published PCT patent application WO 97/12903 shows the only published example of which we are aware of cellular activity of any phosphate mimic. Specifically, WO 97/12903 refers to peptidomimetics incorporating $CF_2PO_3H_2$ and monoesters thereof (see Table 4 on page 112).

Another major hurdle to producing effective Src family SH2 domain inhibitors has been the high negative charge carried by native ligands of Src family SH2 domain binding proteins. For example, sequences containing pTyr-Glu-Glu-Ile have been reported as the optimal binding sequence for Src family SH2 domains (Z. Songyang et al., *Cell*, 72, pp. 767–78 (1993)). Five negatively charged groups are associated with this sequence. The presence of these multiple negative charges, although useful for binding affinity, is not amenable for use in a bioavailable drug substance. As most of the above-referenced documents reveal, attempts to replace all of these negative charges with neutral- or positively charged-amino acids or amino acid mimics met with limited success due to reduced binding affinity (Gilmer, et al., supra,).

A limited number of reports discuss the use of particular Src family SH2 domain inhibitors in whole cells. However, the majority of these trials have required the use of artificial means (e.g., extraneous agents or special microinjection techniques) to allow the Src family SH2 domain inhibitors to successfully enter the cell (Xiao, et al., *J. Biol. Chem.* 269, pp. 21244–8 (1994) and Wange, et al., *J. Biol. Chem.* 270, pp. 944–8 (1995)). To date, aside from WO 97/12903, no reported Src family SH2 inhibitor has been shown to possess high activity levels in whole cells without cell permeabilizers, signal peptides, prodrugs and the like.

Accordingly, the need exists for Src family SH2 inhibitors that overcome the above-mentioned deficiencies.

SUMMARY OF THE INVENTION

This invention satisfies the need for potent Src family SH2 inhibitors by providing a compound of formula (I):

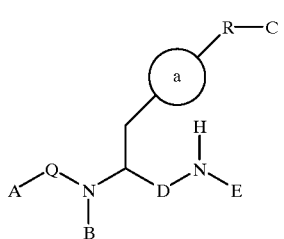

wherein:
Ring a is selected from the group consisting of cycloalkyl, aryl or heterocyclyl;
A is selected from the group consisting of alkyl; alkenyl; alkynyl; alkoxy; cycloalkyl; cycloalkenyl; heterocyclyl and aryl; wherein said cycloalkyl, heterocyclyl or aryl is optionally linked to Q or N via an alkoxy, —O—, amino, lower alkyl, lower alkyl amino, carbonyl, amido, amido alkyl, alkoxycarbonyl, carbonylalkyloxy, cycloalkyl or heterocyclyl linker;
Q is selected from the group consisting of a bond, >C═O, >S(O)$_2$ and >C═S;
B is selected from the group consisting of H; lower alkyl and a nitrogen-protecting group;
R is a bond or an alkyl, aryl, heterocyclyl or cycloalkyl linker;
C is an acidic functionality that carries one or two negative charges at physiological pH;
D is >CH$_2$; >C═O or >C═S;
E is a six-membered unsaturated heterocycle having two double bonds within the ring and the following ring members:
(a) one or two nitrogen ring members optionally substituted with R$_b$,
(b) one ring member selected from the group consisting of >C═O; >C═S; >C═NH; >C═N-lower alkyl and >C═N-nitrogen-protecting group;
(c) one >C—R$_a$ or >N—R$_a$ ring member positioned meta to the point of attachment of the heterocycle E to the adjacent nitrogen; and
(d) two or three additional carbon ring members, wherein said additional carbon ring members are optionally substituted with alkyl; alkoxy: halo; aryl; alkyloxy carbonyl or alkylamino and, if two optionally substituted ring members are present in adjacent positions on heterocycle E, said adjacent ring members may be linked together to form a fused 5–8 membered heterocyclic or carbocyclic ring which may be aromatic, partially unsaturated or fully saturated;
R$_a$ is selected from the group consisting of alkyl; alkenyl; alkynyl; heterocyclyl; cycloalkyl and aryl; wherein said cycloalkyl or aryl may optionally be linked to the adjacent carbon or nitrogen via a lower alkyl, lower alkoxy, lower alkylamino, lower alkylurea, or lower alkyl carbonyloxy linker; and
each R$_b$ is selected from the group consisting of H; alkyl; alkoxy; halo; aryl; alkyloxy carbonyl and alkylamino
and the pharmaceutically acceptable tautomers, salts and esters thereof.

Yet another object of this invention is to provide pharmaceutical compositions comprising the compounds of formula (I) and methods for their use in disrupting Src family SH2 domain binding interactions, in inhibiting T-cell activation, in modulating signal transduction, in immunomodulation and in the treatment or prevention of disorders associated with Src family SH2 domain binding interactions.

A further object of this invention is to provide convenient methods for producing the compounds of formula (I).

These and other objects will be readily apparent to those of ordinary skill in the art based upon the following detailed disclosure of this invention.

DETAILED DESCRIPTION OF THE INVENTION

In order that the invention herein described may be more fully understood, the following detailed description is set forth. As used herein, the following abbreviations are used:
Bn=Benzyl
BOC or t-BOC=tertiary butoxycarbonyl
chloranil=2,3,5,6-tetrachloro-1,4-benzoquinone
DDQ=2,3-dichloro-5,6-dicyano-1,4-benzoquinone
DMAP=4-dimethylamino pyridine
Et=ethyl
Me=methyl
Ph=phenyl
Pr=propyl
Pyr=pyridine
TFA=trifluoroacetic acid
THF=tetrahydrofuran
EDC=1-(3-dimethylaminopropyl)3-ethylcarbodiimide hydrochloride
DBU=1,8-diazabicyclo[5.4.0]undec-7-ene
TBTU=O-Benzotriazolyl-N,N,N',N'-tetramethyluronium tetrafluoroborate
NMM=N-methylmorpholine
DIEA=Diisopropylethylamine
HOBT =1-hydroxybenzotriazole
HOAT=1-Hydroxy-7-azabenzotriazole
HATU=O-(7-azabenzotriazol-1-yl)-N,N,N',N'-tetramethyluronium hexafluorophosphate
NPG=Nitrogen protecting group
OPG=Oxygen protecting group As used herein, each of the following terms, used alone or in conjunction with other terms, are defined as follows (except where noted to the contrary):

The term "alkyl" refers to a saturated aliphatic radical containing from one to ten carbon atoms. "Alkyl" refers to both branched and unbranched alkyl groups. Preferred alkyl groups are alkyl groups containing from one to eight carbon atoms and branched alkyl groups containing from three to eight carbon atoms. More preferred alkyl groups are straight chain alkyl groups containing from one to six carbon atoms and branched alkyl groups containing from three to six carbon atoms.

The term "cycloalkyl" refers to the cyclic analog of an alkyl group, as defined above. Preferred cycloalkyl groups are saturated cycloalkyl groups containing from three to eight carbon atoms, and more preferably, three to six carbon atoms. "Alkyl" and "cycloalkyl", as used herein, include unsubstituted alkyl and cycloalkyl radicals, those radicals that are partially or fully halogenated and those radicals substituted with one to four, preferably one or two, substituents selected from halo, amino, cyano, nitro, methoxy, ethoxy and hydroxy.

The terms "alkenyl" and "alkynyl" refer to mono- or polyunsaturated aliphatic hydrocarbon radical containing from two to twelve carbon atoms, containing at least one double or triple bond, respectively. "Alkenyl" and "alkynyl" refer to both branched and unbranched alkenyl and alkynyl groups. Preferred alkenyl and alkynyl groups are straight chain alkenyl or alkynyl groups containing from two to eight carbon atoms and branched alkenyl or alkynyl groups containing from five to ten carbon atoms. More preferred alkenyl and alkynyl groups are straight chain alkenyl or alkynyl groups containing from two to six carbon atoms and branched alkenyl or alkynyl groups containing from five to eight carbon atoms. The term "cycloalkenyl" refers to the cyclic analog of an alkenyl group, as defined above. Preferred cycloalkenyls include cycloalkenyl rings containing from three to eight carbon atoms, and more preferably, from three to six carbon atoms. "Alkenyl", "alkynyl" and "cycloalkenyl", as used herein, include unsubstituted alkenyl or alkynyl radicals, those radicals that are partially or fully halogenated and those radicals substituted with one to four, preferably one or two, substituents selected from halo, amino, cyano, nitro, methoxy, ethoxy and hydroxy.

The term "aryl" refers to phenyl and naphthyl, phenyl and naphthyl that are partially or fully halogenated and phenyl and naphthyl substituted with halo, alkyl; hydroxyl; nitro; —COOH; —CO(lower alkoxy); —CO(lower alkyl); amino; alkylamino; dialkylamino; alkoxy; —NCOH; —NCO(lower alkyl); —NSO$_2$—Ph(halo)$_{0-3}$, Ph; —O—Ph; naphthyl; —O-naphthyl; pyrrolyl; pyrrolyl subsituted with lower alkyl; pyridyl; pyridinyl; pyrazinyl; pyrimidinyl and pyridazinyl. Preferred aryl groups in position A in compounds of formula (I) and position $R_6$ in compounds of formula (II) include unsubstituted phenyl and phenyl substituted as defined above (preferably in the para-position).

The term "carboxy alkyl" refers to an alkyl radical containing a —COOH substituent.

The term "halo" refers to a halogen radical selected from fluoro, chloro, bromo or iodo. Preferred halo groups are fluoro, chloro and bromo.

The terms "heterocyclyl" refers to a stable 5–8 membered (but preferably, 5 or 6 membered) monocyclic or 8–11 membered bicyclic heterocycle radical which may be either saturated or unsaturated, aromatic or non-aromatic, and which may be optionally benzo- or pyridofused if monocyclic. Each heterocycle consists of carbon atoms and from 1 to 4 heteroatoms selected from the groups consisting of nitrogen, oxygen and sulfur. As used herein, "nitrogen" and "sulfur" include any oxidized form of nitrogen and sulfur and the quaternized form of any basic nitrogen. The heterocycle may be attached by any atom of the cycle which results in the creation of a stable structure. Preferred heterocycles include, for example, benzimidazolyl, furazanyl; imidazolyl, imidazolinoyl, imidazolidinyl, quinolyl, isoquinolyl, indolyl, oxazolyl, pyridyl, pyrrolyl, pyrrolinyl, pyrazolyl, pyrazinyl. pyrimidinyl, pyridazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazoyl, benzodioxolyl, tetrahydrothiophenyl and sulfolanyl. Most preferred heterocycles of this invention include imidazolyl, pyridyl, pyrrolyl, pyrazolyl, piperidinyl, morpholinyl, furyl, thienyl, thiazolyl and the benzo- and pyridofused derivatives thereof. Even more preferred are pyridyl. "Heterocyclyl" refers to unsubstituted heterocycle radicals, those radicals that are partially or fully halogenated and those radicals substituted with alkyl; hydroxyl; nitro; —COOH; —CO(lower alkoxy); —CO(lower alkyl); amino; alkylamino; dialkylamino; alkoxy; —NCOH; —NCO(lower alkyl); —NSO$_2$—Ph(halo)$_{0-3}$, Ph; —O—Ph; naphthyl; —O-naphthyl; pyrrolyl; pyrrolyl subsituted with lower alkyl; pyridyl; pyridinyl; pyrazinyl; pyrimidinyl and pyridazinyl.

The term "high level of activity" used in reference to a cellular assay refers to an $IC_{50}$ level <200 $\mu$M and preferably, <100 $\mu$M.

The term "lower", used in conjunction with other terms (e.g., "alkyl", "alkoxy" and the like), refers to a radical containing from one to six, preferably from one to five and more preferably, from one to four carbon atoms. For example, a "lower alkyl" group is a branched or unbranched alkyl radical containing from one to five carbon atoms.

The term "nitrogen protecting group" (NPG) refers to a substituent that is capable of protecting a reactive nitrogen functional group from undesired chemical reactions. Such nitrogen protecting groups include, for example, amino protecting groups such as acyl groups (including formyl, acetyl, benzoyl and the like) and urethanyl groups (including aromatic urethanyl groups, such as carbonylbenzyloxy (Cbz) and the like, and aliphatic urethanyl groups, such as t-butoxycarbonyl (Boc) or 9-fluorenylmethoxycarbonyl (Fmoc) and the like).

The term "oxygen protecting group" (OPG) refers to a substituent that is capable of protecting a reactive oxygen functional group from undesired chemical reactions. Such oxygen protecting groups include, for example, carboxylic acid protecting groups such as ester groups (including methyl, ethyl 'butyl, benzyl, trimethylsilylethyl and the like).

The term "patient" refers to a warm-blooded mammal and preferably, a human.

The term "phosphate mimic" refers to a group which mimics the role of phosphate in native ligands of Src family SH2 domains (most notably, Lck). Preferably, the phosphate mimic is an acidic functionality that carries one or two negative charges (preferably, one negative charge) at physiological pH. Such phosphate mimics include:

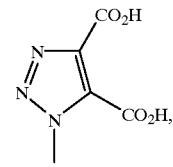

phosphonyl, phosphonyl monoester and carboxy alkyl or cycloalkyl (preferably, carboxy (lower alkyl or lower cycloalkyl), such as carboxy (methyl, ethyl, propyl, cyclopropyl, cyclopentyl or cyclohexyl)). Preferred phosphate mimics include (but are not limited to):

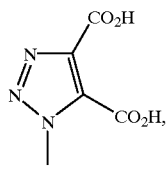

CH(COOH)$_2$; CH$_2$COOH; CHOHCOOH, CH(alkyl)COOH (preferably, CH(lower alkyl)COOH and more preferably CHCH$_3$COOH); C(alkyl)(alkyl)COOH (preferably, C(lower alkyl)(lower alkyl)COOH and more preferably, C(CH$_3$)$_2$COOH); CH(aryl)COOH, cycloalkylCOOH (preferably, cyclopropyl or cyclopentylCOOH); CH(cycloalkyl)COOH, CH(alkenyl)COOH, CH(alkynyl) COOH, CH(lower alkyl)(alkynyl)COOH, CH(alkoxy) COOH, C(lower alkyl)(alkoxy)COOH, CH(alkylthio) COOH, CH(lower alkyl)(alkylthio)COOH; CH$_2$SO$_3$H, CH(alkyl or cycloalkyl)SO$_3$H, C(lower alkyl)(lower alkyl) SO$_3$H, cycloalkylSO$_3$H; CH$_2$PO$_3$H$_2$, CH(alkyl or cycloalkyl)PO$_3$H$_2$, C(lower alkyl)(lower alkyl) PO$_3$H$_2$, cycloalkylPO$_3$H$_2$, CF$_2$PO$_3$H$_2$; NOHCOCOOH and NHCO-COOH. Especially preferred phosphate mimics are —C(H or C$_1$–C$_4$ alkyl)(C$_1$–C$_4$ alkyl)COOH; CF$_2$PO$_3$H$_2$; NHCO-COOH; CH$_2$SO$_3$H; C(H or C$_1$–C$_4$ alkyl)(C$_1$–C$_4$ alkyl) SO$_3$H; C(OH)COOH and

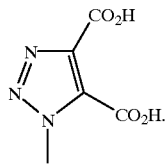

The terms "prodrug", "diester" and "ester" refer to the C$_1$–C$_8$, preferably, the C$_1$–C$_3$, and more preferably, the methyl or ethyl derivatives and the C$_3$–C$_8$, and preferably, the C$_3$–C$_6$, cycloalkyl or cycloalkenyl derivatives, or the aryl derivatives of the acidic functionality or functionalities of these groups. Acidic functionalities in this context includes carboxylic acids, sulfonic acids, phosphonic acids and the like. Such derivatives may be more bioavailable analogues of compounds of formula (I).

The term "prevention" or "prophylaxis" refers to a measurable reduction in the likelihood of patient acquiring a disease or disorder. The term "treatment" refers to either the alleviation of the physical symptoms of a disease or an improvement in the physiological markers used to measure progression of a disease state.

The term "pharmaceutically acceptable carrier" of "pharmaceutically acceptable adjuvant" refers to a non-toxic carrier or adjuvant that may be administered to a patient together with a compound of this invention and which does not destroy the pharmacological activity of that compound.

The terms "pharmaceutically effective amount" and "therapeutically effective amount" are used interchangeably and refer to an amount effective in curing or alleviating the symptoms of a disorder involving an interaction between a Src family SH2 domain of a protein and its ligand. Such treatment generally results in immunosuppression. Suppressed immunity can be readily measured by observing the degree of inhibition of IL-2 production in human T-cells (PBLs) by known techniques. Alternatively, a "pharmaceutically" or "therapeutically effective amount" refers to an amount which is effective, upon single or multiple dose administration to the patient, in controlling the growth of a neoplasm, in alleviating, in whole or in part, the symptoms of the chronic inflammatory disorder, prolonging the survivability or improving the clinical disposition or physical well-being of the patient. The term "prophylactically effective amount" refers to an amount effective in preventing or reducing the likelihood of initial onset or progression of a disorder involving an interaction between a Src family SH2 domain of a protein and its ligand.

It should be understood that any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations. In the case of compounds of formula (I), the S-isomer is preferred.

The compounds of this invention are defined to include pharmaceutically acceptable derivatives thereof. A "pharmaceutically acceptable derivative" refers to any pharmaceutically acceptable salt, ester, or salt of an ester of a compound of this invention, or any other compound which, upon administration to a patient, is capable of providing (directly or indirectly) a compound of this invention, a pharmacologically active metabolite or pharmacologically active residue thereof.

"Pharmaceutically acceptable salts" of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—(C$_1$–C$_4$ alkyl)$_4^+$ salts.

Combinations of substituents and variables encompassed by this invention are only those that result in the formation of stable compounds. It should also be understood that any radical described herein may be linked via any point of attachment so long as the resultant structure is stable. The term "stable" as used herein, refers to compounds which possess stability sufficient to permit manufacture and administration to a patient by conventional methods known in the art. Typically, such compounds are stable at a temperature of 40° C. or less, in the absence of moisture or other chemically reactive conditions, for at least a week.

The compounds of this invention also include those compounds with quaternization of any basic nitrogen-containing groups contained therein. The basic nitrogen can be quaternized with any agents known to those of ordinary skill in the art, including for example, lower alkyl halides, such as methyl, ethyl, propyl and butyl chlorides, bromides and iodides; dialkyl sulfates including dimethyl, dibutyl and diamyl sulfates; long chain halides such as decyl, lauryl, myristyl and stearyl chlorides, bromides and iodides; and aralkyl halides including benzyl and phenethyl bromides. Water or oil soluble or dispersible products may be obtained by such quaternization.

In addition, the compounds of this invention include prodrugs of the compounds of formula (I). Prodrugs include those compounds that, upon simple chemical transformation, are modified to produce a compound of formula (I). Simple chemical transformations include hydrolysis, oxidation and reduction. Specifically, when a prodrug of this invention is administered to a patient, the prodrug may be transformed into a compound of formula (I), thereby imparting the desired pharmacological effect.

The compounds of this invention are represented by formula (I):

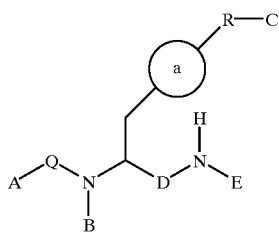

(I)

wherein:
Ring a is selected from the group consisting of cycloalkyl, aryl or heterocyclyl;
A is selected from the group consisting of alkyl; alkenyl; alkynyl; alkoxy; cycloalkyl; cycloalkenyl; heterocyclyl and aryl; wherein said cycloalkyl, heterocyclyl or aryl is optionally linked to Q or N via an alkoxy, —O—, amino, lower alkyl, lower alkyl amino, carbonyl, amido, amido alkyl, alkoxycarbonyl, carbonylalkyloxy, cycloalkyl or heterocyclyl linker;
Q is selected from the group consisting of a bond, >C=O, >S(O)$_2$ and >C=S;
B is selected from the group consisting of H; lower alkyl and a nitrogen-protecting group;
R is a bond or an alkyl, aryl, heterocyclyl or cycloalkyl linker;
C is an acidic functionality that carries one or two negative charges at physiological pH;
D is >CH$_2$; >C=O or >C=S;
E is a six-membered unsaturated heterocycle having two double bonds within the ring and the following ring members:
(a) one or two nitrogen ring members optionally substituted with R$_b$,
(b) one ring member selected from the group consisting of >C=O; >C=S; >C=NH; >C=N-lower alkyl and >C=N-nitrogen-protecting group;
(c) one >C—R$_a$ or >N—R$_a$ ring member positioned meta to the point of attachment of the heterocycle E to the adjacent nitrogen; and
(d) two or three additional carbon ring members, wherein said additional carbon ring members are optionally substituted with alkyl; alkoxy; halo; aryl; alkyloxy carbonyl or alkylamino
and, if two optionally substituted ring members are present in adjacent positions on heterocycle E, said adjacent ring members may be linked together to form a fused 5–8 membered heterocyclic or carbocyclic ring which may be aromatic, partially unsaturated or fully saturated;
R$_a$ is selected from the group consisting of alkyl; alkenyl; alkynyl; heterocyclyl; cycloalkyl and aryl; wherein said cycloalkyl or aryl may optionally be linked to the adjacent carbon or nitrogen via a lower alkyl, lower alkoxy, lower alkylamino, lower alkylurea, or lower alkyl carbonyloxy linker; and
each R$_b$ is selected from the group consisting of H; alkyl; alkoxy; halo; aryl; alkyloxy carbonyl and alkylamino and the pharmaceutically acceptable tautomers, salts and esters thereof.

In a preferred embodiment, Ring a is para-substituted phenyl.

In another preferred embodiment, the heterocycle E is selected from the group consisting of the following unsaturated heterocycles:

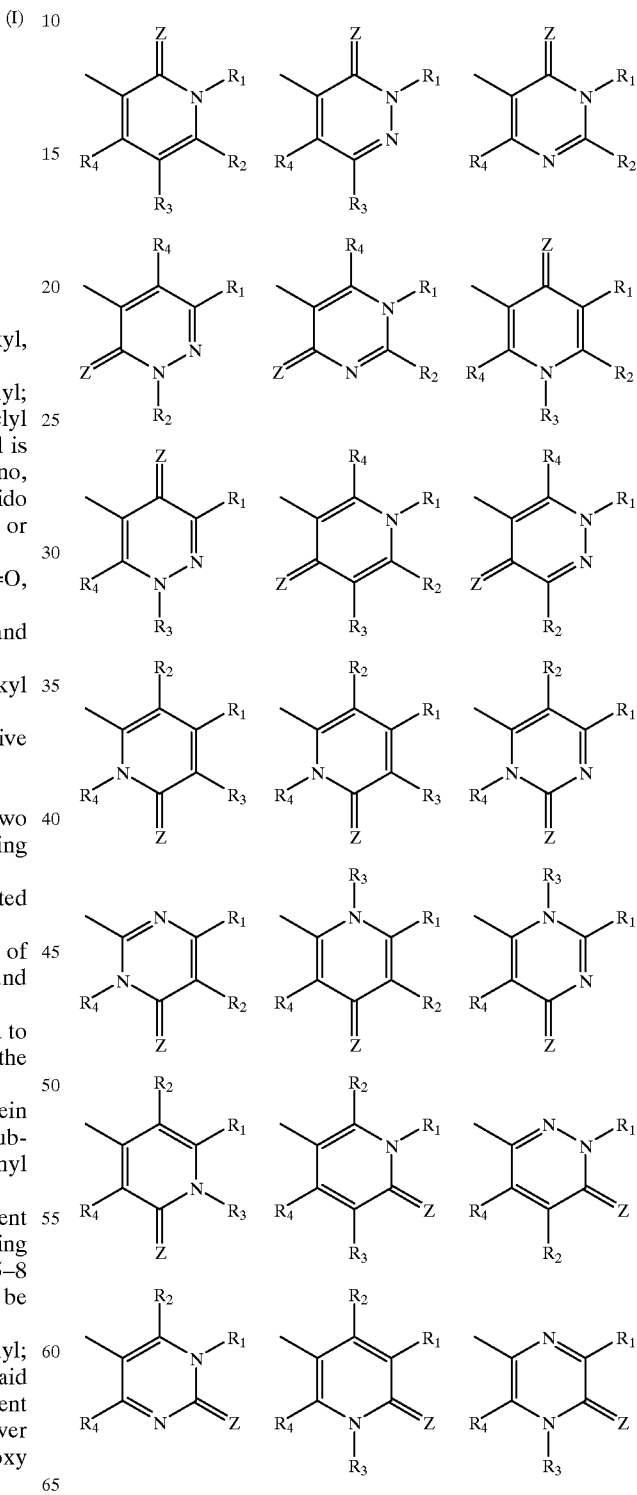

wherein
R₁ is alkyl; alkenyl; alkynyl; heterocyclyl; cycloalkyl or aryl; wherein said cycloalkyl or aryl may optionally be linked to the adjacent N or C via a lower alkyl, lower alkoxy, lower alkylamino, lower alkylurea, or lower alkyl carbonyloxy linker, R₂ and R₃ are each independently selected from the group consisting of H; alkyl; alkoxy; halo; aryl; alkyloxy carbonyl and alkylamino; wherein R₂ and R₃ are the same or different;

R₄ is alkyl; alkoxy; aryl; halo or alkylamino;

or any two of the substituents R₁–R₄, when present in adjacent positions on heterocycle E, may be linked together to form a fused 5–8 membered heterocyclic or carbocyclic ring which may be aromatic, partially unsaturated or fully saturated; and Z is O; S; NH; N-lower alkyl; or N-nitrogen-protecting group.

More preferably, E is selected from the group consisting of:

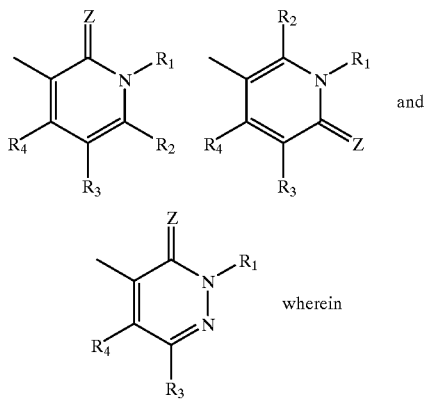

wherein

R₁ is alkyl; alkenyl; alkynyl; heterocyclyl; cycloalkyl or aryl; wherein said cycloalkyl or aryl may optionally be linked to the adjacent N via a lower alkyl, lower alkoxy, lower alkylamino, lower alkylurea, or lower alkyl carbonyloxy linker, R₂ and R₃ are each independently selected from the group consisting of H; alkyl; alkoxy; halo; aryl; alkyloxy carbonyl and alkylamino; wherein R₂ and R₃ are the same or different;

R₄ is alkyl; alkoxy; aryl; halo or alkylamino;

or any two of the substituents R₁–R₄, when present in adjacent positions on heterocycle E, may be linked together to form a fused 5–8 membered heterocyclic or carbocyclic ring which may be aromatic, partially unsaturated or fully saturated; and Z is O; S; NH; N-lower alkyl; or N-nitrogen-protecting group.

In a preferred embodiment, one or more of the following definitions apply in connection with compounds of formula (I):

A is alkoxy; cycloalkyl; aryl; or heterocyclyl; wherein said cycloalkyl. hetercycloalkyl or aryl is optionally linked to Q via an alkoxy; amino; lower alkyl; lower alkyl amino; amido, amido alkyl; cycloalkyl or heterocyclyl linker;

B is H or lower alkyl;

C is a phosphate mimic;

D is —CH₂— or >C=O (preferably >C=O);

Q is selected from the group consisting of >C=O, >S(O)₂ and >C=S;

R is a bond, a C₁–C₃ alkyl linker or a C₃–C₆ cycloalkyl linker;

E is a group of formula

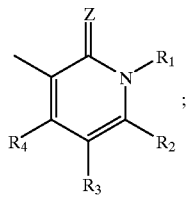

wherein

R₁ is alkyl; cycloalkyl or aryl; wherein said cycloalkyl or aryl may be linked to N via a lower alkyl linker, R₂ and R₃ are each independently H, halo or lower alkyl, wherein R₂ and R₃ are the same or different;

R₄ is lower alkyl; and

Z is O.

In a more preferred embodiment, one or more of the following definitions apply in connection with compounds of formula (I):

A is aryl or heterocyclyl, wherein said aryl or heterocyclyl is optionally linked to Q via an alkoxy, lower alkyl; amido or amido alkyl linker;

B is H or methyl;

C is —C(C₁–C₄ alkyl)(C₁–C₄ alkyl)COOH; CF₂PO₃H₂; NHCOCOOH; CH₂SO₃H or CHOHCOOH;

R is a bond;

D is >C=O;

E is a group of formula

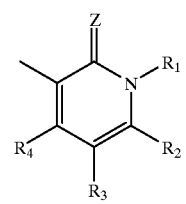

wherein

R₁ is alkyl; cycloalkyl or aryl; wherein said cycloalkyl or aryl may be linked to the adjacent N via a lower alkyl linker, R₂ and R₃ are each independently H; halo or lower alkyl, wherein R₂ and R₃ are the same or different;

R₄ is methyl; and

Z is O.

In another embodiment of the invention there are provided compounds of the formula (II):

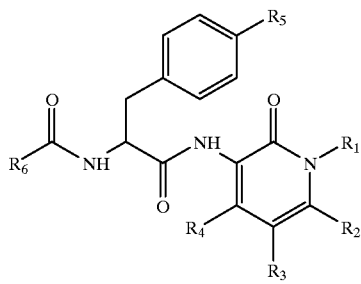

(II)

wherein:
R₁ is alkyl cycloalkyl or aryl; wherein said cycloalkyl or aryl may be linked to the adjacent N via a lower alkyl linker,
R₂ and R₃ are each independently H; halo: alkyl; alkoxy; aryl or alkylamino, wherein R₂ and R₃ are the same or different;
R₄ is alkyl; alkoxy; aryl or alkylamino;
R₅ is a phosphate mimic; and
R₆ is alkyl; alkenyl; alkynyl, alkoxy; cycloalkyl, cycloalkenyl; heterocyclyl or aryl; wherein said cycloalkyl, heterocyclyl or aryl is optionally linked to the adjacent carbonyl via an alkoxy; —O—; amino; lower alkyl; lower alkyl amino; carbonyl; amido; amido alkyl; alkoxycarbonyl; carbonylalkyloxy; cycloalkyl or heterocyclyl linker.

Preferably, the compounds of formula (II) are those in the S-configuration.

In a further preferred embodiment, one or more of the following definitions apply in connection with compounds of formula (II):
R₁ is cycloalkyl or aryl linked to the adjacent N via a lower alkyl linker,
R₂ and R₃ are each independently H, halo or lower alkyl, wherein R₂ and R₃ are the same or different
R₄ is lower alkyl;
R₅ is selected from the group consisting of ):

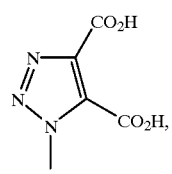

CH(COOH)₂; CH₂COOH; CHOHCOOH, CH(alkyl)COOH (preferably, CH(lower alkyl)COOH and more preferably, CHCH₃COOH); C(alkyl)(alkyl)COOH (preferably, C(lower alkyl)(lower alkyl)COOH and more preferably, C(CH₃)₂COOH); CH(aryl)COOH, cycloalkylCOOH (preferably, cyclopropyl or cyclopentylCOOH); CH(cycloalkyl)COOH, CH(alkenyl)COOH, CH(alkynyl)COOH, CH(lower alkyl)(alkynyl)COOH, CH(alkoxy)COOH, C(lower alkyl)(alkoxy)COOH, CH(alkylthio)COOH, CH(lower alkyl)(alkylthio)COOH; CH₂SO₃H, CH(alkyl or cycloalkyl) SO₃H C(lower alkyl)(lower alkyl) SO₃H, cycloalkylSO₃H; CH₂PO₃H₂, CH(alkyl or cycloalkyl)PO₃H₂, C(lower alkyl)(lower alkyl)PO₃H₂, cycloalkylPO₃H₂, CF₂PO₃H₂; NOHCOCOOH and NHCOCOOH; and R₆ is heterocyclyl or aryl; wherein said heterocyclyl or aryl is optionally linked to the adjacent carbonyl via an amino; lower alkyl; lower alkyl amino; amido or amido alkyl linker.

In a more preferred embodiment, one or more of the following definitions apply in connection with compounds of formula (II):
R₁ is benzyl or benzyl para-substituted with lower alkoxy;
R₂ and R₃ are independently selected from H and halo;
R₄ is methyl or ethyl;
R₅ is selected from the group consisting of C(CH₃)₂COOH; CF₂PO₃H₂; NHCOCOOH; CH₂SO₃H; and CHOHCOOH; and
R₆ is phenyl, phenyl para-substituted with a group consisting of halo, hydroxy, lower alkyl which may be partially or fully halogenated; naphthyl or benzimidazolyl; wherein said phenyl, substituted phenyl, naphthyl or benzimidazolyl is optionally linked to the adjacent carbonyl via a lower alkyl, amino or amido lower alkyl linker.

Preferred specific compounds of the invention are shown in formulas (II)–(III) of Fables 1–2. In these Tables, the point of attachment for variables R₁–R₅ is the left-most position, while for R₆, the point of attachment is the right-most position. A few of the compounds shown in Table 1 are N-methylated. N2-CH₃ refers to methylation at the left core nitrogen (i.e., the nitrogen attached directly to —CO—R₆). N1-CH3 refers to methylation of the right core nitrogen (i.e., the nitrogen attached directly to the pyridonyl ring). Compounds are of the S-configuration, unless otherwise noted.

TABLE 1

| Cmpd. | Kd (μM) | R₁ | R₂ | R₃ | R₄ | R₅ | R₆ |
|---|---|---|---|---|---|---|---|
| 1 | 2.3 | 4-methoxyphenylethyl | H | H | CH₃ | N-hydroxy oxamide | 1-ethylnaphthyl |
| 2 | 0.57 | 4-methoxyphenylethyl | H | H | CH₃ | 2,2-dimethylpropanoic acid | 1-ethylnaphthyl |
| 3 | 5.1 | 4-methoxyphenylethyl | H | H | CH₃ | 2-methylpropanoic acid | 1-ethylnaphthyl |

TABLE 1-continued
(II)
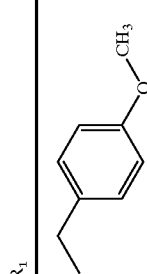
| Cmpd. | Kd (μM) | R₁ | R₂ | R₃ | R₄ | R₅ | R₆ |
|---|---|---|---|---|---|---|---|
| 4 | 42.5 | 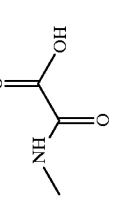 | H | H | CH₃ | 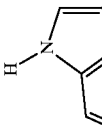 | 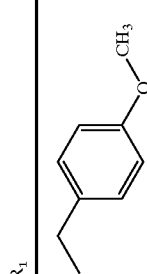 |
| 5 | 1.3 | 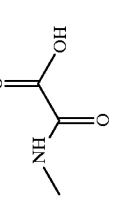 | H | H | CH₃ | 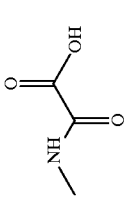 | 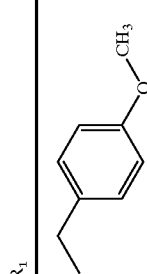 |
| 6 | 8.3 | 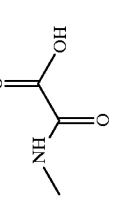 | H | H | CH₃ | 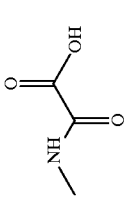 | |
| 7 | >11 | 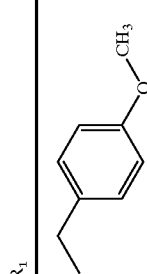 | H | H | CH₃ | 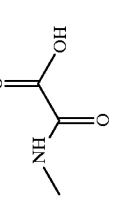 | 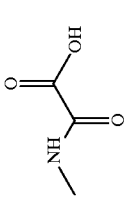 |

TABLE 1-continued (II)

| Cmpd. | Kd (µM) | R₁ | R₂ | R₃ | R₄ | R₅ | R₆ |
|---|---|---|---|---|---|---|---|
| 8 | 0.99 | 4-methoxybenzyl | H | H | CH₃ | lactic acid (CH(OH)CH₃-COOH) | 1-ethylnaphthalene |
| 9 | 64.5 | 4-methoxybenzyl | H | H | CH₃ | NH-C(O)-COOH | 1-(methylamino)naphthalene |
| 10 | 6.7 | 4-methoxybenzyl | H | H | CH₃ | NH-C(O)-COOH | 2-amino-4-ethylthiazole |
| 11 | 2.9 | 4-methoxybenzyl | H | H | CH₃ | NH-C(O)-COOH | 2-amino-5-ethyl-4-phenylthiazole |

TABLE 1-continued
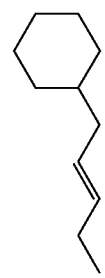
(II)
| Cmpd. | Kd (µM) | R₁ | R₂ | R₃ | R₄ | R₅ | R₆ |
|---|---|---|---|---|---|---|---|
| 12 | >250 | 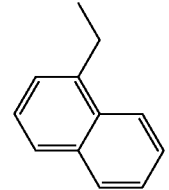 | H | H | CH₃ | 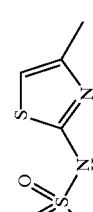 |  |
| 13 | 4.6 |  | H | H | CH₃ |  |  |
| 14 | 4.2 |  | H | H | CH₃ |  |  |
| 15 | 1.8 |  | H | H | CH₃ |  | |

TABLE 1-continued

| Cmpd. | Kd (μM) | R₁ | R₂ | R₃ | R₄ | R₅ | R₆ |
|---|---|---|---|---|---|---|---|
| 16 | 4.9 | 4-methoxybenzyl | H | H | CH₃ | -NHC(O)C(O)OH | 2-phenyl-4-ethyl-oxazol-5-one |
| 17 | 3.4 | (5-methoxypyridin-2-yl)methyl | H | H | CH₃ | -NHC(O)C(O)OH | 4-ethyl-2-(pyrazin-2-yl)thiazole |
| 18 | 17.7 | benzyl | H | H | CH₃ | -CH₂C(O)OH | 4-ethylnaphthalene |
| 19 | 37.2 | 2-methoxybenzyl | H | H | CH₃ | -CH₂C(O)OH | 4-ethylnaphthalene |

TABLE 1-continued
(II)
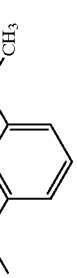
| Cmpd. | Kd (μM) | R₁ | R₂ | R₃ | R₄ | R₅ | R₆ |
|---|---|---|---|---|---|---|---|
| 20 | 19.4 | 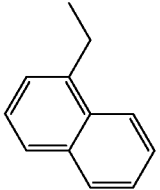 | H | H | CH₃ | 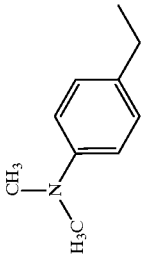 | 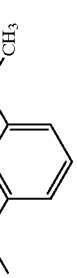 |
| 21 | 30.5 | 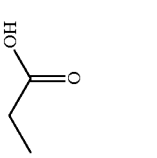 | H | H | CH₃ | 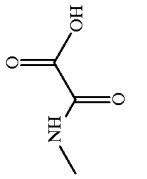 | 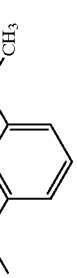 |
| 22 | 1.8 | 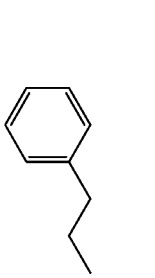 | H | H | CH₃ | 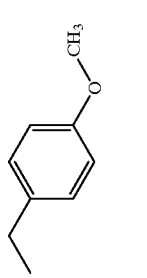 | |

TABLE 1-continued
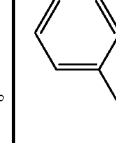
(II)
| Cmpd. | Kd (μM) | R₁ | R₂ | R₃ | R₄ | R₅ | R₆ |
|---|---|---|---|---|---|---|---|
| 23 | 55.7 | 2-ethylpyridine | H | H | CH₃ | propanoic acid | 1-ethylnaphthalene |
| 24 | 2.9 | 4-ethyl-methoxybenzene | H | H | CH₃ | N-hydroxy-N-methyl oxamic acid | 3-ethyl-1H-indole |
| 25 | 2.1 | 4-ethyl-methoxybenzene | H | H | CH₃ | N-methyl oxamic acid | N-methyl-1-naphthylamine |
| 26 | 4.3 | 4-ethyl-methoxybenzene | H | H | CH₃ | N-hydroxy-N-methyl oxamic acid | 4-ethyl-N,N-dimethylaniline |

TABLE 1-continued

| Cmpd. | Kd (μM) | R₁ | R₂ | R₃ | R₄ | R₅ | R₆ |
|---|---|---|---|---|---|---|---|
| 27 | 2.5 | 4-methoxybenzyl | H | H | CH₃ | NHCH₂COOH (oxamide) | 5-hydroxy-3-ethyl-1H-indol-yl |
| 28 | 1.1 | 4-methoxybenzyl | H | H | CH₃ | NHCH₂COOH (oxamide) | 2-thio-3-ethyl-1H-indol-yl |
| 29 | 1.2 | 4-methoxybenzyl | H | H | CH₃ | NHCH₂COOH (oxamide) | 2-ethyl-1,2,3,4-tetrahydroisoquinolin-yl |

TABLE 1-continued
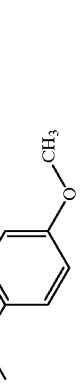
(II)
| Cmpd. | Kd (μM) | R₁ | R₂ | R₃ | R₄ | R₅ | R₆ |
|---|---|---|---|---|---|---|---|
| 30 | 0.35 | 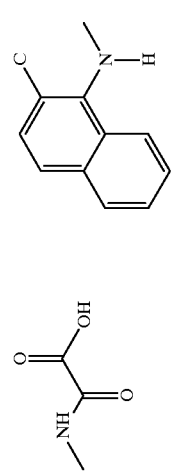 | H | H | CH₃ | 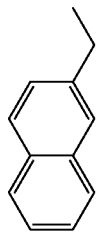 | 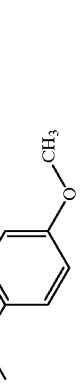 |
| 31 | 0.68 | 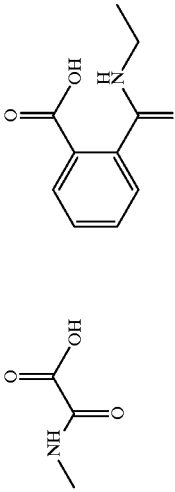 | H | H | CH₃ | 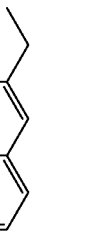 | 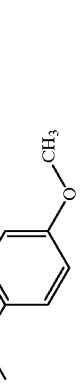 |
| 32 | 0.35 | 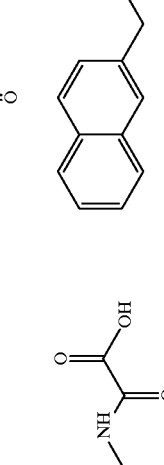 | H | H | CH₃ |  |  |

TABLE 1-continued
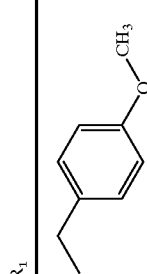
(II)
| Cmpd. | Kd (μM) | R$_1$ | R$_2$ | R$_3$ | R$_4$ | R$_5$ | R$_6$ |
|---|---|---|---|---|---|---|---|
| 33 | 3.7 | 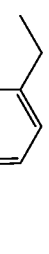 | H | H | CH$_3$ |  | 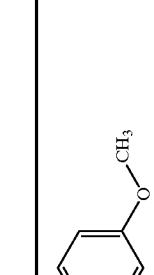 |
| 34 | 2.4 |  | H | H | CH$_3$ | 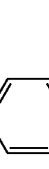 | 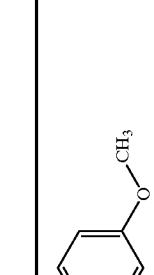 |
| 35 | 4.0 |  | H | H | CH$_3$ | 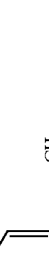 | 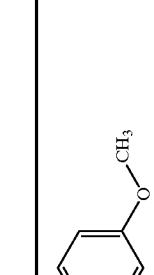 |
| 36 | 1.5 |  | H | H | CH$_3$ | 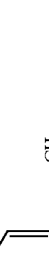 | (4-Br-phenyl) |

TABLE 1-continued
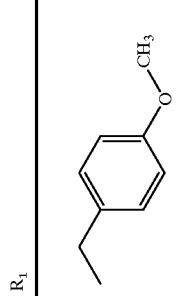
| Cmpd. | Kd (μM) | R1 | R2 | R3 | R4 | R5 | R6 |
|---|---|---|---|---|---|---|---|
| 37 | 0.65 | 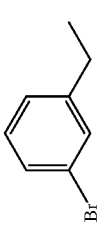 | H | H | $CH_3$ | 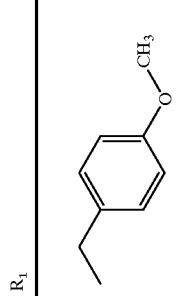 | 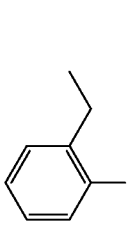 |
| 38 | 3.2 | 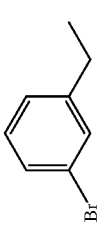 | H | H | $CH_3$ | 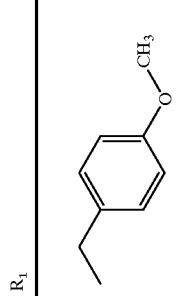 | 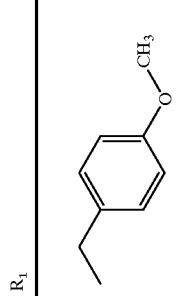 |
| 39 | 2.3 | 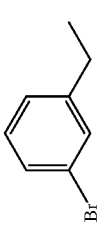 | H | H | $CH_3$ | 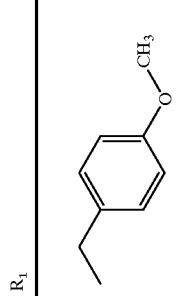 | 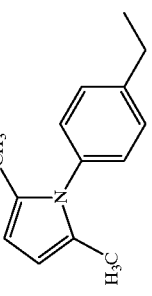 |
| 40 | 1.9 | 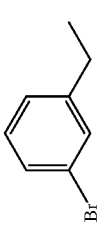 | H | H | $CH_3$ | 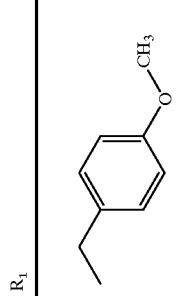 | 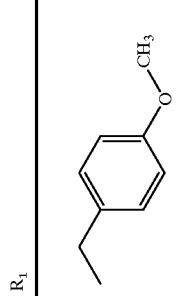 |

TABLE 1-continued (II)

| Cmpd. | Kd (μM) | R₁ | R₂ | R₃ | R₄ | R₅ | R₆ |
|---|---|---|---|---|---|---|---|
| 41 | 4.7 | 4-methoxybenzyl | H | H | CH₃ | propanoic acid | 2-ethyl-1H-indole |
| 42 | 1.5 | 4-methoxybenzyl | H | H | CH₃ | ethanesulfonic acid | 1-ethylnaphthalene |
| 43 | 1.9 | 4-methoxybenzyl | H | H | CH₃ | N-methyl oxamic acid | 1-(4-ethylphenyl)ethyl |
| 44 | 1.5 | 4-methoxybenzyl | H | H | CH₃ | 2,2-dimethylpropanoic acid | (S)-1-(naphthalen-1-yl)ethyl |

TABLE 1-continued
| Cmpd. | Kd (μM) | R1 | R2 | R3 | R4 | R5 | R6 |
|---|---|---|---|---|---|---|---|
| 45 | 3.4 | 4-ethoxyphenyl | H | H | CH3 | 2-methyl-2-carboxypropyl | 1-(1-naphthyl)ethyl |
| 46 | 2.3 | 4-ethoxyphenyl | H | H | CH3 | 2-methyl-2-carboxypropyl | 1-(2-naphthyl)ethyl |
| 47 | 2.1 | 4-ethoxyphenyl | H | H | CH3 | N-methyl oxamide | 1-(4-ethylphenylamino)ethyl |
| 48 | 0.50 | 4-ethoxyphenyl | H | H | CH3 | N-methyl oxamide | (4-ethylphenylamino)-2,2-dimethylpropyl |

TABLE 1-continued
| Cmpd. | Kd (μM) | R1 | R2 | R3 | R4 | R5 | R6 |
|---|---|---|---|---|---|---|---|
| 49 | 2.1 | 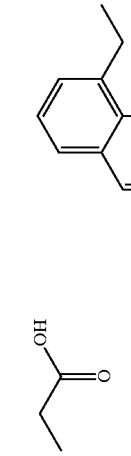 | H | H | CH₃ | 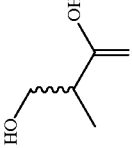 | 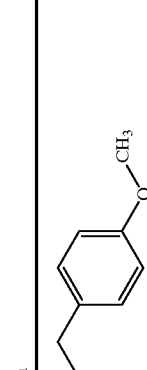 |
| 50 | 39 | 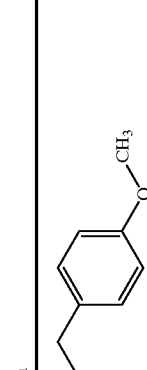 | H | H | CH₃ | 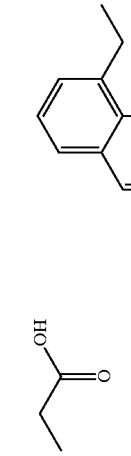 | 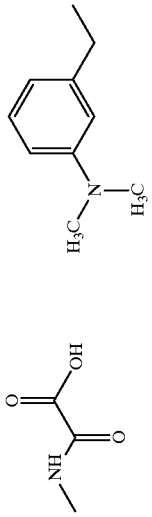 |
| 51 | >69 | 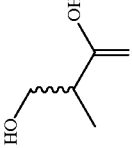 | H | H | CH₃ | 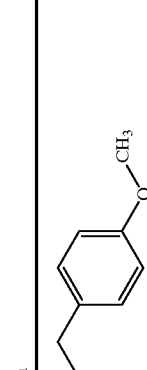 | 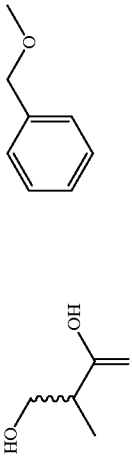 |
| 52 | 0.24 | 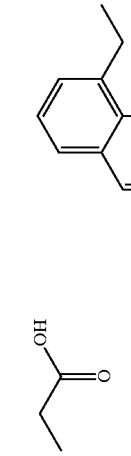 | H | H | CH₃ | 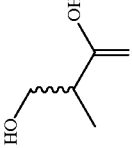 | 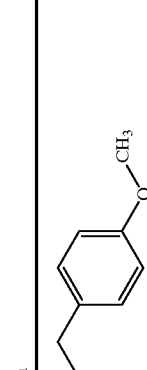 |

TABLE 1-continued
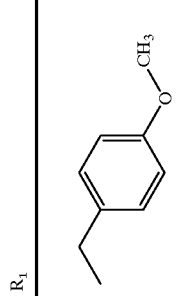
(II)
| Cmpd. | Kd (μM) | R₁ | R₂ | R₃ | R₄ | R₅ | R₆ |
|---|---|---|---|---|---|---|---|
| 53 | 12.7 | 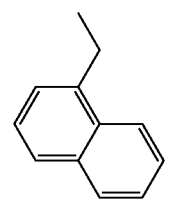 | H | H | CH₃ | 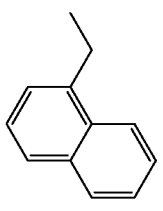 | 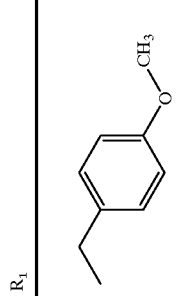 |
| 54 | >500 | 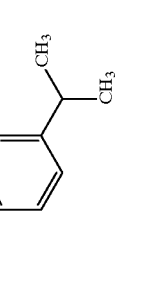 | H | H | CH₃ | 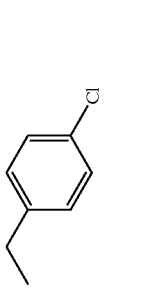 | 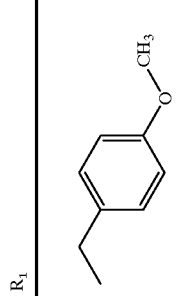 |
| 55 | 15 | 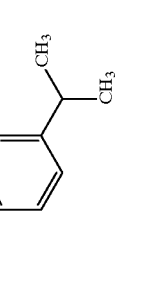 | H | H | CH₃ | 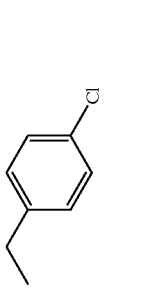 |  |

TABLE 1-continued
| Cmpd. | Kd (μM) | R₁ | R₂ | R₃ | R₄ | R₅ | R₆ |
|---|---|---|---|---|---|---|---|
| 56 | 7.1 | 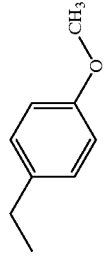 | H | H | CH₃ | 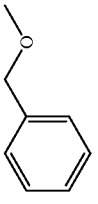 | 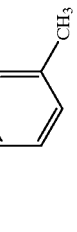 |
| 57 | 15 | 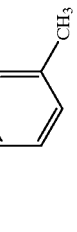 | H | H | CH₃ | 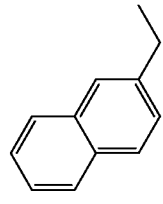 | 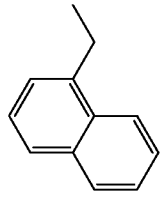 |
| 58 | 5.6 | 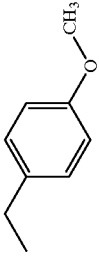 | H | H | CH₃ | 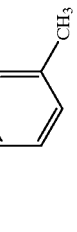 | 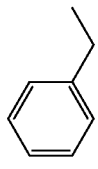 |
| 59 | 1.5 | 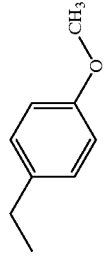 | H | H | CH₃ | 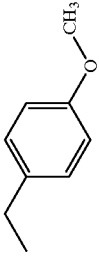 | 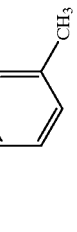 |

TABLE 1-continued (II)

| Cmpd. | Kd (μM) | R₁ | R₂ | R₃ | R₄ | R₅ | R₆ |
|---|---|---|---|---|---|---|---|
| 60 | 1.9 | 4-ethoxyphenyl (CH₃O-C₆H₄-CH₂-) | H | H | CH₃ | CH₂CH₂COOH | 3-methyl-2-ethylnaphthyl |
| 61 | 3.3 | 4-ethoxyphenyl | H | H | CH₃ | CH₂CH₂COOH | 3-ethylphenoxyphenyl |
| 62 | 8.8 | 4-ethoxyphenyl | H | H | CH₃ | CH₂CH₂COOH | (1-methyl)-6-methoxynaphthyl |

TABLE 1-continued
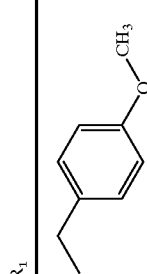
(II)
| Cmpd. | Kd (μM) | R₁ | R₂ | R₃ | R₄ | R₅ | R₆ |
|---|---|---|---|---|---|---|---|
| 63 | 12 | 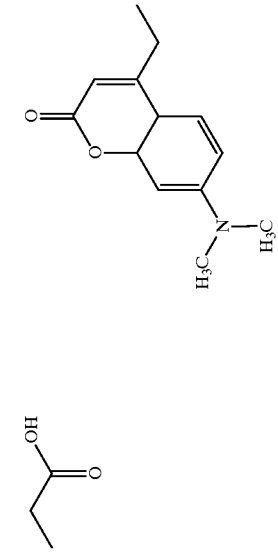 | H | H | CH₃ |  | 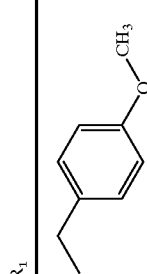 |
| 64 | 17 | 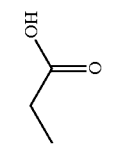 | H | H | CH₃ |  | |
| 65 | 1.3 | 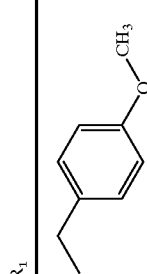 | H | H | CH₃ | 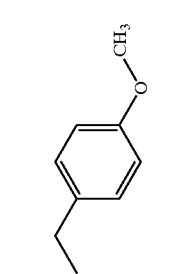 | |

TABLE 1-continued (II) [structure shown: pyridinone with R1, R2, R3, R4 substituents connected via NH-C(O)-CH(NHC(O)R6)-CH2-phenyl-R5]

| Cmpd. | Kd (μM) | R1 | R2 | R3 | R4 | R5 | R6 |
|---|---|---|---|---|---|---|---|
| 66 | 0.43 | 4-methoxybenzyl (CH2-C6H4-OCH3) | H | H | CH3 | CH3-C(F)(F)-P(O)(OH)2 | 1-ethylnaphthyl |
| 67 | 64 | cyclohexylmethyl | H | H | CH3 | CH2-C(O)-OH | C(CH3)2-CH2-CH3 (tert-pentyl) |
| 68 | 12 | cyclohexylmethyl | H | H | CH3 | CH2-C(O)-OH | 1-ethylnaphthyl |
| 69 | 89 | n-pentyl (CH2CH2CH2CH2CH3) | H | H | CH3 | CH2-C(O)-OH | C(CH3)2-CH2-CH3 (tert-pentyl) |

TABLE 1-continued (II) structure shown with R1, R2, R3, R4, R5, R6 substituents on a pyridone-containing compound.

| Cmpd. | Kd (μM) | R1 | R2 | R3 | R4 | R5 | R6 |
|---|---|---|---|---|---|---|---|
| 70 | 24 | CH₃ | H | H | CH₃ | CH₂CH₂COOH | 1-ethylnaphthalene |
| 71 | 14 | 4-methoxybenzyl (CH₂-C₆H₄-OCH₃) | H | H | CH₃ | CH₂CH₂COOH | 4-phenoxyphenyl-ethyl |
| 72 | 2.5 | 4-methoxybenzyl (CH₂-C₆H₄-OCH₃) | H | H | CH₃ | CH₂CH₂COOH | 1-ethoxynaphthalene |

TABLE 1-continued (II)

| Cmpd. | Kd (μM) | R₁ | R₂ | R₃ | R₄ | R₅ | R₆ |
|---|---|---|---|---|---|---|---|
| 73 | >250 | 4-ethyl-phenyl methyl ether | H | H | CH₃ | propanoic acid | 2-ethylphenyl phenyl ether |
| 74 | 14 | 4-ethyl-phenyl methyl ether | H | H | CH₃ | propanoic acid | propyl |
| 75 | 6.7 | 4-ethyl-phenyl methyl ether | H | H | CH₃ | propanoic acid | isobutyl |
| 76 | 8.6 | 4-ethyl-phenyl methyl ether | H | H | CH₃ | propanoic acid | 2-phenylpropan-2-yl |

TABLE 1-continued
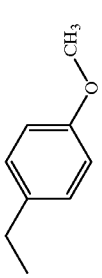
(II)
| Cmpd. | Kd (μM) | R₁ | R₂ | R₃ | R₄ | R₅ | R₆ |
|---|---|---|---|---|---|---|---|
| 77 | 20 | 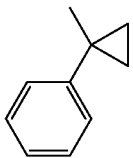 | H | H | CH₃ | 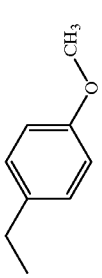 | 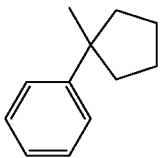 |
| 78 | 13 | 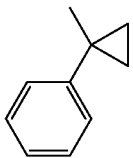 | H | H | CH₃ | 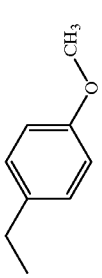 | 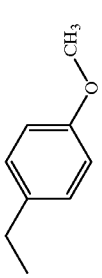 |
| 79 | 11 | 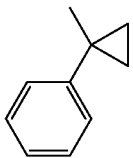 | H | H | CH₃ | 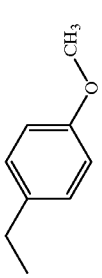 | 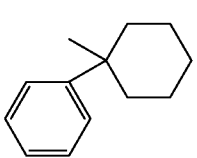 |

TABLE 1-continued
(II)
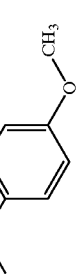
| Cmpd. | Kd (μM) | R₁ | R₂ | R₃ | R₄ | R₅ | R₆ |
|---|---|---|---|---|---|---|---|
| 80 | 20 | 4-methoxy-α-ethylbenzyl | H | H | CH₃ | CH₂CH₂COOH | 4-methyl-4-phenyltetrahydropyran |
| 81 | 23 | 4-methoxy-α-methylbenzyl | H | H | CH₃ | CH₂CH₂COOH | CH₃ |
| 82 | 32 | 4-methoxy-α-methylbenzyl | H | H | CH₃ | CH₂CH₂COOH | C(CH₃)₃ |

TABLE 1-continued (II)

| Cmpd. | Kd (μM) | R₁ | R₂ | R₃ | R₄ | R₅ | R₆ |
|---|---|---|---|---|---|---|---|
| 83 | 2.1 | 4-methoxyphenyl-CH(CH₃)- | H | H | CH₃ | CH₂CH₂COOH | 1-ethylnaphthalene |
| 84 | 400 | 4-methoxyphenyl-CH₂CH₂- | H | H | CH₃ | CH₂CH₂COOH | 5-ethoxyisoquinoline |
| 85 | 2.6 | 4-methoxyphenyl-CH₂CH₂- | H | H | CH₃ | CH₂CH₂COOH | 1-ethoxyisoquinoline |
| 86 | 3.3 | 4-methoxypyridyl-CH₂CH₂- | H | H | CH₃ | CH₂CH₂COOH | 3-ethoxyisoquinoline |

TABLE 1-continued (II)

| Cmpd. | Kd (μM) | R₁ | R₂ | R₃ | R₄ | R₅ | R₆ |
|---|---|---|---|---|---|---|---|
| 87 | 18 | 4-methoxybenzyl | H | H | CH₃ | CH₂CH₂COOH | CF₃ |
| 88 | 4.4 | 4-methoxybenzyl | H | H | CH₃ | CH₂CH₂COOH | 1-ethylnaphthyl |
| 89 | 19 | 4-methoxybenzyl | H | H | CH₃ | CH₂CH₂COOH | CH₃ |
| 90 | >250 | 4-methoxybenzyl | H | H | H | CH₂CH₂COOH | 1-ethylnaphthyl |

TABLE 1-continued (II)

| Cmpd. | Kd (μM) | R₁ | R₂ | R₃ | R₄ | R₅ | R₆ |
|---|---|---|---|---|---|---|---|
| 91 | 4.8 | 4-ethylphenyl methyl ether | H | H | CH₃ | propanoic acid | 8-ethylnaphthalen-1-yl |
| 92 | 3.8 | 4-ethylphenyl methyl ether | H | H | Et | propanoic acid | 8-ethylnaphthalen-1-yl |
| 93 | 12 | 4-ethylphenyl methyl ether | H | H | CH₃ | propanoic acid | N-methyl-N-(4-ethylphenyl)amino |
| 94 | 0.21 | 4-ethylphenyl methyl ether | H | H | CH₃ | 2,2-dimethylpropanoic acid | 1-(4-ethylphenyl)ethyl |

TABLE 1-continued (II)

| Cmpd. | Kd (μM) | R₁ | R₂ | R₃ | R₄ | R₅ | R₆ |
|---|---|---|---|---|---|---|---|
| 95 | 5.4 | 4-ethylphenyl methyl ether | H | H | CH₃ | N-hydroxy-N-methyl oxamide | CH₃ |
| 96 | 23 | 1-(4-ethylphenyl)ethyl | H | H | CH₃ | N-hydroxy-N-methyl oxamide | 4-(N,N-dimethylamino)phenyl |
| 97 | 0.14 | 4-ethylphenyl methyl ether | H | H | CH₃ | 2,2-dimethyl propionic acid | 2-naphthyl |
| 98 | 0.43 | 4-ethylphenyl methyl ether | H | H | CH₃ | 2,2-dimethyl propionic acid | 3-indolyl |

TABLE 1-continued
(II)
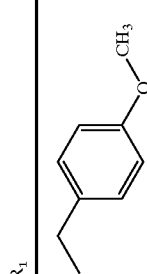
| Cmpd. | Kd (μM) | R₁ | R₂ | R₃ | R₄ | R₅ | R₆ |
|---|---|---|---|---|---|---|---|
| 99 | 0.13 | 4-methoxyphenylethyl | H | H | CH₃ | C(CH₃)₂COOH | 4-(N,N-dimethylamino)phenylethyl |
| 100 | 1.5 | 4-(1-methylethyl)phenylethyl | H | H | CH₃ | C(CH₃)₂COOH | 3-ethylindolyl |
| 101 | 4.3 | 4-(1-methylethyl)phenylethyl | H | H | CH₃ | C(CH₃)₂COOH | 1-ethylnaphthyl |
| 102 | 1.9 | 4-methoxyphenylethyl | H | H | CH₃ | NHC(O)COOH | phenylethyl |

TABLE 1-continued

| Cmpd. | Kd (µM) | R₁ | R₂ | R₃ | R₄ | R₅ | R₆ |
|---|---|---|---|---|---|---|---|
| 103 | 12 | 4-methoxyphenethyl | H | H | CH₃ | -NHCH₂-C(O)-C(O)OH | 1-(4-cyanophenyl)ethyl |
| 104 | 0.65 | 4-methoxyphenethyl | H | H | CH₃ | -NHCH₂-C(O)-C(O)OH | 2-methyl-2-((4-ethylphenyl)amino carbonyl)propyl (isobutyramide with 4-ethylaniline) |
| 105 | 0.82 | 4-methoxyphenethyl | H | H | CH₃ | -NHCH₂-C(O)-C(O)OH | 3-nitrophenyl |

TABLE 1-continued
| Cmpd. | Kd (μM) | R₁ | R₂ | R₃ | R₄ | R₅ | R₆ |
|---|---|---|---|---|---|---|---|
| 106 | 0.47 | 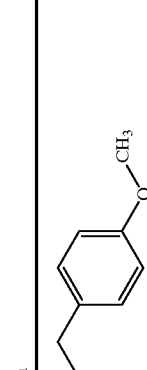 | H | H | CH₃ | 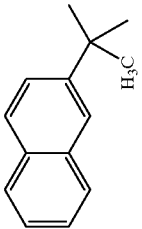 | 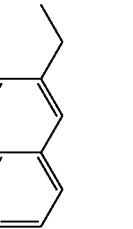 |
| 107 | 0.68 | 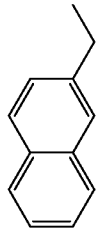 | H | H | CH₃ | 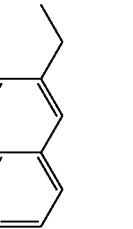 | 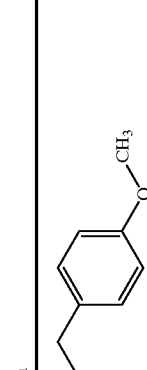 |
| 108 | 2.8 | 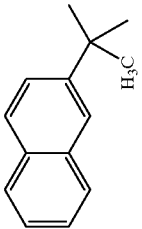 | H | H | CH₃ | 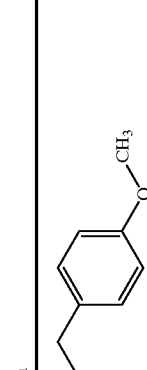 | 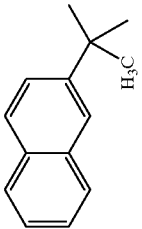 |
| 109 | 0.33 | 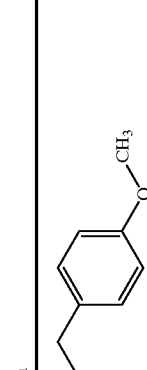 | H | H | CH₃ | 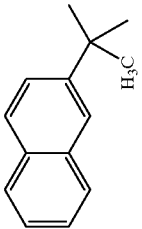 | 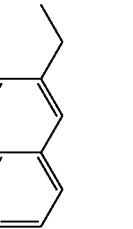 |

TABLE 1-continued (II)

| Cmpd. | Kd (μM) | R1 | R2 | R3 | R4 | R5 | R6 |
|---|---|---|---|---|---|---|---|
| 110 | 0.18 | 4-methoxybenzyl | H | H | CH₃ | C(CH₃)₂COOH | 4-bromophenyl (ethyl substituted) |
| 111 | 0.51 | 4-methoxybenzyl | H | H | CH₃ | C(CH₃)₂COOH | 1-bromo-4-ethylnaphthyl |
| 112 | 1.5 | 4-methoxybenzyl | H | H | CH₃ | C(CH₃)₂COOH | 4-(isobutyl)phenyl, α-methyl |
| 113 | 0.87 | 4-methoxybenzyl | H | H | CH₃ | C(CH₃)₂COOH | 2-methyl-ethylphenyl |

TABLE 1-continued (II)

| Cmpd. | Kd (µM) | R₁ | R₂ | R₃ | R₄ | R₅ | R₆ |
|---|---|---|---|---|---|---|---|
| 114 | 0.19 | 4-methoxybenzyl | H | H | CH₃ | C(CH₃)₂COOH | 4-methylphenyl-ethyl |
| 115 (R,S) | 1.2 | cinnamyl | H | H | CH₃ | C(CH₃)₂COOH | 2-ethylnaphthyl |
| 116 (R,S) | 3.2 | cinnamyl | H | H | CH₃ | C(CH₃)₂COOH | 2-(2-methylpropan-2-yl)naphthyl |

TABLE 1-continued
| Cmpd. | Kd (μM) | R₁ | R₂ | R₃ | R₄ | R₅ | R₆ |
|---|---|---|---|---|---|---|---|
| 117 | 0.37 | 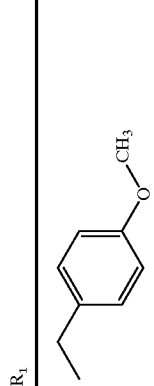 | H | H | CH₃ |  | 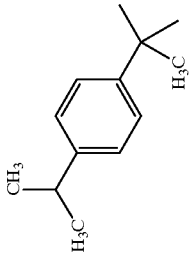 |
| 118 | 0.61 | 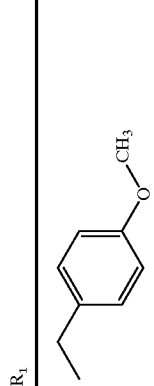 | H | H | CH₃ |  | 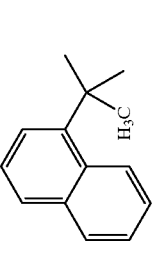 |
| 119 | 3.6 | 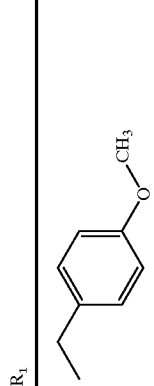 | H | H | CH₃ |  | 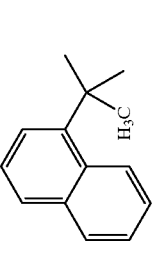 |
| 120 | 0.43 | 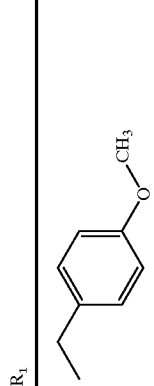 | H | H | CH₃ |  | 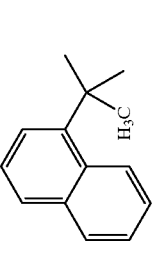 |

TABLE 1-continued (II)

[Structure of compound (II): pyridone ring with R1, R2, R3, R4 substituents, connected via NH-C(=O) to a central CH with NH-C(=O)-R6 group, and a benzyl group with R5 para-substituent]

| Cmpd. | Kd (μM) | R1 | R2 | R3 | R4 | R5 | R6 |
|---|---|---|---|---|---|---|---|
| 121 (R,S) | 2.7 | n-hexyl | H | COOCH$_3$ | CH$_3$ | -C(CH$_3$)$_2$-COOH | 2-(2-methylpropan-2-yl)naphthalene |
| 122 (R,S) | 5.3 | 4-methoxybenzyl-CH(CH$_3$)- | H | Br | CH$_3$ | -C(CH$_3$)$_2$-COOH | 4-tert-butylphenyl (Br-substituted) |
| 123 | 0.84 | 4-methoxybenzyl-CH(CH$_3$)- | H | H | CH$_3$ | -C(CH$_3$)$_2$-COOH | 2-(2-methylbut-2-yl)naphthalene |

TABLE 1-continued (II)

| Cmpd. | Kd (μM) | R₁ | R₂ | R₃ | R₄ | R₅ | R₆ |
|---|---|---|---|---|---|---|---|
| 124 | 1.5 | 4-methoxybenzyl | H | H | CH₃ | 2-methyl-2-(carboxy)propyl | 2-methyl-2-(4-tert-butylphenyl)... |
| 125 (R,S) | >15 | 4-methoxybenzyl | H | H | CH₃ | 1-methylcyclopentane-1-carboxylic acid | 2-(naphth-2-yl)-2-methylpropyl |
| 126 | 0.68 | 4-methoxybenzyl | H | H | CH₃ | 2-methyl-2-(carboxy)propyl | 1-(naphth-1-yl)ethyl |

TABLE 1-continued (II) [structure of compound with R1–R6 substituents]

| Cmpd. | Kd (μM) | R1 | R2 | R3 | R4 | R5 | R6 |
|---|---|---|---|---|---|---|---|
| 127 | 1.4 | 4-methoxyphenylethyl | H | H | CH₃ | C(CH₃)₂COOH | 1-(4-substituted-phenyl)ethyl with isobutyl |
| 128 | 1.6 | 6-ethyl-3-(trifluoromethyl)pyridin-2-yl-methyl | H | H | CH₃ | C(CH₃)₂COOH | 6-ethylnaphthalen-2-yl |
| 129 | 2.8 | 3-chloro-6-ethyl-5-(trifluoromethyl)pyridin-2-yl | H | H | CH₃ | C(CH₃)₂COOH | 6-ethylnaphthalen-2-yl |

TABLE 1-continued

| Cmpd. | Kd (μM) | R1 | R2 | R3 | R4 | R5 | R6 |
|---|---|---|---|---|---|---|---|
| 130 | 0.84 | 4-ethoxyphenyl (with OCH3) | H | H | CH3 | (CH3)2C-COOH | benzyl-NH-(4-ethylphenyl) |
| 131 | >1.3 | 4-ethoxyphenyl (with OCH3) | H | H | CH3 | (CH3)2C-COOH | N(benzyl)(benzyl)(4-ethylphenyl) |
| 132 | 0.25 | 4-ethoxyphenyl (with OCH3) | H | H | CH3 | (CH3)2C-COOH | neopentyl-NH-(4-ethylphenyl) |

TABLE 1-continued (II)

| Cmpd. | Kd (μM) | R₁ | R₂ | R₃ | R₄ | R₅ | R₆ |
|---|---|---|---|---|---|---|---|
| 133 | 0.78 | 4-(methoxy)phenylmethyl | H | H | CH₃ | C(CH₃)₂COOH | N-methyl-N-(1-naphthyl)carbamoyl |
| 134 | 5.7 | 4-(hydroxy)phenylmethyl | H | H | CH₃ | C(CH₃)₂COOH | 2-(1-naphthyl)-2-methylpropyl |
| 135 (R,S) | 1.3 | 4-(ethoxy)phenylmethyl | H | H | CH₃ | C(CH₃)₂COOH | 2-naphthylethyl |
| 136 | 5.6 | 4-(methoxy)phenylmethyl | H | H | CH₃ | CH(CH₃)CH₂OH COOH | 1-naphthylethyl |

TABLE 1-continued

| Cmpd. | Kd (μM) | R₁ | R₂ | R₃ | R₄ | R₅ | R₆ |
|---|---|---|---|---|---|---|---|
| 137 (R,S) | 0.51 | n-heptyl | H | H | CH₃ | C(CH₃)₂COOH | 2-ethylnaphthalen-6-yl |
| 138 (R,S) | 0.83 | n-octyl | H | H | CH₃ | C(CH₃)₂COOH | 2-ethylnaphthalen-6-yl |
| 139 (R,S) | 2.9 | 4-(2-methoxyethoxy)phenyl | H | H | CH₃ | C(CH₃)₂COOH | 2-tert-butylnaphthalen-6-yl |
| 140 (R,S) | 0.63 | 4-(2-methoxyethoxy)phenyl | H | H | CH₃ | C(CH₃)₂COOH | 1-ethylnaphthalen-4-yl |

TABLE 1-continued
(II)
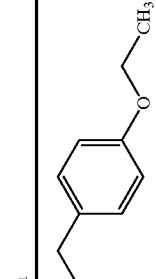
| Cmpd. | Kd (μM) | R₁ | R₂ | R₃ | R₄ | R₅ | R₆ |
|---|---|---|---|---|---|---|---|
| 141 (R,S) | 8.8 | 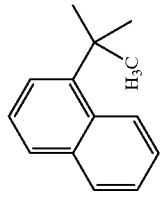 | H | H | CH₃ | 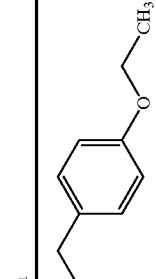 | 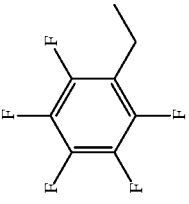 |
| 142 (R,S) | 1.3 | 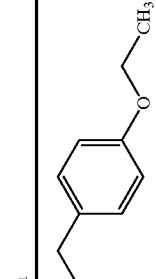 | H | H | CH₃ | 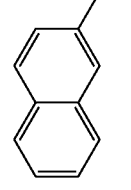 | 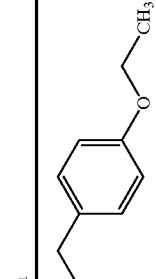 |
| 143 (R,S) | 6.0 | 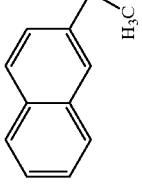 | H | H | CH₃ | (same as above) | (same as above) |
| 144 (R,S) | 20 | (same as 143) | H | H | CH₃ | (same as above) | (same as above) |

TABLE 1-continued
| Cmpd. | Kd (μM) | R₁ | R₂ | R₃ | R₄ | R₅ | R₆ |
|---|---|---|---|---|---|---|---|
| 145 (R,S) | 0.84 |  | H | H | CH₃ | 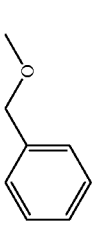 |  |
| 146 (R,S) | 1.3 |  | H | H | CH₃ |  | 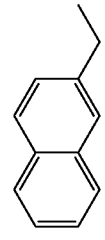 |
| 147 (R,S) | 1.9 |  | H | H | CH₃ |  | 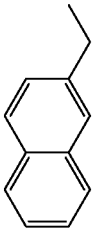 |
| 148 (R,S) | 3.6 |  | H | H | CH₃ |  |  |

TABLE 1-continued
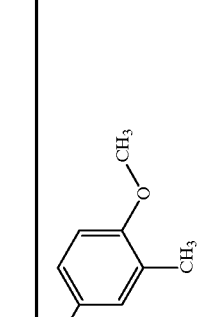
| Cmpd. | Kd (μM) | R1 | R2 | R3 | R4 | R5 | R6 |
|---|---|---|---|---|---|---|---|
| 149 (R,S) | 3.8 | 4-ethyl-2-methyl-1-methoxybenzene | H | H | $CH_3$ | $(CH_3)_2C(COOH)$ | 2-ethylnaphthalene |
| 150 (R,S) | 4.6 | 4-ethyl-1-methylbenzene | H | H | $CH_3$ | $(CH_3)_2C(COOH)$ | 2-ethylnaphthalene |
| 151 (R,S) N1-$CH_3$ | >200 | 4-ethyl-1-methoxybenzene | H | H | $CH_3$ | $(CH_3)_2C(COOH)$ | 2-ethylnaphthalene |
| 152 (R,S) N2-$CH_3$ | 4.5 | 4-ethyl-1-methoxybenzene | H | H | $CH_3$ | $(CH_3)_2C(COOH)$ | 2-ethylnaphthalene |

TABLE 1-continued
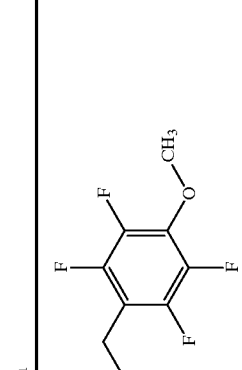
(II)
| Cmpd. | Kd (μM) | R1 | R2 | R3 | R4 | R5 | R6 |
|---|---|---|---|---|---|---|---|
| 153 (R,S) | 2.1 | 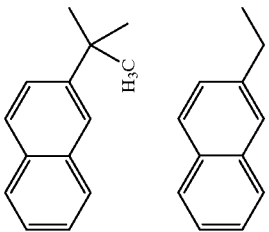 | H | H | CH3 | 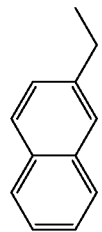 | 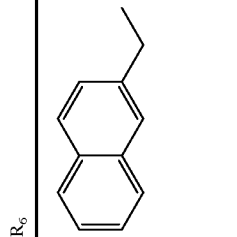 |
| 154 (R,S) | 1.2 | 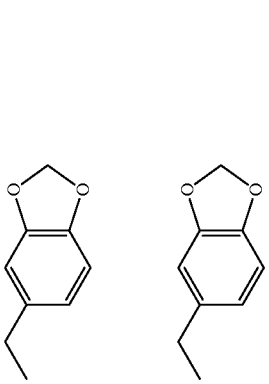 | H | H | CH3 | 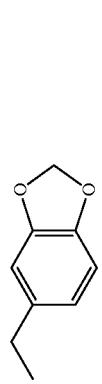 | 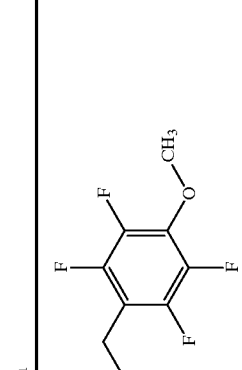 |
| 155 (R,S) | 0.37 | 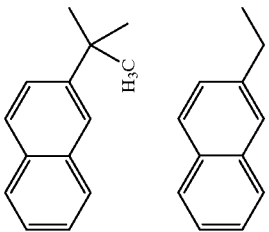 | H | H | CH3 | 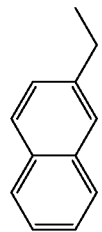 | (same as above) |

TABLE 1-continued
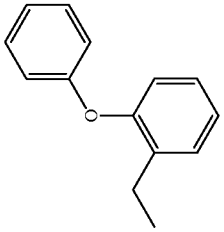
(II)
| Cmpd. | Kd (μM) | R₁ | R₂ | R₃ | R₄ | R₅ | R₆ |
|---|---|---|---|---|---|---|---|
| 156 (R,S) | 4.0 | 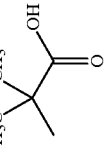 | H | H | CH₃ | 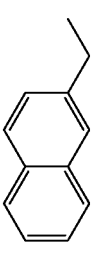 | 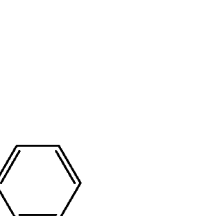 |
| 157 (R,S) | 21 | 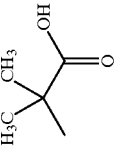 | H | H | CH₃ | 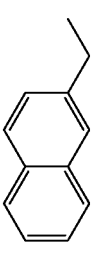 | 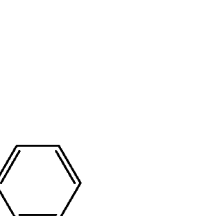 |
| 158 (R,S) | 1.7 | 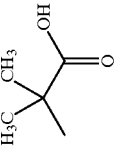 | H | H | CH₃ | 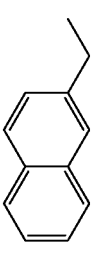 |  |

TABLE 1-continued (II)

| Cmpd. | Kd (μM) | R1 | R2 | R3 | R4 | R5 | R6 |
|---|---|---|---|---|---|---|---|
| 159 (R,S) | 1.4 | 4-ethyl-phenyl, OCH3 | H | H | CH3 | C(CH3)2COOH | 4-(2-methylbut-3-en-2-yl)phenyl (cumyl-like with vinyl) |
| 160 (R,S) | 5.8 | 4-ethyl-2-hydroxy-phenyl, OCH3 | H | H | CH3 | C(CH3)2COOH | naphth-2-yl (ethyl substituted) |
| 161 (R,S) N2-CH3 | 460 | 4-ethyl-phenyl, OCH3 | H | H | CH3 | C(CH3)2COOH | 6-(2-methylprop-2-yl)naphth-2-yl |
| 162 | 1.0 | 4-ethyl-phenyl, OCH3 | H | H | CH3 | CH2CH2COOH | 4-(2-methylprop-2-yl)phenyl ethyl |

TABLE 1-continued
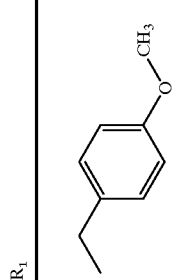
| Cmpd. | Kd (μM) | R₁ | R₂ | R₃ | R₄ | R₅ | R₆ |
|---|---|---|---|---|---|---|---|
| 163 | 1.1 | 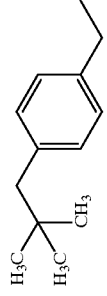 | H | H | CH₃ | 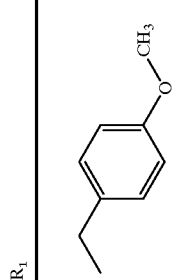 | 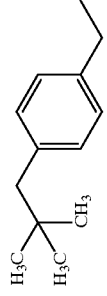 |
| 164 | 1.6 | 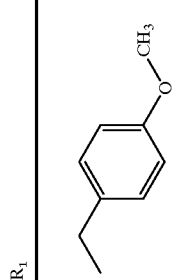 | H | H | CH₃ | 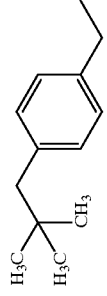 | 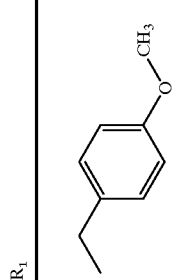 |
| 165 | 2.8 | 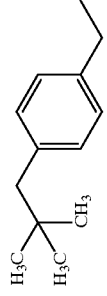 | H | H | CH₃ |  |  |
| 166 | 1.7 |  | H | H | CH₃ |  |  |

TABLE 1-continued
(II)
| Cmpd. | Kd (μM) | R₁ | R₂ | R₃ | R₄ | R₅ | R₆ |
|---|---|---|---|---|---|---|---|
| 167 | 1.2 | 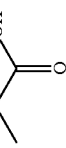 | H | H | CH₃ | 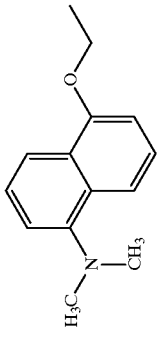 |  |
| 168 | 1.2 | 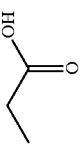 | H | H | CH₃ | 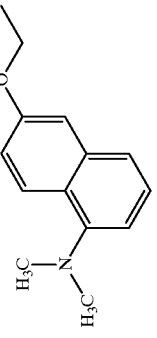 |  |
| 169 (R,S) | 0.52 | 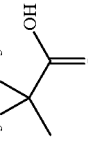 | H | H | CH₃ | 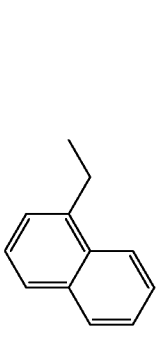 |  |
| 170 (R,S) | 3.9 | 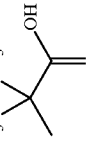 | H | H | CH₃ |  | H₃C–CH–CH₃ |

TABLE 1-continued

| Cmpd. | Kd (μM) | R₁ | R₂ | R₃ | R₄ | R₅ | R₆ |
|---|---|---|---|---|---|---|---|
| 171 (R,S) | 4.3 | 4-methoxybenzyl (-CH₂-C₆H₄-OCH₃) | H | H | CH₃ | -C(CH₃)₂-COOH | -C(CH₃)₂-C₆H₄-O-C₆H₅ |
| 172 (R,S) | 0.66 | 4-methoxybenzyl | H | H | CH₃ | -C(CH₃)₂-COOH | -C(CH₃)₂-C₆H₄-CH₂CH₃ |
| 173 (R,S) | 0.31 | 4-methoxybenzyl | H | H | CH₃ | -C(CH₃)₂-COOH | 1-ethoxynaphthyl |
| 174 (R,S) | 1.0 | 4-methoxybenzyl | H | H | CH₃ | -C(CH₃)₂-COOH | |

TABLE 1-continued

| Cmpd. | Kd (μM) | R1 | R2 | R3 | R4 | R5 | R6 |
|---|---|---|---|---|---|---|---|
| 175 (R,S) | 0.78 | 4-methoxyphenethyl | H | H | CH3 | C(CH3)2COOH | 5-ethoxy-1-(N-methyl)naphthylamine |
| 176 (R,S) | 1.8 | 4-methoxyphenethyl | H | H | CH3 | C(CH3)2COOH | CF3 |
| 177 (R,S) | 3.2 | cinnamyl | H | H | CH3 | C(CH3)2COOH | 6-tert-butyl-2-naphthyl |
| 178 (R,S) | 0.68 | 1-(4-methoxyphenyl)ethyl | H | H | CH3 | C(CH3)2COOH | 4-ethyl-1-naphthyl |

TABLE 1-continued (II)

| Cmpd. | Kd (μM) | R₁ | R₂ | R₃ | R₄ | R₅ | R₆ |
|---|---|---|---|---|---|---|---|
| 179 (R,S) | 5.8 | sec-pentyl | H | H | CH₃ | C(CH₃)₂COOH | ethylnaphthyl |
| 180 (R,S) | 2.5 | 4-methoxyphenethyl | H | H | CH₃ | C(CH₃)₂COOH | cumyl |
| 181 (R,S) | 0.41 | 4-methoxyphenethyl | H | H | CH₃ | C(CH₃)₂COOH | ethylnaphthyl |

TABLE 1-continued

| Cmpd. | Kd (μM) | R₁ | R₂ | R₃ | R₄ | R₅ | R₆ |
|---|---|---|---|---|---|---|---|
| 182 (R,S) | 2.1 | phenylbutyl | H | H | CH₃ | C(CH₃)₂COOH | ethylnaphthyl |
| 183 (R,S) | 3.6 | CH=CH-C(O)NH₂ | H | H | CH₃ | C(CH₃)₂COOH | ethylnaphthyl |
| 184 (R,S) | 1.3 | 1-(4-methoxyphenyl)ethyl | H | H | CH₃ | C(CH₃)₂COOH | 2-(tert-butyl)naphthyl |

TABLE 1-continued

| Cmpd. | Kd (μM) | R₁ | R₂ | R₃ | R₄ | R₅ | R₆ |
|---|---|---|---|---|---|---|---|
| 185 (R,S) | 1.2 | cinnamyl | H | H | CH₃ | C(CH₃)₂COOH | 2-ethylnaphthyl |
| 186 (R,S) | 0.78 | 4-methoxy-benzyl-ethyl | H | H | CH₃ | C(CH₃)₂COOH | 4-tert-butyl-α,α-dimethylbenzyl |
| 187 (R,S) | 0.18 | 4-methoxy-benzyl-ethyl | H | H | CH₃ | C(CH₃)₂COOH | 1-ethyl-2-methoxynaphthyl |

TABLE 1-continued
(II)
| Cmpd. | Kd (μM) | R₁ | R₂ | R₃ | R₄ | R₅ | R₆ |
|---|---|---|---|---|---|---|---|
| 188 (R,S) | 45 | 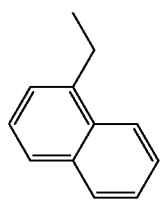 | H | H | CH₃ | 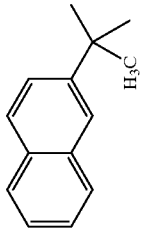 |  |
| 189 (R,S) | 13 | 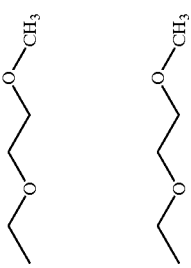 | H | H | CH₃ | 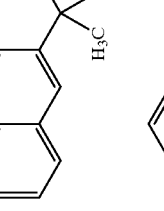 |  |
| 190 (R,S) | 43 | 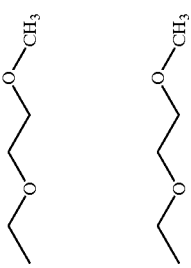 | H | H | CH₃ | 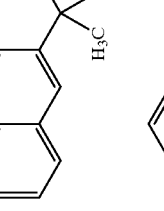 |  |
| 191 (R,S) | 3.1 | 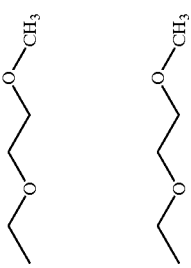 | H | H | CH₃ | 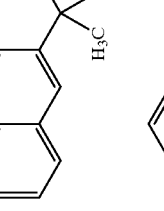 |  |

TABLE 1-continued

| Cmpd. | Kd (µM) | R₁ | R₂ | R₃ | R₄ | R₅ | R₆ |
|---|---|---|---|---|---|---|---|
| 192 (R,S) | 1.2 | n-pentyl (CH₂CH₂CH₂CH₂CH₃) | H | H | CH₃ | C(CH₃)₂COOH | 2-ethylnaphthyl |
| 193 (R,S) | 4.1 | n-pentyl (CH₂CH₂CH₂CH₂CH₃) | H | H | CH₃ | C(CH₃)₂COOH | 2-(tert-butyl)naphthyl |
| 194 (R,S) | 2.3 | cyclohexylmethyl | H | H | CH₃ | C(CH₃)₂COOH | 1-ethylnaphthyl |
| 195 (R,S) | 1.1 | cyclohexylmethyl | H | H | CH₃ | C(CH₃)₂COOH | 2-ethylnaphthyl |

TABLE 1-continued
| Cmpd. | Kd (μM) | R₁ | R₂ | R₃ | R₄ | R₅ | R₆ |
|---|---|---|---|---|---|---|---|
| 196 (R,S) | 5.4 | 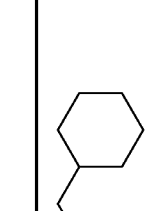 | H | H | CH₃ | 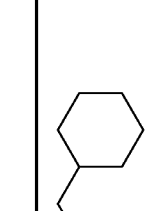 | 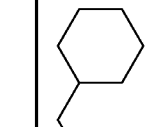 |
| 197 (R,S) | 9.0 | 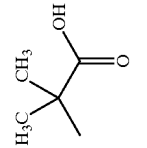 | H | H | CH₃ | 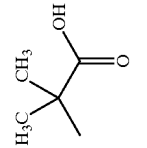 | 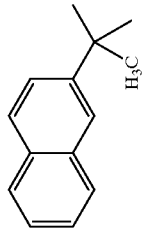 |
| 198 (R,S) | 2.5 | 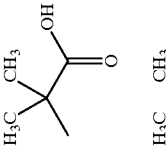 | H | H | CH₃ | 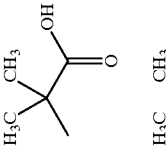 | 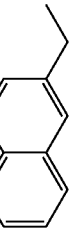 |
| 199 (R,S) | 9.1 | 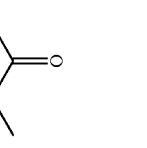 | H | H | CH₃ | 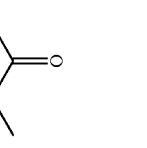 | 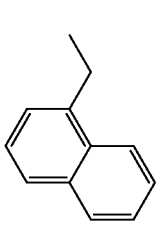 |

TABLE 1-continued
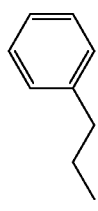
(II)
| Cmpd. | Kd (μM) | R₁ | R₂ | R₃ | R₄ | R₅ | R₆ |
|---|---|---|---|---|---|---|---|
| 200 (R,S) | 2.2 | 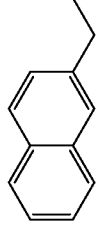 | H | H | CH₃ | 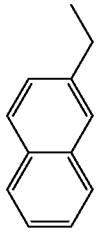 | 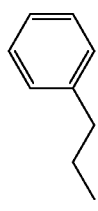 |
| 201 (R,S) | 6.7 | 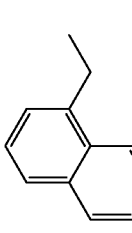 | H | H | CH₃ | 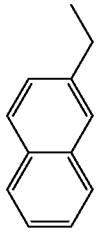 | 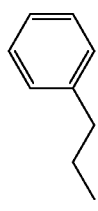 |
| 202 (R,S) | 2.5 | 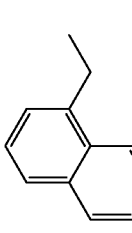 | H | H | CH₃ | 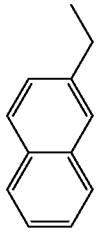 | 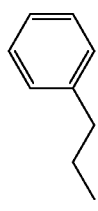 |
| 203 (R,S) | 11 | 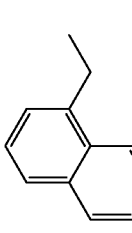 | H | H | CH₃ | 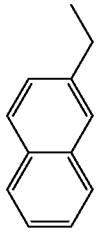 | (2-tert-butyl naphthyl) |

TABLE 1-continued

| Cmpd. | Kd (μM) | R₁ | R₂ | R₃ | R₄ | R₅ | R₆ |
|---|---|---|---|---|---|---|---|
| 204 (R,S) | 10 | n-hexyl | H | H | CH₃ | C(CH₃)₂COOH | CH₂CH₂-phenyl |
| 205 (R,S) | 1.9 | n-hexyl | H | H | CH₃ | C(CH₃)₂COOH | CH₂-O-phenyl |
| 206 (R,S) | 0.89 | n-hexyl | H | H | CH₃ | C(CH₃)₂COOH | CH₂-(2-thienyl) |
| 207 (R,S) | 1.7 | n-hexyl | H | H | CH₃ | C(CH₃)₂COOH | CH₂-(2-methoxyphenyl) |

TABLE 1-continued

| Cmpd. | Kd (μM) | R$_1$ | R$_2$ | R$_3$ | R$_4$ | R$_5$ | R$_6$ |
|---|---|---|---|---|---|---|---|
| 208 (R,S) | 0.80 | pentyl | H | H | CH$_3$ | -C(CH$_3$)$_2$COOH | 4-methoxyphenyl |
| 209 (R,S) | 0.19 | hexyl | H | H | CH$_3$ | -C(CH$_3$)$_2$COOH | 4-(trifluoromethyl)phenyl |
| 210 (R,S) | 15 | (tetrahydrofuran-3-yl)methyl | H | H | CH$_3$ | -C(CH$_3$)$_2$COOH | naphthalen-1-yl |
| 211 (R,S) | 4.9 | (tetrahydrofuran-3-yl)methyl | H | H | CH$_3$ | -C(CH$_3$)$_2$COOH | naphthalen-2-yl |

TABLE 1-continued (II)

| Cmpd. | Kd (μM) | R₁ | R₂ | R₃ | R₄ | R₅ | R₆ |
|---|---|---|---|---|---|---|---|
| 212 (R,S) | 23 | 4-ethyl-tetrahydrofuran-3-yl | H | H | CH₃ | 2-methyl-2-carboxypropyl | 6-tert-butylnaphthalen-2-yl |
| 213 (R,S) | 2.0 | 1-ethyl-1-phenylcyclopropyl | H | H | CH₃ | 2-methyl-2-carboxypropyl | 8-ethylnaphthalen-1-yl |
| 214 (R,S) | 1.2 | 1-ethyl-1-phenylcyclopropyl | H | H | CH₃ | 2-methyl-2-carboxypropyl | 6-ethylnaphthalen-2-yl |
| 215 (R,S) | 5.9 | 1-ethyl-1-phenylcyclopropyl | H | H | CH₃ | 2-methyl-2-carboxypropyl | 6-tert-butylnaphthalen-2-yl |

TABLE 1-continued

| Cmpd. | Kd (μM) | R1 | R2 | R3 | R4 | R5 | R6 |
|---|---|---|---|---|---|---|---|
| 216 (R,S) | 190 | 4-ethoxyphenyl (OCH3 para to ethyl) | H | H | CH3 | 2-methyl-2-(carboxy)propyl (H3C-C(CH3)-COOH) | 1-ethylnaphthalenyl |
| 217 (R,S) | 1.3 | 4-ethoxyphenyl | H | H | CH3 | 2-methyl-2-(carboxy)propyl | 4-(trifluoromethyl)-tert-butylphenyl |
| 218 | 1.8 | 4-ethoxyphenyl | H | H | CH3 | 1-methylcyclopropanecarboxylic acid | 2-ethylnaphthalenyl |
| 219 | 2.2 | 4-ethoxyphenyl | CH3 | H | CH3 | 2-methyl-2-(carboxy)propyl | 2-ethylnaphthalenyl |

TABLE 1-continued
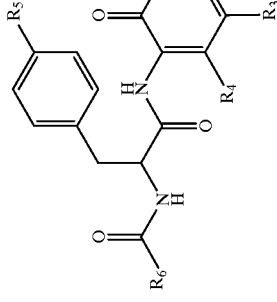
| Cmpd. | Kd (μM) | R₁ | R₂ | R₃ | R₄ | R₅ | R₆ |
|---|---|---|---|---|---|---|---|
| 220 | 0.17 | 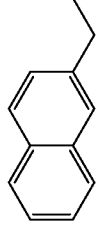 | H | Br | CH₃ | 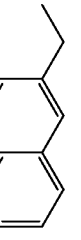 | 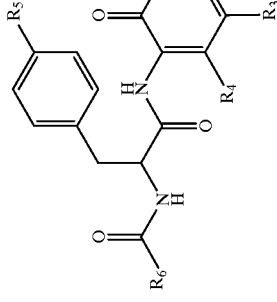 |
| 221 (R,S) | 0.17 |  | H | 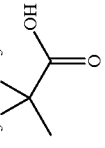 | CH₃ |  | 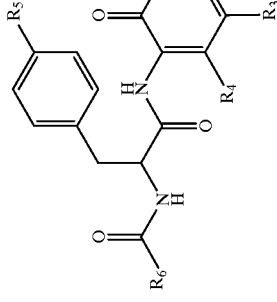 |
| 222 (R,S) | 1.2 | 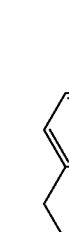 | H | 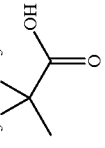 | CH₃ |  | 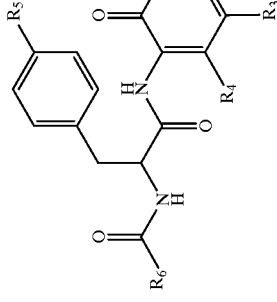 |
| 223 (R,S) | 2.4 |  | H | H | CH₂CH₂OH | 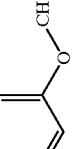 | 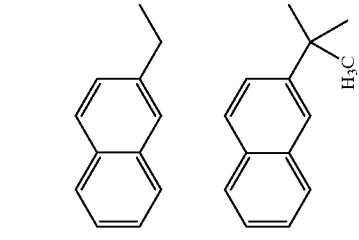 |

TABLE 1-continued

| Cmpd. | Kd (μM) | R1 | R2 | R3 | R4 | R5 | R6 |
|---|---|---|---|---|---|---|---|
| 224 (R,S) | 2.5 | 4-methoxyphenyl-ethyl | H | H | CH3 | C(CH3)2COOH | 2-tert-butyl-naphthyl |
| 225 (R,S) | 41 | 4-(trifluoroacetyl)phenyl-ethyl | H | H | CH3 | C(CH3)2COOH | 2-tert-butyl-naphthyl |
| 226 (R,S) | 33 | 4-(trifluoroacetyl)phenyl-ethyl | H | H | CH3 | C(CH3)2COOH | 2-ethyl-naphthyl |
| 227 | 0.37 | 4-methoxyphenyl-ethyl | H | Br | CH3 | C(CH3)2COOH | 4-tert-butyl-(trifluoromethyl)phenyl |

TABLE 1-continued

| Cmpd. | Kd (μM) | R₁ | R₂ | R₃ | R₄ | R₅ | R₆ |
|---|---|---|---|---|---|---|---|
| 228 | 0.08 | 4-methoxybenzyl | H | Br | CH₃ | C(CH₃)₂COOH | 4-(trifluoromethyl)phenyl |
| 229 (R,S) | 0.14 | 4-methoxybenzyl | H | I | CH₃ | C(CH₃)₂COOH | naphthalen-2-yl |
| 230 (R,S) | 0.51 | 4-methoxybenzyl | H | H | CH₃ | C(CH₃)₂COOH | 4-(dimethylamino)phenyl-C(CH₃)₂- |
| 231 (R,S) | <8 | pentyl | H | phenyl | CH₃ | C(CH₃)₂COOH | naphthalen-2-yl |

TABLE 1-continued
(II)
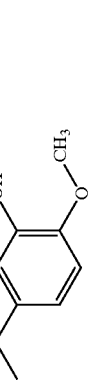
| Cmpd. | Kd (μM) | R₁ | R₂ | R₃ | R₄ | R₅ | R₆ |
|---|---|---|---|---|---|---|---|
| 232 (R,S) | 33 | 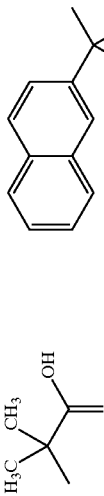 | H | H | CH₃ | 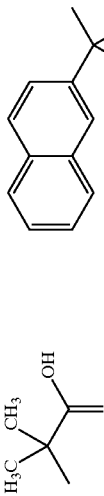 | 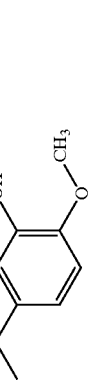 |
| 233 | 0.42 | 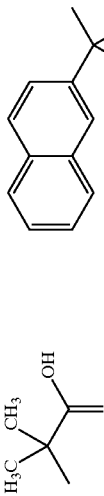 | H | Br | CH₃ | 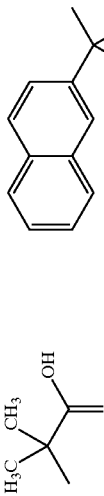 | 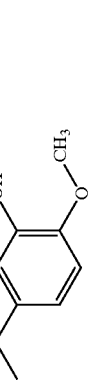 |
| 234 | 1.6 | 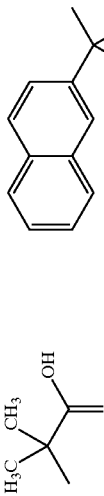 | H | Br | CH₃ | 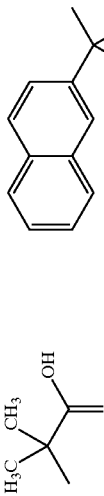 | 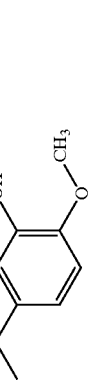 |
| 235 (R,S) | 6.2 | 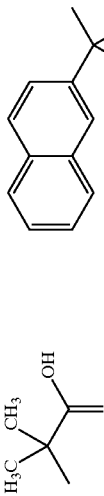 | H | H | CH₃ | 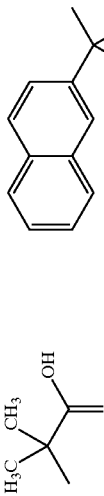 | 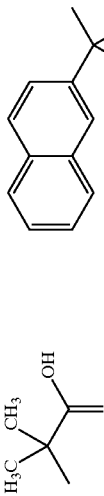 |

TABLE 1-continued

| Cmpd. | Kd (μM) | R1 | R2 | R3 | R4 | R5 | R6 |
|---|---|---|---|---|---|---|---|
| 236 (R,S) | 1.4 | pentyl-O-CH3 | H | H | CH3 | C(CH3)2COOH | 2-tert-butyl-naphthyl |
| 237 (R,S) | 3.1 | pentyl-O-CH3 | H | H | CH3 | C(CH3)2COOH | 2-ethyl-naphthyl |
| 238 (R,S) | 0.72 | hexyl-CH3 | H | Br | CH3 | C(CH3)2COOH | 2-ethyl-naphthyl |
| 239 (R,S) | 3.2 | cyclohexyl-OMe-ethyl | H | H | CH3 | C(CH3)2COOH | 2-ethyl-naphthyl |

TABLE 1-continued (II) [Structure of compound II shown: R5-phenyl-CH2-CH(NH-C(O)-R6)-C(O)-NH-pyridinone with R1, R2, R3, R4 substituents]

| Cmpd. | Kd (μM) | R1 | R2 | R3 | R4 | R5 | R6 |
|---|---|---|---|---|---|---|---|
| 240 (R,S) | 0.74 | n-hexyl (CH2)5CH3 | H | COOCH3 | CH3 | (CH3)2C(COOH)- | 2-ethylnaphthyl |
| 241 | 0.06 | 4-methoxy-ethylphenyl | H | Br | CH3 | 1-methyl-1H-1,2,3-triazole-4,5-dicarboxylic acid | 2-ethylnaphthyl |

More preferred specific compounds of formula (II) are compounds 2, 44, 45, 46, 94, 97–101, 106–135, 137–161, 169, 172–175, 177–197, 199–202 and 213–240 as set forth in Table 1. Most preferred specific compounds of formula (II) are compounds 2, 44–46, 94, 97–99, 106–114, 117–120, 122–127, 130–133, 150, 158–159, 161, 169, 172–174, 180–181, 184, 216–220, 222, 224, 227–230 and 233–234 as set forth in Table 1.

Additional compounds of formula (I) are represented by the compounds of formulas (III), (IV) and (V), specific examples of (III) are set forth in Table 2. The preferred definitions of substituents for compounds of formulas (I) and (II) also apply to the compounds of formulas (III), (IV) and (V).

TABLE 2

| Cmpd. | Kd (μM) | R₁ | R₂ | R₄ | R₅ | R₆ |
|---|---|---|---|---|---|---|
| 242 | 0.53 | 4-methoxybenzyl | H | CH₃ | C(CH₃)₂COOH | 2-naphthylmethyl |
| 243 | 35 | 4-methoxybenzyl | H | CH₃ | CH₂COOH | 1-naphthylmethyl |
| 244 | 6.0 | 4-methoxybenzyl | CH₃ | CH₃ | CH₂COOH | 1-naphthylmethyl |
| 245 | 23 | 4-methoxybenzyl | H | CH₃ | C(CH₃)₂COOH | benzyl |
| 246 | 30 | 4-methoxybenzyl | H | CH₃ | C(CH₃)₂COOH | 2-aminobenzyl |
| 247 | 5.2 | 4-methoxybenzyl | H | CH₃ | C(CH₃)₂COOH | 2-nitrobenzyl |

The compounds of this invention may be prepared by the following general synthetic schemes. Modifications of these schemes can be made to produce any of the compounds of this invention. Such modifications are routine and are well within the skill of the art.

In general, synthesizing the compounds of this invention couples an appropriate heterocyclic system, E, with a modified amino acid fragment. The heterocycles used for E may either be purchased directly or readily produced from commercially available heterocycles. The following demonstrates an appropriate synthetic scheme for producing a wide variety of compounds of formula (I):

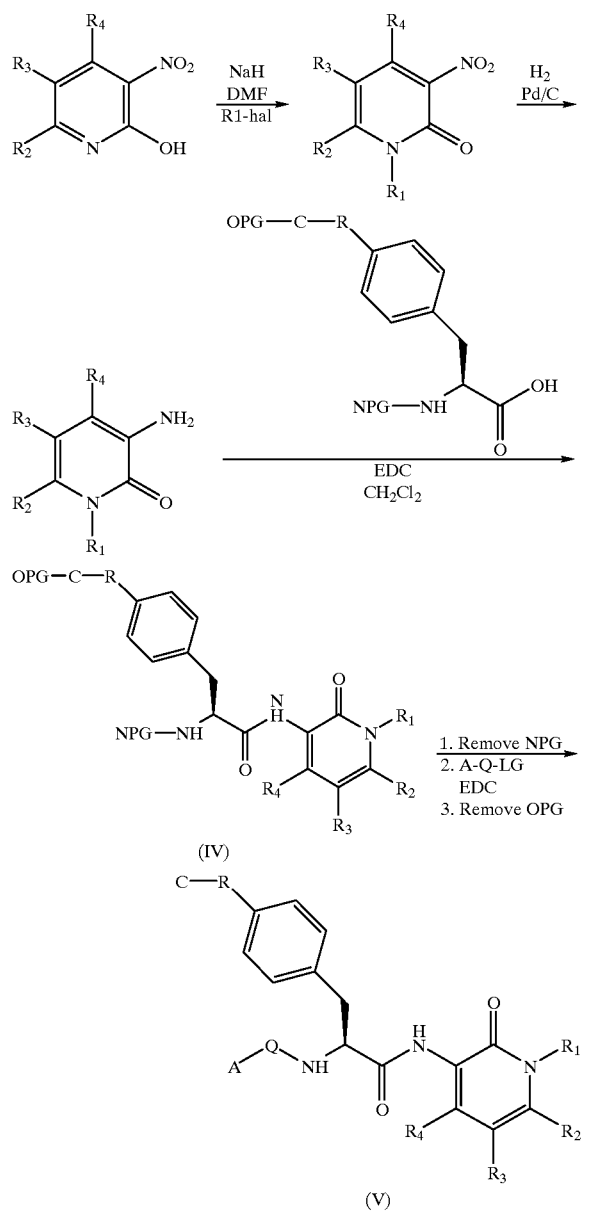

Synthesis of Amino Acid Fragments

The following describes synthetic schemes for amino acid fragments of the formula (VII) useful for producing compounds of formula (I).

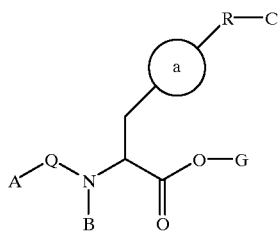

(VII)

wherein:

Ring a is selected from the group consisting of cycloalkyl, aryl or heterocyclyl;

A is selected from the group consisting of alkyl; alkenyl; alkynyl; alkoxy; cycloalkyl; cycloalkenyl; heterocyclyl and aryl; wherein said cycloalkyl, heterocyclyl or aryl is optionally linked to Q or N via an alkoxy, —O—, amino, lower alkyl, lower alkyl amino, carbonyl, amido, amido alkyl, alkoxycarbonyl, carbonylalkyloxy, cycloalkyl or heterocyclyl linker;

Q is selected from the group consisting of a bond, >C=O, >S(O)$_2$ and >C=S;

B is selected from the group consisting of H; lower alkyl and a nitrogen-protecting group;

G is selected from the group consisting of H; lower alkyl and an oxygen-protecting group;

R is a bond or an alkyl, aryl, heterocyclyl or cycloalkyl linker;

C is an acidic functionality that carries one or two negative charges at physiological pal optionally covalently attached to an OPG;

Or a salt or ester thereof.

More preferably, A-Q of the compound of formula (VII) form an amino protecting group (NPG), 'a' is an aryl, preferably phenyl, and B, G are both hydrogen such being the general amino acid fragment formula:

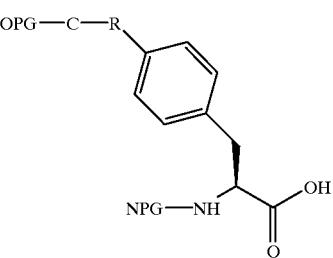

Even more preferable is an amino acid fragment of the formula (VII) wherein R is a branched alkyl; yet even more preferable is an amino acid fragment of the formula(VII) wherein R is —CH$_2$—(CH$_3$)$_2$ and C is a carboxyl group.

2-(S)-Benzyloxycarbonylamino-3-(4'-tbutoxycarbonylmethyl)benzenepropanoic Acid.

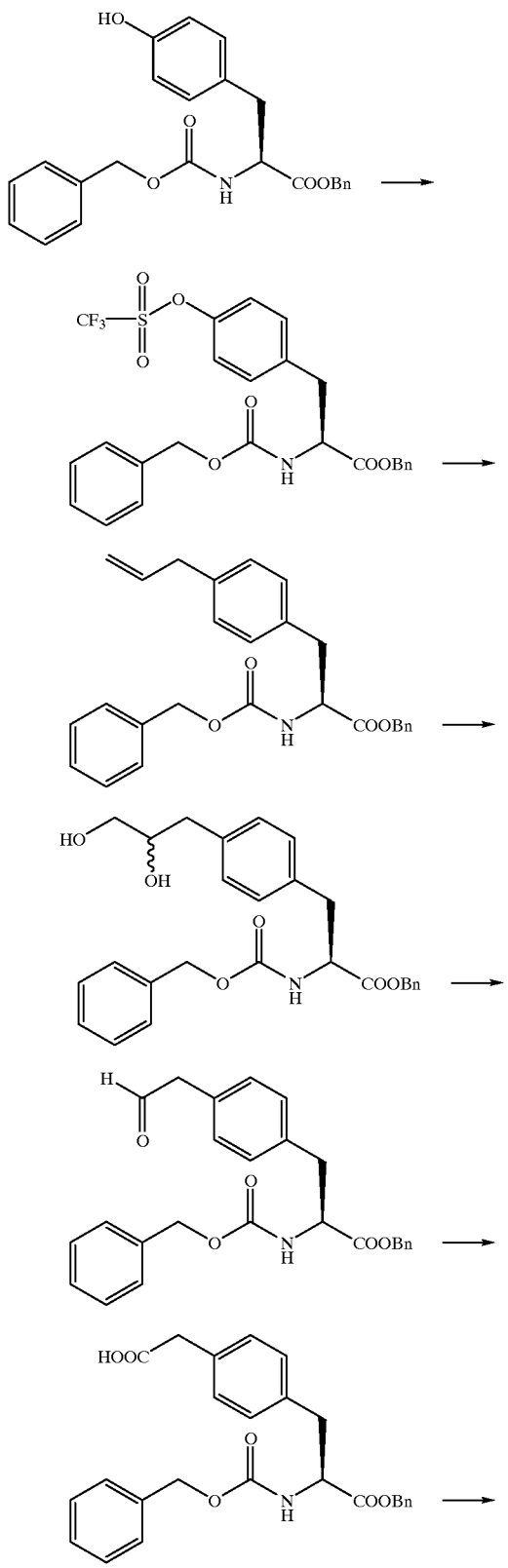

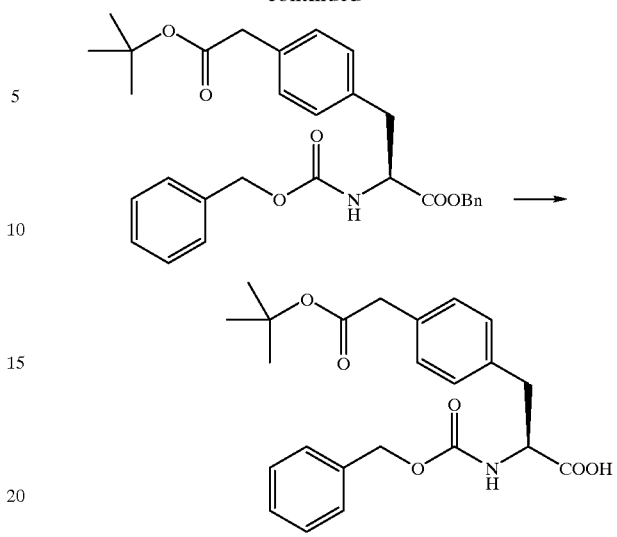

2-(S)-Benzyloxycarbonylamino-3-(4'-trifluoromethanesulfonyloxy)benzenepropanoic Acid Benzyl Ester.

To a stirred solution of 2-(S)-benzyloxycarbonylamino-3-(4'-hydroxy)benzenepropanoic acid benzyl ester (Wade, R.; Bergel F., *J. Chem. Soc.* (C), pp. 592–5 (1967)) (18.9 g, 46.7 mmol) in methylene chloride (120 mL) and triethylamine (8.5 mL). cooled to 0° C., was added slowly triflic anhydride (8.4 mL, 51 mmol). The mixture was allowed to warm to rt and stirred for 1 hour. Ether was added, and the organic phase was washed with water, 1N sodium hydroxide and brine, dried and filtered. Evaporation of the solvents gave 2-(S)-benzyloxycarbonylamino- 3-(4'-trifluoromethanesulfonyloxy)benzenepropanoic acid benzyl ester (24.7 g, 99%).

2-(S)-Benzyloxycarbonylamino-3-(4'-allyl) benzenepropanoic Acid Benzyl Ester.

To a solution of 2-(S)-benzyloxycarbonylamino-3-(4'-trifluoromethanesulfonyloxy)benzenepropanoic acid benzyl ester (24.7 g, 46.5 mmol) in DMF (120 mL) was added lithium chloride (5.85 g) and allyltributyltin (12.7 mL, 41 mmol). The mixture was twice degassed tinder vacuum and covered with argon. Bis(triphenylphosphine)palladium(II) chloride (0.65 g) was added and degassing was repeated three times. The mixture was stirred and heated at 90° C. for 1.5 hours, and then cooled to rt. Ether was added, and the organic phase was washed with water, aqueous potasium fluoride and brine, and dried (MgSO$_4$). Evaporation of the solvent followed by chromatography over silica gel (15% ethyl acetate/hexane) gave 2-(S)-benzyloxycarbonylamino-3-(4'-allyl)benzenepropanoic acid benzyl ester (13.5 g, 68%).

2-(S)-Benzyloxycarbonylamino-3-(4'-carboxymethyl) benzenepropanoic Acid Benzyl Ester.

A mixture of 2-(S)-benzyloxycarbonylamino-3-(4'-allyl) benzenepropanoic acid benzyl ester (15.4 g, 35.9 mmol), N-methylmorpholine-N-oxide (5.81 g), and osmium tetroxide (4% in water, 0.3 mL) in water (120 mL) and dioxane (350 mL) was stirred overnight at rt. The solvents were removed under vacuum. The residue was taken up in ethyl acetate, washed with water and brine, and dried (MgSO$_4$).

Evaporation of the solvent gave the crude diol. A mixture of the crude diol and sodium periodate (10 g) in THF (175 mL) and water (150 mL) was stirred at rt for 15 minutes. The THF was evaporated and the residue was extracted with ethyl acetate. The organic phase was washed with water and brine, dried (MgSO$_4$), filtered and evaporated to give crude 2-(S)-benzyloxycarbonylamino-3-(4'-formylmethyl) benzenepropanoic acid benzyl ester which was used without additional purification.

To a stirred solution of 2-(S)-benzyloxycarbonylamino-3-(4'-formylmethyl)benzenepropanoic acid benzyl ester in 'butanol (350 mL) was added 2-methyl-2-butene (100 mL) and a solution of NaClO$_2$ (32.6 g) and NaH$_2$PO$_4$.H$_2$O (49.7 g) in water (200 mL). After 1.5 hours the 'butanol was removed under reduced pressure. The residue was taken up in aqueous sodium bicarbonate, and washed with ether. The aqueous phase was acidified, and extracted with ethyl acetate. Evaporation of the ethyl acetate gave 2-(S)-benzyloxycarbonylamino-3-(4'-carboxymethyl) benzenepropanoic acid benzyl ester (7.5 g, 16.8 mmol, 47% from 2-(S)-benzyloxycarbonylamino-3-(4'-allyl) benzenepropanoic acid benzyl ester).

2-(S)-Benzyloxycarbonylamino-3-(4'-'butoxycarbonylmethyl)benzenepropanoic Acid Benzyl Ester.

To a solution of 2-(S)-benzyloxycarbonylamino-3-(4'-carboxymethyl)benzenepropanoic acid benzyl ester (7.5 g, 16.8 mmol) in methylene chloride (75 mL), cooled to −78° C., in a pressure bottle was added isobutylene (75 mL) and sulfuric acid (0.5 mL). The pressure bottle was sealed, and the mixture was stirred at rt overnight. The mixture was cooled to −78° C., the cap was removed, and the mixture was allowed to warm to rt with stirring. The solution was washed with water and aqueous NaHCO$_3$, dried and concentrated. Chromatography of the residue over silica gel (15% ethyl acetate/hexane) gave 2-(S)-benzyloxycarbonylamino-3-(4'-'butoxycarbonylmethyl)benzenepropanoic acid benzyl ester (4.0 g, 48%).

2-(S)-Benzyloxycarbonylamino-3-(4'-'butoxycarbonylmethyl)benzenepropanoic Acid.

To a stirred mixture of 2-(S)-benzyloxycarbonylamino-3-(4'-'butoxycarbonylmethyl)benzenepropanoic acid benzyl ester (1.1 g, 2.0 mmol) in methanol (16 mL) and water (4 mL), cooled to 0° C., was added a solution of lithium hydroxide hydrate (0.168 g) in water (1 mL). After 30 minutes at 0° C. and 1.5 hours at rt, the mixture was filtered, and the methanol was removed under reduced pressure. The residue was diluted with water, cooled to 0° C., and 1N H$_2$SO$_4$ was added dropwise to adjust to pH 3. The precipitated solid was collected by filtration, washed with water, and dried to give 2-(S)-benzyloxycarbonylamino-3-(4'-'butoxycarbonylmethyl)benzenepropanoic acid (0.85 g 100%).

2-(S)-Benzyloxycarbonylamino-3-[4'-(1"-'butoxycarbonyl-2"-trimethylsilylethyloxy)ethyl]benzenepropanoic Acid.

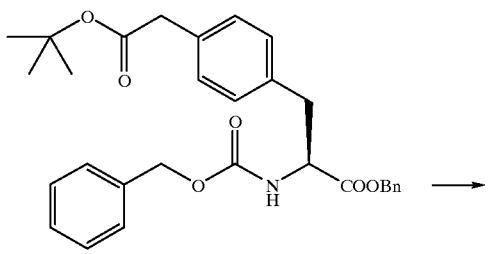

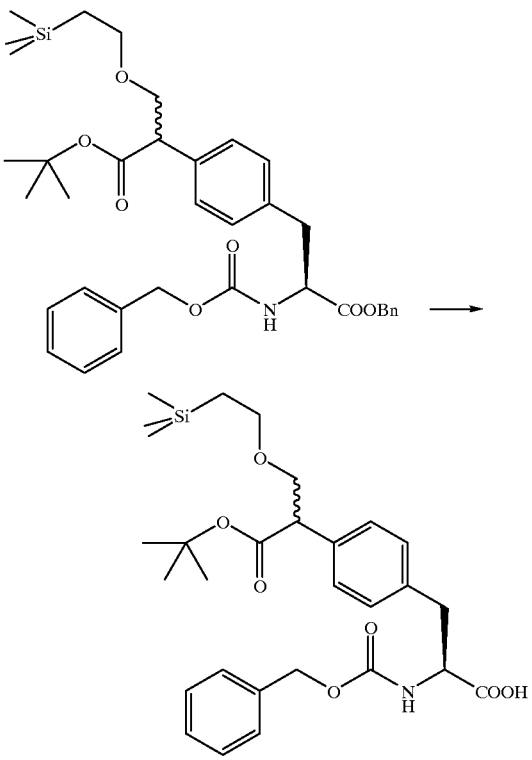

2-(S)-Benzyloxycarbonylamino-3-[4'-(1"-'butoxycarbonyl-2"-trimethylsilylethyloxy)ethyl]benzenepropanoic Acid Benzyl Ester.

To a stirred solution of 2-(S)-benzyloxycarbonylamino-3-(4'-'butoxycarbonylmethyl)benzenepropanoic acid benzyl ester (3.01 g, 5.97 mmol) in THF (50 mL) cooled to −78° C. was added sodium bis(trimethylsilyl)amide (1M in THF, 13.1 mL). After 30 minutes. TMSCH$_2$CH$_2$° C.H$_2$Cl (1.27 mL, 7.17 mmol) was added. The mixture was stirred for 1 hour, quenched with saturated ammonium chloride, and warmed to rt. The solvent was evaporated and the residue was taken up in ethyl acetate. The organic phase was washed with water, dried (MgSO$_4$), filtered, and evaporated. Chromatography of the residue over silica gel (ethyl acetate/hexane 1/9) gave 2-(S)-benzyloxycarbonylamino-3'-[4'-(1"-'butoxycarbonyl-2"-trimethylsilylethyloxy)ethyl] benzenepropanoic benzyl ester (2.87 g, 4.5 mmol, 75%)

2-(S)-Benzyloxycarbonylamino-3-[4'-(1"-'butoxycarbonyl-2"-trimethylsilylethyloxy)ethyl]benzenepropanoic Acid.

A mixture of 2-(S)-benzyloxycarbonylamino-3-[4'-(1"-'butoxycarbonyl-2"-trimethylsilylethyloxy)ethyl] benzenepropanoic benzyl ester (1.18 g 1.86 mmol) and lithium hydroxide hydrate (0.098 g, 2.32 mmol) in THF (30 mL) and water (4 mL) was stirred at rt for 2 days. The mixture was concentrated, diluted with 1M HCl (2.5 mL), and extracted with ethyl acetate. The organic phase was washed with water, dried (MgSO$_4$), filtered, and evaporated. Chromatography of the residue over silica gel (methylene chloride/methanol/acetic acid 95/5/0.05) gave 2-(S)-benzyloxycarbonylamino-3-[4'-(1"-'butoxycarbonyl-2"-trimethylsilylethyloxy)ethyl]benzenepropanoic acid (0.93 g, 1.69 mmol, 91%).

2-(S)-'Butoxycarbonylamino-3-4'-(1"-'butoxycarbonyl-1"-methyl)ethyl]benzenepropanoic Acid.

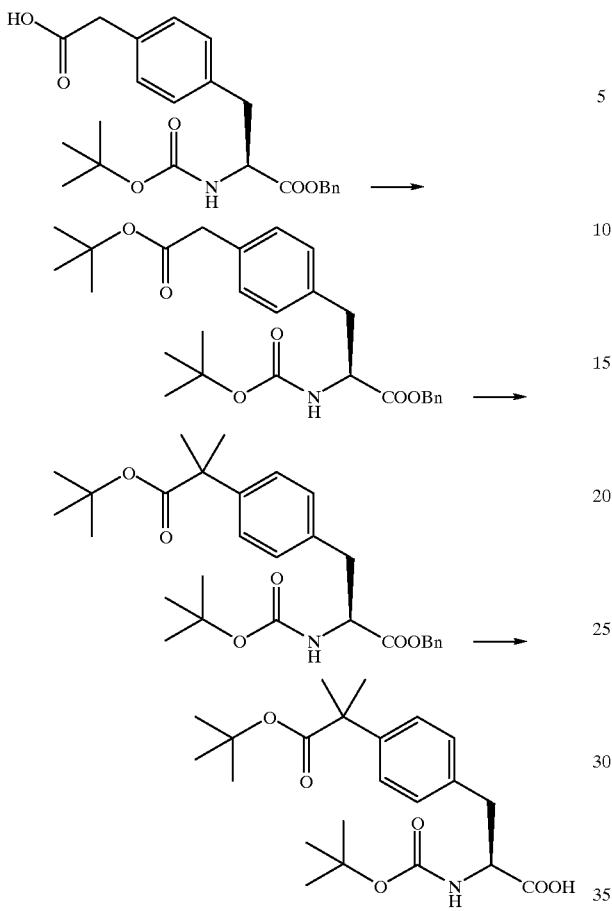

2-(S)-'Butoxycarbonylamino-3-(4'-'butoxycarbonylmethyl) benzenepropanoic Acid Benzyl Ester.

A mixture of 2-(S)-'butoxycarbonylamino-3-[(4'-carboxymethyl)benzene]propanoic acid benzyl ester (J. W. Tilley et al., *J. Org. Chem.*, 55, pp. 906–10 (1990)) (6.67 g, 16.2 mmol) and dimethylformamide di-'butyl acetal (19.4 mL, 80.9 mmol) in toluene (120 mL) was heated at 85°C. for 2 hours under nitrogen. The mixture was diluted with ethyl acetate, washed with water, dried, filtered and evaporated. Chromatography of the residue over silica gel (15% ethyl acetate/hexane) gave 2-(S)-'butoxycarbonylamino-3-(4'-'butoxycarbonylmethyl)benzenepropanoic acid benzyl ester (3.77 g, 50%).

2-(S)-'Butoxycarbonylamino-3-[4'-(1"-'butoxycarbonyl-1"-methyl)ethyl]benzenepropanoic Acid Benzyl Ester.

A cooled (−78° C.) solution of 2-(S)-'butoxycarbonylamino-3-[4'-('butoxycarbonylmethyl) benzene]propanoic acid benzyl ester (3.77 g, 8.06 mmol) in THF (20 mL) was cannulated, over 25 minutes, into a stirred solution of potassium bis(trimethylsilyl)amide (0.8 M in THF, 21.2 mL, 16.9 mmol) at −78° C. After 30 minutes at −78° C., iodomethane (0.75 mL, 12 mmol) was added. After 1 hour 45 minutes at −78° C., the mixture was poured into cold 10% citric acid (300 mL). The aqueous phase was extracted with ethyl acetate. The organic phase was washed with aqueous $Na_2S_2O_3$, saturated $NaHCO_3$, and brine, dried ($MgSO_4$), filtered and concentrated. The residue was subjected twice more to the same alkylation conditions to introduce the second methyl group. Chromatography over silica gel gave 2-(S)-'butoxycarbonylamino-3-[4'-(1"-'butoxycarbonyl-1"-methyl)ethyl]benzenepropanoic acid benzyl ester (3.36 g, 6.78 mmol, 84%).

2-(S)-'Butoxycarbonylamino-3-[4'-(1"-'butoxycarbonyl-1"-methyl)ethyl]benzenepropanoic Acid.

A mixture of 2-(S)-'butoxycarbonylamino-3-[4'-(1"-'butoxyoxycarbonyl-1"-methyl)ethyl]benzenepropanoic acid benzyl ester (3.92 g, 7.91 mmol), 10% Pd/C (1.25 g) and cyclohexene (8.01 mL, 79 mmol) in ethanol (125 mL) was heated at 70–75° C. for 15 minutes. The mixture was cooled and filtered. Evaporation of the solvents gave 2-(S)-'butoxycarbonylamino-3-[4'-(1"-'butoxycarbonyl-1"-methyl)ethyl]benzenepropanoic acid (3.20 g, 99%).

2-(S)-'Butoxycarbonylamino-3-[4'-(1"-benzyloxycarbonvy-1"-methyl)ethyl]benzenepropanoic Acid.

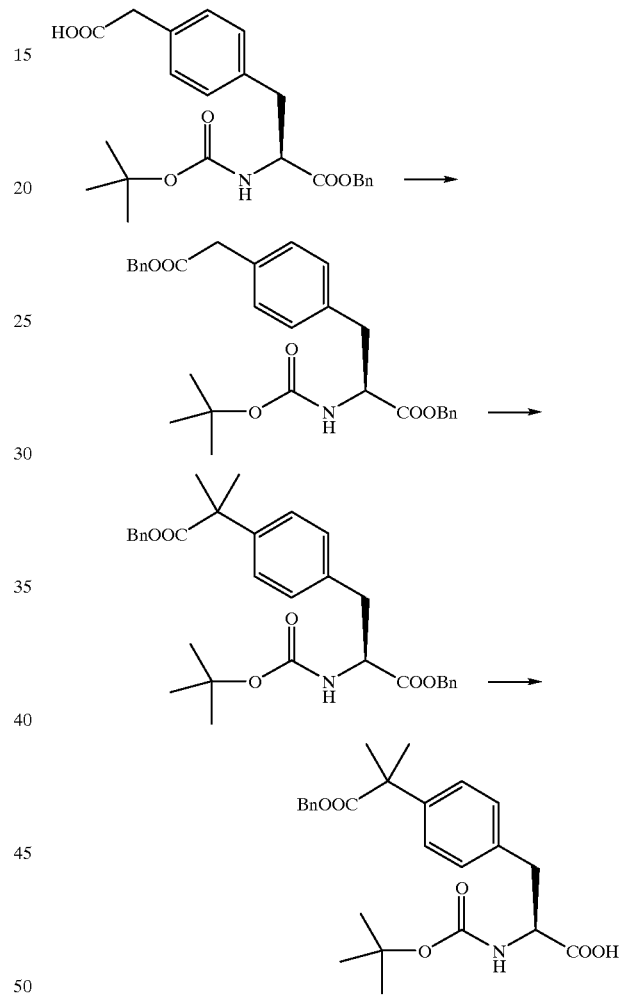

2-(S)-'Butoxycarbonylamino-3-(4'-benzyloxycarbonylmethyl)benzenepropanoic Acid Benzyl Ester.

To a stirred solution of 2-(S)-'butoxycarbonylamino-3-(4'-carboxymethyl)benzene]propanoic acid benzyl ester (7.6 g, 18.4 mmol) in acetonitrile (150 mL), cooled to 0° C., under nitrogen was added DBU (3.03 mL, 20.3 mmol) and benzyl bromide (2.41 mL, 20.3 mmol). The cooling bath was removed and the mixture was stirred at rt for 5 hours. Aqueous ammonium chloride was added, and the mixture was extracted with ethyl acetate. The organic phase was dried, filtered and evaporated. Chromatography of the residue over silica gel (10% to 20% ethyl acetate/hexane) gave 2-(S)-'butoxycarbonylamino-3-(4'-benzyloxycarbonylmethyl)benzenepropanoic acid benzyl ester (9.7 g, 100%).

2-(S)-'Butoxycarbonylamino-3-[4'-(1"-benzyloxycarbonyl-1"-methyl)ethyl]benzenepropanoic Acid Benzyl Ester.

A cold (−78° C.) solution of 2-(S)-'butoxycarbonylamino-3-[4'-(benzyloxycarbonylmethyl)benzene]propanoic acid benzyl ester (7.20 g, 14.3 mmol) in THF (48 mL) was slowly cannulated into a stirred solution of potassium bis(trimethylsilyl)amide (0.8M in THF, 37.5 mL, 30.0 mmol) at −78° C. After 30 minutes at −78° C., iodomethane (1.3 mL, 21 mmol) was added. After 1 hour 45 minutes at −78° C., the mixture was poured into cold 10% citric acid (300 mL). The aqueous phase was extracted with ethyl acetate and the organic phase was washed with 10% $Na_2S_2O_3$, saturated $NaHCO_3$, water and brine. The organic phase was dried ($MgSO_4$), filtered, and concentrated. The residue was subjected to the same reaction conditions in order to introduce the second methyl group. Chromatography over silica gel (10% to 15% ethyl acetate/hexane) gave 2-(S)-'butoxycarbonylamino-3-[4'-(1"-benzyloxycarbonyl-1"-methyl)ethyl]benzenepropanoic acid benzyl ester (6.10 g, 11.5 mmol, 80%).

2-(S)-'Butoxycarbonylamino-3-[4'-(1"-benzyloxycarbonyl-1"-methyl)ethyl]benzenepropanoic Acid To a stirred solution of 2-(S)-'butoxycarbonylamino-3-[4'-(1"-benzyloxycarbonyl-1"-methyl)ethyl]benzenepropanoic acid benzyl ester (5.39 g, 10.2 mmol) in methanol (125 mL) and THF (230 mL) at 0° C. was added a cold solution of lithium hydroxide (0.86 g, 20.4 mmol) in water (125 mL). After 2.5 hours at 0° C., the mixture was diluted with water (250 mL), and washed 3 times with ether. The aqueous phase was acidified with 10% citric acid, and extracted with ethyl acetate. The combined organic phase was washed with water and brine, dried ($Na_2SO_4$), filtered, and concentrated to give 2-(S)-'butoxycarbonylamino-3-[4'-(1"-benzyloxycarbonyl-1"-methyl)ethyl]benzenepropanoic acid (4.13 g, 9.36 mmol, 92%).

2-(S)-'Butoxycarbonylamino-3-[4'-(1"-trimethylsilylethyloxycarbonyl-1"-methyl)ethyl]benzenepropanoic Acid.

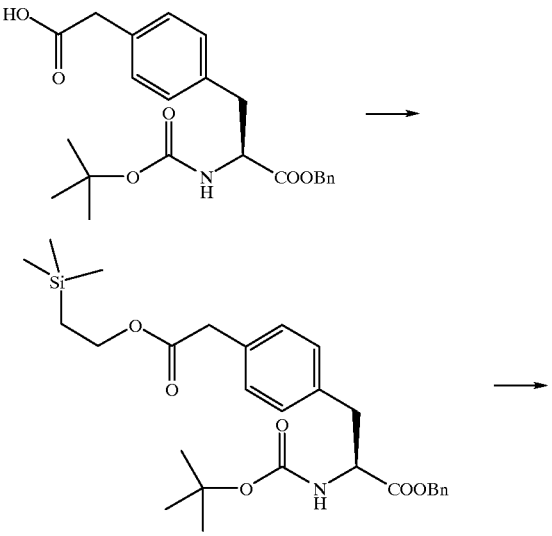

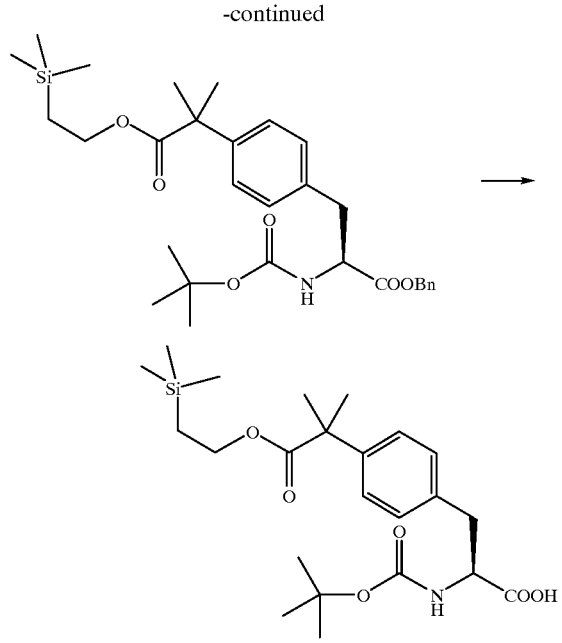

2-(S)-'Butoxycarbonylamino-3-(4'-trimethylsilylethyloxycarbonylmethyl)benzenepropanoic Acid Benzyl Ester.

To a stirred suspension of 2-chloro-1-methylpyridinium iodide (2.02 g, 7.89 mmol) in methylene chloride (3 mL) was added 2-(S)-'butoxycarbonylamino-3-(4'-carboxymethyl)benzenepropanoic acid benzyl ester (2.17 g, 5.26 mmol), 2-trimethylsilylethanol (1.13 mL, 7.89 mmol), and triethylamine (2.27 mL, 16.3 mmol) in methylene chloride (12 mL). After 10 hours, water and ethyl acetate were added, and the organic phase was washed with water and brine, dried ($MgSO_4$), filtered, and evaporated. Chromatography of the residue over silica gel (5% ethyl acetate/hexane) gave 2-(S)-'butoxycarbonylamino-3-(4'-trimethylsilylethyloxycarbonylmethyl)benzenepropanoic acid benzyl ester (2.72 g, 100%).

2-(S)-'Butoxycarbonylamino-3-[4'-(1"-trimethylsilylethyloxycarbonyl-1"-methyl)ethyl] benzenepropanoic Benzyl Ester.

To a stirred solution of 2-(S)-'butoxycarbonylamino-3-(4'-trimethylsilylethyloxycarbonylmethyl)benzenepropanoic acid benzyl ester (4.29 g. 8.8 mmol) in THF (40 mL), cooled to −78° C., was added a solution of lithium bis(trimethylsilyl)amide (1M in THF, 19.2 mL, 19 mmol). After 45 minutes, iodomethane (1.04 mL, 18 mmol) was added and stirring was continued for an additional 1.5 hours. Acetic acid (5 mL) was added, and the mixture was allowed to warm to rt. Ether (500 mL) was added, and the organic phase was washed with 10% citric acid, 10% $NaHCO_3$, 1M NaOH, and brine, dried ($MgSO_4$), and concentrated. The residue was subjected to the same reaction conditions but using potassium bis(trimethylsilyl)amide as the base in order to introduce the second methyl group. 2-(S)-'Butoxycarbonylamino-3-[4'-(1"-trimethylsilylethyloxycarbonyl-1"-methyl)ethyl] benzenepropanoic benzyl ester was obtained as a yellow oil (2.0 g, 69%).

2-(S)-'Butoxycarbonylamino-3-[4'-(1"-trimethylsilylethyloxycarbonyl-1"-methyl)ethyl] benzenepropanoic Acid.

A mixture of 2-(S)-'butoxycarbonylamino-3-[4'-(1"-trimethylsilylethyloxycarbonyl-1"-methyl)ethyl]

benzenepropanoic benzyl ester (0.823 g, 1.52 mmol) and 10% Pd/C (0.082 g) in ethanol (10 mL) was hydrogenated at 1 atmosphere for 1 hour. The catalyst was removed by filtration, and the solvent was evaporated to give 2-(S)-*t*butoxycarbonylamino-3-[4'-(1"-trimethylsilylethyloxycarbonyl-1"-methyl)ethyl]benzenepropanoic acid as a colorless oil (0.65 g, 96%).

2-(S)-*t*Butoxycarbonylamino-3-[4'-(1"-(R,S)-trimethylsilylethyloxycarbonyl)ethyl]benzenepropanoic Acid.

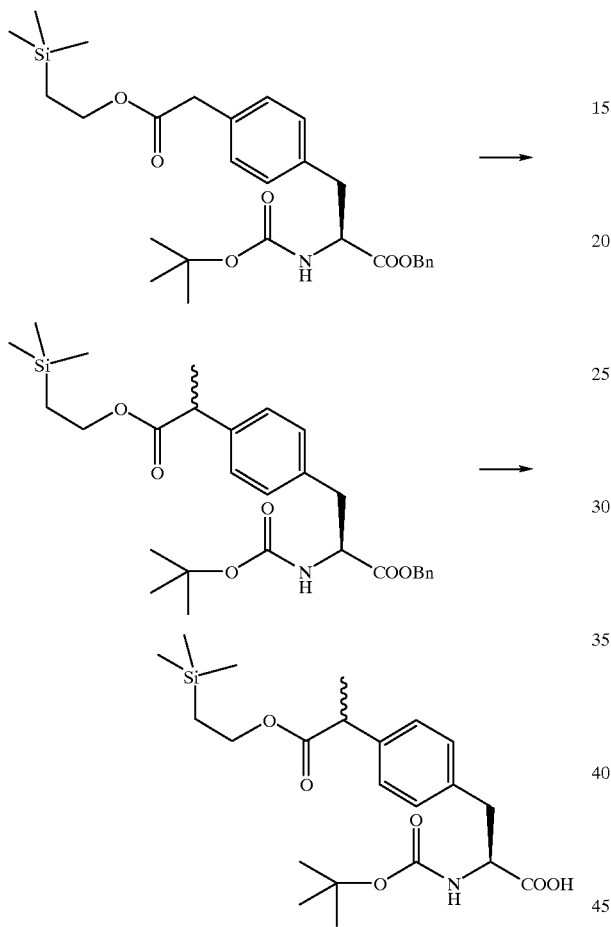

2-(S)-*t*Butoxycarbonylamino-3-[4'-(1"-(R,S)-trimethylsilylethyloxycarbonyl)ethyl]benzenepropanoic Acid Benzyl Ester.

To a stirred solution of 2-(S)-*t*butoxycarbonylamino-3-(4'-trimethylsilylethyloxycarbonylmethyl)benzenepropanoic acid benzyl ester (4.29 g, 8.8 mmol) in THF (40 mL) cooled to −78° C. was added a solution of lithium bis(trimethylsilyl)amide (1M in THF, 19.2 mL, 19.2 mmol). After 45 minutes, iodomethane (1.04 mL, 18 mmol) was added, and stirring was continued for 1.5 hours. Acetic acid (5 mL) was added, the mixture warmed to rt, and ether (500 mL) was added. The solution was washed with 10% citric acid, 10% NaHCO$_3$, 1M NaOH and brine. The organic phase was dried (MgSO$_4$), and concentrated to give 2-(S)-*t*butoxycarbonylamino-3-[4'-(1"-(R,S)-trimethylsilylethyloxycarbonyl)ethyl]benzenepropanoic acid benzyl ester (4.35 g, 98%).

Conversion to 2-(S)-*t*butoxycarbonylamino-3-[4'-(1"-(R,S)-trimethylsilylethyloxycarbonyl)ethyl]benzenepropanoic acid was carried out in the same manner as described above for the deprotection of 2-(S)-*t*butoxycarbonylamino-3-[4'-(1"-trimethylsilylethyloxycarbonyl-1"-methyl)ethyl]benzenepropanoic benzyl ester.

2-(R,S)-Benzyloxycarbonylamino-3-[4'-(1"-*t*butoxycarbonyl)cyclopentyl]benzenepropanoic Acid.

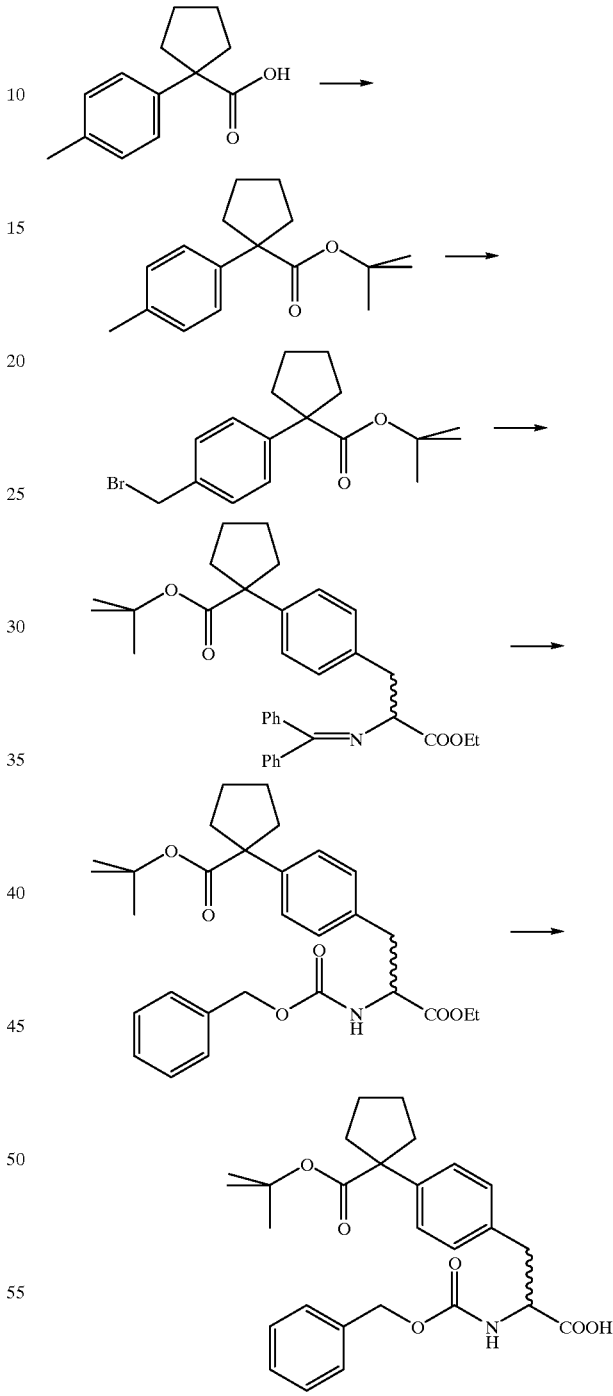

1-(4-Methylphenyl)cyclopentane Carboxylic Acid *t*butyl Ester.

To a suspension of 1-(4-methylphenyl)cyclopentane carboxylic acid (3.00 g, 14.7 mmol) in dichloromethane (50 mL) at 0° C. was added oxalyl chloride (1.54 mL, 17.4 mmol) and DMF (2 drops). The mixture was stirred at 0° C. for 1 hour, and at rt for 2 hours. The solution was concentrated, diluted with THF (40 mL), and cooled to 0° C. Potassium ᵗbutoxide (1.80 g 16.2 mmol) in THF (20 mL) was slowly added, and the mixture was stirred overnight at rt. Additional potassium ᵗbutoxide (0.660 g, 5.88 mmol) was added. After 20 minutes the solution was concentrated to dryness, and taken up in ethyl acetate. The organic phase was washed with 10% citric acid, saturated NaHCO₃ and brine, dried (MgSO₄), and concentrated. Flash column chromatography (10% ethyl acetate/hexane) gave 1-(4-methylphenyl)cyclopentane carboxylic acid ᵗbutyl ester (3.27 g, 87%).

1-(4-Bromomethylphenyl)cyclopentane Carboxylic Acid ᵗbutyl Ester.

To a solution of 1-(4-methylphenyl)cyclopentane carboxylic acid ᵗbutyl ester (2.00 g, 7.68 mmol) in CCl₄ (80 mL) was added N-bromosuccinimide (1.37 g, 7.68 mmol) and benzoyl peroxide (0.050 g). This mixture was brought to reflux by heating, and maintained at reflux for 2 hours using a sun lamp (250 W). Additional N-bromosuccinimide (0.34 g, 1.9 mmol) was added, and after 20 minutes the solution was concentrated to 40 mL. The white precipitate was removed by filtration. The filtrate was concentrated to give 1-(4-bromomethylphenyl)cyclopentane carboxylic acid ᵗbutyl ester (2.9 g, 100%) as a yellow oil which was used without additional purification.

2-(R,S)-Benzyloxycarbonylamino-3-[4'-(1"-ᵗbutoxycarbonyl)cyclopentyl]benzenepropanoic Acid Ethyl Ester.

To a stirred solution of 1-(4-bromomethylphenyl) cyclopentane carboxylic acid ᵗbutyl ester (1.00 g, 2.95 mmol) and N-(diphenylmethylene)glycine ethyl ester (0.788 g, 2.95 mmol) in THF (12 mL) at 0° C. was added, over 10 minutes, sodium bis(trimethylsilyl)amide (1M in THF, 3.54 mL, 3.54 mmol). After 40 minutes, the mixture was filtered and concentrated. The residue was dissolved in ethyl acetate, washed with 10% citric acid, saturated NaHCO₃ and brine, and dried (MgSO₄). Evaporation of the solvent gave 2-(R, S)-diphenylmethyleneamino-3-[4'-(1"-ᵗbutoxycarbonyl) cyclopentyl]benzenepropanoic acid ethyl ester which was hydrolysed by stirring in methanol (6 mL), water (3 mL) and acetic acid (3 mL) for 2 hours. The mixture was basified with sodium carbonate, and benzyl chloroformate (0.422 mL, 2.95 mmol) was added. After 1 hour, water and ethyl acetate were added. The organic phase was washed with 10% citric acid, saturated NaHCO₃ and brine. dried (MgSO₄), and concentrated. Flash chromatography (20% ethyl acetate/hexane) gave 2-(R,S)-benzyloxycarbonylamino-3-[4'-(1"-ᵗbutoxycarbonyl)cyclopentyl]benzenepropanoic acid ethyl ester (0.475 g, 0.958 mmol, 32% from 1-(4-bromomethylphenyl)cyclopentane carboxylic acid ᵗbutyl ester).

2-(R,S)-Benzyloxycarbonylamino-3-[4'-(1"'ᵗbutoxycarbonyl)cyclopentyl]benzenepropanoic Acid A mixture of 2-(R,S)-benzyloxycarboiylamino-[4'-(1"-ᵗbutoxycarbonyl)cyclopentyl]benzenepropanoic acid ethyl ester (0.475 g, 0.96 mmol) and aqueous LiOH (1M, 1.44 mL) in THF (3 mL) was stirred for 2 hours. Aqueous HCl (1M, 2 mL) was added, and the mixture was extracted with ethyl acetate. The organic phase was washed with brine, dried (MgSO₄), and concentrated to give 2-(R,S)-benzyloxycarbonylamino-3-[4'-(1"-ᵗbutoxycarbonyl) cyclopentyl]benzenepropanoic acid (0.430 g, 96%).

2-(R,S)-Benzyloxycarbonylamino-3-[4'-(1"-ᵗbutoxycarbonyl-1"-methyl)ethyl]benzenepropanoic Acid.

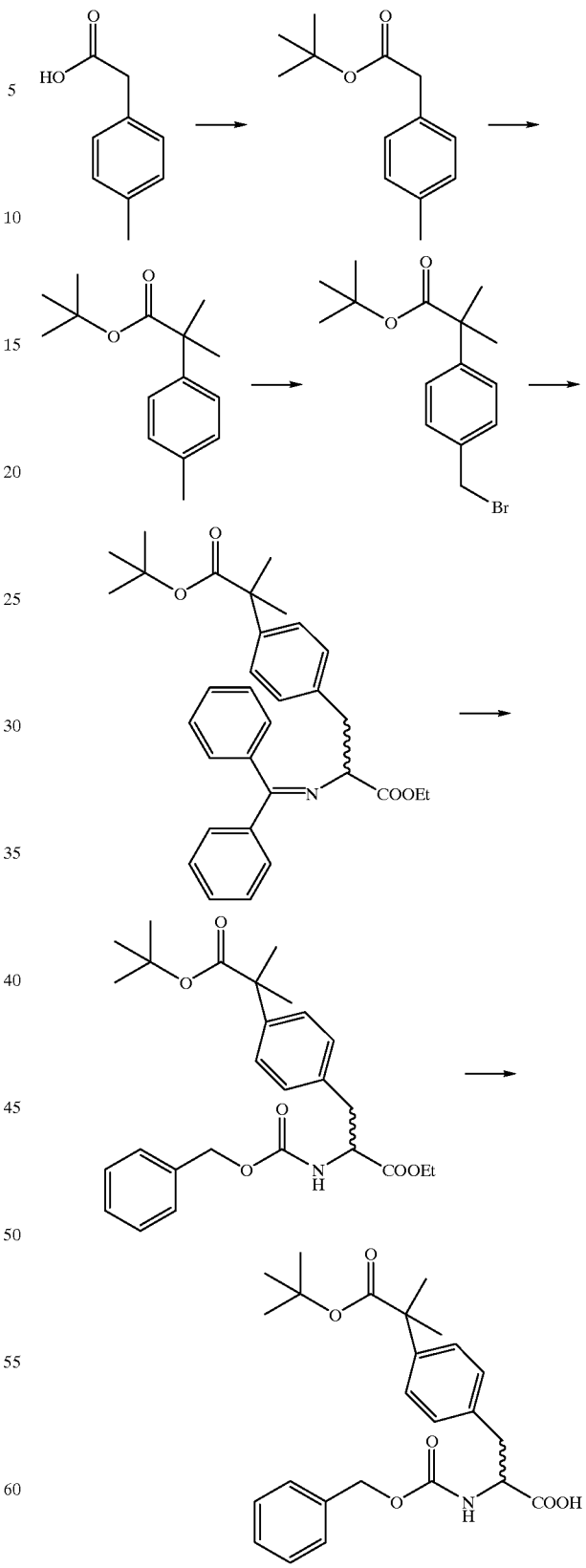

ᵗButyl 4-methylphenylacetate.

To a stirred solution of 4-methylphenylacetic acid (20.6 g, 137 mmol) in methylene chloride (100 mL) in a pressure flask cooled on a dry-acetone bath was added isobutene (190 mL) followed by concentrated sulfuric acid (2.5 mL). After 36 hours, the mixture was cooled (dry ice/acetone bath) and isobutene was removed in a slow stream of nitrogen. The residue was treated with 10% NaHCO$_3$, and extracted with methylene chloride (3×100 mL). The combined methylene chloride extract was washed with 10% NaHCO$_3$ and brine, and dried (Na$_2$SO$_4$). Evaporation of the solvent gave $^t$butyl 4-methylphenylacetate as a colorless oil (25 g, 90%).

$^t$Butyl 2-(4-methylphenyl)-2,2-dimethylacetate.

To a stirred solution of potassium $^t$butoxide (1M in THF, 100 mL) under argon in THF (150 mL) cooled to 0° C. was added $^t$butyl 4-methylphenylacetate (19.3 g, 93.5 mmol) in THF (50 mL). After 30 minutes, iodomethane (7 mL) in THF (10 mL) was added over 15 minutes and the mixture was stirred for 45 min. Additional potassium $^t$butoxide (1M in THF, 120 mL) was added followed, after 1 hour, by iodomethane (8 mL) in THF (25 ml). The mixture was allowed to warm to rt overnight, and the solvent was evaporated. The residue was taken up in 1N sulfuric acid (250 mL), and extracted with ether (3×100 mL). The combined organic phase was washed with brine, dried (Na$_2$SO$_4$), and evaporated to give $^t$butyl 2-(4-methylphenyl)-2,2-dimethylacetate as a light yellow oil (19.4 g, 83 mmol, 89%).

$^t$Butyl 2-(4-bromomethylphenyl)-2,2-dimethylacetate.

To a solution of $^t$butyl 2-(4-methylphenyl)-2,2-dimethylacetate (19.4 g, 83 mmol) in carbon tetrachloride (350 mL) was added N-bromosuccinimide (16.2 g, 92 mmol) and benzoyl peroxide (0.5 g). The mixture was heated under reflux for 1 hour. The mixture was cooled to rt, and the precipitate was removed by filtration. The filtrate was washed with 10% NaHCO$_3$ and brine, dried (Na$_2$SO$_4$), and evaporated to give $^t$butyl 2-(4-bromomethylphenyl)-2,2-dimethylacetate as a light yellow oil (26.4 g, 100%).

2-(R,S)-Benzyloxycarbonylamino-3-[4'-(1"-$^t$butoxycarbonyl-1"-methyl)ethyl]benzenepropanoic Acid Ethyl Ester.

To a stirred solution of $^t$butyl 2-(4-bromomethylphenyl)-2,2-dimethylacetate (6.3 g, 20 mmol) in THF (60 mL) cooled on ice was added N-(diphenylmethylene)glycine ethyl ester (5.6 g, 21 mmol). After 10 minutes, sodium bis(trimethylsilyl)amide (2M in THF, 11 mL) was added all at once. The mixture was stirred at 0° C. for 1 hour. The precipitated solid was removed, and the solvent was evaporated. The residue was taken up in acetic acid (20 mL), water (20 mL) and methanol (40 mL), and stirred at rt for 3 hours. The methanol was evaporated, and the aqueous phase was washed with 1/1 hexane/ether (2×50 mL). The combined organic phase was extracted with water (2×25 mL), and the combined aqueous phase was cooled on ice. The pH was adjusted to approximately pH 7 with sodium carbonate. Dioxane (60 mL) was added followed by benzyl chloroformate (3.6 mL, 25 mmol). The mixture was stirred on ice for 1 hour, diluted with water (100 mL), acidified to pH 3 with 1N sulfuric acid, and extracted with ethyl acetate (3×100 mL). The combined ethyl acetate extract was washed with brine, dried (Na$_2$SO$_4$), and evaporated to give crude 2-(R,S)-benzyloxycarbonylamino-3-[4'-(1"-$^t$butoxycarbonyl-1"-methyl)ethyl]benzenepropanoic acid ethyl ester as a light yellow oil (9.4 g). This reaction was repeated with 20 g (63.6 mmol) of $^t$butyl 2-(4'-bromomethylphenyl)-2,2-dimethylacetate to give additional 2-(R,S)-benzyloxycarbonylamino-[4'-(1"-$^t$butoxycarbonyl-1"-methyl)ethyl]benzenepropanoic acid ethyl ester (30 g). The two batches were combined and purified by chromatography over silica gel (hexane/ethyl acetate 9/1) to give 2-(R,S)-benzyloxycarbonylamino-3-[4'-(1"-$^t$butoxycarbonyl-1"-methyl)ethyl]benzenepropanoic acid ethyl ester as a colorless oil (23.7 g, 50.6 mmol, 54% from $^t$butyl 2-(4-bromomethyl)phenyl-2,2-dimethylacetate).

2-(R,S)-Benzyloxycarbonylamino-3-[4'-(1"-$^t$butoxycarbonyl-1"-methyl)ethyl]benzenepropanoic Acid was obtained by lithium hydroxide hydrolysis of 2-(R,S)-benzyloxycarbonylamino-[4'-(1-$^t$butoxycarbonyl-1"-methyl)ethyl]benzenepropanoic acid ethyl ester by a procedure similar to that described above in the synthesis of 2-(R,S)-benzyloxycarbonylamino-3-[4'-(1"-$^t$butoxycarbonyl)cyclopentyl]benzenepropanoic acid.

2-(S)-$^t$Butoxycarbonylamino-3-[4'-(1"-$^t$butoxycarbonyl)cyclopropyl]benzenepropanoic Acid.

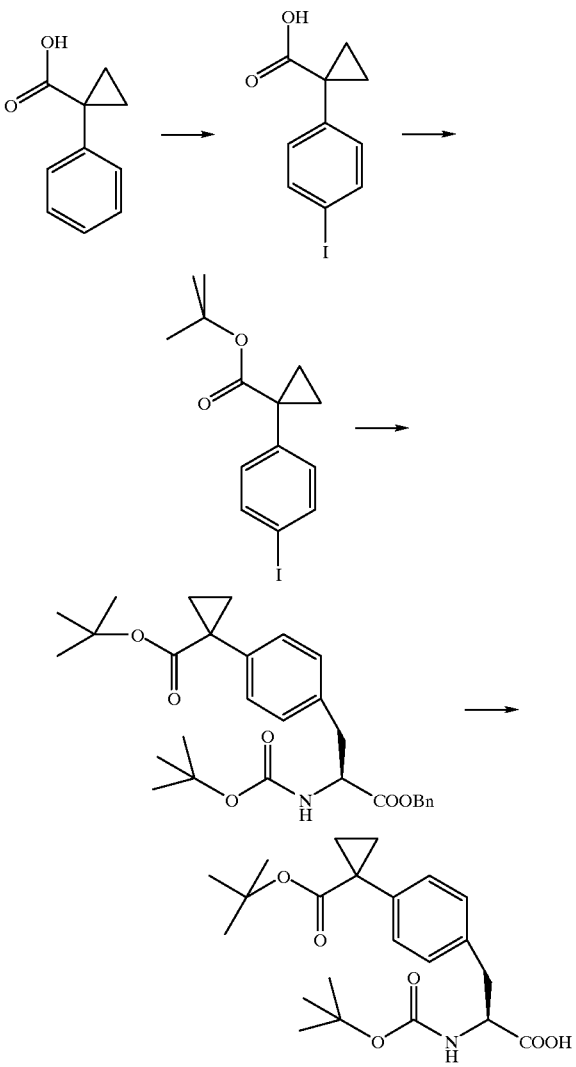

1-(4-Iodophenyl)cyclopropane-1-carboxylic Acid.

A mixture of 1-phenylcyclopropane carboxylic acid (16.5 g, 101 mmol), sodium iodate (5.04 g) and concentrated sulfuric acid (1 mL) in acetic acid (70 mL) was stirred and heated at 70° C. for 2 days. Additional sodium iodate (1.88 g) and sulfuric acid (1 mL) were added, and stirring was continued for 1 day. The acetic acid was evaporated, and the residue was partitioned between ethyl acetate and water. The organic phase was washed with aqueous sodium thiosulfate, dried, filtered, and evaporated. The solid residue was recrystallized from methanol/water to give 1-(4-iodophenyl)cyclopropane-1-carboxylic acid (7.98 g, 27 mmol, 27%).

ᵗButyl 1-(4-iodophenyl)cyclopropane-1-carboxylate.

To a solution of 1-(4-iodophenyl)cyclopropane-1-carboxylic acid (7.98 g, 27 mmol) in methylene chloride (200 mL) containing DMF (0.25 mL) was added dropwise over 30 minutes oxalyl chloride (3.2 mL). The mixture was stirred for 1 hour, and the solvent was removed under reduced pressure. The residue was taken up in THF (100 mL), and potassium ᵗbutoxide (1M in THF, 35 mL) was added. After 30 minutes, the mixture was diluted with hexane, washed with water, dried, filtered and evaporated. The solid residue was recrystallized from methanol to give ᵗbutyl 1-(4-iodophenyl)cyclopropane-1-carboxylate (5.74 g, 16.6 mmol, 62%).

2-(S)-ᵗButoxycarbonylamino-3-[4'-(1"-ᵗbutoxycarbonyl)cyclopropyl]benzenepropanoic Acid Benzyl Ester.

A suspension of zinc (0.874 g) in THF with dibromoethane (0.02 mL) was sonicated at 40° C. for 40 minutes under argon. N-Boc-iodo-L-alanine benzyl ester (4.20 g, 10.4 mmol) and dimethylacetamide (5 mL) were added, and the mixture was heated at 55° C. for 1 hour. ᵗbutyl 1-(4-iodophenyl)cyclopropane-1-carboxylate (3.26 g, 9.48 mmol) in dimethylacetamide (10 mL) was added followed by tris(dibenzylideneacetone)dipalladium(0) (0.33 g) and tri-o-tolylphosphine (0.398 g). Heating was continued under argon for 16 hours. The mixture was diluted with ethyl acetate, washed with water, dried, filtered and evaporated. Chromatography of the residue over silica gel (methylene chloride/hexane 1/3 to methylene chloride/ethyl acetate 95/5) gave 2-(S)-ᵗbutoxycarbonylamino-3-[4'-1"-ᵗbutoxycarbonyl)cyclopropyl]benzenepropanoic acid benzyl ester (3.15 g, 6.36 mmol, 67%).

2-(S)-ᵗButoxycarbonylamino-3-[4'-(1"-ᵗbutoxycarbonyl)cyclopropyl]benzenepropanoic Acid.

A mixture of 2-(S)-ᵗbutoxycarbonylamino-3-[4'-(1"-ᵗbutoxycarbonyl)cyclopropyl)benzene]propanoic acid benzyl ester (3.92 g, 7.92 mmol) and lithium hydroxide hydrate (0.60 g) in THF (10 mL) and water (5 mL) was stirred at rt for 16 hours. The mixture was acidified with potassium bisulfate (2N), and partitioned between ethyl acetate and water. The organic phase was separated, dried, filtered and evaporated. Chromatography of the residue over silica gel (methylene chloride/hexane to methylene chloride/ethyl acetate) gave 2-(S)-ᵗbutoxycarbonylamino-3-[4'-(1"-ᵗbutoxycarbonyl)cyclopropyl]benzenepropanoic acid (2.13 g 5.25 mmol, 66%) as an oil that crystallized on standing.

2-(R,S)-ᵗButoxycarbonylamino-3-[4'-(1"-ᵗbutoxycarbonyl-1"-methyl)ethyl]benzenepropanoic Acid.

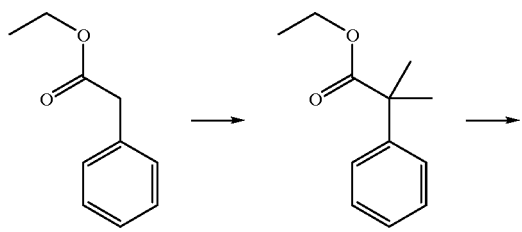

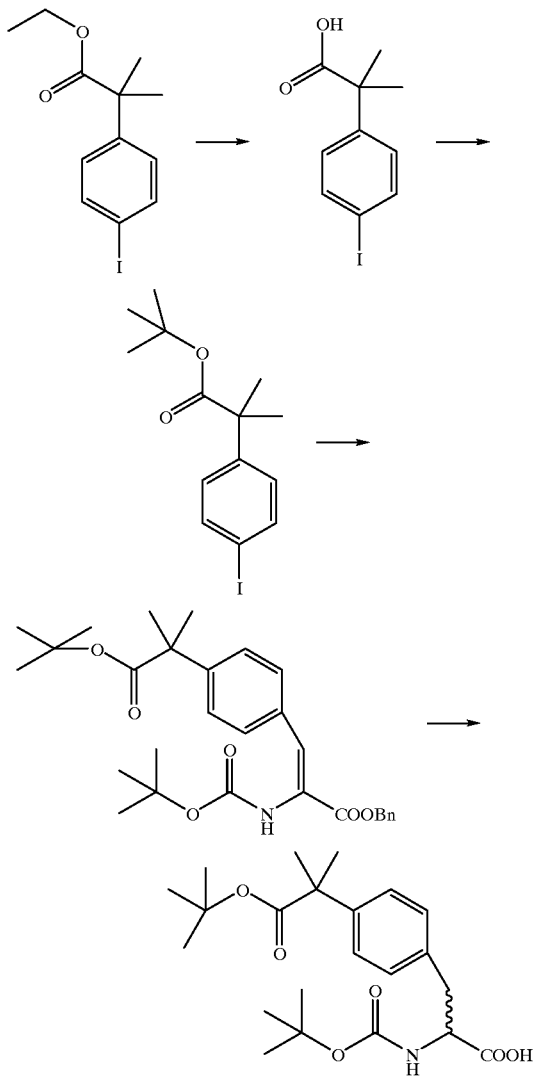

(1'-Ethoxycarbonyl-1'-methyl)ethylbenzene

To a solution of ethyl phenylacetate (32.8 g, 200 mmol) in THF (1000 mL) under argon was added sodium bistrimethylsilylamide (2M in THF, 100 mL). After 45 minutes, methyl iodide (13 mL) was added over 15 minutes and the mixture was stirred at rt for 30 minutes. Additional sodium bistrimethylsilylamide (2M in THF, 100 mL) was added, followed, after 30 minutes, by methyl iodide (14 mL). After 30 minutes the mixture was diluted with hexane and washed with water. The organic phase was dried, filtered and evaporated to give (1'-ethoxycarbonyl-1'-methyl)ethylbenzene (28.0 g, 146 mmol, 73%).

4-Iodo-(1'-carboxy-1'-methyl)ethylbenzene.

A mixture of (1'-ethoxycarbonyl-1'-methyl)ethylbenzene (28.0 g, 146 mmol), iodine (24.7 g), sodium iodate (7.1 g) and concentrated sulfuric acid (4 mL) in acetic acid (200 mL) was stirred and heated at 55° C. for 90 hours. The solvent was evaporated and the residue was partitioned between water and hexane. The organic phase was washed with aqueous sodium thiosulfate, dried, filtered, and evaporated. The residue was taken up in ethanol (200 mL) and water (100 mL), and potassium hydroxide (20 g) was added. The mixture was heated under reflux for 5 hours, and cooled to rt. The mixture was washed with hexane. The aqueous phase was acidified with concentrated hydrochloric acid, and extracted with hexane. The organic phase was dried, filtered and evaporated to give 4-iodo-(1'-carboxy-1'-methyl)ethylbenzene as a solid (19.6 g. 67 mmol, 46%).

4-Iodo-(1'-'butoxycarbonyl-1'-methyl)ethylbenzene.

To a solution of 4-iodo-(1'-carboxy-1'-methyl) ethylbenzene (18.7 g, 64.3 mmol) in methylene chloride (150 mL) was added dimethylformamide (0.5 mL) followed by oxalyl chloride (10 mL) dropwise. After 1 hour the solvent was evaporated and the residue was taken up in THF (100 mL), and cooled on ice. Potassium 'butoxide (1M in THF, 75 mL) was added over 20 minutes. The mixture was diluted with hexane, washed with water, dried, filtered and evaporated. The residue was triturated with methanol/water to give 4-iodo-(1'-'butoxycarbonyl-1'-methyl)ethylbenzene as a solid (18.1 g, 52.1 mmol, 81%).

2-'Butoxycarbonylamino-3-[4'-(1"-'butoxycarbonyl-1"-methyl)ethyl]benzenepropenoic Acid, Benzyl Ester.

A mixture of benzyl (2-'butoxycarbonylamino)acrylate (8.00 g, 27.9 mmol), 4-iodo-(1'-'butoxycarbonyl-1'-methyl)ethylbenzene (7.03 g, 20.3 mmol), sodium bicarbonate (4.03 g), tetrabutylammonium chloride hydrate (6.47 g) and palladium acetate (0.41 g) in dimethylformamide (100 mL) was degassed and covered with argon three times. The mixture was heated under argon at 80° C. for 5 hours. The mixture was cooled, diluted with ethyl acetate/hexane and washed with water. The organic phase was dried, filtered and evaporated. Chromatography of the residue over silica gel (ethyl acetate/hexane 98/2 to 9/1) gave 2-'butoxycarbonylamino-3-[4'-(1"-'butoxycarbonyl-1"-methyl)ethyl] benzenepropenoic acid, benzyl ester as an oil that solidified upon trituration with hexane (7.24 g, 14.6 mmol, 72%).

2-(R, S)-'Butoxycarbonylamino-3-[4'-(1"-'butoxycarbonyl-1"-methyl)ethyl]benzenepropanoic Acid.

A mixture of 2''butoxycarbonylamino-3-[4'-(1"-'butoxycarbonyl-1"-methyl)ethyl]benzenepropenoic acid, benzyl ester (7.39 g. 14.9 mmol) and 10% Pd/C (0.202 g)in ethanol (75 mL) was hydrogenated at 45 psi in a Parr apparatus for 26 hours. The catalyst was removed by filtration and the solvent was evaporated. The residue crystallized from hexane giving 2-(R, S)'butoxycarbonylamino-3[4'-(1"-'butoxycarbonyl 1"-methyl)ethyl]benzenepropanoic acid (4.67 g, 1 1.5 mmol, 77%).

2-(S)-'Butoxycarbonylamino-3-[4'-1"-hydroxy-1"-methoxycarbonyl)methyl]benzenepropanoic Acid.

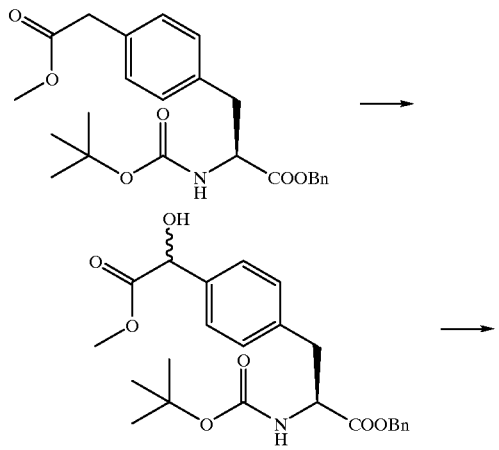

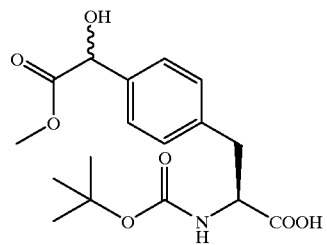

2-(S)-'Butoxycarbonylamino-3-[4'-(1"-hydroxy-1"-methoxycarbonyl)methyl]benzenepropanoic Acid Benzyl Ester.

To a stirred solution of 2-(S)-'butoxycarbonylamino-3-(4'-methoxycarbonylmethyl)benzenepropanoic acid benzyl ester (1.28 g, 3.0 mmol) in dry THF (15 mL) cooled to −78° C. under argon was added a cooled (−78° C.) solution of potassium bis(trimethylsilyl)amide (0.81 M in THF, 9.3 mL, 7.5 mmol). After 45 minutes. N-phenylsulfonylphenyloxaziridine (1.18 g, 4.5 mmol) in THF (15 mL) cooled to −78° C. was added, and the mixture was stirred for 40 minutes at −78° C. The reaction was quenched with saturated $NH_4Cl$ (10 mL), and the mixture was extracted with ether and ethyl acetate. The combined extract was washed with saturated $NH_4Cl$, 5% $NaHCO_3$, 0.5N HCl and brine, dried ($MgSO_4$), and evaporated. Chromatography of the residue over silica gel (hexane/ethyl acetate 4/1) gave 2-(S)-'butoxycarbonylamino-)-[4'-(1"-hydroxy-1"-methoxycarbonyl)methyl]benzenepropanoic acid benzyl ester (1.02 g. 77%).

2-(S)-'Butoxycarbonylamino-3-[4'-(1"-hydroxy-1"-methoxycarbonyl)methyl]benzenepropanoic Acid.

A mixture of 2-(S)-'butoxycarbonylamino-3-[4'-(1"-hydroxy-1"-methoxycarbonyl)methyl]benzenepropanoic acid benzyl ester (0.330 g, 0.744 mmol) and 5% Pd/C (0.050 g) in ethanol (10 mL) was hydrogenated at 1 atmosphere for 30 minutes. The catalyst was removed by filtration, and the solvent was evaporated to give 2-(S)-'butoxycarbonylamino-[4'-(1"-hydroxy-1"-methoxycarbonyl)methyl]benzenepropanoic acid.

2-(R,S)-(N-methyl-N-benzyloxycarbonylamino)-3-[4'-(1"-'butoxycarbonyl-1"-methyl)ethyl]benzenepropanoic Acid

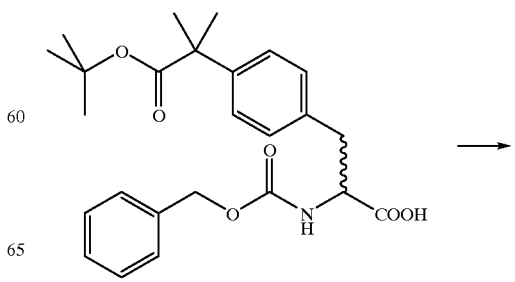

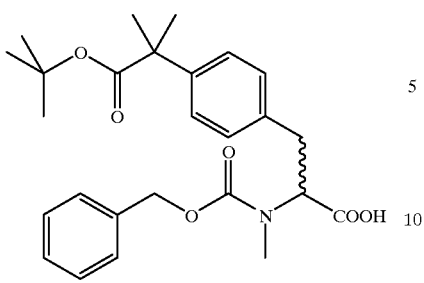

To a solution of 2-(R,S)-benzyloxycarbonylamino-3-[4'-(1"-ᵗbutoxycarbonyl-1"-methyl)ethyl]benzenepropanoic acid (0.53 g, 1.2 mmol) in THF (20 mL) cooled to 0° C. was added iodomethane (0.60 mL, 9.6 mmol) followed by sodium hydride (60% in oil, 0.145 go 3.6 mmol). The mixture was allowed to warm to rt and stirred for 25 hours. Ethyl acetate and water were added and the solvents were evaporated. The residue was partitioned between water and ether, and the organic phase was extracted with saturated NaHCO$_3$. The combined aqueous phase was acidified to pH 2 with 6N HCl, and extracted with ethyl acetate. The organic phase was dried (MgSO$_4$), filtered and evaporated to give 2-(R,S)-(N-methyl-N-benzyloxycarbonylamino)-3-[4'-(1"-ᵗbutoxycarbonyl-1"-methyl)ethyl]benzenepropanoic acid as an oil (0.50 g, 91%).

2-(S)-Fluorenylmethoxycarbonylamino-3-[4'-(4", 5"-di-ᵗbutoxycarbonyltriazolyl)]benzenepropanoic Acid.

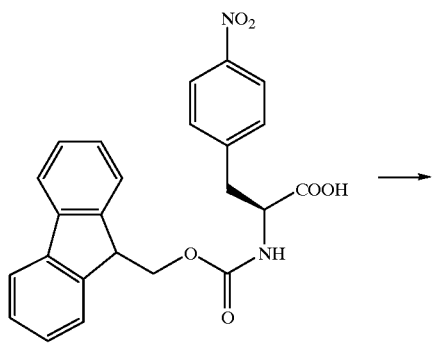

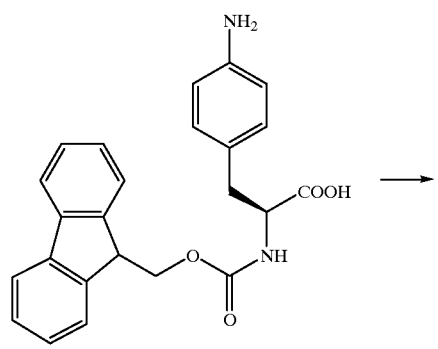

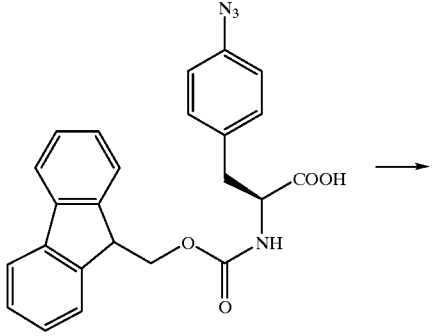

2-(S)-Fluorenylmethoxycarbonylamino-3-(4'-aminobenzene)propanoic Acid.

2-(S)-Fluorenylmethoxycarbonylamino-3-(4'-nitrobenzene)propanoic acid (6.00 g, 13.9 mmol) was heated in acetic acid (300 mL) to dissolve, and 10% Pd/C (0.18 g) was added. The mixture was hydrogenated at 35 psi in a Parr apparatus for 4 hours. The catalyst was removed by filtration and the solvent was evaporated. Trituration of the residue with ethyl acetate gave 2-(S)-fluorenylmethoxycarbonylamino-3-(4'-aminobenzene)propanoic acid (3.99 g, 9.93 mmol, 71%).

2-(S)-Fluorenylmethoxycarbonylamino-3-(4'-azidobenzene)propanoic Acid.

To a suspension of 2-(S)-fluorenylmethoxycarbonylamino-3-(4'-aminobenzene)propanoic acid (4.02 g, 10.0 mmol) in a mixture of water (200 mL) and concentrated HCl (3 mL), cooled to 5° C., was added a solution of sodium nitrite (0.71 g) in water (5 mL). The mixture was stirred for 4 hours at 5–10° C.. Sodium azide (0.71 g) in water (5 mL) was added and the mixture was allowed to warm to rt. After 90 minutes the precipitate was collected by filtration and air dried to give 2-(S)-fluorenylmethoxycarbonylamino-3-(4'-azidobenzene) propanoic acid (4.02 g, 9.4 mmol, 94%).

2-(S)-Fluorenylmethoxycarbonylamino-3-[4'-(4", 5"-di-ᵗbutoxycarbonyltriazolyl)]benzenepropanoic Acid A mixture of 2-(S)-fluorenylmethoxycarbonylamino-3-(4'-azidobenzene)propanoic acid (3.25 g 7.59 mmol) and di-ᵗbutyl acetylenedicarboxylate (1.75 g, 7.74 mmol) in dioxane (15 mL) was heated at 80–90° C. for 24 hours. The solvent was evaporated and the residue was fractionated over silica gel (chloroform/hexane/ethanol/acetic acid 1/1/0.01/0.01 to chloroform/ethanol/acetic acid 1/0.01/0.01 gradient) to give 2-(S)-fluorenylmethoxycarbonylamino-3-[4'-(4",5"-di-$^t$butoxycarbonyltriazolyl)]benzenepropanoic acid (2.56 g, 3.91 mmol, 51%).

2-(R,S)-Benzyloxycarbonylamino-3-[4'-(1"-ethyloxysulfonyl-1"-methyl)ethyl)benzene]propanoic Acid.

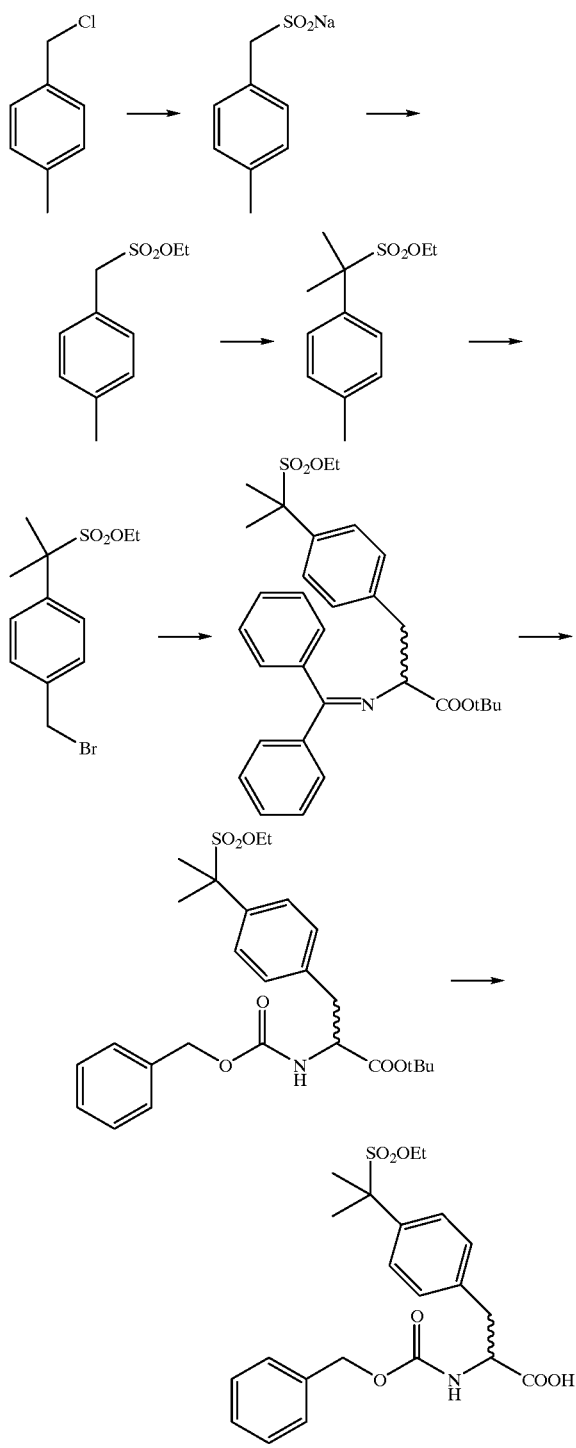

4-Methylphenylmethanesulfonic Acid, Sodium Salt.

To a solution of sodium sulfite (14.3 g 113 mmol) in water (60 mL) was added 4-methylbenzyl chloride (15.0 mL, 113 mmol). The mixture was stirred under reflux for 12 hours, and cooled to rt. The precipitate was collected by filtration, and washed with water and ether to give 4-methylphenylmethanesulfonic acid sodium salt (12.5 g, 60 mmol, 53%).

Ethyl 4-methylphenylmethanesulfonate.

To 4-methylphenylmethanesulfonic acid, sodium salt (9.22 g, 44.3 mmol) cooled on ice in a flask fitted with an overhead stirrer was added phosphorus pentachloride (9.22 g, 44.3 mmol) and phosphorus oxychloride (1.5 mL). The mixture was stirred for 2 hours at 0° C., and allowed to warm to rt. The phosphorus oxychloride was removed under vacuum, and the residue was cooled to −10° C.. Ethanol (13 mL) was added, followed by pyridine (18 mL) added slowly over 2 hours. The mixture was left in the freezer overnight, and then allowed to warm to rt. Methylene chloride was added, the mixture was washed with 1N HCl and brine, and dried (K$_2$CO$_3$). Evaporation of the solvent followed by chromatography of the residue over silica gel (15% ethyl acetate/hexane) gave ethyl 4-methylphenylmethanesulfonate (3.13 g, 14.6 mmol, 33%).

Ethyl 1-methyl-1-(4-methylphenyl)ethanesulfonate.

To a solution of butyllithium (2.5M in hexanes, 2.94 mL) in THF (3.5 mL) cooled to −60° C. was added ethyl 4-methylphenylmethanesulfonate (1.05 g, 4.91 mmol) in THF (5 mL). After 15 minutes, iodomethane (0.61 mL, 9.8 mmol) was added, and the mixture was stirred for 1 hour at −50 to −30° C.. The mixture was recooled to −60° C., and further butyllithium (2.94 mL) and iodomethane (0.61 mL) were added. The reaction was quenched with aqueous ammonium chloride, and extracted with ether. The organic phase was dried (K$_2$CO$_3$), filtered and evaporated. Chromatography of the residue over silica gel (15% ethyl acetate/hexane) gave ethyl 1-methyl-1-(4-methylphenyl)ethanesulfonate (0.917 g, 3.79 mmol, 77%).

Ethyl 1-methyl-1-(4-bromomethylphenyl)ethanesulfonate.

To a solution of ethyl 1-methyl-1-(4-methylphenyl)ethanesulfonate (0.458 g, 1.89 mmol) in carbon tetrachloride (8 mL) was added N-bromosuccinimide (0.370 g, 2.08 mmol) and benzoyl chloride (0.009 g). The mixture was heated under reflux for 1.5 hours, cooled to rt, and filtered. The filtrate was washed with aqueous sodium bicarbonate and brine, dried, filtered and evaporated to give crude ethyl 1-methyl-1-(4-bromomethylphenyl)ethanesulfonate (0.64 g, 100%) which was used directly in the next reaction.

2-(R,S)-Benzyloxycarbonylamino-3-[4'-(1"-ethyloxysulfonyl-1"-methyl)ethyl)benzene]propanoic Acid To a solution of ethyl 1-methyl-1-(4-bromomethylphenyl)ethanesulfonate (0.64 g, 1.89 mol) and N-diphenylmethyleneglycine $^t$butyl ester (0.586 g. 1.98 mmol) in THF (6.5 mL) cooled on ice was added sodium bis(trimethylsilyl)amide (2M in THF, 1.04 mL). After 30 minutes the solvent was evaporated, the residue was taken up in acetic acid (2 mL), water (2 mL) and methanol (4 mL), and stirred at rt for 4 hours. The methanol was evaporated, water was added, and the mixture was washed with hexane/ether 1/1 (2×20 mL). The organic phase was washed with water. The combined aqueous phase was cooled on ice, and adjusted to pH 7 with sodium bicarbonate. Dioxane was added followed by benzyl chloroformate (0.38 mL, 2.65 mmol) and the mixture was stirred coming to rt overnight. Water was added, and the mixture was acidified to pH 3 with 1N H$_2$SO$_4$. The mixture was extracted with ethyl acetate, and the organic phase was dried, filtered and evaporated. Chromatography of the residue over silica gel (10% to 20% ethyl acetate/hexane) gave crude 2-(R,S)-benzyloxycarbonylamino-3-[4'-(1"-ethyloxysulfonyl-1"-methyl)ethyl)benzene]propanoic acid $^t$butyl ester (0.645 g, 68%). To a solution of the crude ester in methylene chloride (9 mL) cooled on ice was added trifluoroacetic acid (1.5 mL). The mixture was stirred for 4 hours, warming to rt. The reaction was quenched with cold aqueous sodium bicarbonate, and extracted with methylene chloride. The solvent was evaporated, and chromatography of the residue over silica gel (methylene chloride to 10% methanol/methylene chloride) gave 2-(R,S)-benzyloxycarbonylamino-3-[4'-(1"-ethyloxysulfonyl-1"-methyl)ethyl)benzene]propanoic acid (0.396 g, 0.88 mmol, 69%).

Synthesis of Aminopyridone Fragments
3-Amino-1-(4-methoxybenzyl)-4-methyl-2-pyridone.

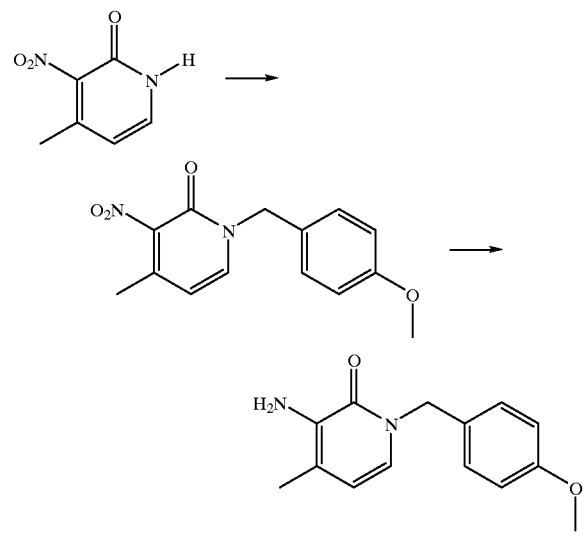

1-(4-Methoxybenzyl)-4-methyl-3-nitro-2-pyridone.

To a stirred suspension of 4-methyl-3-nitro-2-pyridone (2.0 g, 3 mmol) in DMF (60 mL) was added NaH (60% suspension in oil, 0.52 g). After 1 hour, 4-methoxybenzyl chloride (1.8 mL) was added, and the mixture was stirred at rt overnight. Ethyl acetate was added, and the organic phase was washed with water, dried, filtered and evaporated. Chromatography of the residue over silica gel (ethyl acetate/hexane) gave 1-(4-methoxybenzyl)-4-methyl-3-nitro-2-pyridone (2.0 g, 7.3 mmol, 56%).

3-amino-1-(4-methoxybenzyl)-4-methyl-2-pyridone.

A mixture of 1-(4-methoxybenzyl)-4-methyl-3-nitro-2-pyridone (1.5 g, 5.5 mmol) and 10% Pd/C (0.15 g) in ethanol (150 mL) was hydrogenated at 40 psi in a Parr apparatus for 5.5 hours. The catalyst was removed by filtration, and the solvent was evaporated to give 3-amino-1-(4-methoxybenzyl)-4-methyl-2-pyridone (1.3 g, 5.3 mmol, 96%).

The following aminopyridone fragments were prepared in an analogous manner:

For compound 53, 3-amino-4-methyl-1-(4-trifluoromethoxybenzyl)-2-pyridone;
For compounds 54, 96, 100 and 101, 3-amino-1-(4-isopropylbenzyl)-4-methyl-2-pyridone;
For compound 55, 3-amino-1-(4-chlorobenzyl)-4-methyl-2-pyridone;
For compound 56, 3-amino-1-(4-methylbenzyl)-4-methyl-2-pyridone;
For compound 149, 3-amino-1-(4-methoxy-3-methylbenzyl)-4-methyl-2-pyridone;
For compound 150, 3-amino-1-(4-ethylbenzyl)-4-methyl-2-pyridone;
For compound 153, 3-amino-1-(4-methoxy-2,3,5,6-tetrafluorobenzyl)-4-methyl-2-pyridone;
For compounds 154 and 155, 3-amino-1-(3,4-methylenedioxybenzyl)-4-methyl-2-pyridone;
For compound 156, 3-amino-1-(2-phenoxybenzyl)-4-methyl-2-pyridone;
For compounds 160 and 232, 3-amino-1-(4-methoxy-3-'butoxycarbonyloxybenzyl)-4-methyl-2-pyridone;
For compound 51, 3-amino-1-(4-isopropyloxybenzyl)-4-methyl-2-pyridone;
For compounds 135, 139, 140 and 141, 3-amino-1-(4-ethoxybenzyl)-4-methyl-2-pyridone;
For compounds 145 and 146, 3-amino-1-(5-methylhexyl)-4-methyl-2-pyridone;
For compounds 143 and 144, 3-amino-1-(methoxyethoxyethyl)-4-methyl-2-pyridone;
For compounds 188, 189 and 190, 3-amino-1-(methoxyethoxymethyl)-4-methyl-2-pyridone;
For compounds 236 and 237, 3-amino-1-(4-methoxybutyl)-4-methyl-2-pyridone;
For compounds 69, 70, 191, 192 and 193, 3-amino-1-pentyl-4-methyl-2-pyridone;
For compounds 81, 82, 83, 178 and 184, 3-amino-1-((x-methylbenzyl)-4-methyl-2-pyridone;
For compounds 137, 142, 204, 205, 206, 207, 208 and 209, 3-amino-1-hexyl-4-methyl-2-pyridone;
For compound 138, 3-amino-1-heptyl-4-methyl-2-pyridone;
For compound 179, 3-amino-1-(4-methylbutyl)-4-methyl-2-pyridone;
For compound 183, 3-amino-1-(4-methylpentyl)-4-methyl-2-pyridone;
For compounds 199 and 200, 3-amino-1-(4-phenylethyl)-4-methyl-2-pyridone;
For compound 182, 3-amino-1-(4-phenylpropyl)-4-methyl-2-pyridone;
For compounds 213, 214 and 215, 3-amino-1-(1-phenylcyclopropylmethyl)-4-methyl-2-pyridone;
For compound 91, 3-amino-1-(4-methoxybenzyl)-4,6-dimethyl-2-pyridone;
For compound 12, 3-amino-1-(cyclohexylbut-2-enyl)-4-methyl-2-pyridone;
For compounds 67, 68, 194, 195 and 196, 3-amino-1-(cyclohexylmethyl)-4-methyl-2-pyridone;
For compounds 18, 197 and 198, 3-amino-1-benzyl-4-methyl-2-pyridone;
For compound 19, 3-amino-1-(2-methoxybenzyl)-4-methyl-2-pyridone;
For compound 20, 3-amino-1-(3-methoxybenzyl)-4-methyl-2-pyridone;
For compound 21, 3-amino-1-phenethyl-4-methyl-2-pyridone;
For compound 23, 3-amino-1-(2-pyridyl)-4-methyl-2-pyridone,
For compounds 93 and 219,3-amino-1-(4-methoxybenzyl)-4,6-dimethyl-2-pyridone.

3-Amino-1-(3-furanylmethyl)-4-methyl-2-pyridone and 3-amino-1-(3-tetrahydrofuranylmethyl)-4-methyl-2-pyridone (for compounds 201, 202, 203, 210, 211 and 212).

A mixture of 1-(3-furanylmethyl)-4-methyl-3-nitro-2-pyridone (0.362 g) and 10% Pd/C (0.082 g) in ethanol (15 mL) was hydrogenated at 40 psi in a Parr apparatus for 5 hours. The catalyst was removed by filtration, and the solvent was evaporated to give a mixture of 3-amino-1-(3-furanylmethyl)-4-methyl-2-pyridone and 3-amino-1-(3-tetrahydrofuranylmethyl)-4-methyl-2-pyridone (ratio approx 1:3, 0.294 g).

3-Amino-1-(4-methoxybenzyl)-4-ethyl-2-pyridone (For Compound 92)

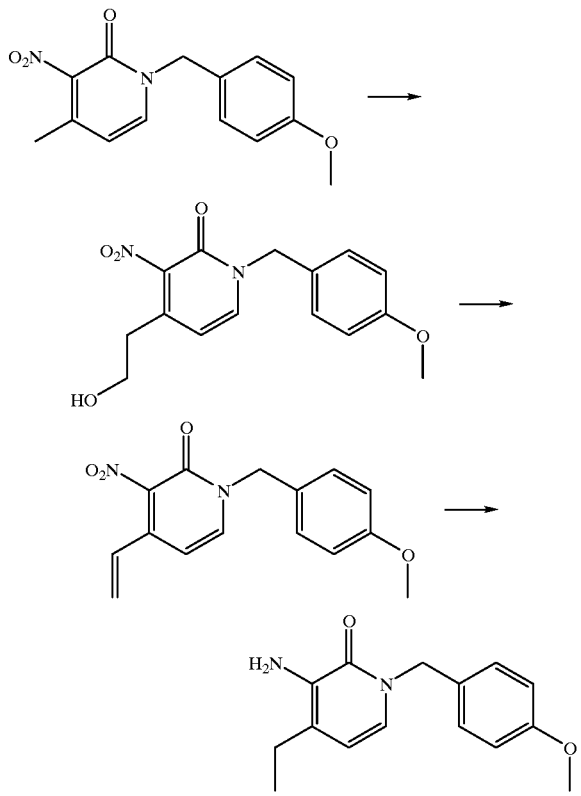

1-(4-Methoxybenzyl)-4-hydroxyethyl-3-nitro-2-pyridone.

To a stirred mixture of 1-(4-methoxybenzyl)-4-methyl-3-nitro-2-pyridone (1.38 g, 5.0 mmol) and paraformaldehyde (0.152 g) in dimethylsulfoxide (8 mL) was added sodium methoxide (0.018 g). After 2 hours, the mixture was diluted with ethyl acetate and washed with water. The aqueous phase was extracted with ethyl acetate, and the combined organic phase was dried, filtered and evaporated. The residual solid was triturated with chloroform/ethyl acetate (10 mL, 1/1) and 1-(4-methoxybenzyl)-4-hydroxyethyl-3-nitro-2-pyridone was collected by filtration (0.496 g). Fractionation of the supernatant over silica gel (chloroform/ethyl acetate to ethyl acetate/methanol 99/1) gave additional product (0.404 g) (total yield, 2.96 mmol, 59%).

1-(4-Methoxybenzyl)-4-vinyl-3-nitro-2-pyridone.

To a solution of 1-(4-methoxybenzyl)-4-hydroxyethyl-3-nitro-2-pyridone (0.35 g, 1.2 mmol) in pyridine (4 mL) was added benzenesulfonyl chloride (0.2 mL). After 4 days, the mixture was diluted with ethyl acetate, and washed with dilute hydrochloric acid. The aqueous phase was basified to pH 13 with aqueous KOH, and after 30 minutes was extracted with ethyl acetate. The organic phase was dried, filtered and evaporated to give 1-(4-methoxybenzyl)-4-vinyl-3-nitro-2-pyridone (0.29 g, 1.0 mmol, 83%).

3-Amino-1-(4-methoxybenzyl)-4-ethyl-2-pyridone.

A mixture of 1-(4-methoxybenzyl)-4-vinyl-3-nitro-2-pyridone (0.21 g, 0.73 mmol) in ethanol (30 mL) with 10% Pd/C (0.26 g) was hydrogenated at 40 psi in a Parr apparatus for 4 hours. The catalyst was removed by filtration and the solvent was evaporated to give 3-amino-1-(4-methoxybenzyl)-4-ethyl-2-pyridone (0.17 g, 0.56 mmol, 76%).

3-Amino-1-(4-methoxybenzyl)-4-(2'-tetrahydropyranyloxy) ethyl-2-pyridone (For Compound 223).

1-(4-methoxybenzyl)-4-(2'-tetrahydropyranyloxy)ethyl-3-nitro-2-pyridone.

To a stirred solution of 1-(4-methoxybenzyl)-4-hydroxyethyl-3-nitro-2-pyridone (0.26 g, 0.85 mmol) in methylene chloride (7 mL) was added dihydropyran (0.4 mL) and p-toluenesulfonic acid (0.002 g). After 2 hours the mixture was washed with water, dried, filtered and evaporated. Chromatography of the residue over silica gel (ethyl acetate/hexane 1/1) gave 1-(4-methoxybenzyl)-4-(2'-tetrahydropyranyloxy)ethyl-3-nitro-2-pyridone (0.32 g, 96%).

3-Amino-1-(4-methoxybenzyl)-4-(2'-tetrahydropyranyloxy) ethyl-2-pyridone.

A mixture of 1-(4-methoxybenzyl)-4-(2'-tetrahydropyranyloxy)ethyl-3-nitro-2-pyridone (0.32 g, 0.82 mmol) and 10% Pd/C (0.035 g) in ethanol (50 mL) was hydrogenated at 40 psi in a Parr apparatus for 5 hours. The catalyst was removed by filtration, and the solvent was evaporated to give 3-amino-1-(4-methoxybenzyl)-4-(2'-tetrahydropyranyloxy)ethyl-2-pyridone (0.27 g, 92%).

3-Amino-1-(4-methoxybenzyl)-5-bromo-4-methyl-2-pyridone (For Compound 220).

5-Bromo-4-methyl-3-nitro-2-pyridone.

To a stirred solution of 4-methyl-3-nitro-2-pyridone (0.45 g, 2.9 mmol) in glacial acetic acid (3 mL) was added sodium acetate (0.24 g) followed by bromine (0.15 mL) dropwise. After 5.5 hours, the mixture was diluted with ethyl acetate, washed with water, dried, filtered and concentrated to give 5-bromo-4-methyl-3-nitro-2-pyridone (0.62 g, 2.6 mmol, 90%).

1-(4-Methoxybenzyl)-5-bromo-4-methyl-3-nitro-2-pyridone.

To a stirred solution of 5-bromo-4-methyl-3-nitro-2-pyridone (0.60 g, 2.5 mmol) in DMF (15 mL) was added sodium hydride (60% suspension in oil, 0.103 g). After 30 minutes, 4-methoxybenzyl chloride (0.35 mL) was added, and the mixture was stirred overnight at rt. Ethyl acetate was added and the organic phase was washed with water, dried ($Na_2SO_4$), filtered and evaporated. Chromatography of the residue over silica gel (ethyl acetate/hexane 1/1) gave 1-(4-methoxybenzyl)-S-bromo-4-methyl-3'-nitro-2-pyridone (0.60 g, 1.7 mmol, 68%).

3-Amino-1-(4-methoxybenzyl)-5-bromo-4-methyl-2-pyridone.

To a stirred solution of 1-(4-methoxybenzyl)-5-bromo-4-methyl-3-nitro-2-pyridone (0.23 g 0.65 mmol) in glacial acetic acid (3 mL) was added a solution of stannous chloride dihydrate (1.0 g) in concentrated HCl (2 mL). After 3.5 hours, the reaction mixture was diluted with water, neutralized with $NaHCO_3$, and extracted with methylene chloride. The organic phase was dried, filtered, and evaporated to give 1-(4-methoxybenzyl)-5-bromo-4-methyl-3-amino-2-pyridone (0.13 g, 0.40 mmol, 61%).

3-Amino-1-(hexyl)-5-bromo-4-methyl-2-pyridone (For Compound 238) was synthesized in an analogous manner.

3-Amino-5-ethyl-4-methyl-2-pyridone (For Compound 222).

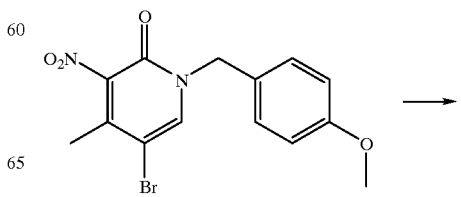

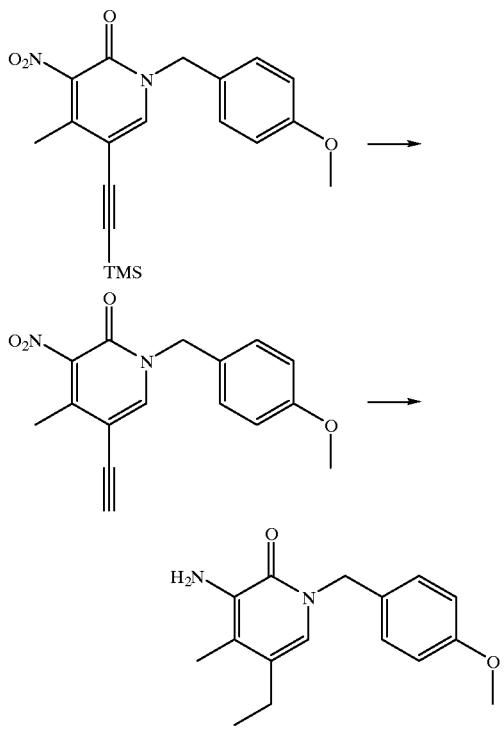

5-Trimethylsilylethynyl-4-methyl-3-nitro-2-pyridone.

A mixture of 5-bromo-4-methyl-3-nitro-2-pyridone (1.0 g, 2.8 mmol), trimethylsilylacetylene (1.2 mL, 8.5 mmol), bis(triphenylphosphine)Pd(II) chloride (0.100 g) and cuprous iodide (0.025 g) in DMF (4 mL) and triethylamine (2 mL) was heated at 90° C. in a sealed tube for 7 hours. Ethyl acetate was added, and the mixture was washed with water, dried, filtered and evaporated. Chromatography of the residue over silica gel (40% ethyl acetate/hexane) gave 5-trimethylsilylethynyl-4-methyl-3-nitro-2-pyridone (1.0 g, 2.7 mmol, 96%)

5-Ethynyl-4-methyl-3-nitro-2-pyridone.

To a stirred solution of 5-trimethylsilylethynyl-4-methyl-3-nitro-2-pyridone (1.0 g, 2.7 mmol) in THF (10 mL) was added tetrabutylammoniun fluoride (1M in THF, 2 mL). After 30 minutes the mixture was diluted with ethyl acetate, washed with water, dried, filtered and evaporated. Chromatography of the residue over silica gel (40% ethyl acetate/hexane) gave 5-ethynyl-4-methyl-3'-nitro-2-pyridone (0.18 g, 22%).

3-Amino-5-ethyl-4-methyl-2-pyridone.

A mixture of 5-ethynyl-4-methyl-3-nitro-2-pyridone (0.18 g, 0.6 mmol) and 10% Pd/C (0.02 g) in ethanol/ethyl acetate (50 mL, 1/1) was hydrogenated at 35 psi in a Parr apparatus overnight. The catalyst was removed by filtration, and the solvents were evaporated to give 3-amino-5-ethyl-4-methyl-2-pyridone.

3-Amino-1-(4-methoxybenzyl)-5-iodo-4-methyl-2-pyridone (for compound 229). 5-Iodo-4-methyl-3-nitro-2-pyridone.

To a solution of 4-methyl-3-nitro-2-pyridone (2.00 g, 13 mmol) in acetic acid (12 mL) and concentrated sulfuric acid (1.6 mL) was added iodine (1.32 g) and sodium iodate (0.55 g). The mixture was heated at 75° C. for 2.5 hours and then stirred at rt overnight. Water (100 mL) was added, and the precipitated 5-iodo-4-methyl-3-nitro-2-pyridone was collected by filtration (2.97 g, 82%).

1-(4-Methoxybenzyl)-5-iodo-4-methyl-3-nitro-2-pyridone.

A mixture of 5-iodo-4-methyl-3-nitro-2-pyridone (2.90 g, 10.4 mmol) and sodium hydride (60% in oil, 0.44 g, 11 mmol) was stirred at rt for 2.5 hours. 4-Methoxybenzyl chloride (1.50 mL) was added, and the mixture was stirred at rt for 18 h. Water was added, and the mixture and extracted with ethyl acetate. The organic phase was washed, dried and evaporated. Chromatography of the residue over silica gel (35% ethyl acetate/petroleum ether) followed by crystallization from water gave 1-(4-methoxybenzyl)-5-iodo-4-methyl-3-nitro-2-pyridone (3.11 g, 75%).

3-Amino-1-(4-methoxybenzyl)-5-iodo-4-methyl-2-pyridone.

To a stirred solution of 1-(4-methoxybenzyl)-5-iodo-4-methyl-3-nitro-2-pyridone (1.00 g, 2.5 mmol) in acetic acid (12 mL), cooled on ice, was added a solution of stannous chloride dihydrate (2.85 g, 12.6 mmol) in concentrated HCl (8 mL). After 1 hour the mixture was filtered, and the filtrate was neutralized with solid sodium carbonate (adding water as necessary). The mixture was extracted with methylene chloride, and the organic phase was washed, dried, and evaporated to give 3-amino-1-(4-methoxybenzyl)-5-iodo-4-methyl-2-pyridone (0.265 g, 29%) as an oil.

3-Amino-1-hexyl-5-phenyl-4-methyl-2-pyridone (For Compound 231).

1-Hexyl-5-iodo-4-methyl-3-nitro-2-pyridone.

A mixture of 5-iodo-4-methyl-3-nitro-2-pyridone (8.0 g. 28.6 mmol) and sodium hydride (1.03 g, 43 mmol) in DMF (150 mL) was stirred at rt for 1 hour. n-Hexyl bromide (8.03 mL, 57.2 mmol) was added, and the mixture was stirred for 24 hours. Water was added, and the mixture was extracted with ethyl acetate. The organic phase was washed, dried, filtered and evaporated. Chromatography of a portion of the residue over silica gel (20% petroleum ether/methylene chloride) gave 1-hexyl-5-iodo-4-methyl-3-nitro-2-pyridone.

1-Hexyl-4-methyl-3-nitro-5-phenyl-2-pyridone.

A mixture of bis(triphenylphosphine)Pd(II) chloride (0.014 g), lithium chloride (0.067 g), 1-hexyl-5-iodo-4-methyl-3-nitro-2-pyridone (0.15 g, 0.41 mmol) and phenyl-tributyltin (0.11 mL, 0.62 mmol) in THF (15 mL) was heated under reflux for 2 days. The mixture was cooled, diluted with ethyl acetate, and washed with aqueous potassium fluoride and water. The organic phase was dried, filtered and evaporated. Chromatography of the residue over silica gel (petroleum ether/methylene chloride 1/1 to methylene chloride gradient) gave 1-hexyl-4-methyl-3'-nitro-5-phenyl-2-pyridone (0.093 g, 72%).

3-Amino-1-hexyl-4-methyl-5-phenyl-2-pyridone.

A mixture of 1-hexyl-4-methyl-3-nitro-5-phenyl-2-pyridone (0.093 g, 0.30 mmol) and 10% Pd/C in ethyl acetate (100 mL) was hydrogenated at 45 psi in a Parr apparatus for 4 hours. The catalyst was removed by filtration, and the solvent was evaporated to give 3-amino-1-hexyl-4-methyl-5-phenyl-2-pyridone (0.083 g, 97%).

3-Amino-1-hexyl-4-methyl-5-methoxycarbonyl-2-pyridone (for compounds 240 and 121).

1-Hexyl-4-methyl-3-nitro-5-methoxycarbonyl-2-pyridone.

A mixture of 1-hexyl-5-iodo-4-methyl-3-nitro-2-pyridone (0.500 g, 1.37 mmol), tris(dibenzylideneacetone) dipalladium (0.003 g), diphenylphosphinoferrocene (0.154 g) and potassium acetate (0.565 g) in DMSO (10 mL) and methanol (10 mL) was stirred and heated at 60° C. under an atmosphere of carbon monoxide for 4 hours. The mixture was diluted with ethyl acetate, washed with aqueous sodium bicarbonate, dried (MgSO$_4$), filtered, and evaporated. Chromatography of the residue over silica gel (30% ethyl acetate/petroleum ether) gave 1-hexyl-4-methyl-3-nitro-5-methoxycarbonyl-2-pyridone (0.305 g, 75%).

3-Amino-1-hexyl-4-methyl-5-methoxycarbonyl-2-pyridone.

A mixture of 1-hexyl-4-methyl-3-nitro-5-methoxycarbonyl-2-pyridone (0.145 g, 0.49 mmol) and a catalytic amount of 10% Pd/C in ethyl acetate (100 mL) was hydrogenated at 45 psi in a Parr apparatus for 5 hours. The catalyst was removed by filtration and the solvent was evaporated to give 3-amino-1-hexyl-4-methyl-5-methoxycarbonyl-2-pyridone (0.133 g, 100%).

Cis and trans, 3-amino-1-(4-methoxycyclohexylmethyl)-4-methyl-2-pyridone (For Compounds 147, 148, 235 and 239).

4-Methoxycyclohexylmethylbromide.

To a stirred solution of 4-methoxycyclohexylmethanol (mixture of cis and trans) (1.8 g, 12 mmol) in acetonitrile (90 mL) and pyridine (1.29 g) cooled on ice was added dibromotriphenylphosphorane (6.3 g, 15 mmol). The mixture was allowed to warm to rt, and stirred for 2 days. The mixture was washed through a short pad of silica gel, and concentrated. The residue was taken up in ethyl acetate, washed with 2N HCl and water, dried, and evaporated. The residue was treated with hexane, and the solid was removed by filtration. Concentration of the filtrate gave 4-methoxycyclohexylmethylbromide as an oil (1.6 g, 61%. mixture of cis and trans isomers).

Cis and trans, 3-nitro-1-(4-methoxycyclohexylmethyl)-4-methyl-2-pyridone.

A mixture of 4-methyl-3-nitro-2-pyridone (0.93 g, 6.0 mmol) and sodium hydride (60% in oil, 0.25 g, 6.3 mmol) in DMF (20 mL) was stirred at rt for 1 hour. 4-Methoxycyclohexylmethylbromide (1.5 g, 7.2 mmol) in DMF (5 mL) was added. After 60 hours, the mixture was diluted with water, and extracted with ethyl acetate. The organic phase was washed, dried (MgSO$_4$), and evaporated. Chromatography of the residue over silica gel (ethyl acetate/hexane 1/1 to 3/1) gave cis-3-nitro-1-(4-methoxycyclohexylmethyl)-4-methyl-2-pyridone which crystallized from ethyl acetate/hexane (0.16 g, 10%) and trans-3-nitro-1-(4-methoxycyclohexylmethyl)-4-methyl-2-pyridone which crystallized from ethyl acetate/hexane (0.18 g, 11%).

Cis-3-amino-1-(4-methoxycyclohexylmethyl)-4-methyl-2-pyridone.

A mixture of cis-3-nitro-1-(4-methoxycyclohexylmethyl)-4-methyl-2-pyridone (0.16 g, 0.57 mmol) and 10% Pd/C (0.06 g) in ethanol was hydrogenated at 50 psi in a Parr apparatus for 22 hours. The catalyst was removed by filtration, and the solvent was evaporated to give cis-3-amino-1-(4-methoxycyclohexylmethyl)-4-methyl-2-pyridone (0.13 g, 0.52 mmol, 91%).

Trans-3-amino-1-(4-methoxycyclohexylmethyl)-4-methyl-2-pyridone was obtained in an analogous manner.

4-Amino-2-(4-methoxybenzyl)-5-methyl-3-pyridazinone (For Compound 242).

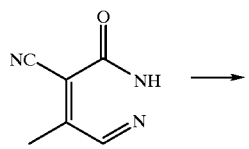

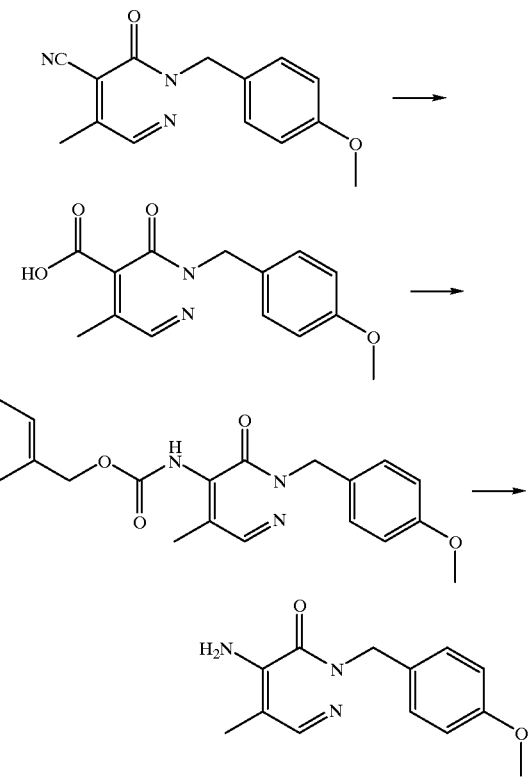

4-Cyano-2-(4-methoxybenzyl)-5-methyl-3-pyridazinone.

A mixture of 4-cyano-5-methyl-3-pyridazinone (P. Schmidt and J. Drucy, *Helvetica Chemica Acta*, 37, 1467 (1954)) (0.93 g, 6.9 mmol) and NaH (50% in oil, 0.344 g, 8.6 mmol) in DMF (15 mL) was stirred at rt for 1 hour. 4-Methoxybenzyl chloride (1.34 g, 8.6 mmol) was added, and the mixture was stirred for 16 hours. The mixture was diluted with water. and extracted with ethyl acetate. The organic phase was washed with water, dried, filtered and evaporated. Trituration of the residue with ethyl acetate gave 4-cyano-2-(4-methoxybenzyl)-5-methyl-3-pyridazinone (0.83 , 3.2 mmol, 46%).

4-Carboxy-2-(4-methoxybenzyl)-5-methyl-3-pyridazinone.

To a stirred suspension of 4-cyano-2-(4-methoxybenzyl)-5-methyl-3-pyridazinone (0.51 g, 2.0 mmol) in water was added 5N aqueous KOH (2.61 mL). The mixture was heated under reflux for 24 hours. The mixture was cooled, filtered, and acidified with 10% HCl. The solid 4-carboxy-2-(4-methoxybenzyl)-5-methyl-3-pyridazinone was collected by filtration (0.54 g, 2.0 mmol, 100%).

4-Benzyloxycarbonylamino-2-(4-methoxybenzyl)-5-methyl-3-pyridazinone.

To a stirred solution of 4-carboxy-2-(4-methoxybenzyl)-5-methyl-3-pyridazinone (0.50 g, 1.8 mmol) in benzene (20 mL) was added diphenylphosphoryl azide (0.63 g, 2.3 mmol) and triethylamine (0.76 mL, 5.5 mmol). The mixture was stirred at rt for 30 minutes, heated under reflux for 30 minutes, and cooled. Benzyl alcohol (0.24 g, 2.2 mmol) was added, and the mixture was heated under reflux for 17 hours. The mixture was cooled, washed with aqueous citric acid, water, aqueous sodium bicarbonate and brine, dried, filtered and evaporated. Chromatography of the residue over silica gel (15% to 25% ethyl acetate/hexane) gave 4-benzyloxycarbonylamino-2-(4-methoxybenzyl)-5-methyl-3-pyridazinone (0.39 g, 1.0 mmol, 56%).

4-Amino-2-(4-methoxybenzyl)-5-methyl-3-pyridazinone.

181

A mixture of 4-benzyloxycarbonylamino-2-(4-methoxybenzyl)-5-methyl-3-pyridazinone (0.39 g, 1.0 mmol) and 10% Pd/C (0.10 g) in ethanol (40 mL) and ethyl acetate (5 mL) was hydrogenated at 45 psi in a Parr apparatus for 1.3 hours. The catalyst was removed by filtration and the solvents were evaporated to give 4-amino-2-(4-methoxybenzyl)-5-methyl-3-pyridazinone (0.23 g) 1.0 mmol, 910%).

Synthesis of N-Terminus Fragments 2,2-Dimethyl-(4'-biphenyl)acetic Acid (For Compound 159).

4-Biphenylacetic Acid, Methyl Ester.

To a solution of 4-biphenylacetic acid (10 g, 47 mmol) in methanol (150 mL) was added concentrated HCl (3 mL). The mixture was heated under reflux for 16 hours, cooled to rt, and the solvent was evaporated. Chromatography of the residue over silica gel (petroleum ether followed by ethyl acetate/petroleum ether 1/4) gave 4-biphenylacetic acid methyl ester (10.4 g, 98%).

2,2-Dimethyl-(4-biphenyl)acetic Acid, Methyl Ester.

To a solution of 4-biphenylacetic acid methyl ester (10 g, 44 mmol) in THF (200 ml) was added sodium bis(trimethylsilyl)amide (1M in THF, 48 mL). The mixture was stirred at rt for 15 minutes, and iodomethane (2.9 mL) was added. After 15 minutes additional sodium bis(trimethylsilyl)amide (1M in THF, 48 mL) was added. After 15 minutes iodomethane (2.9 mL) was added, and the mixture was stirred at rt for 3 hours. Brine was added, and the mixture was extracted with two portions of ether. The combined organic phase was dried (MgSO$_4$), filtered, and evaporated to give 2,2-dimethyl-(4-biphenyl)acetic acid, methyl ester (10.9 g, 43 mmol, 98%).

2,2-Dimethyl-(4-biphenyl)acetic Acid.

A mixture of 2,2-dimethyl-(4-biphenyl)acetic acid, methyl ester (4.18 g, 16.5 mmol) and sodium hydroxide (3.29 g) in ethanol (57 mL) and water (25 mL) was heated under reflux for 18 hours. The mixture was cooled to rt and acidified to pH 2 with 6N HCl. The precipitate was collected by filtration and recrystallized from ether to give 2,2-dimethyl-(4-biphenyl)acetic acid (1.37 g 5.7 mmol, 35%).

2-(S)-Methyl-2-naphthylacetic Acid (For Compound 46).

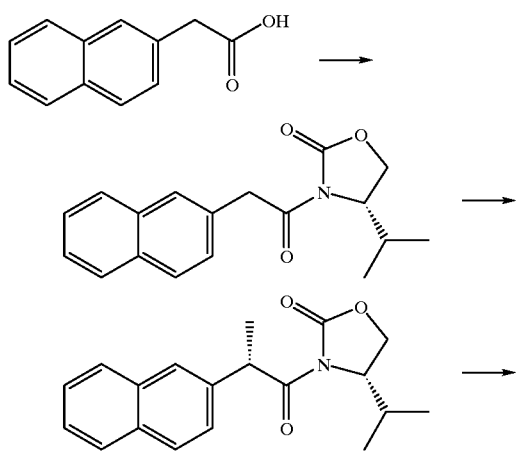

182

-continued

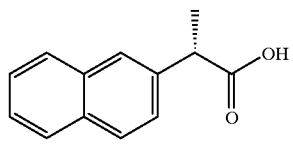

4-(S)-4-Isopropyl-3-(2-naphthylacetyl)-2-oxazolidinone.

To a stirred solution of 2-naphthylacetic acid (0.960 g, 5.15 mmol) in methylene chloride (10 mL) was added oxalyl chloride (0.58 mL, 6.7 mmol) and DMF (1 drop). After 1.5 hours, the solvent was evaporated to give 2-naphthylacetyl chloride. A solution of the 2-naphthylacetyl chloride in THF (3 ml), cooled to −78° C., was slowly cannulated into a stirred solution of the lithium salt of 4-(S)-(+)-4-isopropyl-2-oxazolidinone (prepared by treating, at −78° C., a solution of 4-(S)-(+)-4-isopropyl-2-oxazolidinone (0.60 g, 5.2 mmol) in THF (4 mL) with a solution of butyllithium (1.6 M in hexane) for 15 min). After 2 hours, 10% citric acid and ethyl acetate were added. The organic phase was washed with NaHCO$_3$ and brine, dried (MgSO$_4$), and concentrated. Flash column chromatography of the residue (15% ethyl acetate/hexanes) gave 4-(S)-4-isopropyl-3-(2-naphthylacetyl)-2-oxazolidinone as a slightly yellow oil (0.91 g, 60%).

4-(S)-4-isopropyl-3-(2-(S)-methyl-2-naphthylacetyl)-2-oxazolidinone.

4-(S)-4-isopropyl-3-($^2$-naphthylacetyl)-2-oxazolidinone (0.9 g, 3.0 mmol) in THF (5 mL) was added slowly to a cold (−78° C.) solution of lithium bis(trimethylsilyl)amide (1 M in THF, 3.34 mL). After 30 minutes, iodomethane (0.19 mL, 3.04 mmol) was added. The mixture was stirred at −78° C. for 30 minutes and at 0° C. for 2 hours. Acetic acid was added followed by ethyl acetate and water. The organic phase was washed with aqueous NaHCO$_3$ and brine, dried (MgSO$_4$), and concentrated. Flash column chromatography of the residue (10% ethyl acetate/hexane) gave 4-(S)-4-isopropyl-3-(2-(S)-methyl-2-naphthylacetyl)-2-oxazolidinone (0.25 g. 30%).

2-(S)-Methyl-2-naphthylacetic Acid.

To a stirred solution of 4-(S)-4-isopropyl-3-(2-(S)-methyl-2-naphthylacetyl)-2-oxazolidinone (0.25 g, 0.8 mmol) in THF (6 mL) and water (2 mL) at 0° C. was added LiOH.H$_2$O (0.067 g, 1.6 mmol). After 4 hours., Na$_2$SO$_4$ (0.64 g, 4.5 mmol) and water were added. The THF was evaporated and the aqueous phase was washed with methylene chloride. The aqueous phase was acidified with 1N HCl and extracted with ethyl acetate.

The organic phase was dried (MgSO$_4$), and concentrated to give 2-(S)-methyl-2-naphthylacetic acid as a slightly yellow solid (0.15 g, 95%).

2-(S)-Methyl-1-naphthylacetic A (For Compound 45) was prepared in an analogous manner using 1-naphthyl acetic acid as the starting material.

2-(S)-Methyl-1-naphthylacetic Acid (For Compound 44) was prepared in an analogous manner using 1-naphthyl acetic acid and (4R)-(-)-isopropyl-2-oxazolidinone as the starting materials.

2,2-Dimethyl-2-naphthylacetic Acid (For Compound 107).

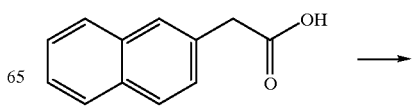

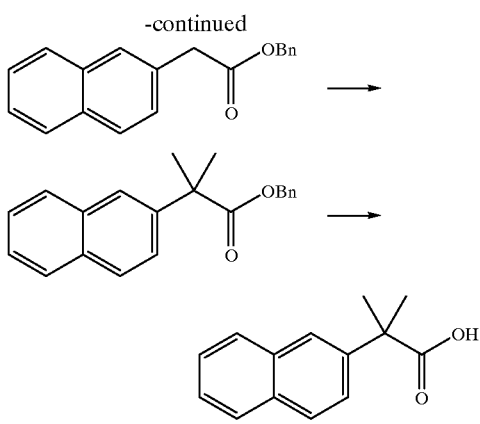

2-Naphthylacetic Acid Benzyl Ester.

To a stirred solution of 2-naphthylacetic acid (1 g, 5.4 mmol) in acetonitrile (10 mL) were added DBU (0.97 mL, 6.4 mmol) and benzyl bromide (0.77 mL, 6.4 mmol). After 3 hours the mixture was concentrated, and the residue was taken up in ethyl acetate. The organic phase was washed with 10% citric acid, 10% NaHCO$_3$ and brine, dried (MgSO$_4$), and concentrated to give 2-naphthylacetic acid benzyl ester as a white solid (1.5 g, 100%).

2,2-Dimethyl-(2-naphthyl)acetic Acid Benzyl Ester.

2-Naphthylacetic acid benzyl ester (0.750 g, 2.72 mmol) in THF (4 ml) was slowly added to a cold (0° C.) solution of sodium bis(trimethylsilyl)amide (1M in THF, 4.1 mL) and iodomethane (0.25 mL). After 30 minutes at rt, additional sodium bis(trimethylsilyl)amide (4.1 mL) and iodomethane (0.25 mL) were added. After 1 hour, ethyl acetate was added, and the mixture was washed with 10% citric acid, 10% NaHCO$_3$ and brine. The solvent was evaporated, and flash column chromatography of the residue (10% ethyl acetate/hexane) gave 2,2-dimethyl-(2-naphthyl)acetic acid benzyl ester as a colorless oil (0.46 g, 1.5 mmol, 55%).

2,2-Dimethyl-(2-naphthyl)acetic Acid.

A mixture of 2,2-dimethyl-(2-naphthyl)acetic acid benzyl ester (0.46 g, 1.5 mmol) and 10% Pd/C (0.040 g) in ethanol (5 mL) was hydrogenated at 1 atmosphere for 16 hours. The catalyst was removed by filtration, and the solvent was evaporated to give 2,2-dimethyl-(2-naphthyl)acetic acid (0.33 g, 1.5 mmol. 100%).

(4-Dimethylaminophenyl)-2,2-dimethylacetic Acid (For Compound 230).

Ethyl 4-nitrophenyl-2,2-dimethylacetate.

To a stirred solution of ethyl 4-nitrophenylacetate (7.50 g, 35.9 mmol) in THF (200 mL) was added sodium bis(trimethylsilyl)amide (1M in THF, 39 mL). After 15 minutes, iodomethane (2.35 mL) was added. After 30 minutes, additional sodium bis(trimethylsilyl)amide (39 mL) was added followed by iodomethane (2.35 mL). After 17 hours, the mixture was diluted with brine, and extracted with ether. The organic phase was dried, filtered and evaporated. Chromatography of the residue over silica gel (8% ethyl acetate/petroleum ether) gave ethyl (4-nitrophenyl)-2.2-dimethylacetate (3.3 g, 39%) as a colorless oil.

Ethyl (4-aminophenyl)-2,2-dimethylacetate.

A mixture of ethyl (4-nitrophenyl)-2,2-dimethylacetate (3.30 g, 13.9 mmol) and 10% Pd/C in methanol (40 mL) was hydrogenated in a Parr apparatus at 50 psi for 2 hours. The catalyst was removed by filtration, and the solvent was evaporated to give ethyl (4-aminophenyl)-2,2-dimethylacetate (2.63 g, 91%) as a colorless oil.

Ethyl (4-dimethylaminophenyl)-2,2-dimethylacetate.

To a solution of ethyl (4-aminophenyl)-2,2-dimethylacetate (1.00 g, 4.82 mmol) in THF (30 mL) was added sodium bis(trimethylsilyl)amide (1M in THF, 5 mL). After 15 minutes. iodomethane (0.33 mL) was added. After 2 hours, the mixture was diluted with water, and extracted with ethyl acetate. The organic phase was dried, filtered and evaporated. Chromatography of the residue over silica gel (5% ethyl acetate/petroleum ether) gave ethyl (4-dimethylaminophenyl)-2,2-dimethylacetate (1.05 g, 92%).

(4-Dimethylaminophenyl)-2,2-dimethylacetic Acid.

A mixture of ethyl (4-dimethylaminophenyl)-2,2-dimethylacetate (1.00 g, 4.25 mmol) and sodium hydroxide (0.85 g) in ethanol (20 mL) and water (9 mL) was heated under reflux for 18 hours. The mixture was cooled, acidified with 10% HCl, and washed with ethyl acetate. The aqueous phase was evaporated. The residue was dissolved in aqueous saturated sodium bicarbonate, and extracted with ethyl acetate. The organic phase was dried, filtered and evaporated to give (4-dimethylaminophenyl)-2,2-dimethylacetic acid as a faint red solid (0.81 g, 92%).

Representative Synthesis of Final Compounds
3-[2'-(S)-(2'''-Naphthylacetyl)amino-3'-(4''-carboxymethyl) benzene]propanoylamino-1-(4-methoxybenzyl)-4-methyl-2-pyridone (Compound 59).

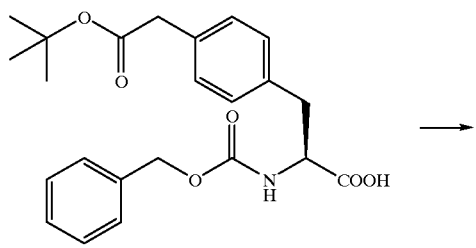

-continued

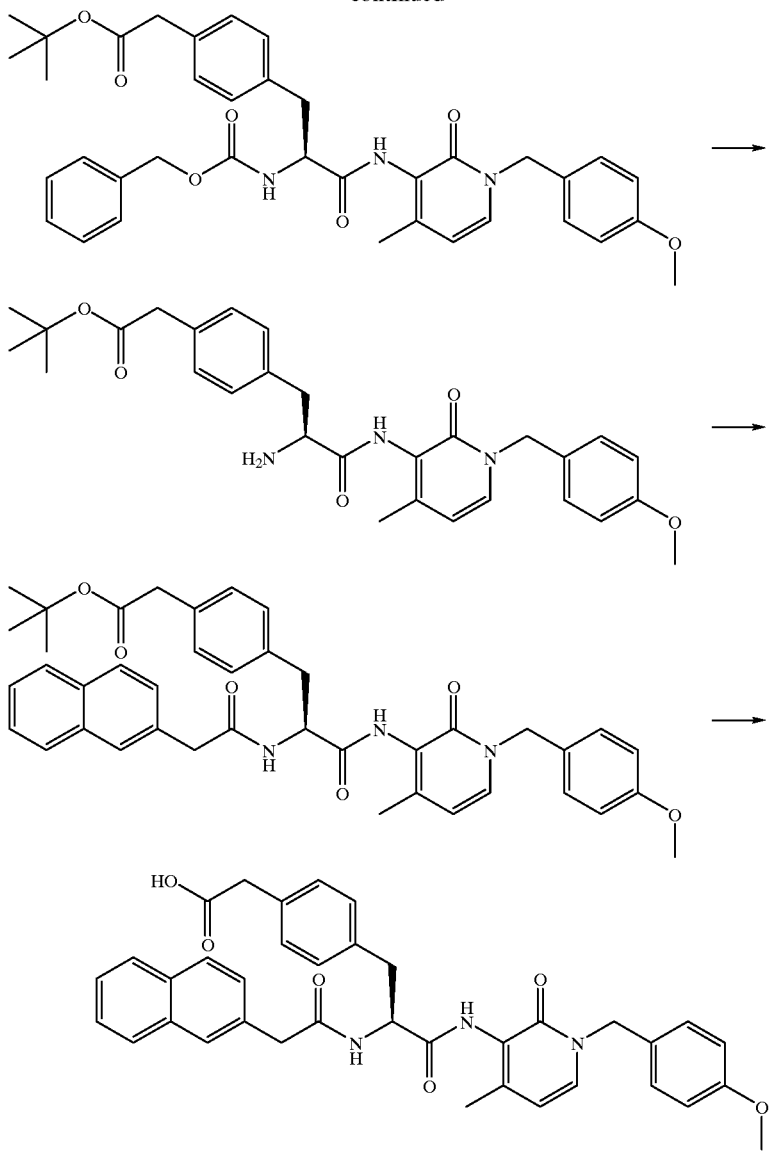

3-[2'-(S)-Benzyloxycarbonylamino-3'-(4"-ᵗbutoxycarbonylmethyl)benzene]propanoylamino-1-(4-methoxybenzyl)-4-methyl-2-pyridone.

A mixture of 2-(S)-benzyloxycarbonylamino-3-(4'-ᵗbutoxycarbonylmethyl)benzene]propanoic acid (0.412 g, 1.00 mmol) and EDC (0.211 g) in methylene chloride (10 mL) was stirred at 0° C. for 15 minutes. 3-Amino-1-(4-methoxybenzyl)-4-methyl-2-pyridone (0.244 g, 1.00 mmol) was added, and the mixture was stirred at it overnight. Chromatography of the mixture over silica gel (methylene chloride/ethyl acetate 3/2) gave 3-[2'-(S)-benzyloxycarbonylamino-3'-(4"-ᵗbutoxycarbonylmethyl)benzene]propanoylamino-1-(4-methoxybenzyl)-4-methyl-2-pyridone (0.441 g, 0.69 mmol, 69%).

3-[2'-(S)-Amino-3'-(4"-ᵗbutoxycarbonylmethyl)benzene]propanoylamino-1-(4-methoxybenzyl)-4-methyl-2-pyridone.

A mixture of 3-[2'-(S)-benzyloxycarbonylamino-3'-(4"-ᵗbutoxycarbonylmethyl)benzene]propanoylamino-1-(4-methoxybenzyl)-4-methyl-2-pyridone (0.441 g, 0.69 mmol), 10% Pd/C (0.146 g) and cyclohexene (1.4 mL) in ethanol (13 mL) was heated at 60–65° C. for 30 minutes. The catalyst was removed by filtration and the solvents were evaporated to give 3-[2'-(S)-amino-3'-(4"-ᵗbutoxycarbonylmethyl)benzene]propanoylamino-1-(4-methoxybenzyl)-4-methyl-2-pyridone (0.323 g, 0.65 mmol, 95%).

3-[2'-(S)-(2'"-Naphthylacetyl)amino-3'-(4"-ᵗbutoxycarbonylmethyl)benzene]propanoylamino-1-(4-methoxybenzyl)-4-methyl-2-pyridone.

3-[2'-(S)-Amino-3'-(4"-ᵗbutoxycarbonylmethyl)benzene]propanoylamino-1-(4-methoxybenzyl)-4-methyl-2-pyridone was coupled with 2-naphthylacetic acid using EDC as described above to give 3-[2'-(S)-(2"-naphthylacetyl)amino-3'-(4"-ᵗbutoxycarbonylmethyl)benzene]propanoylamino-1-(4-methoxybenzyl)-4-methyl-2-pyridone.

3-[2'-(S)-(2'"-Naphthylacetyl)amino-3'-(4"-carboxymethyl)benzene]propanoylamino-1-(4-methoxybenzyl)-4-methyl-2-pyridone.

187

A solution of 3-[2'-(S)-(2'''-naphthylacetyl)amino-3'-(4''-'butoxycarbonylmethyl)benzene]propanoylamino-1-(4-methoxybenzyl)-4-methyl-2-pyridone (0.036 g) in trifluoroacetic acid (1 mL) was stirred at rt for 1 hour. The solvent was removed and the residue was purified by HPLC to give 3-[2'-(S)-(2'''-naphthylacetyl)amino-3'-(4''-carboxymethyl)benzene]propanoylamino-1-(4-methoxybenzyl)-4-methyl-2-pyridone (0.0078 g).

188

Compounds 57, 58, 60, 61, 62, 63, 64, 67, 68, 69, 70, 71, 72, 73, 74, 75, 76, 77, 78, 79, 80, 81, 82, 83, 84, 85, 86, 87, 162, 163, 164, 165, 166, 167 and 168 were synthesized in an analogous manner.

3-[2'-(S)-(1'''-Naphthyl)acetlyamino-3'-(4''-carboxymethyl)benzene]propanoylamino-1-(4-trifluoromethoxybenzyl)-4-methyl-2-pyridone (Compound 53).

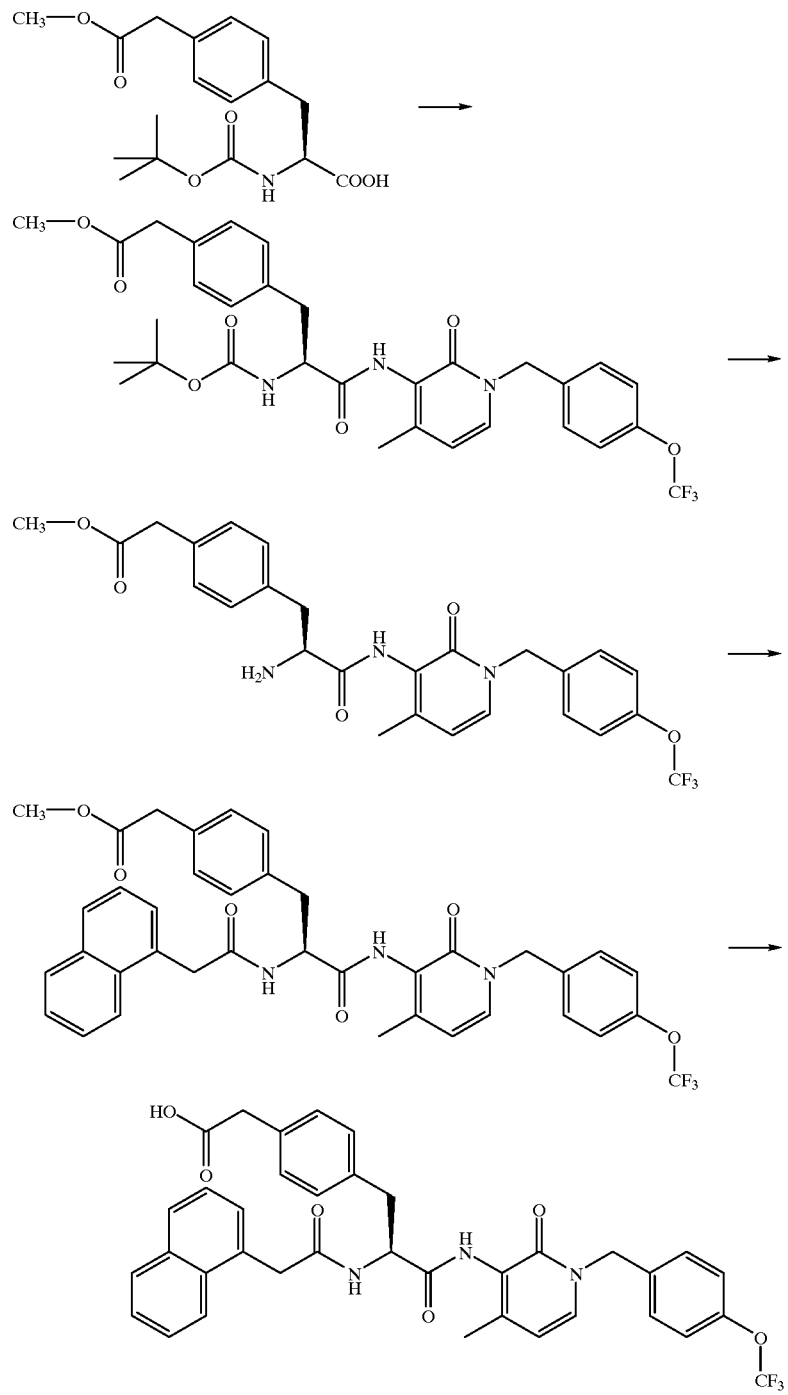

3-[2'-(S)-'Butoxycarbonylamino-3'-(4"-methoxycarbonylmethyl)benzene]propanoylamino-1-(4-trifluoromethoxybenzyl)-4-methyl-2-pyridone.

This compound was obtained by EDC coupling of 2-(S)-'butoxycarbonylamino-3-(4'-methoxycarbonylmethyl)benzene]propanoic acid with 3-amino-4-methyl-1-(4-trifluoromethoxybenzyl)-2-pyridone (42%).

3-[2'-(S)-(1'"-Naphthyl)acetylamino-3'-(4"-methoxycarbonylmethyl)benzene]propanoylamino-1-(4-trifluoromethoxybenzyl)-4-methyl-2-pyridone.

This compound was obtained from 3-[2'-(S)-'butoxycarbonylamino-3'-(4"-methoxycarbonylmethyl)benzene]propanoylamino-1-(4-trifluoromethoxybenzyl)-4-methyl-2-pyridone by standard removal of the 'butoxycarbonyl protecting group, followed by EDC coupling with 1-naphthylacetic acid (52% for the two steps).

3-[2'-(S)-(1'"-Naphthyl)acetylamino-3'-(4"-carboxymethyl)benzene]propanoylamino-1-(4-trifluoromethoxybenzyl)-4-methyl-2-pyridone.

To a solution of 3-[2'-(S)-(1'"-naphthyl)acetylamino-3'-(4"-methoxycarbonylmethyl)benzene]propanoylamino-1-(4-trifluoromethoxybenzyl)-4-methyl-2-pyridone (0.024 g, 0.035 mmol) in methanol (0.5 mL) was added aqueous NaOH (1M, 0.05 mL). The mixture was stirred at rt for 3 hours, acidified with a slight excess of 1N HCl, and evaporated to a small volume. The precipitate was filtered, washed with water, and redissolved in ethyl acetate. The organic phase was dried (MgSO₄), and evaporated. The residue was triturated with ether, methanol, ethyl acetate and methylene chloride. The residue was recrystallized from warm ethyl acetate to give 3-[2'-(S)-(1'"-naphthylacetyl)amino-3'-(4"-carboxymethyl)benzene]propanoylamino-1-(4-trifluoromethoxybenzyl)-4-methyl-2-pyridone (0.017 g, 45%).

Compounds 54, 55 and 56 were obtained in an analogous manner.

3-[2'-(S)-(1'"-Naphthylacetyl)amino-3'-(4"-carboxymethyl)benzene]propanoylamino-1-(4-methoxybenzyl-4-methyl-2-pyridone (Compound 88).

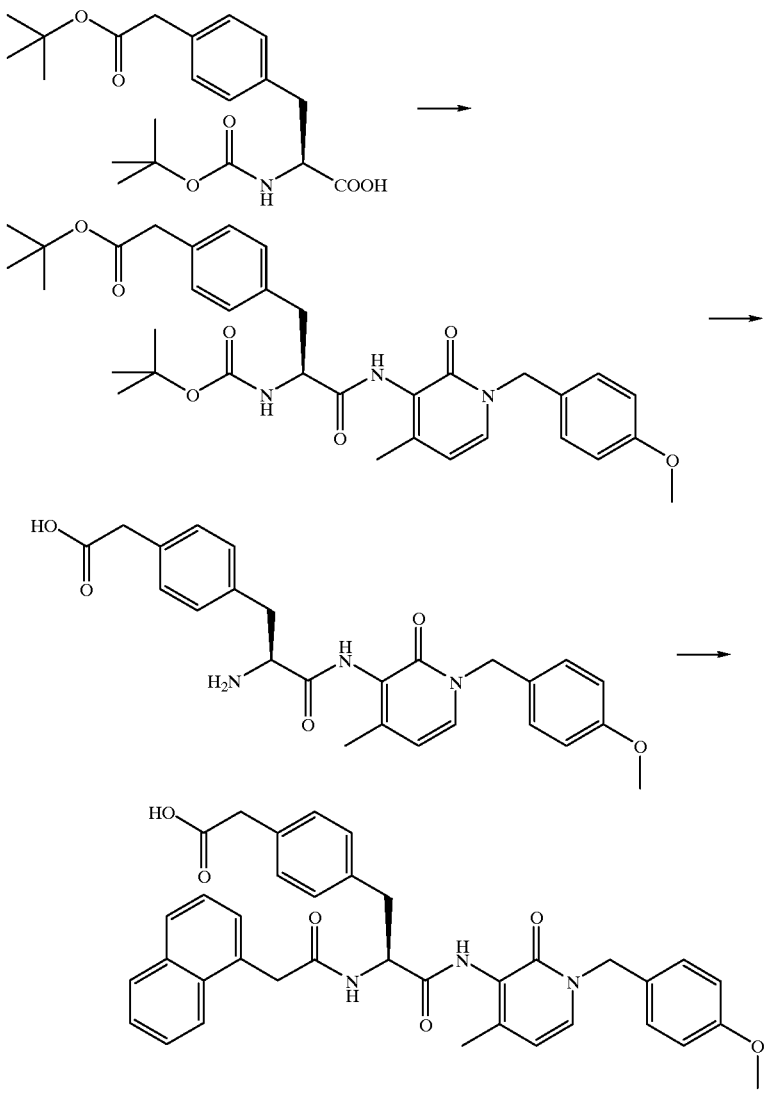

3-[2'-(S)-ᵗButoxycarbonylamino-3'-(4"-ᵗbutoxycarbonylmethyl)benzene]propanoylamino-1-(4-methoxybenzyl)-4-methyl-2-pyridone.

To a stirred solution of 2-(S)-ᵗbutoxycarbonylamino-3-(4'-ᵗbutoxycarbonylmethylbenzene)propanoic acid (0.388 g, 1.02 mmol) in methylene chloride (3 mL) at 0° C. under nitrogen was added EDC (0.211 g). After 15 minutes, 1-(4-methoxybenzyl)-4-methyl-3-amino-2-pyridone (0.250 g, 1.02 mmol) in methylene chloride (2 mL.) was added. The mixture was stirred at 0° C. for 1 hour, and at rt overnight. Dimethylaminopyridine (0.002 g) was added and stirring was continued for 2 hours. The mixture was diluted with methylene chloride, washed with water, dried (Na₂SO₄), filtered and evaporated. Chromatography of the residue over silica gel (ethyl acetate/hexane 1/1) gave 3'-[2'-(S)-ᵗbutoxycarbonylamino-'-(4"-ᵗbutoxycarbonylmethyl)benzene]propanoylamino-1-(4-methoxy)benzyl-4-methyl-2-pyridone (0.45 g, 0.74 mmol, 73%).

3-[2'-(S)-(1'''-Naphthylacetyl)amino-3'-(4"-carboxymethyl)benzene]propanoylamino-1-(4-methoxy)benzyl-4-methyl-2-pyridone.

A solution of 3-[2'-(S)-ᵗbutoxycarbonylamino-3'-(4"-ᵗbutoxycarbonylmethyl)benzene]propanoylamino-1-(4-methoxybenzyl)-4-methyl-2-pyridone (0.45 g, 0.74 mmol) in methylene chloride (10 mL) and trifluoroacetic acid (1 mL) was stirred at rt for 2 hours. The solvents were evaporated. The residue was taken up in ether/hexane 1/1 and evaporated to dryness to give the trifluoroacetate salt of 3-[2'-(S)-amino-3'-(4"-carboxymethyl)benzene]propanoylamino-1-(4-methoxybenzyl)-4-methyl-2-pyridone (0.33 g). To this salt (0.10 g) in methylene chloride (5 mL) was added diisopropylethylamine to adjust the pH to ≈pH 7. The mixture was cooled to 0° C., and 1-naphthylacetyl chloride (0.050 g) in methylene chloride (5 mL) was added. The mixture was stirred at 0° C. for 1 hour, allowed to warm to rt, and stirred at rt for 2 hours. The solvent was evaporated, and the residue was purified by chromatography over silica gel followed by preparative layer chromatography to give 3-[2'-(S)-(1'''-naphthylacetyl)amino-3'-(4"-carboxymethyl)benzene]propanoylamino-1-(4-methoxybenzyl)-4-methyl-2-pyridone (0.03 g, 0.05 mmol, 7%).

Compounds 89 and 243 were prepared in an analogous manner.

3-[2'-(S)-(1'''-Naphthylacetyl)amino-3'-(4"-carboxymethyl)benzene]propanoylamino-1-(4-methoxy)benzyl-4-ethyl-2-pyridone (Compound 92).

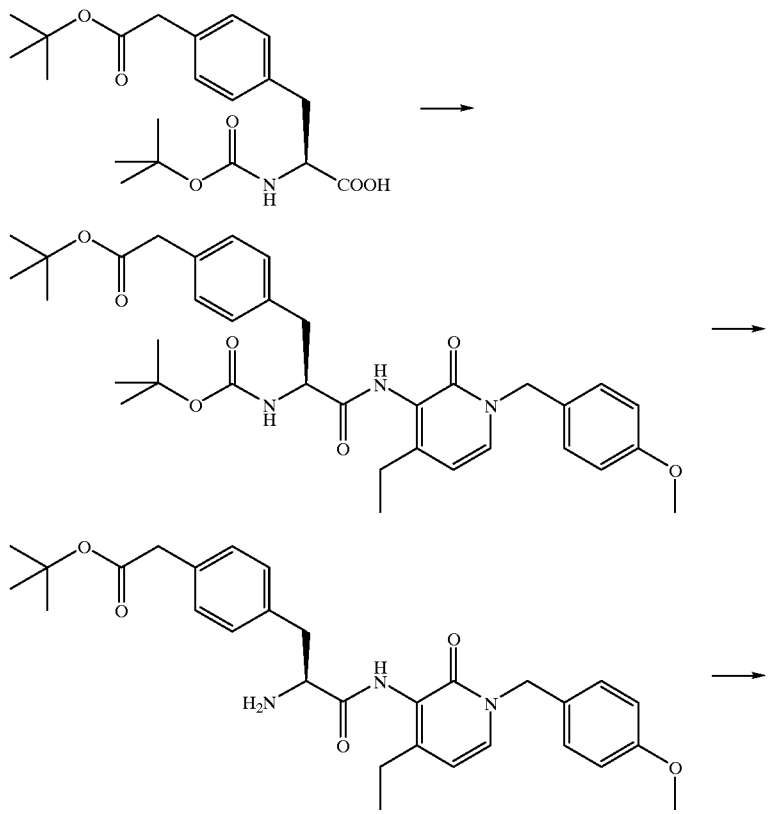

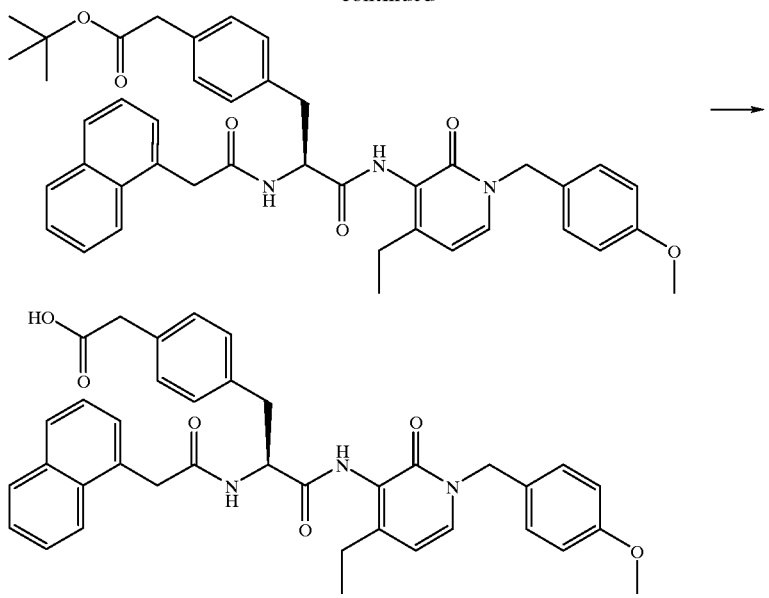

3-[2'-(S)-ᵗButoxycarbonylamino-3'-(4"-ᵗbutoxycarbonylmethyl)benzene]propanoylamino-1-(4-methoxybenzyl)-4-ethyl-2-pyridone.

To a stirred solution of 2-(S)-ᵗbutoxycarbonylamino-3-(4'-ᵗbutoxycarbonylmethyl)benzene]propanoic acid (0.29 g, 0.77 mmol) in methylene chloride (5 mL) at 0° C. under nitrogen was added EDC (0.163 g). After 20 minutes, 1-(4-methoxybenzyl)-4-ethyl-3-amino-2-pyridone (0.20 g, 0.78 mmol) in methylene chloride (5 mL) was added. The mixture was stirred at 0° C. for 1 hour and at rt for 3 days. The to mixture was diluted with methylene chloride, washed with water, dried (Na₂SO₄), filtered and evaporated. Chromatography of the residue over silica gel (ethyl acetate/hexane 3/1) gave 3-[2'-(S)-ᵗbutoxycarbonylamino-3'-(4"-ᵗbutoxycarbonylmethyl)benzene]propanoylamino-1-(4-methoxybenzyl)-4-ethyl-2-pyridone (0.165 g, 0.26 mmol, 34%).

3-[2'-(S)-Amino-3'-(4'-ᵗbutoxycarbonylmethyl)benzene]propanoylamino-1-(4-methoxybenzyl)-4-ethyl-2-pyridone.

To a stirred solution of 3-[2'-(S)-ᵗbutoxycarbonylamino-3'-(4"-ᵗbutoxycarbonylmethyl)benzene]propanoylamino-1-(4-methoxybenzyl)-4-ethyl-2-pyridone (0.15 g, 0.24 mmol) in methylene chloride (4 mL,) at −5° C. was added trifluoroacetic acid (0.5 mL). After 4.5 hours, NaHCO₃ was added at 0° C., and the mixture was extracted with two portions of methylene chloride. The organic phase was dried, filtered and evaporated. Chromatograpy of the residue over silica gel (5% methanol in methylene chloride) gave 3-[2'-(S)-amino-3'-(4'-ᵗbutoxycarbonylmethyl)benzene]propanoylamino-1-(4-methoxybenzyl)-4-ethyl-2-pyridone (0.065 g, 0.12 mmol, 50%).

3-[2'-(S)-(1'''-Naphthylacetyl)amino-3'-(4"-ᵗbutoxycarbonylmethyl)benzene]propanoylamino-1-(4-methoxybenzyl)-4-ethyl-2-pyridone.

To a stirred solution of 1-naphthylacetic acid (0.023 g, 0.12 mmol) in methylene chloride (3 mL) at 0° C. under nitrogen was added EDC (0.026 g). After 20 minutes, 3-[2'-(S)-amino-3-(4"-ᵗbutoxycarbonylmethyl)benzene]propanoylamino-1-(4-methoxybenzyl)-4-ethyl-2-pyridone (0.065 g, 0.12 mmol) in methylene chloride was added. The mixture was stirred at 0° C. for 2 hours, and allowed to warm to rt overnight. The mixture was diluted with methylene chloride, washed with water, dried, filtered and evaporated. Chromatography of the residue over silica gel (5% methanol in methylene chloride) gave 3-[2'-(S)-(1'''-naphthylacetyl)amino-3'-(4"-ᵗbutoxycarbonylmethyl)benzene]propanoylamino-1-(4-methoxybenzyl)-4-ethyl-2-pyridone (0.088 g. 0.12 mmol, 100%).

3-[2'-(S)-(1'''-Naphthylacetyl)amino-3'-(4"-carboxymethyl)benzene]propanoylamino-1-(4-methoxy)benzyl-4-ethyl-2-pyridone.

To a solution of 3-[2'-(S)-(1'''-naphthylacetyl)amino-3'-(4"-ᵗbutoxycarbonylmethyl)benzcne]propanoylamino-1-(4-methoxybenzyl)-4-ethyl-2-pyridone (0.086 g, 0.12 mmol) in methylene chloride (3 mL) was added trifluoroacetic acid (1 mL). The mixture was stirred at rt under nitrogen for 8 hours. Additional trifluoroacetic acid (0.5 mL) was added, and after 3 hours the solvents were evaporated. Methylene chloride/ether was added to the residue, and the solid 3-[2'-(S)-(1'''-naphthylacetyl)amino-3'-(4"-carboxymethyl)benzene]propanoylamino-1-(4-methoxybenzyl)-4-ethyl-2-pyridone (0.038 g, 0.06 mmol, 50%) was collected by filtration.

Compounds 91, 93, 51 and 244 were prepared in an analogous manner.

3-[2'-(R,S)-(2''''-Naphthylacetyl)amino-3'-[4"-(1'''-carboxy-1"-methyl)ethyl]benzene]propanoylamino-1-(4-methoxy-3-methylbenzyl)-4-methyl-2-pyridone (Compound 149).

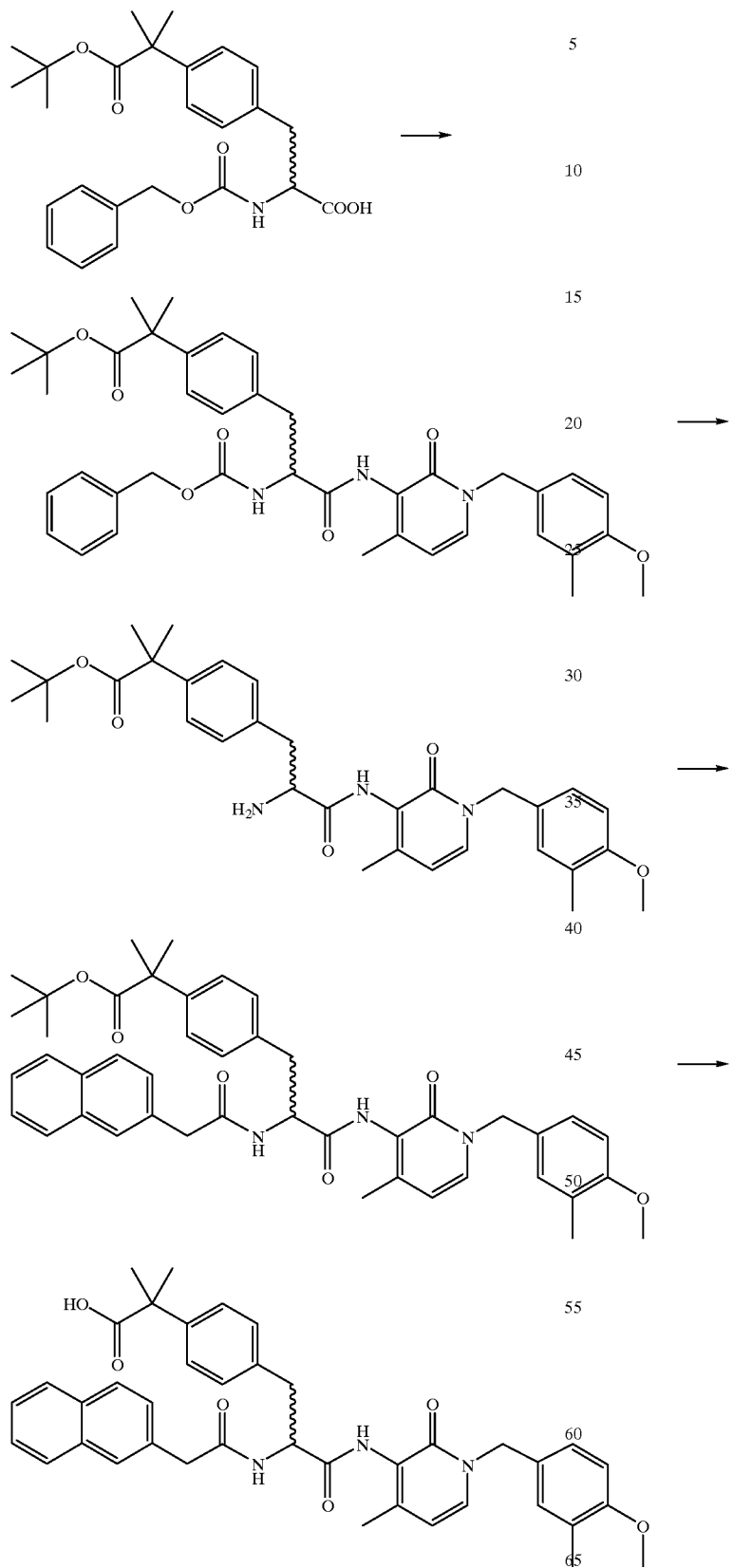

3-[2'-(R,S)-Benzyloxycarbonylamino-3-[4"-(1'"-$^t$butoxycarbonyl-1'"-methyl)ethyl]benzene] propanoylamino-1-(4-methoxy-3-methylbenzyl)-4-methyl-2-pyridone.

To a solution of 2-(R,S)-benzyloxycarbonylamino-3-[4'-(1"-$^t$butoxycarbonyl-1"-methyl)ethylbenzene]propanoic acid (0.250 g, 0.57 mmol) in methylene chloride (25 mL) at 0° C. under nitrogen was added EDC (0.125 g). The mixture was stirred at 0° C. for 20 minutes. 3-Amino-1-(4-methoxy-3-methylbenzyl)-4-methyl-2-pyridone (0.13 g, 0.50 mmol) in methylene chloride (2 mL) was added, and the mixture was stirred coming to rt for 1 hour. The solvent was evaporated, and chromatography of the residue over silica gel (ethyl acetate/petroleum ether 45/65) gave 3-[2'-(R,S)-benzyloxycarbonylamino-3'-[4"-(1'"-$^t$butoxycarbonyl-1'"-methyl)ethyl]benzene]propanoylamino-1-(4-methoxy-3-methyl)benzyl-4-methyl-2-pyridone (0.252 g, 0.37 mmol, 65%).

3-[2'-(R,S)-Amino-3'-[4"-(1'"-$^t$butoxycarbonyl-1'"-methyl) ethyl]benzene]propanoylamino-1-(4-methoxy-3-methylbenzyl)-4-methyl-2-pyridone.

A mixture of 3-[2'-(R,S)-benzyloxycarbonylamino-3'-[4"-(1'"-$^t$butoxycarbonyl-1'"-methyl)ethyl]benzene] propanoylamino-1-(4-methoxy-3-methylbenzyl)-4-methyl-2-pyridone (0.252 g, 0.37 mmol) and 10% Pd/C in ethanol (40 mL) was hydrogenated at 50 psi in a Parr apparatus for 8 hours. The catalyst was removed by filtration, and the solvent was evaporated to give 3-[2'-(R,S)-amino-3'-[4"-(1'"-$^t$butoxycarbonyl-1'"-methyl)ethyl]benzene] propanoylamino-1-(4-methoxy-3-methylbenzyl)-4-methyl-2-pyridone (0.090 g, 0.16 mmol, 44%) which was used directly in the next step.

3-[2'-(R,S)-(2""-Naphthylacetyl)amino-3-[4"-(1'"-$^t$butoxycarbonyl-1'"-methyl)ethyl]benzene] propanoylamino-1-(4-methoxy-3-methylbenzyl)-4-methyl-2-pyridone.

A mixture of 2-naphthylacetic acid (0.153 g, 0.82 mmol) and EDC (0.16 g) in methylene chloride (15 mL) at 0° C. under nitrogen was stirred for 15 minutes. 3-[2'-(R,S)-Amino-3-[4"-(1'"-$^t$butoxycarbonyl-1'"-methyl)ethyl] benzene]propanoylamino-1-(4-methoxy-3 -methylbenzyl)-4-methyl-2-pyridone (0.090 g, 0.16 mmol) in methylene chloride (3 mL) was added, and the mixture was stirred at rt for 18 hours. The solvent was evaporated, and chromatography of the residue over silica gel (ethyl acetate) gave 3-[2'-(R,S)-(2""-naphthylacetyl)amino-3'-[4"-(1'"-$^t$butoxycarbonyl-1'"-methyl)ethyl]benzene] propanoylamino-1-(4-methoxy-3-methylbenzyl)-4-methyl-2-pyridone (0.067 g, 0.09 mmol, 56%).

3-[2'-(R,S)-(2""-Naphthylacetyl)amino-3'-[4"-(1'"-carboxy-1'"-methyl)ethyl]benzene]propanoylamino-1-(4-methoxy-3-methylbenzyl)-4-methyl-2-pyridone.

A solution of 3-[2'-(R,S)-(2""-naphthylacetyl)amino-3'-[4"-(1'"-$^t$butoxycarbonyl 1'"-methyl)ethyl]benzene] propanoylamino-1-(4-methoxy-3-methylbenzyl)-4-methyl-2-pyridone (0.067 g, 0.09 mmol) in methylene chloride (4 mL) and trifluoroacetic acid (4 mL) was stirred at rt for 3 hours. The solvents were evaporated and the residue was triturated with ether. Recrystallization of the solid from ethyl acetate/ether gave 3-[2'-(R,S)-(2""-naphthylacetyl)amino-3'-[4"-(1'"-carboxy-1'"-methyl)ethyl]benzene] propanoylamino-1-(4-methoxy-3-methylbenzyl)-4-methyl-2-pyridone (0.031 g, 0.047 mmol, 52%).

Compounds 135, 137, 138, 139, 140, 141, 142, 143, 144, 145, 147, 148, 150, 153, 154, 155, 156, 157, 158, 159, 160, 169, 170, 171, 172, 173, 174, 175, 178, 179, 180, 181, 182, 183, 184, 186, 187, 188, 189, 190, 191, 192, 193, 194, 195, 196, 197, 198, 199, 200, 204, 205, 206, 207, 208, 209, 213, 214, 215, 216, 217, 222, 223, 230, 232, 235, 236, 237 and 239 were synthesized in an analogous manner.

3-[2'-(R,S)-Benzyloxycarbonylamino-3'-[4"-(1'"-methyl-1'"-$^t$butoxycarbonyl)ethyl]benzene]propanoylamino-1-(3-furanylmethyl)-4-methyl-2-pyridone and 3-[2'-(R,S)-benzyloxycarbonylamino-3'-[4"-(1'"methyl-1'"-$^t$butoxycarbonyl)ethyl]benzene]propanoylamino-1-(3-tetrahydrofuranylmethyl)-4-methyl-2-pyridone (For Compounds 201, 202, 203, 210, 211 and 212).

2-(R,S)-Benzyloxycarbonylamino-3-[4'-(1'"-methyl-1'"-$^t$butoxycarbonyl)ethyl]benzene propanoic acid (0.953 g, 2.2 mmol) and the mixture of 3-amino-1-(3-furanylmethyl)-4-methyl-2-pyridone and 3-amino-1-(3-tetrahydrofuranylmethyl)-4-methyl-2-pyridone (0.294 g, 1.44 mmol) were coupled using EDC (0.47 g) as described above. Chromatography of the reaction mixture over silica gel (hexane/ethyl acetate 2/3) gave 3-[2'-(R,S)-benzyloxycarbonylamino-3'-[4"-(1'"-methyl-1'"-$^t$butoxycarbonyl)ethyl]benzene]propanoylamino-1-(3-furanylmethyl)-4-methyl-2-pyridone (0.200 g, 0.31 mmol, 14%) and 3-[2'-(R,S)-benzyloxycarbonylamino-3'-[4"-(1'"-methyl-1'"-$^t$butoxycarbonyl)ethyl]benzene] propanoylamino-1-(3-tetrahydrofuranylmethyl)-4-methyl-2-pyridone (0.542 g, 0.86 mmol, 39%). 3-[2'-(R,S)-Benzyloxycarbonylamino-3'-[4"-(1'"-methyl-1'"-$^t$butoxycarbonyl)ethyl]benzene]propanoylamino-1-(3-furanylmethyl)-4-methyl-2-pyridone was converted to compounds 201, 202, and 203 by procedures analogous to those described above. 3-[2'-(R,S)-Benzyloxycarbonylamino-3'-14"-(1'"-methyl-1'"-$^t$butoxycarbonyl)ethyl]benzene]propanoylamino-1-(3-tetrahydrofuranylmethyl)-4-methyl-2-pyridone was converted to compounds 210, 211, and 212 by procedures analogous to those described above.

3-[2'-(R,S)-(N-Methyl-N-(2""-naphthylacetyl)amino-3'-[4"-(1'"-carboxy-1'"-methyl)ethyl]benzene]propanoylamino-1-(4-methoxybenzyl)-4-methyl-2-pyridone (compound 152).

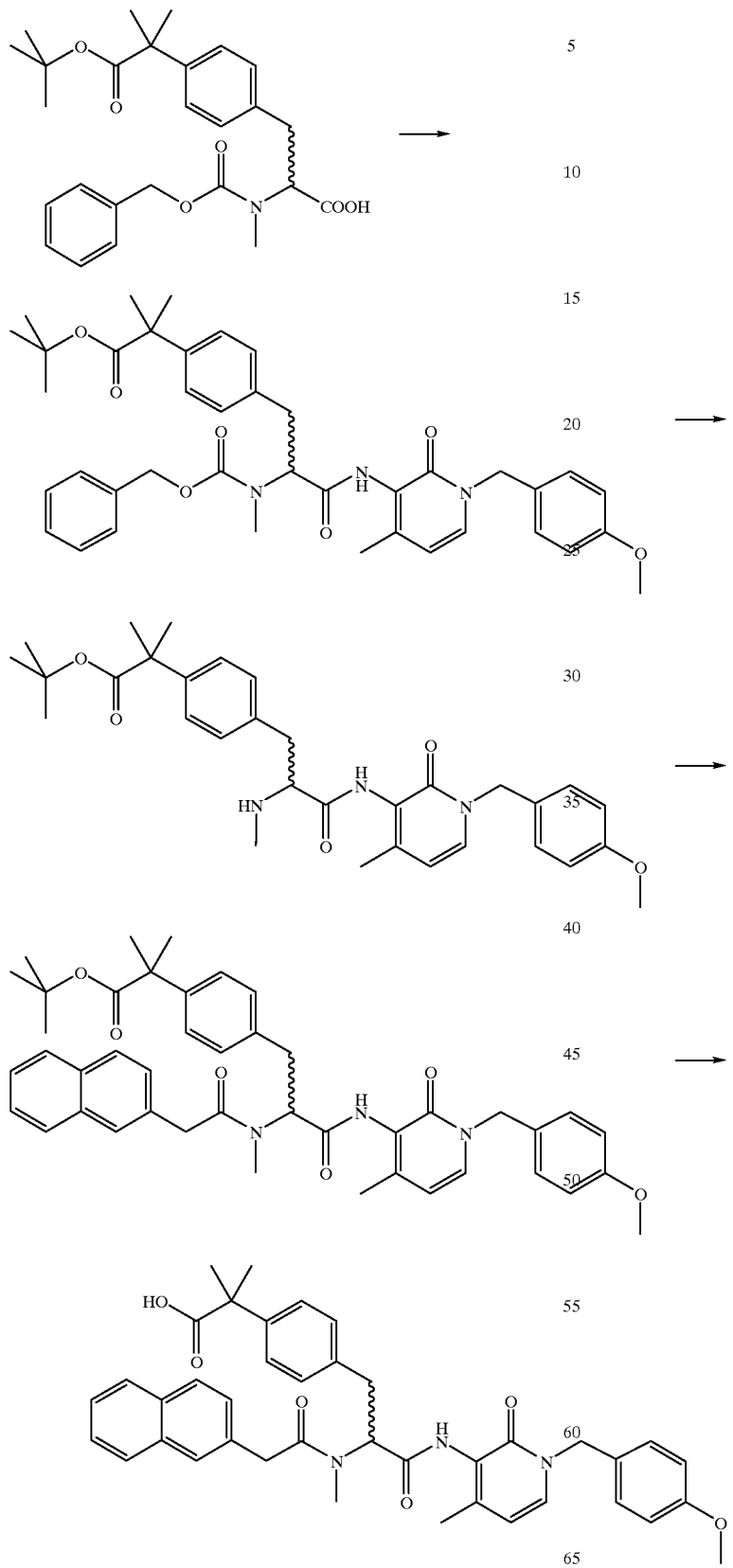

201

3-[2'-(R,S)-(N-Methyl-N-benzyloxycarbonylamino)-3'-[4"-(1'"-ᵗbutoxycarbonyl-1'"-methyl)ethyl]benzene]propanoylamino-1-(4-methoxybenzyl)-4-methyl-2-pyridone.

A mixture of 2-(R,S)-(N-methyl-N-benzyloxycarbonylamino)-3-[4'-(1"-ᵗbutoxycarbonyl-1'"-methyl)ethyl]benzenepropanoic acid (0.50 g, 1.1 mmol) and EDC (0.25 g) in methylene chloride (30 mL) at 0° C. under nitrogen was stirred at 0° C. for 20 minutes. 1-(4-Methoxybenzyl)-4-methyl-3-amino-2-pyridone (0.15 g) in methylene chloride (3 mL) was added, and the mixture was allowed to warm to rt, and stirred overnight. The solvent was evaporated, and chromatography of the residue over silica gel (45% ethyl acetate/petroleum ether) gave 3-[2'-(R,S)-(N-methyl-N-benzyloxycarbonylamino)-3'-[4"-(1'"-ᵗbutoxycarbonyl-1'"-methyl)ethyl]benzene]propanoylamino-1-(4-methoxybenzyl)-4-methyl-2-pyridone as an oil (0.36 g, 0.52 mmol, 85%).

3-[2'-(R,S)-(N-Methyl-N-(2""-naphthylacetyl)amino-3'-[4"-(1'"-ᵗbutoxycarbonyl-1'"-methyl)ethyl]benzene]propanoylamino-1-(4-methoxybenzyl)-4-methyl-2-pyridone.

A mixture of 3-[2'-(R,S)-(N-methyl-N-benzyloxycarbonylamino)-3'-[4"-(1'"-ᵗbutoxycarbonyl-1'"-methyl)ethyl]benzene]propanoylamino-1-(4-methoxybenzyl)-4-methyl-2-pyridone (0.36 g, 0.52 mmol) and 10% Pd/C (0.1 g) in ethanol (12 mL) and cyclohexene was heated at 70° C. for 30 minutes. The catalyst was

202 removed by filtration, and the solvent was evaporated to give 3-[2'-(R,S)-(N-methylamino)-3'-[4"-(1'"-ᵗbutoxycarbonyl-1'"-methyl)ethyl]benzene]propanoylamino-1-(4-methoxybenzyl)-4-methyl-2-pyridone which was used directly in the next step. A mixture of 2-naphthylacetic acid (0.25 g, 1.3 mmol) and EDC (0.29 g) in methylene chloride (10 mL) at 0° C. was stirred for 20 minutes. 3-[2'-(R,S)-(N-methylamino)-3'-[4"-(1'"-ᵗbutoxycarbonyl-1'"-methyl)ethyl]benzene]propanoylamino-1-(4-methoxybenzyl)-4-methyl-2-pyridone in methylene chloride (3 mL) was added, and the mixture was allowed to warm to rt, and stirred for 18 hours. The solvent was evaporated, and chromatography of the residue over silica gel (70% ethyl acetate/petroleum ether) gave 3-[2'-(R,S)-(N-methyl-N-(2""-naphthylacetyl)amino)-1'-[4"(1'-ᵗbutoxycarbonyl-1'"-methyl)ethyl]benzene]propanoylamino-1-(4-methoxybenzyl)-4-methyl-2-pyridone (0.263 g, 0.37 mmol, 70%).

3-[2'-(R,S)-(N-Methyl-N-(2""-naphthylacetyl)amino-3'-[4"-(1'"-carboxy-1'"-methyl)ethyl]benzene]propanoylamino-(4-methoxybenzyl)-4-methyl-2-pyridone.

This compound was obtained in 66% yield by trifluoroacetic acid/methylene chloride 1/1 deprotection of 3-[2'-(R,S)-(N-methyl-N-(2""-naphthylacetyl)amino)-'3'-[4"-((1'"-ᵗbutoxycarbonyl-1'"-methyl)ethyl]benzene]propanoylamino-(4-methoxybenzyl)-4-methyl-2-pyridone.

3-[2'-(R,S)-(2""-Naphthylacetyl)amino-3'4"-(1'"-carboxy-1'"-methyl)ethyl]benzene]propanoylamino-5-iodo-1-(4-methoxybenzyl)-4-methyl-2-pyridone (Compound 229).

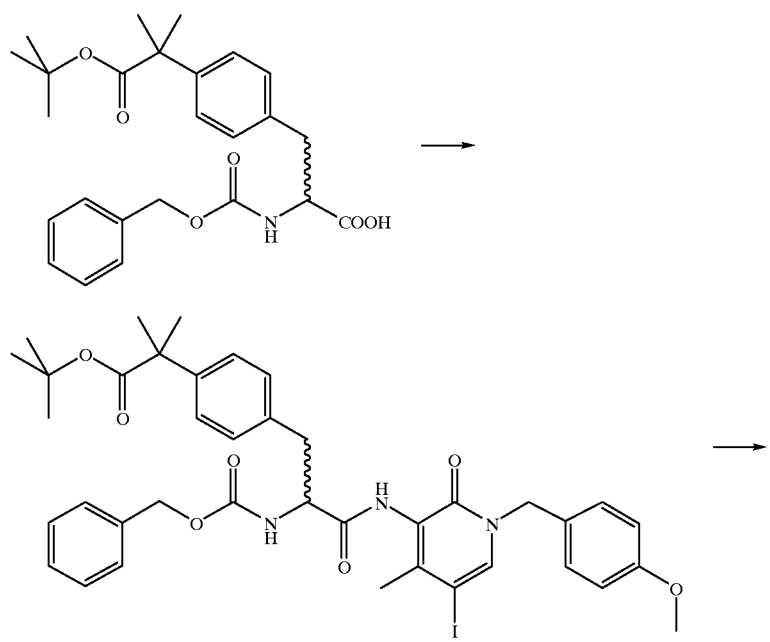

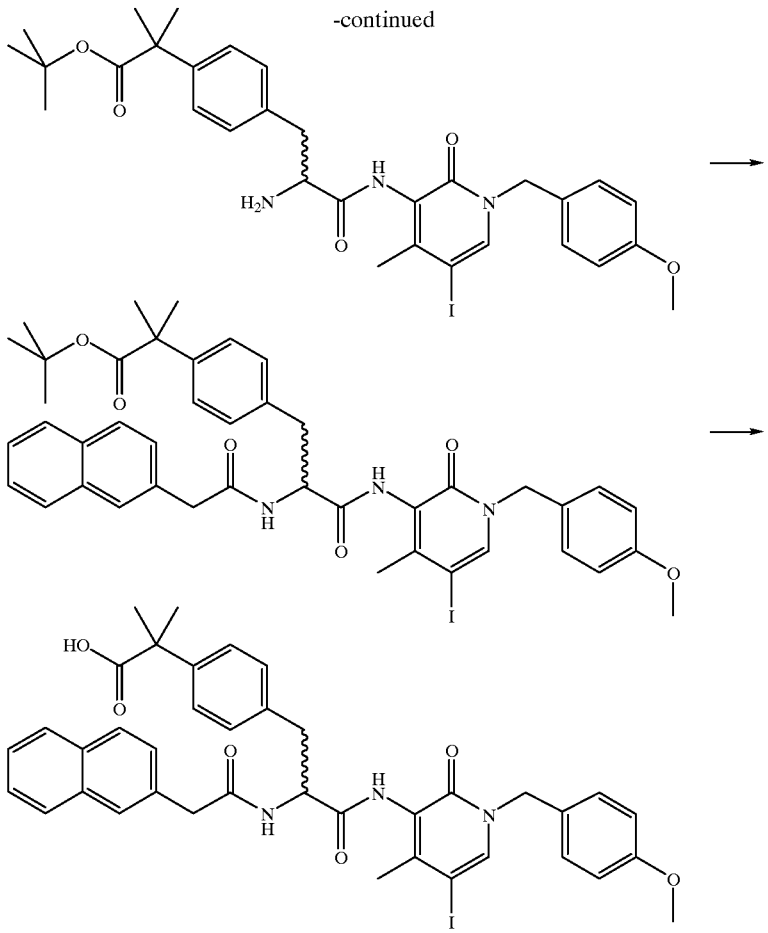

3-[2'-(R,S)-N-Benzyloxycarbonylamino-3'-[4"-(1'"-ᵗbutoxycarbonyl-1'"-methyl)ethyl]benzene]propanoylamino-5-iodo-1-(4-methoxybenzyl)-4-methyl-2-pyridone.

A mixture of 2-(R,S)-N-benzyloxycarbonylamino-3-[4'-(1"-ᵗbutoxycarbonyl-1"-methyl)ethyl]benzenepropanoic acid (0.47 g, 1.1 mmol) and EDC (0.24 g) in methylene chloride (5 mL) at 0° C. under nitrogen was stirred for 15 min. 5-Iodo-1-(4'-methoxybenzyl)-4-methyl-3-amino-2-pyridone (0.26 g, 0.70 mmol) in methylene chloride (5 mL) was added, and the mixture was allowed to warm to rt. After 36 hours the solvent was evaporated, and chromatography of the residue over silica gel (40% ethyl acetate/petroleum ether) gave 3-[2'-(R,S)-N-benzyloxycarbonylamino-3'-[4"-(1-ᵗbutoxycarbonyl-1'"-methyl)ethyl]benzene]propanoylamino-5-iodo-1-(4-methoxybenzyl)-4-methyl-2-pyridone as an oil (0.24 g, 43%).

3-[2'-(R,S)-(2""-Naphthylacetyl)amino-3'-[4"-(1'"-ᵗbutoxycarbonyl-1'"-methyl)ethyl]benzene]propanoylamino-5-iodo-1-(4-methoxybenzyl)-4-methyl-2-pyridone.

To a solution of 3-[2'-(R,S)-N-benzyloxycarbonylamino-3'-[4"-(1'"-ᵗbutoxycarbonyl-1'"-methyl)ethyl]benzene]propanoylamino-5-iodo-1-(4-methoxybenzyl)-4-methyl-2-pyridone (0.125 g, 0.16 mmol) in methylene chloride (1.6 mL) was added diisopropylethylamine (0.055 mL) and trimethylsilyl iodide (0.023 mL, 0.16 mmol). After 1 hour, additional trimethylsilyl iodide (0.012 mL) was added. After 1.5 hours, methanol (0.068 mL) was added, and the solvent was evaporated. Additional methanol (1 mL) was added and the evaporation was repeated to give 3-[2'-(R,S)-amino-3'-[4"-(1'"-ᵗbutoxycarbonyl-1'"-methyl)ethyl]benzene]propanoylamino-5-iodo-1-(4-methoxybenzyl)-4-methyl-2-pyridone which was used directly in the next step.

To a solution of 2-naphthylacetic acid (0.29 g, 1.6 mmol) in methylene chloride (7 mL) at 0° C. was added EDC (0.36 0, 1.9 mmol). After 15 minutes, 3-[2'-(R,S)-amino-3'-[4"-(1'"-ᵗbutoxycarbonyl-1'"-methyl)ethyl]benzene]propanoylamino-5-iodo-1-(4-methoxybenzyl)-4-methyl-2-pyridone in methylene chloride (1 mL) was added. The mixture was allowed to warm to rt, and stirred for 20 hours. The solvent was evaporated, and chromatography of the residue over silica gel (35% ethyl acetate/petroleum ether) gave 3-[2'-(R,S)-(2""-naphthylacetyl)amino-3'-[4"-(1'"-ᵗbutoxycarbonyl-1'"-methyl)ethyl]benzene]propanoylamino-5-iodo-1-(4-methoxybenzyl)-4-methyl-2-pyridone (0.041 g, 31%).

3-[2'-(R,S)-(2""-Naphthylacetyl)amino-3'-[4"-(1'"-carboxy-1'"-methyl)ethyl]benzene]propanoylamino-5-iodo-1-(4-methoxybenzyl)-4-methyl-2-pyridone.

This compound was obtained in 83% yield by trifluoroacetic acid/methylene chloride (1/1) deprotection of 3-[2'-(R,S)-(2""-naphthylacetyl)amino-3'-[4"-(1'"-ᵗbutoxycarbonyl-1'"-methyl)ethyl]benzene]propanoylamino-5-iodo-1-(4-methoxybenzyl)-4-methyl-2-pyridone.

Compound 231 was made in an analogous manner.

3-[2'-(R,S)-Benyloxycarbonylamino-3'-[4"-(1'"-carboxy-1'"-methyl)ethyl]benzene]propanoylamino-1-(5-methylhexyl)-4-methyl-2-pyridone (Compound 146).

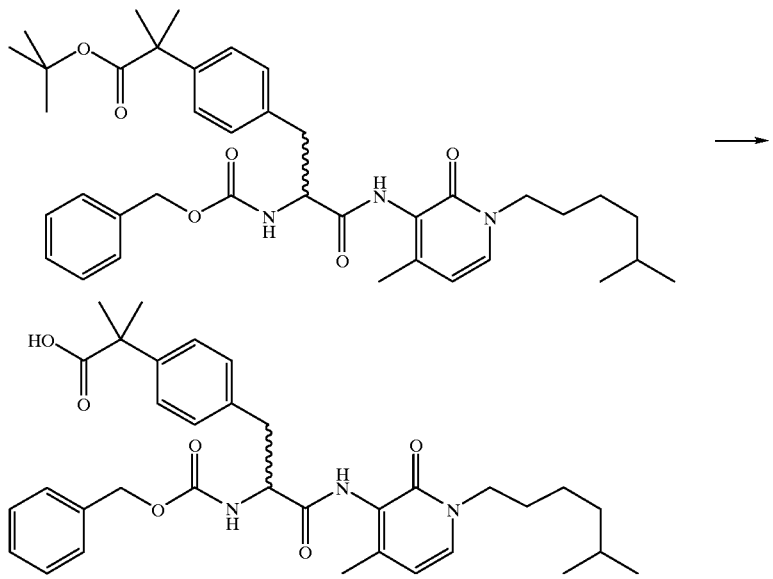

A solution of 3-[2'-(R,S)-benzyloxycarbonylamino-3-[4"-(1'''-*t*butoxycarbonyl-1'''-methyl)ethyl]benzene]propanoylamino-1-(5-methylhexyl)-4-methyl-2-pyridone (obtained as an intermediate in the synthesis of compound 145 above) (0.054 g, 0.08 mmol) in trifluoroacetic acid (2.5 mL) was stirred at rt for 2 hours. The mixture was concentrated, taken up in ether., and evaporated. The residue crystallized from methylene chloride/ether to give 3-[2'-(R,S)-benzyloxycarbonylamino-3'-[4"-(1'''-carboxy-1'''-methyl)ethyl]benzene]propanoylamino-1-(5-methylhexyl)-4-methyl-2-pyridone (0.034 g, 0.06 mmol, 68%).

3-[2'-(R,S)-(2''''-Naphthylacetyl)amino-3'-[4"-(1'''-carboxy-1'''-methyl)ethyl]benzene]propanoylamino-5-acrylamido-1-(4-methoxybenzyl)-4-methyl-2-pyridone (Compound 221).

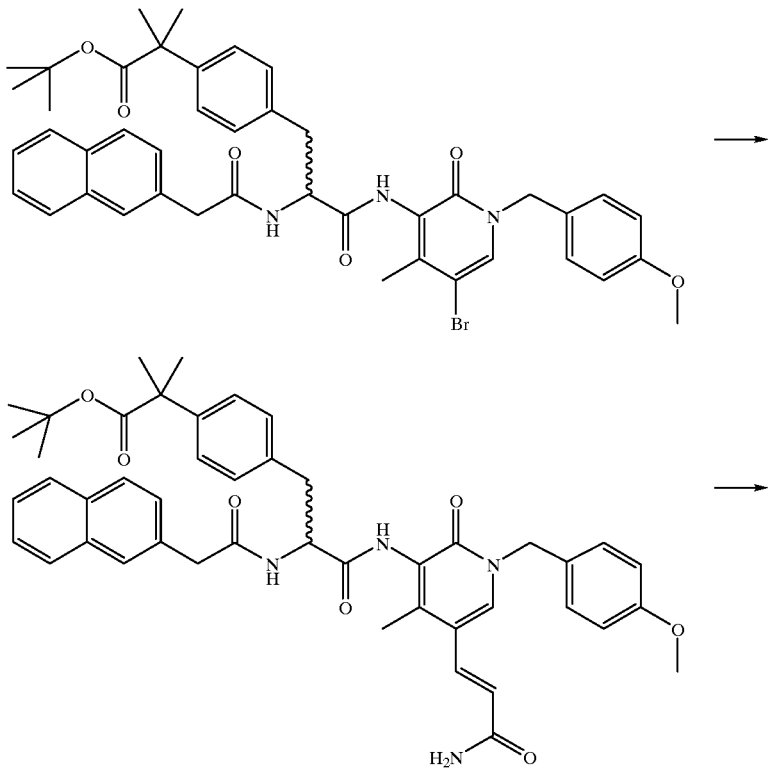

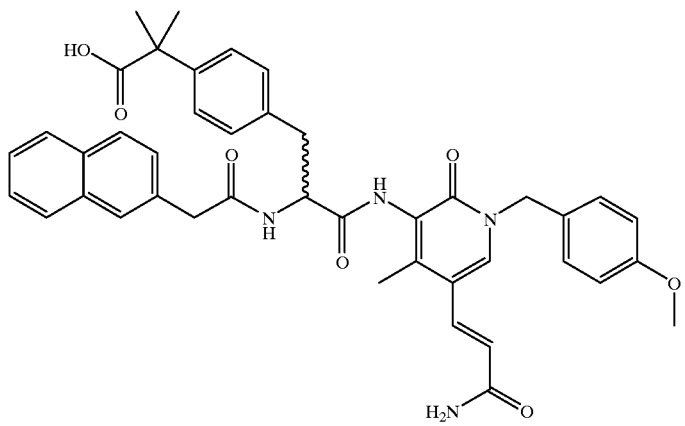

3-[2'-(R,S)-(2''''-Naphthylacetyl)amino-3'-[4''-(1'''-ᵗbutoxycarbonyl-1'''-methyl)ethyl]benzene]propanoylamino-5-acrylamido-1-(4-methoxybenzyl)-4-methyl-2-pyridone.

A mixture of 3-[2'-(R,S)-(2''''-naphthylacetyl)amino-3'-[4''-(1'''-ᵗbutoxycarbonyl-1'''-methyl)ethyl]benzene]propanoylamino-5-bromo-1-(4-methoxybenzyl)-4-methyl-2-pyridone (0.080 g, 0.10 mmol), acrylamide (0.022 g) and bis(triphenylphosphine)Pd(II) chloride (0.010 g) in NMP (2 mL) and triethylamine (1 mL) was heated at 100° C. under nitrogen for 4.5 hours. The mixture was diluted with methylene chloride, and washed with water. The organic phase was dried, filtered and evaporated. Chromatography of the residue over silica gel (5% methanol/methylene chloride) gave crude 3-[2'-(R,S)-(2''''-naphthylacetyl)amino-3'[4''(1'''-ᵗbutoxycarbonyl-1'''-methyl)ethyl]benzene]propanoylamino-5-acrylamido-1-(4-methoxybenzyl)-4-methyl-2-pyridone which was used directly in the next reaction.

3-[2'-(R,S)-(2''''-Naphthylacetyl)amino-3'-[4''-(1'''-carboxy-1'''-methyl)ethyl]benzene]propanoylamino-5-acrylamido-1-(4-methoxybenzyl)-4-methyl-2-pyridone.

A solution of 3-[2'-(R,S)-(2-naphthylacetyl)amino-3'-[4''-(1'''-ᵗbutoxycarbonyl-1'''-methyl)ethyl]benzene]propanoylamino-5-acrylamido-1-(4-methoxybenzyl)-4-methyl-2-pyridone in methylene chloride (3 mL) and trifluoroacetic acid (1 mL) was stirred at rt for hours. The solvent was evaporated. Chromatography of the residue over silica gel (5% methylene chloride/methanol), followed by reverse phase HPLC gave 3-[2'-(R,S)-(2''''-naphthylacetyl)amino-3'-[4''-(1'''-carboxy-1'''-methyl)ethyljbenzene]propanoylamino-5-acrylamido-1-(4-methoxybenzyl)-4-methyl-2-pyridone (0.003 g, 0.004 mmol, 4%).

3-[2'-(S)-(2''''-Naphthylacetyl)amino-3'-[4''-(1'''-carboxy-1'''-methyl)ethyl]benzene]propanoylamino-5-bromo-1-(4-methoxybenzyl)-4-methyl-2-pyridone (Compound 220).

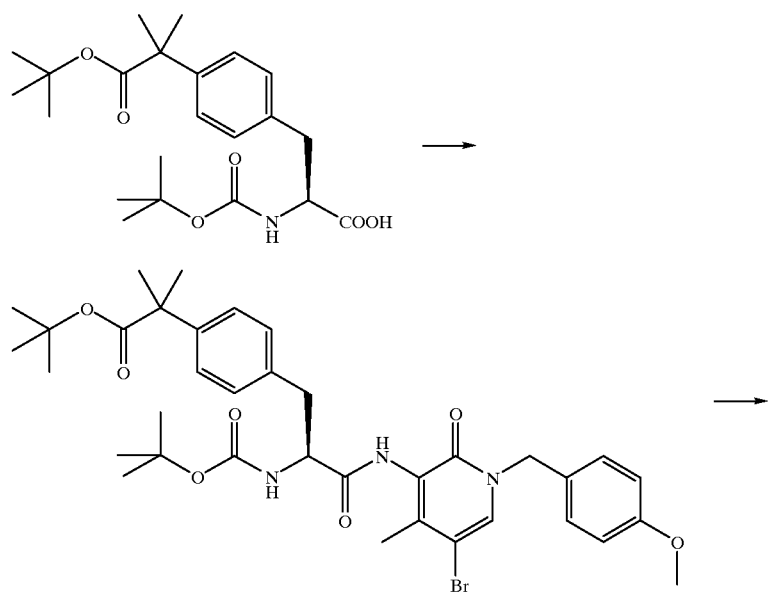

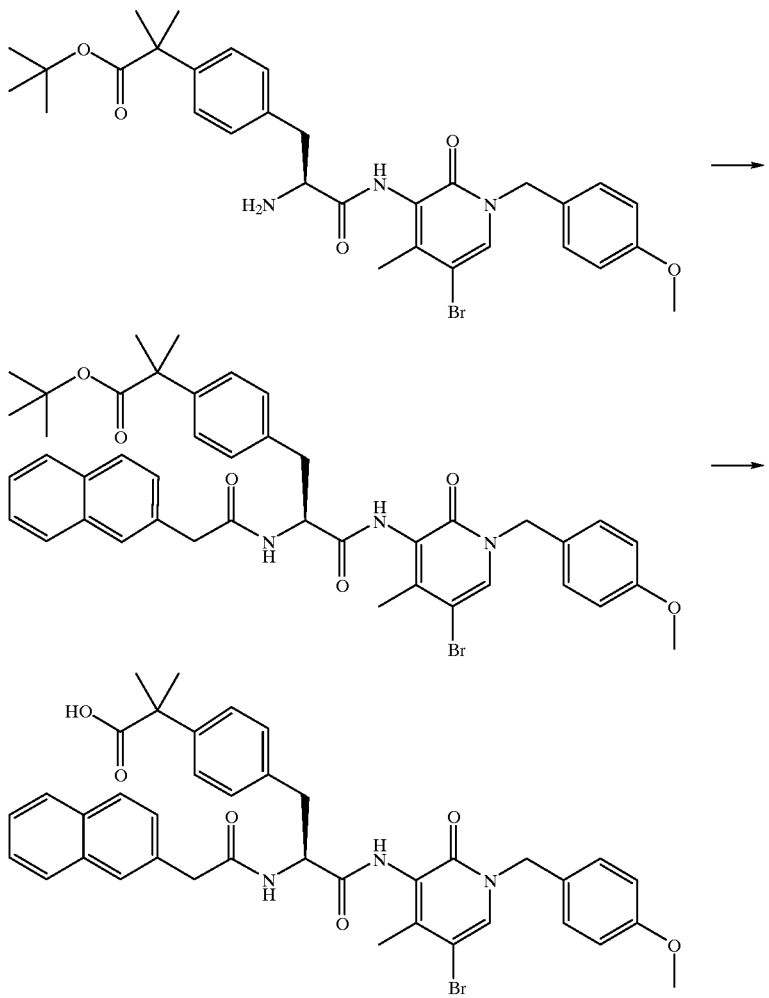

3-[2'-(S)-ʳButoxycarbonylamino-3'-[4"-(1'"-ʳbutoxycarbonyl-1'"-methyl)ethyl]benzene]propanoylamino-5-bromo-1-(4-methoxybenzyl)-4-methyl-2-pyridone.

To a solution of 2-(S)-ʳbutoxycarbonylamino-)-[4'-(1"-ʳbutoxycarbonyl-1"-methyl)ethyl]benzenepropanoic acid (3.20 g, 7.88 mmol) in methylene chloride (20 mL) and DMF (5 mL) at 0° C. were added HOAT (1.07 g) and 1-(4-methoxybenzyl)-5-bromo-4-methyl-3-amino-2-pyridone (2.80 g, 8.67 mmol). EDC (1.66 g) and TMP (1.04 mL) were added, and the mixture was stirred coming to rt overnight. The methylene chloride was evaporated and DMF (25 mL) was added. Additional EDC (0.80 g), HOAT (0.50 g) and TMP (0.5 mL) were added. After 3 hours the mixture was diluted with ethyl acetate, and washed with 1N HCl, aqueous sodium bicarbonate and brine. The organic phase was dried (MgSO₄), filtered and evaporated. Chromatography of the residue over silica gel (ethyl acetate/hexane 1/3) gave 3'-[2'-(S)-ʳbutoxycarbonylamino-3'-[4"-(1'"-ʳbutoxycarbonyl-1'"-methyl)ethyl]benzene]propanoylamino-5-bromo-1-(4-methoxybenzyl)-4-methyl-2-pyridone (2.48 g, 3.49 mmol, 44%).

3-[2'-(S)-Amino-3'-[4"-(1'"-ʳbutoxycarbonyl-1'"-methyl)ethyl]benzene]propanoylamino-5-bromo-1-(4-methoxybenzyl)-4-methyl-2-pyridone.

To 3)-[2'-(S)-ʳbutoxycarbonylamino-3'-[4"-(1'"-ʳbutoxycarbonyl-1'"-methyl)ethyl]benzene]propanoylamino-5-bromo-1-(4-methoxybenzyl)-4-methyl-2-pyridone (0.836 g. 1.18 mmol) in methylene chloride (8 mL) at 0° C. was added a cooled solution of trifluoroacetic acid (2.2 mL) in methylene chloride (9 mL). After 3 hours at 0° C., aqueous NaHCO₃ was added, and the mixture was extracted with methylene chloride. The organic phase was dried (MgSO₄), filtered, and evaporated. Chromatography of the residue over silica gel (1% to 2% methanol in methylene chloride) gave 3-[2'-(S)-amino-3'-[4"-(1'"-ʳbutoxycarbonyl-1'"-methyl)ethyl]benzene]propanoylamino-5-bromo-1-(4-methoxybenzyl)-4-methyl-2-pyridone (0.434 g, 0.708 mmol, 60%).

3-[2'-(S)-(2""-Naphthylacetyl)amino-3'-[4"-(1'"-ʳbutoxycarbonyl-1'"-methyl)ethyl]benzene]propanoylamino-5-bromo-1-(4-methoxybenzyl)-4-methyl-2-pyridone.

A mixture of 2-naphthylacetic acid (0.145 g, 0.778 mmol) and EDC (0.149 g) in methylene chloride (4 mL) cooled to 0° C. was stirred for 20 minutes. 3-[2'-(S)-Amino-3'-[4"-(1'"-ʳbutoxycarbonyl-1'"-methyl)ethyl]benzene]propanoylamino-5-bromo-1-(4-methoxybenzyl)-4-methyl-2-pyridone (0.434 g, 0.708 mmol) in methylene chloride (3 mL) was added and the mixture was allowed to warm to rt. After 40 minutes, the solvent was evaporated. Chromatography of the residue over silica gel (methylene chloride to 2% methanol in methylene chloride) followed by an additional chromatography using 30% ethyl acetate/hexane gave 3-[2'-(S)-(2""-naphthylacetyl)amino-3'-[4"-(1'"-'butoxycarbonyl-1'"-methyl)ethyl]benzene]propanoylamino-5-bromo-1-(4-methoxybenzyl)-4-methyl-2-pyridone (69%).

3-[2'-(S)-(2""-Naphthylacetyl)amino-3'-[4"-(1'"-carboxy-1'"-methyl)ethyl]benzene]propanoylamino-5-bromo-1-(4-methoxybenzyl)-4-methyl-2-pyridone.

To a solution of 3-[2'-(S)-(2""-naphthylacetyl)amino-3'-[4"-(1'"-'butoxycarbonyl-3'-methyl)ethyl]benzene]propanoylamino-5-bromo-1-(4-methoxybenzyl)-4-methyl-2-pyridone (0.729 g, 0.935 mmol) in methylene chloride (36 mL) was added trifluoroacetic acid (10 mL). The mixture was stirred at rt until TLC showed complete conversion of starting material. The solvents were evaporated. The residue was taken up in methylene chloride and evaporated and this procedure was repeated three times. Trituration of the residue with ether gave 3-[2'-(S)-(2""-naphthylacetyl)amino-3'-[4"-(1'"-carboxy-1'"-methyl)ethyl]benzene]propanoylamino-5-bromo-1-(4-methoxybenzyl)-4-methyl-2-pyridone (0.577 gt 0.797 mmol, 85%).

Compounds 233 and 234 were synthesized in an analogous manner using 2-(S)-'butoxycarbonylamino-3-[4'-(1"-'butoxycarbonyl-1"-methyl)ethyl]benzenepropanoic acid as the starting material.

3-[2'-(S)-(2""-Naphthylacetyl)amino-3'-[4"-(1'"-carboxy)cyclopropyl]benzene]propanoylamino-1-(4-methoxybenzyl)-4-methyl-2-pyridone (Compound 218).

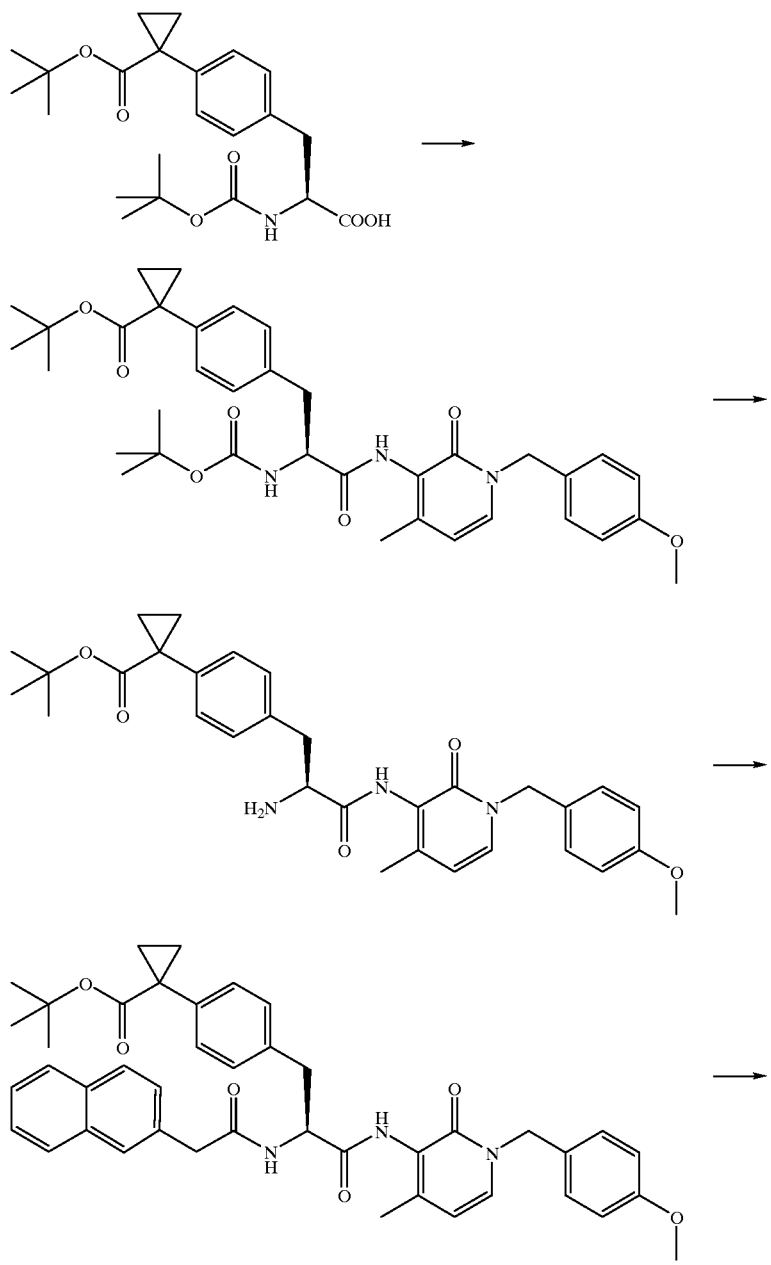

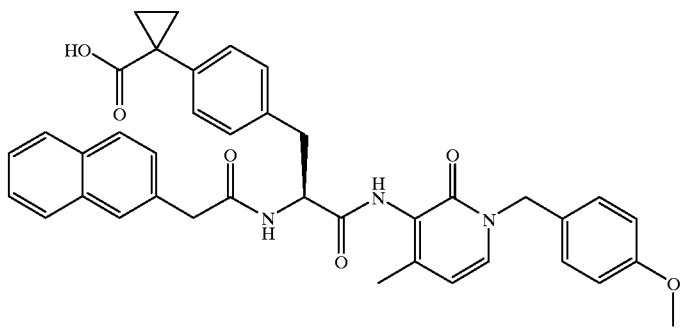

3-[2'-(S)-'Butoxycarbonylamino-3'-4-(1'''-'butoxycarbonyl)cyclopropyl]benzene]propanoylamino-1-(4-methoxybenzyl)-4-methyl-2-pyridone.

To a solution of 2-(S)-'butoxycarbonylamino-3-[4'-(1''-'butoxycarbonyl)cyclopropyl]benzene]propanoic acid (0.30 g, 0.74 mmol) in methylene chloride (3 mL) at 0° C. under nitrogen was added EDC (0.15 g). The mixture was stirred at 0° C. for 20 minutes. 3-Amino-1-(4-methoxybenzyl)-4-methyl-2-pyridone (0.22 g, 0.90 mmol) in methylene chloride (2 mL) was added, and the mixture was stirred coming to rt overnight. The mixture was diluted with ethyl acetate, washed with water, 1N KHSO₄, dried, filtered and evaporated to give 3-[2'-(S)-'butoxycarbonylamino-1'-[4"-(1'''-'butoxycarbonyl)cyclopropyl]benzene]propanoylamino-1-(4-methoxybenzyl)-4-methyl-2-pyridone (0.41 g, 0.65 mmol, 88%) which was used without additional purification.

3-[2'-(S)-Amino-3'-[4"-(1'''-'butoxycarbonyl)cyclopropyl]benzene]propanoylamino-1-(4-methoxybenzyl)-4-methyl-2-pyridone.

To a solution of 3 1-[2'-(S)-'butoxycarbonylamino-3'-[4"-(1'''-'butoxycarbonyl)cyclopropyl]benzene]propanoylamino-1-(4-methoxybenzyl)-4-methyl-2-pyridone (0.41 g, 0.65 mmol) in methylene chloride (1 mL) cooled to 0° C. was added an ice-cooled solution of trifluoroacetic acid (2 mL) in methylene chloride (7 mL). After 3 hours at 0° C., the reaction was quenched with aqueous potassium carbonate. The organic phase was dried, filtered and evaporated. Chromatography of the residue over silica gel (ethyl acetate followed by 10% ethanol in chloroform) gave '3-[2'-(S)-amino-3'-[4"-(1'''-'butoxycarbonyl)cyclopropyl]benzene]propanoylamino-1-(4-methoxybenzyl)-4-methyl-2pyridone (0.067 g, 0.13 mmol, 19%).

3-[2'-(S)-(2""-Naphthylacetyl)amino-3'-[4"-(1'''-'butoxycarbonyl)cyclopropyl]benzene]propanoylamino-1-(4-methoxybenzyl)-4-methyl-2-pyridone To a stirred solution of 2-naphthylacetic acid (0.031 g) in methylene chloride (1 mL), cooled to 0° C., was added EDC (0.032 g) and 3-[2'-(S)-amino-3'-[4"-(1'''-'butoxycarbonyl)cyclopropyl]benzene]propanoylamino-1-(4-methoxybenzyl)-4-methyl-2-pyridone (0.067 g, 0.13 mmol) in methylene chloride. After 3 hours at 0° C., the mixture was chromatographed directly over silica gel (methylene chloride to 2% methanol in methylene chloride) to give 3-[2'-(S)-(2""-naphthylacetyl)amino-3'-[4"-(1'''-'butoxycarbonyl)cyclopropyl]benzene]propanoylamino-1-(4-methoxybenzyl)-4-methyl-2-pyridone (0.080 g. 0.1 1 mmol, 84%).

3-[2'-(S)-(2""-Naphthylacetyl)amino-3'-[4"-(1'''-carboxy)cyclopropyl]benzene]propanoylamino-1-(4-methoxybenzyl)-4-methyl-2-pyridone.

To a stirred solution of 3-[2'-(S)-(2""-naphthylacetyl)amino-3'-[4"-(1'''-'butoxycarbonyl)cyclopropyl]benzene]propanoylamino-1-(4-methoxybenzyl)-4-methyl-2-pyridone (0.080 g, 0.11 mmol) in methylene chloride (1 mL) was added a solution of trifluoroacetic acid (1 mL) in methylene chloride (3 mL). After 90 minutes the solvents were evaporated. The residue was taken up in methylene chloride/ether, and the solvents were evaporated. The co-evaporation with methylene chloride/ether was repeated twice more. The residue was taken up in methylene chloride and filtered. Addition of ether precipitated 3-[2'-(S)-(2""-naphthylacetyl)amino-3'-[4"-(1'''-carboxy)cyclopropyl]benzene]propanoylamino-1-(4-methoxybenzyl)-4-methyl-2-pyridone as a solid (0.05 (J 0.08 mmol, 73%).

3-[2'-(S)-(1'''-Naphthylacetyl)amino-3'-[4"-(1'''-(R,S)-carboxy-2'''-hydroxy)ethyl]benzene]propanoylamino-1-(4-methoxybenzyl)-4-methyl-2-pyridone (Compound 136).

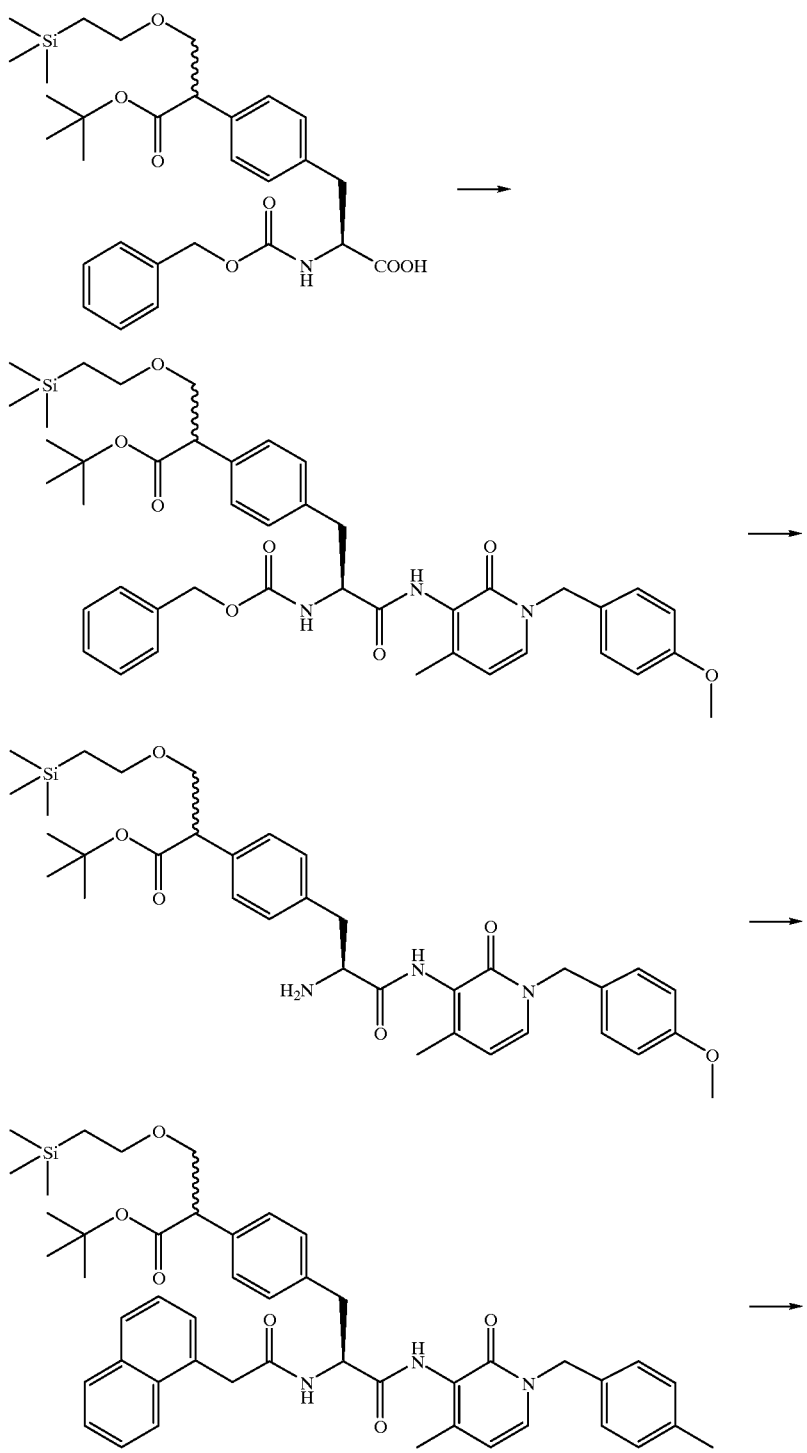

-continued

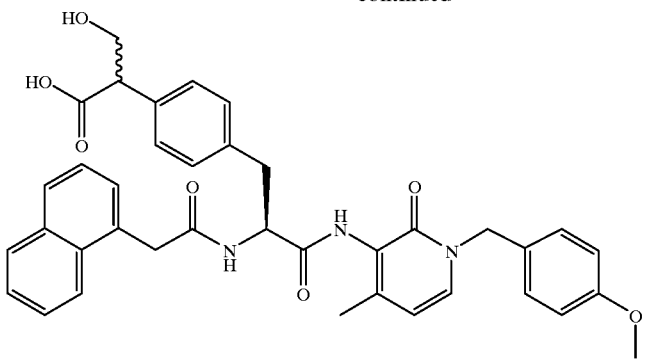

3-[2'-(S)-Benzyloxycarbonylamino-3'-[4"-(1'''-(R,S)-^tbutoxycarbonyl-2'''-trimethylsilylethyloxy)ethyl]benzene]propanoylamino-1-(4-methoxybenzyl)-4-methyl-2-pyridone.

To a solution of 2-(S)-benzyloxycarbonylamino-3-[4'-(1"-(R,S)-^tbutoxycarbonyl-2"-trimethylsilylethyloxy)ethyl]benzene]propanoic acid (0.91 g, 1.7 mmol) in methylene chloride (15 mL), cooled to 0° C., was added EDC (0.39 g, 2.0 mmol). After 15 minutes, 3-amino-1-(4-methoxybenzyl)-4-methyl-2-pyridone (0.40 g. 1.6 mmol) in methylene chloride (8 mL) was added. The mixture was allowed to warm to rt. and was stirred for 20 hours. The mixture was diluted with methylene chloride, washed with water, dried (MgSO$_4$), filtered and evaporated. Chromatography of the residue over silica gel (ethyl acetate/hexane 1/1) gave 3-[2'-(S)-benzyloxycarbonylamino-3'-[4"-(1'''-(R,S)-^tbutoxycarbonyl-2'''-trimethylsilylethyloxy)ethyl]benzene]propanoylamino-1-(4-methoxybenzyl)-4-methyl-2-pyridone (0.81 g, 1.1 mmol, 65%).

3-[2'-(S)-Amino-3'-[4"-(1'''-(R,S)-^tbutoxycarboxy-2'''-trimethylsilylethyloxy)ethyl]benzene]propanoylamino-1-(4-methoxybenzyl)-4-methyl-2-pyridone.

A mixture of 3-[2'-(S)-benzyloxycarbonylamino-3'-[4"-(1'''-(R,S)-^tbutoxycarboxy-2'''-trimethylsilylethyloxy)ethyl]benzene]propanoylamino-1-(4-methoxybenzyl)-4-methyl-2-pyridone (0.25 g, 0.33 mmol) and 10% Pd/C in ethyl acetate (20 mL) with acetic acid (5 drops) was hydrogenated overnight in a Parr apparatus. The mixture was filtered, washed with water, dried, filtered and evaporated. Chromatography of the residue over silica gel (methylene chloride/methanol 99/1 to 95/5) gave 3-[2'-(S)-amino-3'-[4"-(1'''-(R,S)-^tbutoxycarbonyl-2'''-trimethylsilylethyloxy)ethyl]benzene]propanoylamino-1-(4-methoxybenzyl)-4-methyl-2-pyridone (0.10 g, 0.15 mmol, 45%).

3-[2'-(S)-(1''''-Naphthylacetyl)amino-3'-[4"-(1'''-(R,S)-^tbutoxycarbonyl-2'''-trimethylsilylethyloxy)ethyl]benzene]propanoylamino-1-(4-methoxybenzyl)-4-methyl-2-pyridone.

This compound was obtained by EDC coupling of 3-[2'-(S)-amino-3'-[4"-(1'''-(R,S)-^tbutoxycarbonyl-2'''-trimethylsilylethyloxy)ethyl]benzene]propanoylamino-1-(4-methoxybenzyl)-4-methyl-2-pyridone with 1-naphthyl acetic acid.

3-[2'-(S)-(1''''-Naphthylacetyl)amino-3'-[4"-(1"-(R,S)-carboxy-2'''-hydroxy)ethyl benzene]propanoylamino-1-(4-methoxybenzyl)-4-methyl-2-pyridone.

A solution of 3-[2'-(S)-(1''''-naphthylacetyl)amino-3'-[4"-(1'''-(R,S)-^tbutoxycarboxy-2'''-trimethylsilylethyloxy)ethyl]benzene]propanoylamino-1-(4-methoxybenzyl)-4-methyl-2-pyridone (0.064 g. 0.10 mol) in trifluoroacetic acid (5 mL) was stirred at rt for 4 hours. The mixture was concentrated and resubjected to the same reaction conditions. Concentration and co-evaporation of the residue with ether several times gave 3-[2'-(S)-( 1'''-naphthylacetyl)amino-3'-[4"-(1'''-(R,S)-carboxy-2'''-hydroxy)ethyl]benzene]propanoylamino-1-(4-methoxybenzyl)-4-methyl-2-pyridone which crystallized from ethyl acetate/ether (0.003 g, 0.005 mmol, 5%).

3-[2-(S)-Benzyloxycarbonylamino-3-[4'-(1"-(R,S)-carboxy-2"-hydroxy)ethyl]benzene]propanoylamino-1-(4-methoxybentyl)-4-methyl-2-pyridone (Compound 50).

A solution of 3-[2'-(S)-benzyloxycarbonylamino-3'-[4"-(1'''-(R,S)-^tbutoxycarbonyl-2'-trimethylsilylethyloxy)ethylbenzene]propanoylamino-1-(4-methoxybenzyl)-4-methyl-2-pyridone (0.14 g, 0.19 mmol) in trifluoroacetic acid (10 mL) was stirred at rt for 4 hours. The mixture was concentrated and the residue was co-evaporated with ether several times. Trituration with ether gave -[2'-(S)-benzyloxycarbonylamino-3'-[4"-(1'''-(R,S)-carboxy-2'''-hydroxy)ethyl]benzene]propanoylamino-1-(4-methoxybenzyl)-4-methyl-2-pyridone (0.03 g, 0.05 mmol, 26%).

4-[2'-(R,S)-(2''''-Naphthylacetyl)amino-3'-[4"-(1'''-carboxy-1'''-methyl)ethyl]benzene]propanoylamino-2-(4-methoxybenzyl)-5-methyl-3-pyridazinone (Compound 242).

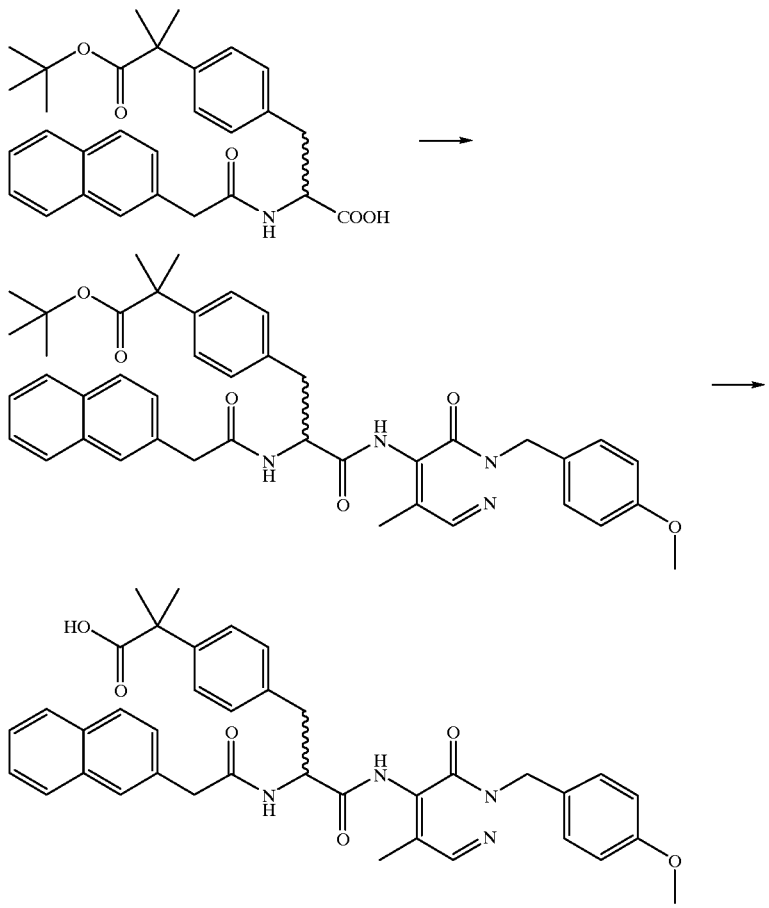

4-[2'-(R,S)-(2""-Naphthylacetyl)amino-3'-[4"-(1"'-'butoxycarbonyl-1"'-methyl)ethyl]benzene]propanoylamino-2-(4-methoxybenzyl)-5-methyl-3-pyridazinone.

To a stirred solution of 2-(R,S)-(2naphthylacetyl)amino -3-[4'-(1"-'butoxycarbonyl-1"-methyl)ethyl]benzenepropanoic acid (0.31 g, 0.66 mmol) in methylene chloride (5 mL) at rt was added dimethylformamide (3 drops) followed by oxalyl chloride (2 M in methylene chloride, 0.33 mL, 0.66 mmol). The mixture was stirred at rt for 1 hour. Triethylamine (0.13 mL), 4-amino-2-(4-methoxybenzyl)-5-methyl-3-pyridazinone (0.12 g, 0.47 mmol) and DMAP (0.005 g) were added. The mixture was stirred overnight at rt, and heated at reflux for 6 hours. The solvents were evaporated, and the residue was fractionated over silica gel (ethyl acetate/hexane 1/1) to give 4-[2'-(R,S)-(2""-naphthylacetyl)amino-3'-[4'¹-(1"'-'butoxycarbonyl-3'-methyl)ethyl]benzene]propanoylamino-2-(4-methoxybenzyl)-5-methyl-3'-pyridazinone (0.08 g, 0.11 mmol, 17%).

4-[2'-(R,S)-(2""-Naphthylacetyl)amino-3'-[4"-(1"'-carboxy-1"'-methyl)ethyl]benzene]propanoylamino-2-(4-methoxybenzyl)-5-methyl-3-pyridazinone.

A solution of 4-[2'-(R,S)-(2""-naphthylacetyl)amino-3'-[4"-(1"'-'butoxycarbonyl-1"'-methyl)ethyl]benzene]propanoylamino-2-(4-methoxybenzyl)-5-methyl-'-)-pyridazinone (0.06 g, 0.09 mmol) in trifluoroacetic acid (2.5 mL) was stirred at rt for 1.3 hours. The solvent was evaporated and the residue was co-evaporated with ether three times. Trituration with ethyl acetate gave 4-[2'-(R,S)-(2""-naphthylacetyl)amino-1"'-[4"-(1"'-carboxy-1"'-methyl)ethyl]benzene]propanoylamino-2-(4-methoxybenzyl)-5-3pyridazinone (0.03 g, 0.04 mmol, 44%).

Compound 238 was synthesized in an analogous manner. 3-[2-(S)-[[2'(S)-Methyl-2'-[4"-(2"'-methylpropyl)]phenyl]acetylamino]3'-amino]-3'-[4"-(1"'-carboxy-1"'-methyl)ethyl]benzene]propanoylamino-1-(4-methoxybenzyl)-4-methyl-2-pyridone (Compound 127).

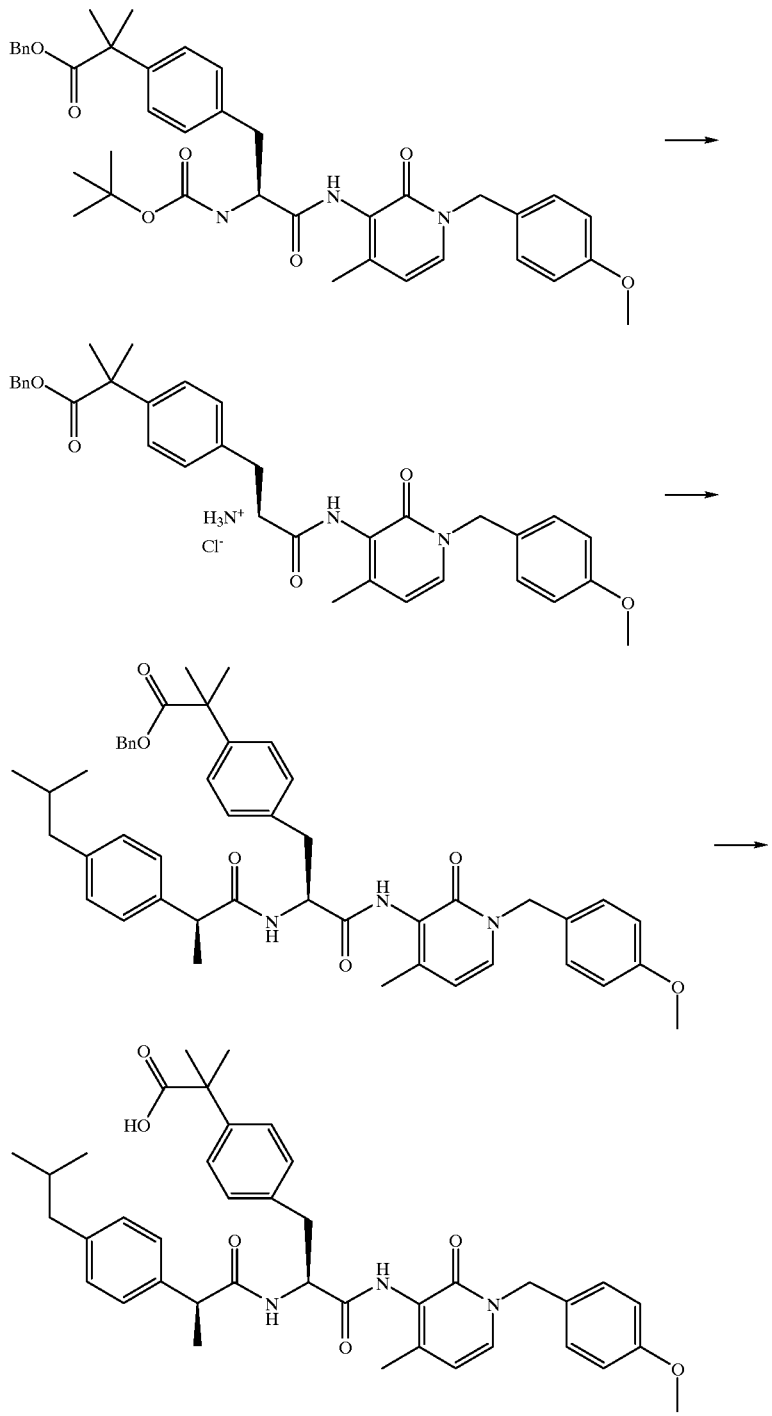

Hydrochloride salt of 3-[2-(S)-amino-3-[4'-(1"-benzyloxycarbonyl-1"-methyl)ethyl]benzene]propanoylamino-1-(4-methoxybenzyl)-4-methyl-2-pyridone.

3-[2'-(S)-ᵗButoxycarbonylamino-3'-[4"-(1'"-benzyloxycarbonyl-1'"-methyl)ethyl]benzene]propanoylamino-1-(4-methoxybenzyl)-4-methyl-2-pyridone (1 g, 1.5 mmol) was dissolved in HCl (4N) in dioxane (11.3 mL). After 30 minutes the mixture was evaporated to dryness to give the hydrochloride salt of 3-[2'-(S)-amino-3'-[4"-(1'"-benzyloxycarbonyl-1'"-methyl)ethyl]benzene]propanoylamino-1-(4-methoxybenzyl)-4-methyl-2-pyridone as a colorless solid.

3-[2'-(S)-[[2"(S)-Methyl-2"-[4'"-(2""-methylpropyl)]phenyl]acetylamino]-3'-[4"-(1'"-carboxy-1'"-methyl)ethyl]benzene]propanoylamino-1-(4-methoxybenzyl)-4-methyl-2-pyridone.

To a solution of 2-(S)-methyl-[4-(2-methylpropyl)]phenylacetic acid (0.031 g, 0. 15 mmol), TBTU (0.058 g, 0.18 mmol) and NMM (0.058 mL. 0.53 mmol) in acetonitrile (3 mL) was added the hydrochloride salt of 3-[2'-(S)-amino-3-1'"-[4(1'"-benzyloxycarbonyl-1'"-methyl)ethyl]

benzene]propanoylamino-1-(4-methoxybenzyl)-4-methyl-2-pyridone (0.091 g, 0.15 mmol). After 2 hours, ethyl acetate (30 mL) was added. The solution was washed with 10% citric acid, brine, dried (MgSO$_4$) and concentrated. 3-[2'-(S)-[[2"(S)-Methyl-2"-[4'"-(2""-methylpropyl)]phenyl] acetylamino]-'-[4"-(1'"-benzyloxycarbonyl-1'"-methyl) ethyl]benzene]propanoylamino-1-(4-methoxybenzyl)-4-methyl-2-pyridone was obtained as a clear oil (0.103 g, 0.135 mmol).

A mixture of 3-[2'-(S)-[[2"(S)-methyl-2"-[4'"-(2""-methylpropyl)]phenyl]acetylamino]-3'-[4"-(1'"-benzyloxycarbonyl-1'"-methyl)ethyl]benzene] propanoylamino-1-(4-methoxybenzyl)-4-methyl-2-pyridone (0.103 g, 0.135 mmol) and 10% Pd/C (0.010 g) in ethanol (4 mL) was stirred under hydrogen at 1 atmosphere for 20 hours. The catalyst was removed by filtration, and the solvent was evaporated to give 3-[2'-(S)-[[2"(S)-methyl-2"-[4'"-(2""-methylpropyl)]phenyl]acetylamino]-3'-[4"-(1'"-carboxy-1'"-methyl)ethyl]benzene]propanoylamino-1-(4-methoxybenzyl)-4-methyl-2-pyridone (0.019 g, 0.03 mmol, 20%) after purification by preparative HPLC.

Compounds 112, 113, 114, 117, 119, 126 and 133 were prepared in an analogous manner.

Compounds 108 and 124 were prepared in an analogous manner using 2-(R,S)-benzyloxycarbonylamino-3-[4'-(1"-$^t$butoxycarbonyl)cyclopentyl]benzenepropanoic acid as the starting material.

3-[2'-(S)-1(4""-Trifluoromethylphenyl)dimethylacelyl] amino-3'-[4"-(1'"-carboxy-1'"-methyl)ethyl]benzene] propanoylamino-5-bromo-1-(4-methoxybenzyl)-4-methyl-2-pyridone (Compound 227).

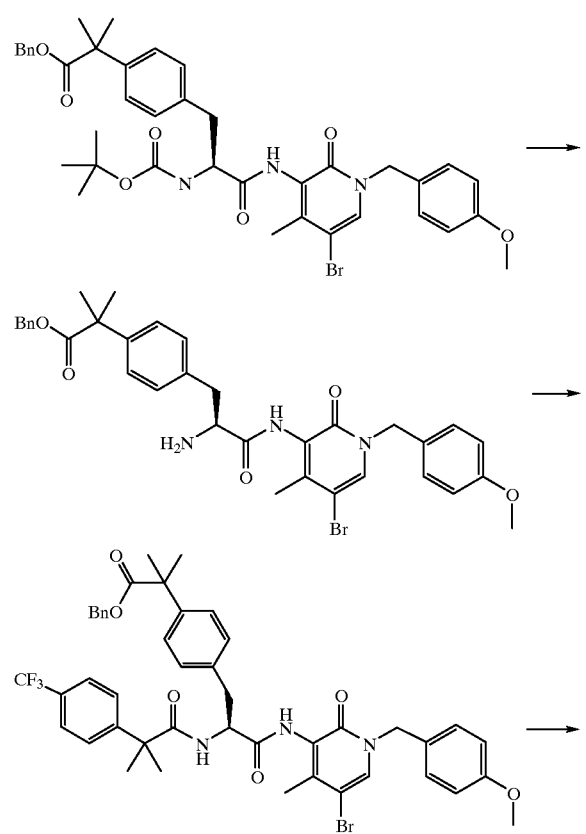

-continued

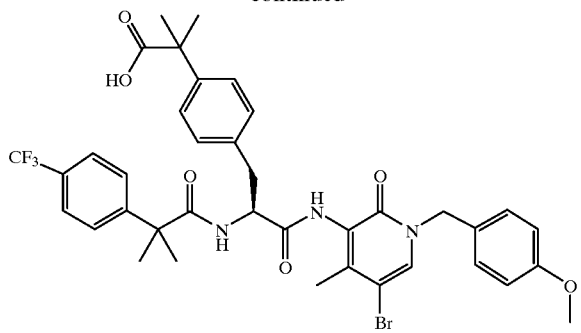

3-[2'-(S)-(4'"-Trifluoromethylphenyl)dimethylacetylamino-3'-[4"-(1'"-benzyloxycarbonyl-1'"-methyl)ethyl]benzene] propanoylamino-5-bromo-1-(4-methoxybenzyl)-4-methyl-2-pyridone.

A solution of 3'-[2'-(S)-$^t$butoxycarbonylamino-3'-[4"-('"-benzyloxycarbonyl-1'"-methyl)ethyl]benzene] propanoylamino-5-bromo-1-(4-methoxybenzyl)-4-methyl-2-pyridone (0.22 g, 0.3 mmol) in trifluoroacetic acid (5 mL) cooled on ice was left for 15 minutes. The solvent was evaporated, and the residue was taken up in methylene chloride (1 mL). Diisopropylethylamine (0.2 mL) was added and half of this reaction mixture was added to a solution of 4-trifluoromethylphenyldimethylacetic acid (0.3 mmol) and EDC (0.33 mmol) in methylene chloride (0.5 mL). The mixture was stirred at rt overnight. Chromatography of the reaction mixture over silica gel (2% to 5% isopropanol/methylene chloride) gave 3'[-2'-(S)-(4""-trifluoromethylphenyl)dimethylacetylamino-3'-[4"-(1'"-benzyloxycarbonyl-1'"-methyl)ethyl]benzene] propanoylamino-5-bromo-1-(4-methoxybenzyl)-4-methyl-2-pyridone (0.10 g).

3-[2'-(S)-(4""-Trifluoromethylphenyl)dimethylacetylamino-3'-[4"-(1'"-carboxy-1'"-methyl)ethyl]benzene] propanoylamino-5-bromo-1-(4-methoxybenzyl)-4-methyl-2-pyridone.

A mixture of 3-[2'-(S)-(4""-trifluoromethylphenyl) dimethylacetylamino-3'-[4"-(1'"-benzyloxycarbonyl-1'"-methyl)ethyl]benzene]propanoylamino-5-bromo-1-(4-methoxybenzyl)-4-methyl-2-pyridone (0.021 g) in 30% HBr/acetic acid (2 mL) was stirred at rt for 2 hours. The solvents were evaporated and the residue was triturated with ether. The residue was purified by preparative HPLC to give 3-[2'-(S)-(4""-trifluoromethylphenyl)dimethylacetylamino-3'-[4"-(1'"-carboxy-1'"-methyl)ethyl]benzene] propanoylamino-5-bromo-1-(4-methoxybenzyl)-4-methyl-2-pyridone (0.013 g, 0.017 mmol).

Compound 228 was prepared in an analogous manner.

3-[2'-(S)-(1"-Naphthylacetyl)amino-3'-[4'"-(1'"-carboxy-1'"-methyl)ethyl]benzene]propanoylamino-1-(4-methoxybenzyl)-4-methyl-2-pyridone (Compound 2).

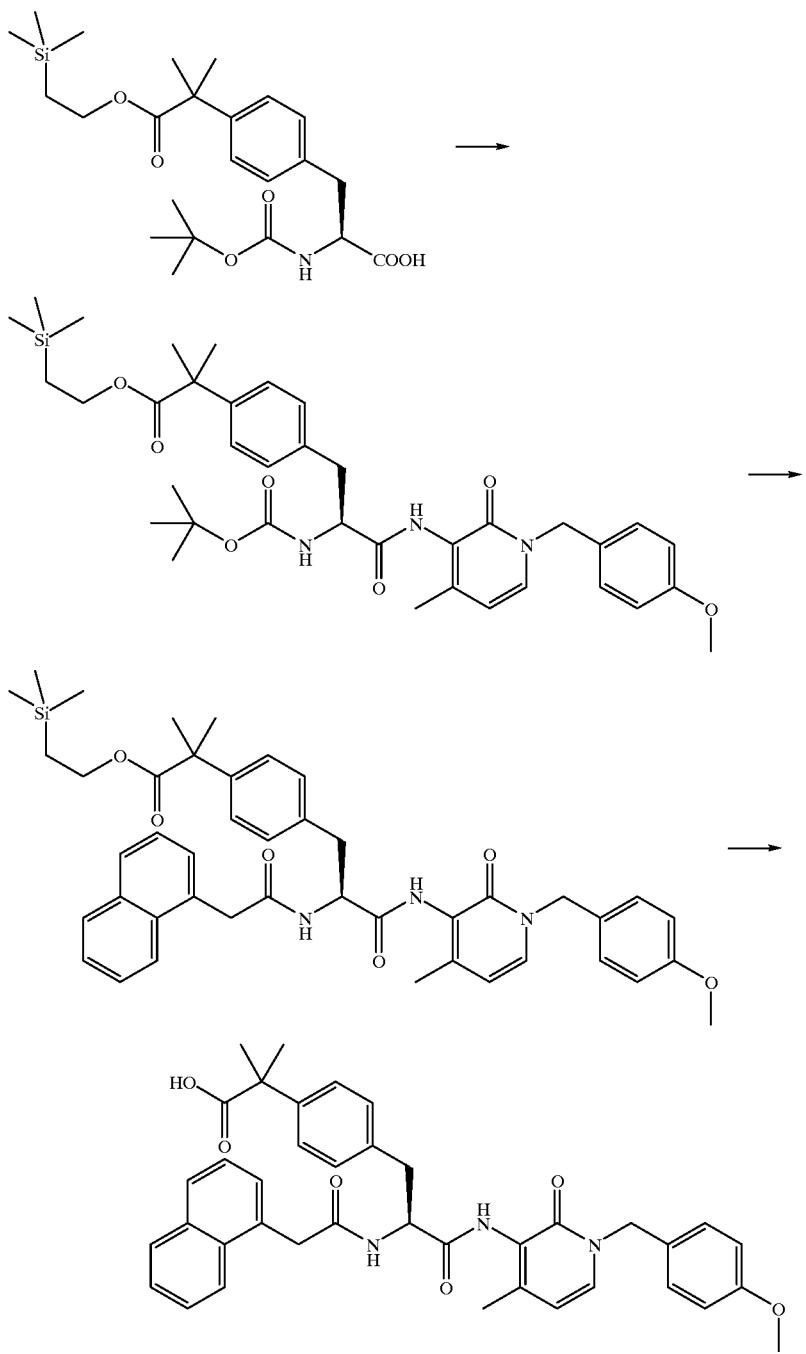

3-[2'-(S)-'Butoxycarbonylamino-3'-[4(1'"-trimethylsilylethyloxycarbonyl-1'"-(1-trimethylsilylethyloxycarbonyl-1'"-methyl)ethyl]benzene]propanoylamino-1-(4-methoxybenzyl)-4-methyl-2-pyridone.

To a solution of 2-(S)-'butoxycarbonylamino-3-[4'-(1"-trimethylsilylethyloxycarbonyl-1"-methyl)ethyl]benzenepropanoic acid (0.685 g, 1.52 mmol) in methylene chloride (5 mL) cooled to 0° C. was added EDC (0.408 g, 2.13 mmol) and 3-amino-1-(4-methoxybenzyl)-4-methyl-2-pyridone (0.371 g, 1.52 mmol). The mixture was warmed to rt, and stirred overnight. Ethyl acetate was added, and the organic phase was washed with 10% citric acid, NaHCO$_3$ and brine, dried (MgSO$_4$) and concentrated. Chromatography of the residue over silica gel (ethyl acetate/hexane 3/2) gave 3-[2'-(S)-'butoxycarbonylamino-3'-[4"-(1'"-trimethylsilylethyloxycarbonyl-1'"-methyl)ethyl]benzene]propanoylamino-1-(4-methoxybenzyl)-4-methyl-2-pyridone as an off-white solid (0.533 g, 52%). 3-[2'-(S)-(1""-Naphthylacetyl)amino-3'-[4"-(1'"-trimethylsilylethyloxycarbonyl-1'"-methyl)ethyl]benzene]propanoylamino-1-(4-methoxybenzyl)-4-methyl-2-pyridone.

3-[2'-(S)-'Butoxycarbonylamino-3'-[4"-(1'"-trimethylsilylethyloxycarbonyl-1'"-methyl)ethyl]benzene]propanoylamino-1-(4-methoxybenzyl)-4-methyl-2- pyridone (0.106 g, 0.15 mmol) was dissolved in 4N HCl/dioxane (4.6 mL). After 45 minutes the mixture was concentrated, and the amine hydrochloride salt was added to a solution of 1-naphthylacetic acid (0.029 g, 0.15 mmol), TBTU (0.060 g, 0.18 mmol), and NMM (0.060 mL, 0.54 mmol) in acetonitrile (4 mL). After 2 hours at rt, ethyl acetate was added and the organic phase was washed with 10% citric acid, aqueous NaHCO₃ and brine. The organic phase was dried and concentrated to give 3-[2'-(S)-(1'''-naphthylacetyl)amino-3'-[4"-(1'"-trimethylsilylethyloxycarbonyl-1'"-methyl)ethyl]benzene]propanoylamino-1-(4-methoxybenzyl)-4-methyl-2-pyridone as a yellow oil (0.124 100%).

3-[2'-(S)-(1'''-Naphthylacetyl)amino-3'-[4"-(1'"-carboxy-1'"-methyl)ethyl]benzene]-propanoylamino-1-(4-methoxybenzyl)-4-methyl-2-pyridone.

3-[2'-(S)-(''"-Naphthylacetyl)amino-3'-[4"-('"-trimethylsilylethyloxycarbonyl-1'"-methyl)ethyl]benzene]propanoylamino-1-(4-methoxybenzyl)-4-methyl-2-pyridone (0.124 g, 0.15 mmol) was treated with a solution of tetrabutylammonium fluoride in THF (1M, 0.24 mL). After stirring at rt for 1 hour, the solution was concentrated and taken up in ethyl acetate. The organic phase was washed with 10% citric acid and brine. The mixture was concentrated, and the residue was purified by prep HPLC to give 3-[2'-(S)-(1'"-naphthylacetyl)amino-3'-[4"-(1'"-carboxy-1'"-methyl)ethyl]benzene]propanoylamino-1-(4-methoxybenzyl)-4-methyl-2-pyridone as a colorless amorphous solid (0.030 g 0.04 mmol, 27%).

Compounds 44, 94, 97, 98, 100 and 101 were prepared in an analogous manner.

Compound 3 was prepared in an analogous manner using 2-(S)-('butoxycarbonylamino)-3-[4'-(1"-methyl-1"-trimethylsilylethyloxycarbonylmethyl)]benzenepropanoic acid.

Compounds 18, 19, 20, 21 and 41 were prepared in an analogous manner using 2-(S)-('butoxycarbonylamino)-3-[4'-(trimethylsilylethyloxycarbonylmethyl)benzene]propanoic acid.

3-[2'-(S)-(1'"-Naphthylacetyl)amino-3'-[4"-(1'"-hydroxy-1'"-carboxy)methyl]benzene]propanoylamino-1-(4-methoxybenzyl)-4-methyl-2-pyridone (Compound 8).

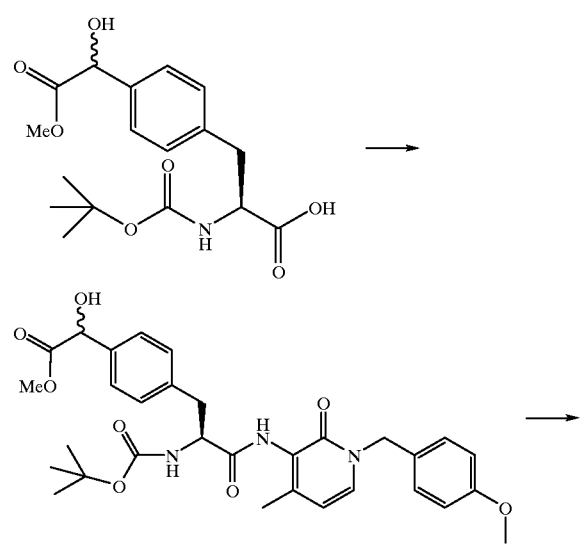

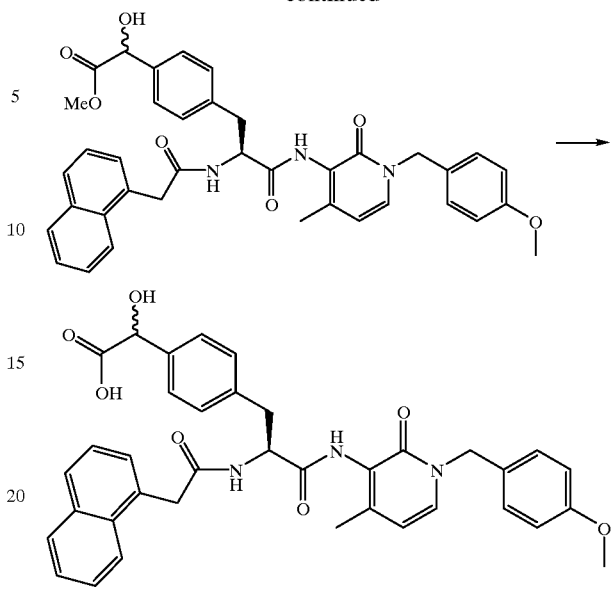

3-[2'-(S)-'Butoxycarbonylamino-3'-[4"-(1'"-hydroxy-1'"-methoxycarbonyl) methyl]benzene]propanoylamino-1-(4-methoxybenzyl)-4-methyl-2-pyridone.

To a solution of 2-(S)-'butoxycarbonylamino-3-[4'-(1'"-hydroxy-1'"-methoxycarbonyl)methyl]benzenepropanoic acid (0.74 mmol) in methylene chloride (10 mL) cooled on ice was added EDC (0.157 g, 0.82 mmol). The mixture was stirred for 15 minutes. 3-Amino-1-(4-methoxybenzyl)-4-methyl-2-pyridone (0.182 g, 0.794 mmol) in methylene chloride (5 mL) was added, and the mixture was stirred for 1 hour at 0° C. and for 20 hours at rt. Additional EDC (0.157 g, 0.82 mmol) was added, and the mixture stirred for 3 hours. Volatiles were removed under reduced pressure. The residue was taken up in ethyl acetate, and washed with water, cold 0.75N HCl and water, dried (MgSO₄), and evaporated. Chromatography of the residue over silica gel (ethyl acetate/hexane 7/3) gave 3-[2'-(S)-'butoxycarbonylamino-3'-[4"-(1'"-hydroxy-1'"-methoxycarbonyl)methyl]benzene]propanoylamino-1-(4-methoxybenzyl)-4-methyl-2-pyridone (0.130 g, 30%). 3-[2'-(S)-(1''"-Naphthylacetyl)amino-3'-[4"-(1'"-hydroxy-1'"-methoxycarbonyl)methyl]benzene] propanoylamino-1-(4-methoxybenzyl)-4-methyl-2-pyridone.

A solution of 3-[2'-(S)-3'butoxycarbonyl)amino-3'-[4"-(1'"-hydroxy-1'"-methoxycarbonyl)methyl]benzene] propanoylamino-1-(4-methoxybenzyl)-4-methyl-2-pyridone (0.130 g, 0.224 mmol) in cold trifluoroacetic acid/CH₁₂Cl₂ (3/2, 10 mL) was stirred for 30 minutes. Volatiles were removed in vacuo to leave the crude trifluoroacetate salt.

To a solution of 1-naphthylacetic acid (0.050 g, 0.269 mmol) in CH₂Cl₂/CH₃CN (1/1, 20 mL) was added TBTU (0.086 g, 0.27 mmol) and N-methylmorpholine (0.094 mL, 0.67 mmol), and the mixture stirred at rt for 15 minutes. The crude trifluoroacetate salt from above was added, and the mixture stirred at rt for 2 hours. Volatiles were removed under reduced pressure. The residue was taken up in ethyl acetate, washed with 5% NaHCO₃, 1N HCl and brine, dried (MgSO₄), and evaporated. Flash chromatography of the residue (ethyl acetate/hexane 9/1) gave 3-[2'-(S)-(1'"-naphthylacetyl)amino-3'-[4"-(1'"-hydroxy- 1'"-methoxycarbonyl)methyl]benzene]propanoylamino-1-(4-methoxybenzyl)-4-methyl-2-pyridone (0.050 g, 34%).

3-[2'-(S)-(1""-naphthylacetyl)amino-3'-[4"-(1'"-hydroxy-1'"-carboxy)methyl]benzene]propanoylamino-1-(4-methoxybenzyl)-4-methyl-2-pyridone.

To a stirred solution of 3-[2'-(S)-(1""-naphthylacetyl) amino-[4"-(1'"-hydroxy-1'"-methoxycarbonyl)methyl] benzene]propanoylamino-1-(4-methoxybenzyl)-4-methyl-2-pyridone (0.049 g, 0.077 mmol) in THF (10 mL) was added LiOH (1N in water, 0.23 mL, 0.23 mmol). After 3 hours, the mixture was acidified to pH 4 with 2N HCl, and the THF was removed under reduced pressure. The precipitate was collected, redissolved in THF (10 mL), and the solution filtered. Concentration and addition of water gave 3-[2'-(S)-(1""-naphthylacetyl)amino-3'-[4"-(1'"-hydroxy-1'"-carboxy)methyl]benzene]propanoylamino-1-(4-methoxybenzyl)-4-methyl-2-pyridone (0.039 g, 80% ) as a colorless solid.

3-[2'-(S)-(1'"-Naphthylacetyl)amino-3'-(4"-sulfonylmethyl) benzene]propanoylamino-1-(4-methoxybenzyl)-4-methyl-2-pyridone (Compound 42).

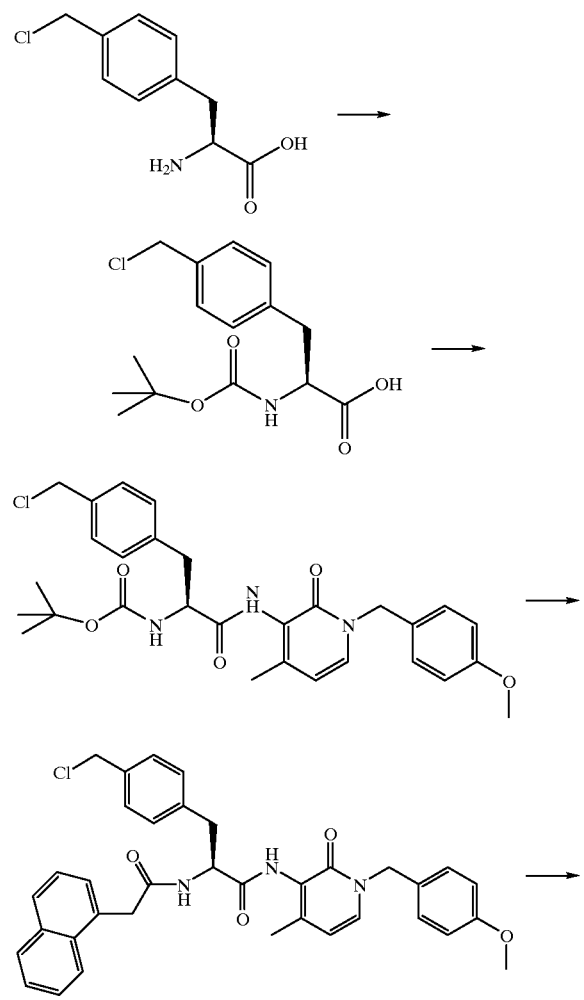

-continued

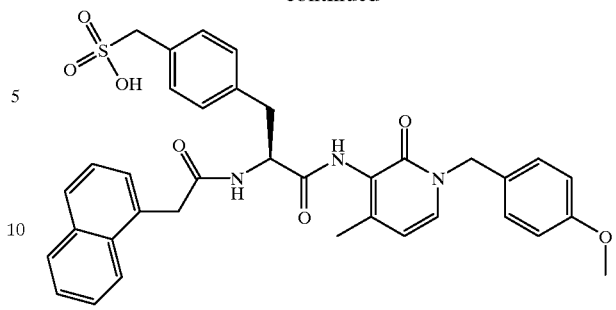

2-(S)-ᵗButoxycarbonylamino-3-(4-chloromethyl) benzenepropanoic Acid 2-(S)-Amino-'-(4'-chloromethyl)benzenepropanoic acid (*J. Med. Chem.*, 36, pps. 1681–1688 (1993)) (1.00 g, 4.0 mmol) was suspended in dioxane (10 mL), and $Na_2CO$ (0.425 g 4.00 mmol) and water (20 mL) were added. ᵗbutyldicarbonate (0.96 h , 4.4 mmol) in dioxane (10 mL) was added and the mixture stirred for 2 hours at rt. 1N HCl (20 mL) was added, and the product was extracted with ether (150 mL). The extract was washed with 1N HCl (25mL) and brine (25 mL), dried ($MgSO_4$) and evaporated to give 2-(S)-ᵗbutoxycarbonylamino-3-(4'chloromethyl) benzenepropanoic acid as a clear gum (0.985 g, 78%).

3-[2-(S)-ᵗButoxycarbonylamino-3-(4-chloromethyl) benzene]propanoylamino-1-(4-methoxybenzyl)-4-methyl-2-pyridone.

To a stirred mixture of 2(S)-ᵗbutoxycarbonylamino-3-(4'-chloromethyl)benzenepropanoic acid (0.420 g, 1.4 mmol) and 3-amino-1-(4-methoxybenzyl)-4-methyl-2-pyridone (0.327 g, 1.34 mmol) in DMF (10 mL) were added DIEA (0.47 mL, 2.68 mmol), 1-HOAt (0.182 g, 1.34 mmol) and HATU (0.509 g, 1.34 mmol). After 3 hours, the mixture was diluted with ether, and the organic phase was washed with 2.5N NaOH, 1N HCl and brine (25 mL), dried ($MgSO_4$) and evaporated. Flash chromatography of the residue over silica gel (ethyl acetate/hexane 3/1) gave 3-[2'-(S)-ᵗbutoxycarbonylamino-3'-(4"-chloromethyl)benzene] propanoylamino-1-(4-methoxybenzyl)-4-methyl-2-pyridone as a light brown foam (0.256 g, 35%).

3-[2'-(S)-(1'"-Naphthylacetyl)amino-3'-(4"-chloromethyl) benzene]propanoylamino-1-(4-methoxybenzyl)-4-methyl-2-pyridone A solution of 3-[2'-(S)-ᵗbutoxycarbonylamino-3'-(4"-chloromethyl)benzene]propanoylamino-1-(4-methoxybenzyl)-4-methyl-2-pyridone (0.234 g, 0.433 mmol) in 4N HCl/dioxane (10 mL) was stirred for 90 minutes. Volatiles were removed under reduced pressure, and the residue was co-evaporated with hexane to give 3-[2'-(S)-amino-3'-(4"-chloromethyl)benzene] propanoylamino-1-(4-methoxybenzyl)-4-methyl-2-pyridone hydrochloride salt as a yellow powder. The hydrochloride salt was dissolved in DMF (10 mL), and 1-naphthylacetic acid (0.081 g, 0.433 mmol), TBTU (0.139 g, 0.433 mmol) and NMM (0.285 mL,, 2.6 mmol) were added. After 90 minutes, ethyl acetate (100 mL) was added. The organic phase was washed with 2.5N NaOH, 1N HCl and brine (25 mL), dried ($MgSO_4$), and concentrated. Trituration of the residue with ether gave 3-[2'-(S)-(1'-naphthylacetyl)amino-3'-(4"-chloromethyl)benzene] propanoylamino-1-(4-methoxybenzyl)-4-methyl-2-pyridone (0.160 g, 60%) as a light yellow solid.

3-[2'-(S)-(1'''-Naphthylacetyl)amino-3'-(4''-sulfonylmethyl)benzene]propanoylamino-1-(4-methoxybenzyl)-4-methyl-2-pyridone.

To a solution of 3)-2'-(S)-(1'''-naphthylacetyl)amino-3'-(4''chloromethyl)benzene]propanoylamino-1-(4-methoxybenzyl)-4-methyl-2-pyridone (0.154 g, 0.25 mmol) in DMF (4 mL) was added sodium sulfite (0.200 g, 1.6 mmol). The mixture was stirred at rt, and water (5×0.5 mL) was added until cloudiness persisted. The mixture was heated to 70° C. and more water (1 mL) was added. After 15 minutes additional water (1.5 mL) was added, and the mixture was stirred and heated at 70° C. for 1 hour. After cooling to rt, 1N HCl (2 mL) was added followed by enough DMF (2 mL) to redissolve the precipitated material. The reaction mixture was subjected to preparative HPLC to give 3-[2'-(S)-(1'''-naphthylacetyl)amino-3'-(4''-sulfonylmethyl)benzene]propanoylamino-1-(4-methoxybenzyl)-4-methyl-2-pyridone as a colorless amorphous solid.

Synthesis of Oxamic Acids

3-[2-S)-(1'''-Naphthylacetyl)amino-3'-(4''-oxalylamino)benzene]propanoylamino-1-(4-methoxybenzyl)-4-methyl-2-pyridone (Compound 52).

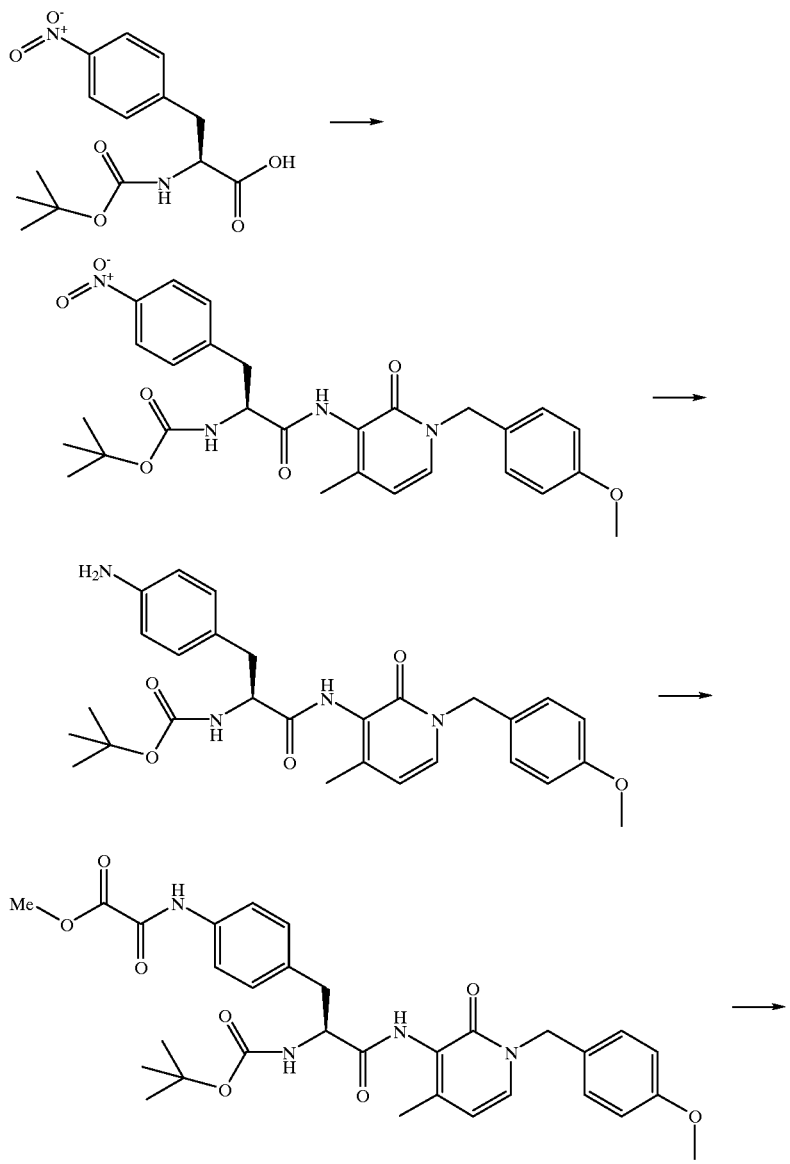

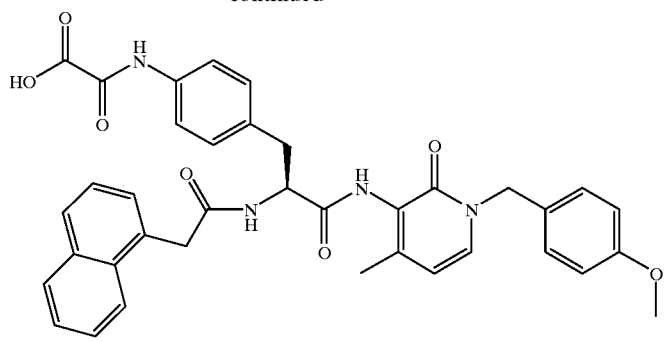

3-[2'-(S)-'Butoxycarbonylamino-3'-(4"-nitro)benzene]propanoylamino-1-(4-methoxybenzyl)-4-methyl-2-pyridone.

To a solution of 3-amino-1-(4-methoxybenzyl)-4-methyl-2-pyridone (5.03 g, 20.6 mmol), DIEA (3.76 mL, 21.6 mmol) and N-Boc-p-nitrophenylalanine (6.71 g, 21.6 mmol) in acetonitrile (100 mL) cooled on ice was added TBTU (7.94 g, 24.7 mmol). The mixture was stirred at rt overnight. Additional DIEA (3.76 mL, 21,6 mmol) was added, and the slurry was stirred for another 6 hours. 1N HCl (50 mL) was added, and the acetonitrile was removed under reduced pressure. Ethyl acetate (300 mL) was added, and the organic suspension was separated and washed with 1N HCl, 2.5N NaOH and brine. Ethyl acetate (50 mL) and THF (100 mL) were added to the suspension to dissolve all solids, and the organic phase was washed with brine, and dried (MgSO₄/silica gel/charcoal). Evaporation of the solvent gave 3-2'-(S)-'butoxycarbonylamino-3'-(4"-nitro)benzene]propanoylamino-1-(4-methoxybenzyl)-4-methyl-2-pyridone as a brown solid (9.73 g, 88%).

3-[2'-(S)-'Butoxycarbonylamino-3'-(4"-amino)benzene]propanoylamino-1-(4-methoxybenzyl)-4-methyl-2-pyridone.

A mixture of -[2'-(S)-'butoxycarbonylamino-3'-(4"-nitro)benzene]propanoylamino-1-(4-methoxybenzyl)-4-methyl-2-pyridone (4.79 g, 8.93 mmol) and 20% Pd(OH)₂/charcoal (0.50 g) in THF (100 mL) was hydrogenated at 1 atmosphere for 2 days. The catalyst was removed by filtration, and the solvent was evaporated to give 3-[2'-(S)-'butoxycarbonylamino-3'-(4"-aminobenzene]propanoylamino-1-(4-methoxybenzyl)-4-methyl-2-pyridone (4.89 g, 100%).

3-[2'-(S)-'Butoxycarbonylamino-3'-(4'-methyloxalyamino)benzene]propanoylamino-1-(4-methoxybenzyl)-4-methyl-2-pyridone.

To a mixture of 3-[2'-(S)-'butoxycarbonylamino-3'-(4"-amino)benzene]propanoylamino-1-(4-methoxybenzyl)-4-methyl-2-pyridone (8.93 mmol) and DIEA (1.56 mL, 8.93 mmol) in CH₂Cl₂ (100 mL), cooled on ice, was added methyloxalyl chloride (0.82 mL, 8.93 mmol) in CH₂Cl₂ (50 mL) over 30 minutes. The mixture was allowed to warm to rt, and stirred for 3 hours. The reaction mixture was washed with 1N HCl and brine, dried (MgSO₄), filtered and evaporated. Chromatography of the residue over silica gel (ethyl acetate/hexane 3/1) gave 3-[2'-(S)-'butoxycarbonylamino-3'-(4"-methyloxalylamino)benzene]propanoylamino-1-(4-methoxybenzyl)-4-methyl-2-pyridone as an orange solid (3.916 g, 75%).

3-[2'-(S)-Amino-3'-(4"-oxalylamino)benzene]propanoylamino-1-(4-methoxybenzyl)-4-methyl-2-pyridone hydrochloride salt.

3-[2'-(S)-('butoxycarbonyl)amino-1'-(4"-methyloxalylamino)benzene]propanoylamino-1-(4-methoxybenzyl)-4-methyl-2-pyridone (3.680 g, 6.21 mmol) was stirred with 4N HCl/dioxane (40 mL) for 1 hour. Volatiles were removed under reduced pressure to give the amine hydrochloride as an orange solid (3.52 g, >100%).

3-[2'-(S)-(1'''-Naphthylacetyl)amino-3'-(4"-oxalylamino)benzene]propanoylamino-1-(4-methoxybenzyl)-4-methyl-2-pyridone.

The crude hydrochloride salt from above (0.100 g, 0.189 mmol) was dissolved in DMF (3 mL). 1-Naphthylacetic acid (0.035 g, 0.189 mmol), DIEA (0.1 mL, 0.567 mmol) and TBTU (0.073 g, 0.227 mmol) were added, and the mixture stirred for 1 hour at rt. 1N NaOH (I mL) was added and the mixture stirred for 1 hour. 1N HCl was added, and the precipitate was collected and washed with water. The crude material was dissolved in DMF (3 mL), and 1N HCl (20 mL) was added dropwise. The slurry was stirred and sonicated for 1 hour. The solid was collected by filtration, washed with water and dried to give 3-[2'-(S)-(1'''-naphthylacetyl)amino-3'-(4"-oxalylamino)benzene]propanoylamino-1-(4-methoxybenzyl)-4-methyl-2-pyridone (0.082 g, 67%).

Compounds 4, 5, 6, 7, 9, 10, 11, 13, 14, 15, 16, 17, 22, 25, 27, 28, 29, 30, 31, 32, 33, 34, 35, 36, 37, 38, 39, 40, 43, 47, 48, 49, 102, 103, 104, 105, were obtained from 3-[2'-(S)-amino-3'-(4"-oxalylamino)benzene]propanoylamino-1-(4-methoxybenzyl)-4-methyl-2-pyridone hydrochloride salt above by reaction with the appropriate carboxylic acid. isocyanate or carbamoyl chloride and subsequent hydrolysis of the methyl ester also as described above.

3-[2'-(S)-(1'''-Naphthylacetyl)amino-3'-[4"-(N-oxalyl, N-hydroxy)amino]benzene]propanoylamino-1-(4-methoxybenzyl)-4-methyl-2-pyridone (Compound 1).

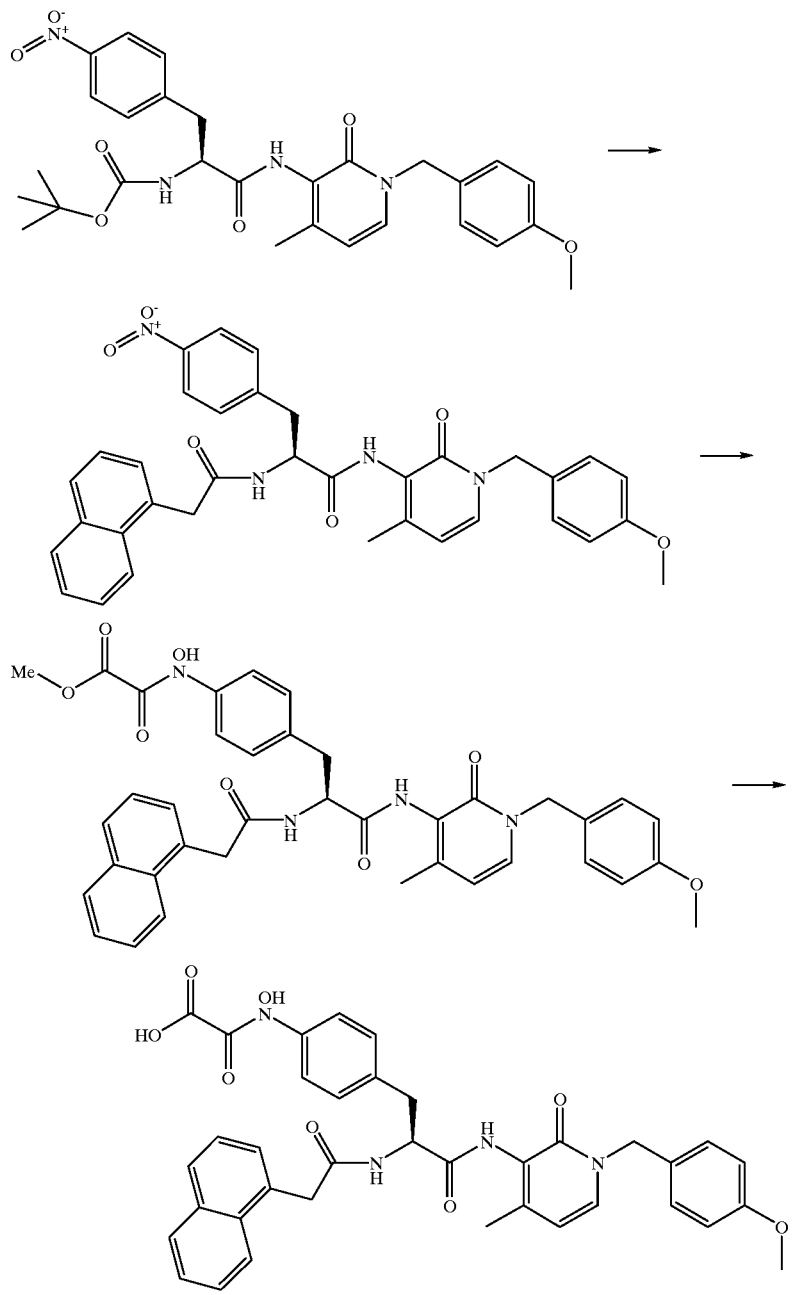

3-[2'-(S)-(1'''-Naphthylacetyl)amino-3'-(4''-nitro)benzene]propanoylamino-1-(4-methoxybenzyl)-4-methyl-2-pyridone.

3-[2'-(S)-'Butoxycarbonylamino-3'-(4''-nitro)benzene]propanoylamino-1-(4-methoxybenzyl)-4-methyl-2-pyridone (1.00 g, 1.86 mmol) was suspended in 4N HCl/dioxane (15 mL) and the mixture was stirred at rt for 1 hour. Volatiles were removed under reduced pressure to give the amine hydrochloride salt which was dissolved in dry DMF (10 mL). N-Methylmorpholine (0.7 ml. 7 mmol) and 1-naphthylacetic acid (0.349 g, 1.87 mmol) were added, followed by TBTU (0.61 g, 1.9 mmol). The mixture was stirred for 2 days at rt. 1N HCl (40 mL) was added, and after 1 hour the precipitate was collected by filtration and washed with water and ether. Drying in vacuo gave 3-[2'-(S)-(1'''-naphthylacetyl)amino-3'-(4''-nitro)benzene]propanoylamino-1-(4-methoxybenzyl)-4-methyl-2-pyridone as a tan-colored solid (0.810 g, 72%).

3-[2'-(S)-(1'''-Naphthylacetyl)amino-3'-[4''-(N-methyloxalyl, N-hydroxy)amino]benzene]propanoylamino-1-(4-methoxybenzyl)-4-methyl-2-pyridone.

Aluminum foil (1 cm$^2$) was stirred for 5 minutes in 3% aqueous HgCl$_2$ (50 mL). The resulting amalgam was washed with MeOH and THF, and used immediately. To a solution of 3-[2'-(S)-(1-naphthylacetyl)amino-3'-(4''-nitro)benzene]propanoylamino-1-(4-methoxybenzyl)-4-methyl-2-pyridone (0.100 g, 0.165 mmol) in THF/water 10/1 (10 mL), cooled in an ice-salt bath, was added aluminum amalgam prepared as above (0.200 g). After 2 hours, the mixture was filtered though celite using THF for washings. The filtrate was cooled in ice, and solid NaHCO₃ (0.100 g, 1.19 mmol) was added followed by methyloxalyl chloride (0.060 g, 0.5 mmol). After stirring for 1 hour at −5° C., water (20 mL) was added, and the mixture was extracted 3 times with methylene chloride. The combined organic phase was washed with brine, dried (MgSO₄), and concentrated to give 3-[2'-(S)-(1'''-naphthylacetyl)amino-3'-[4"-(N-methyloxalyl, N-hydroxy)amino]benzene]propanoylamino-1-(4-methoxybenzyl)-4-methyl-2-pyridone (0.070 g, 71%).

3-[2'-(S)-(1'''-Naphthylacetyl)amino-3'-[4"-(N-oxalyl, N-hydroxy)amino]benzene]propanoylamino-1-(4-methoxybenzyl)-4-methyl-2-pyridone.

3-[2'-(S)-('''-Naphthylacetyl)amino-1'-[4"-(N-methyloxalyl-N-hydroxy)amino]benzene]propanoylamino-1-(4-methoxybenzyl)-4-methyl-2-pyridone (0.065 g. 0.11 mmol) was dissolved in THF/water 2/1 (10 mL) and 5% aqueous NaOH (0.5 mL) was added. After stirring for 75 minutes at rt, the solution was acidified with 2N HCl and volatiles removed under vacuo. The residue was dissolved in DMF-water (5 mL+1 mL) and purified by preparative HPLC) to give 3-[2'-(S)-(1'''-naphthylacetyl)amino-3'-[4"-(N-oxalyl,-N-hydroxy)amino]benzene]propanoylamino-1-(4-methoxybenzyl)-4-methyl-2-pyridone was obtained as a white amorphous solid (0.035 g, 48%).

Compounds 24, 26, 95 and 96 were synthesized in an analogous manner.

3-[2'-(S)-(2''''-Naphthylacetyl)amino-3'-[4"-(4''',5'''-dicarboxytriazolyl)]benzene]propanoylamino-1-(4-methoxybenzyl)-5-bromo-4-methyl-2-pyridone (Compound 241).

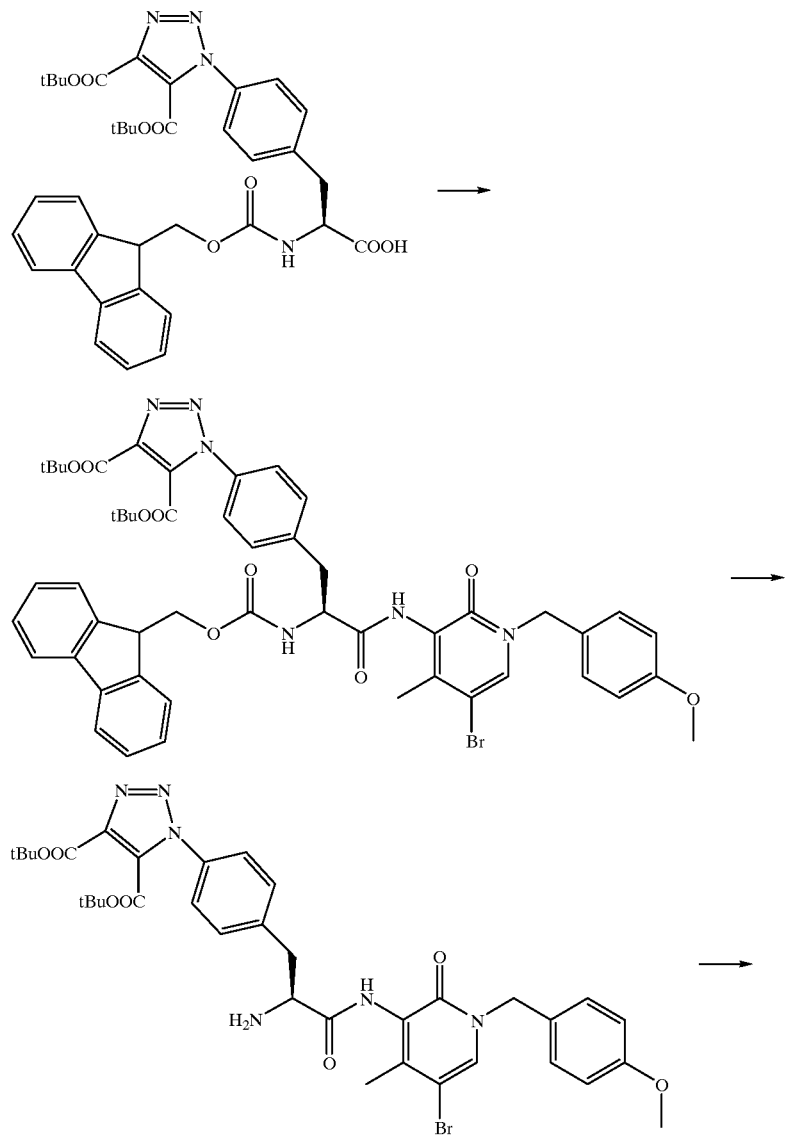

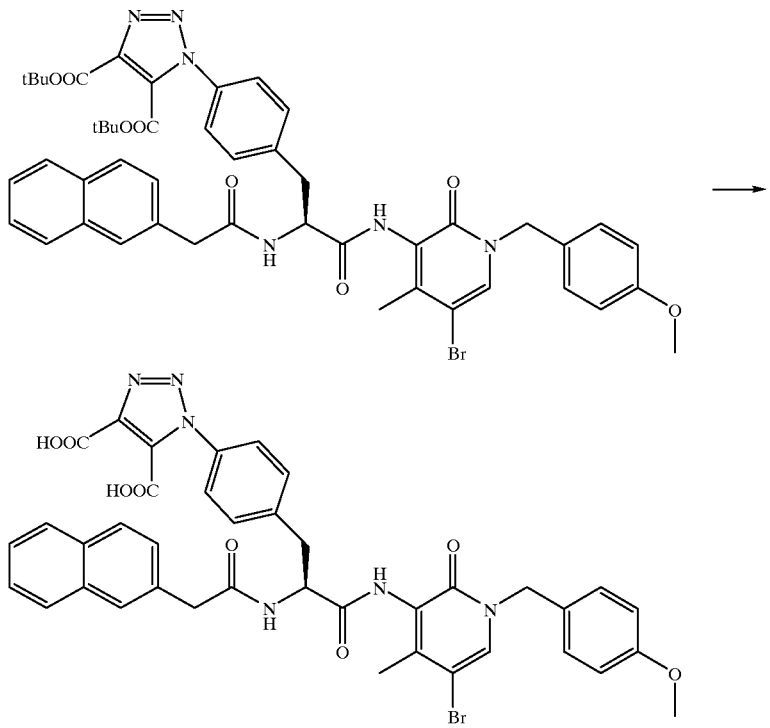

3-[2'-(S)-Fluorenylmethoxycarbonylamino-3'-[4"-(4'",5'"-di-'butoxycarbonyltriazolyl)]benzene]propanoylamino-1-(4-methoxybenzyl)-5-bromo-4-methyl-2-pyridone.

To 2-(S)-fluorenylmethoxycarbonylamino-3-[4'-(4",5"-di-'butoxycarbonyltriazolyl)]benzenepropanoic acid (0.578 g, 0.884 mmol) in methylene chloride (2 mL) at 0° C. was added EDC (0.186 g). The mixture was stirred at 0° C. for 15 minutes, and 1-(4-methoxybenzyl)-5-bromo-4-methyl-3-amino-2-pyridone (0.411 g, 1.28 mmol) was added. The mixture was stirred, warming to rt, for 2.5 hours. The mixture was fractionated directly over silica gel (ethyl acetate/hexane 1/3 to (ethyl acetate/hexane 1/1) to give 3-[2'-(S)-fluorenylmethoxycarbonylamino-3'-[4"-(4'",5'"-di-'butoxycarbonyltriazolyl)]benzene]propanoylamino-1-(4-methoxybenzyl)-5-bromo-4-methyl-2-pyridone (0.568 g, 0.592 mmol, 67%).

3-[2'-(S)-Amino-3'-[4"-(4'",5'"-di-'butoxycarbonyltriazolyl)]benzene]propanoylamino-1-(4-methoxybenzyl)-5-bromo-4-methyl-2-pyridone.

A mixture of 3-[2'-(S)-fluorenylmethoxycarbonylamino-3'-[4'"-(4'",5'"-di-'butoxycarbonyltriazolyl)]benzene]propanoylamino-1-(4-methoxybenzyl)-5-bromo-4-methyl-2-pyridone (0.272 g, 0.284 mmol) and ethanolamine (1 mL) in tetrahydrofuran (1 mL) was heated at 40° C. for 5 minutes. The mixture was diluted with ethyl acetate, washed with water, dried, filtered, and evaporated. Chromatography of the residue over silica gel (methylene chloride/methanol 99.5/0.5 to 97/3 gradient) gave 3-[2'-(S)-amino-3'-[4"-(4'", 5'"-di-'butoxycarbonyltriazolyl)]benzene]propanoylamino-1-(4-methoxybenzyl)-5-bromo-4-methyl-2-pyridone.(0.152 g, 0.206 mmol, 73%).

3-[2'-(S)-(2""-Naphthylacetyl)amino-3'-[4"-(4'",5'"-dicarboxytriazolyl)]benzene]propanoylamino-1-(4-methoxybenzyl)-5-bromo-4-methyl-2-pyridone.

To a solution of 2-naphthylacetic acid (0.035 g, 0.19 mmol) in methylene chloride (1 mL) cooled to 0° C. was added EDC (0.037 g). The mixture was stirred at 0° C. for 15 minutes, and 3-[2'-(S)-amino-3'-[4"-(4'",5'"-di-'butoxycarbonyltriazolyl)]benzene]propanoylamino-1-(4-methoxybenzyl)-5-bromo-4-methyl-2-pyridone (0.076 g, 0.10 mmol) in methylene chloride (1 mL) was added. After 1 hour, the mixture was fractionated directly over silica gel to give 3-[2'-(R,S)-(2""-naphthylacetyl)amino-3'-[4"-(4'", 5'"-di-'butoxycarbonyltriazolyl)]benzene]propanoylamino-5-bromo-1-(4-methoxybenzyl)-4-methyl-2-pyridone (0.081 g). This product was dissolved in methylene chloride (1 mL) and trifluoroacetic acid (1 mL). After 2 hours the solvents were evaporated and the residue was triturated with ether to give 3-[2'-(S)-(2""-naphthylacetyl)amino-3'"-[4"-(4'",5'"-dicarboxytriazolyl)]benzene]propanoylamino-1-(4-methoxybenzyl)-5-bromo-4-methyl-2-pyridone (0.046 g, 0.058 mmol, 31%).

As can be appreciated by chemists possessing ordinary skill in the art, the synthetic schemes described above are for illustrative purposes only and may be modified using conventional synthetic methodology to produce any compound of formula (I), (II), (III), (IV) or (V). Depending on precisely how the synthetic schemes are modified, the specific reaction conditions might also require modification. Such modifications may, for instance, involve the use of higher or lower temperature or pressure conditions than those reported herein or the addition of further synthetic steps, such as functional group transformations. However, since progress of the reactions is easily monitored by techniques such as high performance liquid chromatography, gas chromatography, mass spectroscopy, thin layer chromatography, nuclear magnetic resonance spectroscopy and the like, such modifications are well within the skill of the art.

Biological Methods and Materials

The general methods for the determination of Receptor-Ligand Kinetic and Equilibrium Binding Constants using Surface Plasmon Resonance as applied to the lck SH2 Domain have been described in: M. M. Morelock, R. H. Ingraham, R. Betageri. S. Jakes, *J. Med. Chem.*, 38, pps.1309–1318 (1995).

General Biosensor Methods.

The mobile phase buffer, 10 mM HEPES, pH 7.4, 150 mM NaCl, and 0.05% P-20, was maintained at a flow rate of 5 µL/min in all experiments. All buffers and protein solutions were filtered through a 0.2 um filter and degassed immediately before use.

Surface Preparation.

Strepavidin was diluted to 0.25 mg/ml in 20 mM NaOAc buffer, pH 4.5 and immobilized by free amine coupling to approximately 3000 RU for all 4 flow cells from a single sensor chip. For direct binding Kd determinations, to a 2500 RU strepavidin surface 15 µL of 20 nM biotin-E-aminohexanoic acid-EPQpYEEIPIA was injected. This amount of peptide provided a surface which bound a maximum of 500 RU of p56lck GST-SH2 domain.

Surface Kd Determinations.

p56lck GST-SH2 was titrated over this surface from 100 to 0.31 nM with either a single injection or back to back injections (kinjection) in order to reach equilibrium. The surface was regenerated by 4µL of 20 mM HCl followed by 4 µL of 150 mM Tris base. The values used in the analysis were the equilibrium plateau values from which the sample refractive index has been subtracted. For the data analyzed for linear function the equilibrium plateau values without the sample refractive index subtracted were used. Free solution Kd determinations. In a 96 well microtiter plate 20 nM SH2 domain suspended in running buffer containing 0.2 mg/ml BSA and 1 mM DTT was distributed in 100 µL per well. The highest concentration of compound tested was added to the last well and titrated with 2 fold dilutions for a final of 10 concentrations to be run. 25 µL of the mixture was injected over a strepavidin-biotin-ε-aminohexanoic acid-EGQpYEEIPIA surface and regenerated with 4 µL of 20 mM HCl. 25 pi, of 150 mM Tris base was injected after every 11 samples. Typically 8 assays were run in an overnight programmed run.

Summary of Primary T Cell Assay.

Inhibitors of the lck SH2 domain were assayed for their ability to block Inter-leukin 2 (IL-2) production by activated Human Primary T Lymphocytes. Peripheral blood mononuclear cells were isolated from whole blood by centrifugation in ficoll-Pague partitioning medium. CD4 positive cells were purified using negative selection. The isolated cells were plated at $2 \times 10^5$ cells/well in RPMI 1640 medium supplemented with 1.25 mg/mL bovine serum albumen, 240 nM ferric nitrate, 150 nM transferrin, 18 uM linoleic acid, 80 nM sodium selenite, non-essential amino acid solution, 1 mM sodium pyruvate, 100 u/mL penicillin sodium, 100 u/mL streptomycin sulfate and 2 mM L-glutamine in 96 well flat-bottom plates. The compounds, at the appropriate dilutions, were added, and the cells were incubated for 60 minutes at 37° C. The CD4 positive T cells were then activated by the addition of anti-CD3 (60 ng/mL), anti CD28 (500 ng/mL) and goat anti mouse IgG coated beads, and incubated overnight at 37° C. The cells were pelleted, and the supernatents assayed for IL-2 by ELISA.

Discussion and Demonstration of Activity

Regulation of intracellular metabolic pathways through covalent modification of protein intermediates and enzymes by serine and threonine phosphorylation is a process that has been recognized since the 1930's. It is now understood that protein phosphorylation is the primary means by which cells regulate intracellular metabolism in response extracellular stimuli. This may include environmental stimuli, such as heat, light and stress, cell to cell signaling, such as neurotransmitters and hormones, as well as pharmacological agents. In the early 1980's, an additional form of protein phosphorylation was discovered in which the phosphorylation was directed toward tyrosine residues. Because the first enzymes recognized to perform this phosphorylation were the viral oncogene v-src and the insulin receptor, a mitogenic hormone receptor, the implication was that phosphorylation of proteins on tyrosine appeared to be related to cell growth and transformation. This has been confirmed as the known members of the family of tyrosine kinases and phosphatases has greatly expanded since their discovery. Tyrosine phosphorylation is now known to control nearly every aspect of cellular growth and proliferation, from hormone and antigen induced gene transcription to cell cycle control.

As tyrosine phosphorylation became recognized as a general signaling mechanism research has moved toward understanding the mechanisms of cellular responses to tyrosine phosphorylation. The initial search focused on tyrosine kinase substrates with the assumption that, as receptor tyrosine kinases became activated by hormone binding, second messenger proteins should become phosphorylated, and amplify the response. While a small number of proteins were observed to be transiently tyrosine phosphorylated in response to hormone activation, the magnitude of the mitogenic responses were difficult to explain given the signal amplification models operative for serine and threonine phosphorylation. With the discovery of SH2 domains, the mechanisms of tyrosine phosphorylation became clearer. Rather than amplifying the signal through phosphorylation of a large number of second messenger proteins, the goal of the activated receptor tyrosine kinase is to assemble proteins in an SH2 domain dependent manner into an activation complex around the receptor itself. This often involves "switch kinases" which are activated by tyrosine phosphorylation but are themselves serine/threonine kinases, thereby converting the signal from tyrosine kinases to serine/threonine kinases. Without the SH2 domain on the proteins in the activation complex, the activated receptor tyrosine kinase would be completely ineffective and unable to activate the cell.

Given the dependence on SH2 domains for tyrosine kinase signaling and the observed specificity of the different SH2 domains in a wide variety of signaling pathways, they are excellent candidates for therapeutic targets. Compounds which antagonize the specific SH2 domains of signaling proteins will likely be effective against a large number of diseases related to cellular proliferation (including oncology and autoimmunity).

As SH2 domain containing proteins are intracellular, any therapeutic agent must be able to cross biological membranes. Therefore, the major obstacle to overcome for an effective therapeutic agent is the ability of the compounds to be effective in cell culture. One goal of the synthetic effort detailed hereinabove has been to obtain compounds which possess cell permeability and activity in cell culture. These characteristics may be quantified by observing inhibition in IL-2 production in human blood CD4 positive T-lymphocytes after T cell receptor and CD28 cross-linking. The data set forth in Table 5 illustrate the effectiveness of the compounds of this invention in blocking IL-2 production:

TABLE 5

| Compound | IC50* (uM) | Compound | IC50* (uM) | Compound | IC50* (uM) |
|---|---|---|---|---|---|
|  |  | 135 | 35 | 179 | 106 |
| 2 | 96 | 137 | 75 | 180 | 82 |
| 94 | 156 | 138 | 64 | 182 | 64 |
| 46 | 58 | 139 | 56 | 183 | 71 |
| 97 | 113 | 140 | 82 | 184 | 53 |
| 106 | 82 | 141 | 49 | 186 | 41 |
| 107 | 48 | 142 | 94 | 187 | 52 |
| 108 | 69 | 145 | 56 | 192 | 169 |
| 109 | 78 | 242 | 60 | 194 | 84 |
| 111 | 64 | 149 | 54 | 195 | 63 |
| 112 | 60 | 150 | 60 | 196 | 29 |
| 117 | 108 | 151 | 67 | 200 | 87 |
| 118 | 61 | 154 | 45 | 205 | 136 |
| 119 | 52 | 155 | 76 | 208 | 279 |
| 123 | 35 | 156 | 46 | 209 | 92 |
| 124 | 42 | 158 | 75 | 213 | 166 |
| 125 | 29 | 159 | 25 | 214 | 117 |
| 126 | 39 | 231 | 57 | 215 | 36 |
| 127 | 52 | 169 | 116 | 216 | 193 |
| 128 | 207 | 172 | 96 | 217 | 70 |
| 129 | 107 | 173 | 93 | 218 | 90 |
| 130 | 181 | 174 | 67 | 219 | 70 |
| 132 | 141 | 175 | 108 | 220 | 31 |
| 133 | 112 | 178 | 65 | 222 | 69 |

*Mean IC50 value

As demonstrated by the data in Table 5, the compounds of this invention effectively block IL-2 production. By inhibiting IL-2 production, these compounds will be immunosuppressive agents. More specifically, the compounds of formulas (I)–(V) target the SH2 domain of particular regulatory proteins, and in particular, tyrosine kinases having one or more SH2 domains. The compounds of this invention inhibit the physical association of the SH2 domain of these regulatory proteins and their native ligands. Because this physical interaction is needed for normal signal transduction, the compounds of this invention are capable of modulating signal transduction pathways as immunosuppressant agents. Without wishing to be bound by theory, it is believed that the result of such suppressed immunity includes reduction in the following processes; immunoglobulin synthesis, T-cell activation, cell proliferation of peripheral blood lymphocytes, cellular immune response and proliferation of T- and B-lymphocytes without serious toxicity or undesired side effects. Thus., the disruption of the interaction between the SH2 domain of regulatory proteins and their native ligands is an attractive means for preventing and treating, and preventing, a variety of disorders associated with SH2 binding interactions, such as neoplastic diseases and chronic inflammatory diseases. Representative neoplastic diseases include (but are not limited to): leukemias (including, but not limited to, acute lymphocytic, acute lymphoblastic, chronic lymphocytic, acute myeloblastic and chronic myelocytic), carcinomas (including, but not limited to, adenocarcinoma and that of the colon, ovaries, cervix, esophagus, stomach, small intestines, pancreas and lungs), sarcomas (including, but not limited to oesteroma, osteosarcoma, lepoma, liposarcoma, hemangionma, hemangiosarcoma and Kaposi's sarcoma), malignant melanomas (including, but not limited to, amelanotic and melanotic), mixed types of neoplasias (such as, but not limited to, carcinosarcoma, lymphoid tissue type, follicular reticulum, cell sarcoma and Hodgkin's disease), neuroblastoma, cerebral malaria, capillary leak syndrome, hematological malignancies and the like. Representative chronic inflammatory diseases include (but are not limited to): rheumatoid arthritis, multiple sclerosis, Guillain-Barre syndrome, Crohn's disease, ulcerative colitis, psoriasis, graft versus host disease, lupus erythematosus and insulin-dependent diabetes mellitus. Other disorders associated with SH2 domain binding interactions will be evident to those of ordinary skill in the art.

The compounds of this invention may be administered in any conventional dosage form in any conventional manner. Such methods of treatment, including their dosage levels and other requirements, may be selected by those of ordinary skill in the art from available methods and techniques. For example, a compound of this invention may be combined with a pharmaceutically acceptable carrier or adjuvant for administration to a patient in need of such treatment in a pharmaceutically acceptable manner and in an amount effective to treat (including lessening the severity of symptoms) the immune disorder.

The compounds of this invention may be administered alone or in combination with conventional therapeutics, such as conventional immunosuppressants. Advantageously, such combination therapies utilize lower dosages of the conventional therapeutics, thus avoiding possible toxicity and adverse side effects incurred when those agents are used as monotherapies. The compounds of this invention may be physically combined with the conventional therapeutics into a single pharmaceutical composition. Advantageously, the compounds may then be administered together in a single dosage form. Preferably, the pharmaceutical compositions comprising such combinations of compounds contain at least about 15%, but more preferably at least about 20%, of a compound of formula (I) (w/w). Alternatively, the compounds may be administered separately (either serially or in parallel). Separate dosing allows for greater flexibility in the dosing regime.

According to this invention, the compounds of formula (I)–(V) and the pharmaceutical compositions containing those compounds may be administered to a patient in any conventional manner and in any pharmaceutically acceptable dosage from, including, but not limited to, intravenously, intramuscularly, subcutaneously, intrasynovially, by infusion, sublingually, transdermally, orally, topically or by inhalation. The preferred modes of administration are oral and intravenous.

Dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical Dosage Forms and Drug Delivery Systems, 5th ed., Lea and Febiger (1990)). Dosage levels and requirements are well-recognized in the art and may be selected by those of ordinary skill in the art from available methods and techniques suitable for a particular patient. Typically, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto and the judgment of the treating physician.

The foregoing examples demonstrate production and use of the compounds of this invention. These examples have been included for the purpose of illustrating specific and preferred embodiments of this invention, and are not to be construed as limiting the scope of the invention in any way.

While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments that have been presented herein by way of example.

All information cited hereinabove, including all scientific publications, is hereby incorporated by reference in its entirety.

We claim:
1. A compound of formula (I):

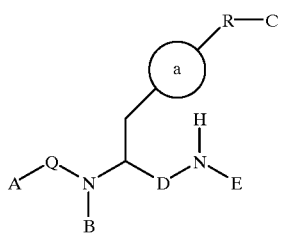

(I)

wherein:

Ring a is aryl;

A is heterocyclyl selected from the group consisting of pyridyl, pyrrolyl, pyrrolinyl, pyrazolyl, piperidinyl, oxopiperidinyl, oxopyrroldinyl and the benzofused derivatives thereof optionally linked to Q or N via an alkoxy, —O—, amino, lower alkyl, lower alkyl amino, carbonyl, amido, amido alkyl, alkoxycarbonyl, carbonylalkyloxy, cycloalkyl or heterocyclyl as defined in this paragraph;

Q is >C=O;
B is H;
R is a bond;
C is —C(CH3)$_2$—COOH or —NHCOCOOH;
D is >C=O;
E is

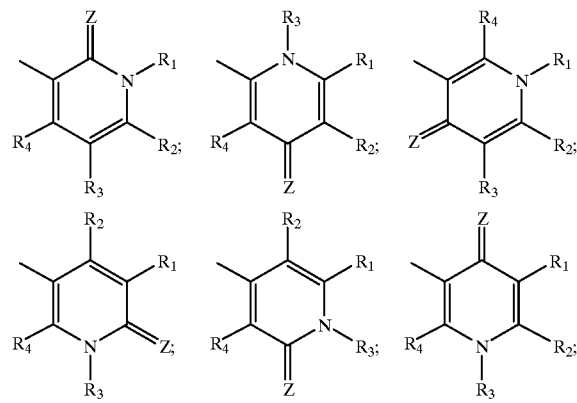

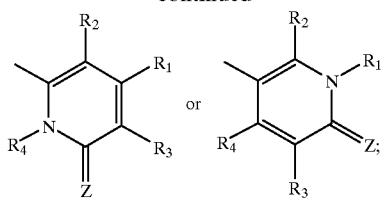

$R_1$ is aryl optionally be linked to the adjacent N or C via a lower alkyl, $R_2$ and $R_3$ are each independently selected from the group consisting of H or alkyl; wherein $R_2$ and $R_3$ are the same or different;

$R_4$ is alkyl;

wherein any two substituents $R_1$–$R_4$, when present in adjacent positions on heterocycle E, may be linked together to form a fused 6-membered carbocyclic ring which may be aromatic, partially unsaturated or fully saturated;

Z is O; S; NH; N-lower alkyl; or N-nitrogen-protecting group;

and the pharmaceutically acceptable tautomers, salts and esters thereof.

2. The compound according to claim 1, wherein:

A is optionally linked to the adjacent carbonyl via an alkoxy, lower alkyl; amido or amido alkyl;

E is a group of formula

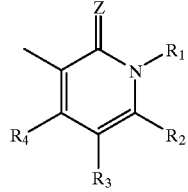

wherein
$R_2$ and $R_3$ are each independently H or methyl, wherein $R_2$ and $R_3$ are the same or different;
$R_4$ is methyl; and
Z is O.

3. A compound of formula (II):

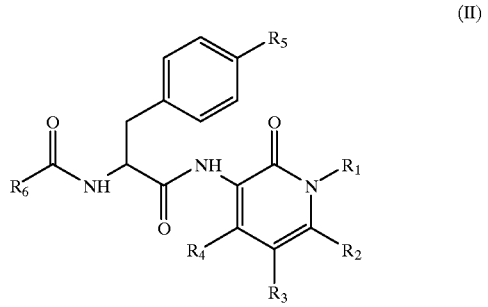

(II)

wherein:
$R_1$ aryl linked to the adjacent N via a lower alkyl,
$R_2$ and $R_3$ are each independently H or alkyl wherein $R_2$ and $R_3$ are the same or different;
$R_4$ is alkyl;
$R_5$ is C(CH$_3$)$_2$COOH or NHCOCOOH; and R$_6$ is heterocyclyl selected from pyridyl, pyrrolyl, pyrrolinyl, piperidinyl, oxopiperidinyl, oxopyrroldinyl, and the benzofused derivatives thereof optionally linked to the adjacent carbonyl via an alkoxy; —O—; amino; lower alkyl; lower alkyl amino; carbonyl; amido; amido alkyl; alkoxycarbonyl; carbonylalkyloxy; cycloalkyl or heterocyclyl as defined in this paragraph.

4. The compound according to claim 3, wherein:

R$_6$ is optionally linked to the adjacent carbonyl via an amino; lower alkyl; lower alkyl amino; amido or amido alkyl.

5. The compound according to claim 4, wherein:

R$_1$ is benzyl or benzyl para-substituted with lower alkoxy; R$_2$ and R$_3$ are each H;

R$_4$ is methyl or ethyl;

R$_6$ is optionally linked to the adjacent carbonyl via a lower alkyl, amino or amido lower alkyl linker.

6. The compound according to claim 5, wherein:

R$_6$ is benzimidazolyl optionally linked to the adjacent carbonyl via a lower alkyl, amino or amido lower alkyl linker.

7. A pharmaceutical composition comprising a compound according to claim 1 and a pharmaceutically acceptable carrier or adjuvant.

8. A compound of the formula(II), wherein R$_1$, R$_2$, R$_3$, R$_4$, R$_5$ and R$_6$ are selected from

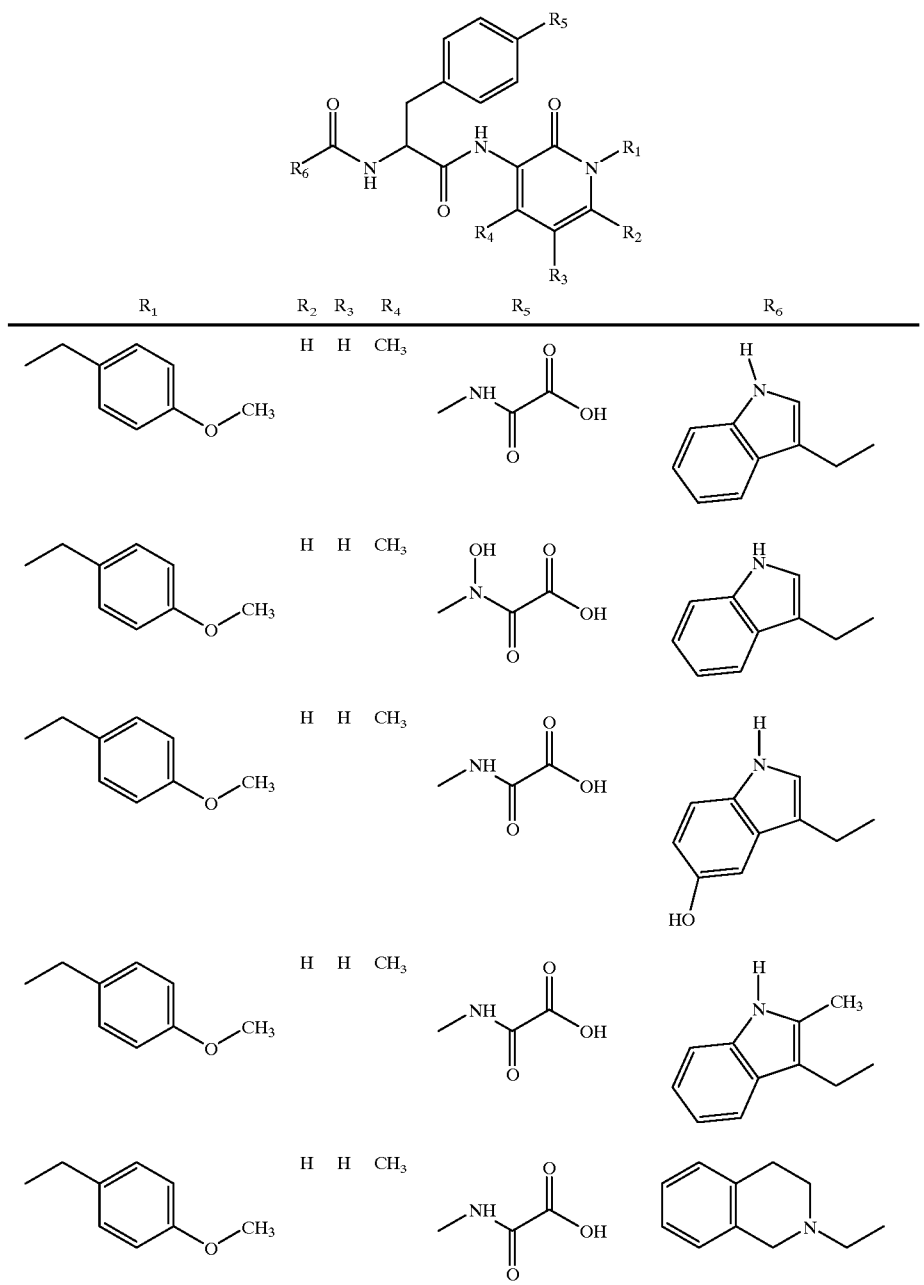

-continued
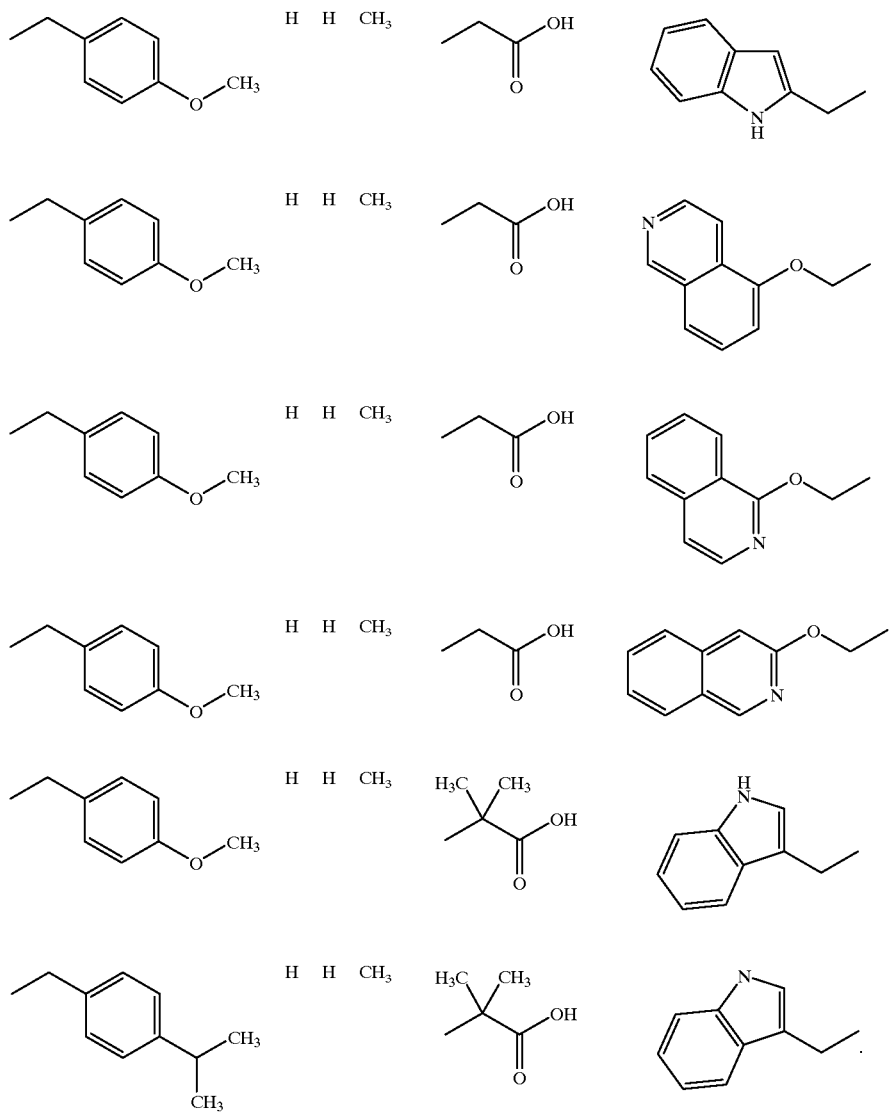

9. The compound according to claim 8 wherein $R_1$, $R_2$, $R_3$, $R_4$, $R_5$ and $R_6$ are selected from:
| $R_1$ | $R_2$ | $R_3$ | $R_4$ | $R_5$ | $R_6$ |
|---|---|---|---|---|---|
| 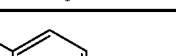 | H | H | $CH_3$ |  |  |
| 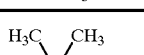 | H | H | $CH_3$ | 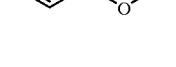 |  |
10. A method for treating rheumatoid arthritis comprising administering to a patient in need thereof a therapeutically effective amount of a compound according to claim 1.
* * * * *